US011432927B2

(12) United States Patent
Lashinski et al.

(10) Patent No.: US 11,432,927 B2
(45) Date of Patent: *Sep. 6, 2022

(54) IMPLANTABLE DEVICE AND DELIVERY SYSTEM FOR RESHAPING A HEART VALVE ANNULUS

(71) Applicant: Boston Scientific Scimed, Inc., Maple Grove, MN (US)

(72) Inventors: Randall Lashinski, Windsor, CA (US); Kristian Kristoffersen, Redding, CA (US); Matthew Rust, Windsor, CA (US); Richard Glenn, Santa Rosa, CA (US); Michael J. Lee, Santa Rosa, CA (US); Patrick E. Macaulay, Windsor, CA (US); Kenny D. Bruner, Windsor, CA (US); Padraig J. Savage, Santa Rosa, CA (US); Nathan D. Brown, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 106 days.

This patent is subject to a terminal disclaimer.

(21) Appl. No.: 16/718,745

(22) Filed: Dec. 18, 2019

(65) Prior Publication Data
US 2020/0146825 A1 May 14, 2020

Related U.S. Application Data

(63) Continuation of application No. 15/893,122, filed on Feb. 9, 2018, now Pat. No. 10,548,731.
(Continued)

(51) Int. Cl.
*A61F 2/02* (2006.01)
*A61F 2/24* (2006.01)

(52) U.S. Cl.
CPC ............ *A61F 2/2445* (2013.01); *A61F 2/243* (2013.01); *A61F 2/2418* (2013.01);
(Continued)

(58) Field of Classification Search
CPC .... A61F 2/2418; A61F 2/2436; A61F 2/2427; A61F 2/2439; A61F 2002/9511;
(Continued)

(56) References Cited

U.S. PATENT DOCUMENTS 9,180,005 B1 * 11/2015 Lashinski ............. A61F 2/2409
9,848,983 B2 * 12/2017 Lashinski ............. A61F 2/2409
(Continued)

*Primary Examiner* — Ann Schillinger
(74) *Attorney, Agent, or Firm* — Seager, Tufte & Wickhem LLP

(57) ABSTRACT

Systems, devices and methods related to various heart valve implants and for delivery of those implants are described. The implants may be used to re-size a native valve annulus or to replace a native heart valve. The implants include a re-sizable frame having angled struts. The implant is secured to tissue with anchors that can rotate without axial advancement to engage tissue while drawing the implant closer to the tissue. Collars are used to decrease the angle between struts of a frame to contract the implant. The implants can include a rotatable shaft, such as a threaded shaft, located internally to an axially translatable collar. Rotation of the shaft transmits force to the collar to cause the collar to translate axially, closing the angle of adjacent struts and decreasing the width of the implant and thus of the annulus. The implants can be delivered, secured and contracted via a catheter. The implants are repositionable and retrievable via catheter.

5 Claims, 71 Drawing Sheets

Related U.S. Application Data

(60) Provisional application No. 62/552,896, filed on Aug. 31, 2017, provisional application No. 62/457,441, filed on Feb. 10, 2017.

(52) U.S. Cl.
CPC .......... *A61F 2/2466* (2013.01); *A61F 2/2409* (2013.01); *A61F 2/2412* (2013.01); *A61F 2220/0016* (2013.01); *A61F 2230/0056* (2013.01); *A61F 2230/0065* (2013.01); *A61F 2230/0091* (2013.01); *A61F 2250/001* (2013.01); *A61F 2250/0006* (2013.01)

(58) Field of Classification Search
CPC .. A61F 2220/0016; A61F 2/24; A61F 2/2445; A61F 2/243; A61F 2/2466; A61F 2/2409; A61F 2/2412; A61F 2230/0056; A61F 2230/0065; A61F 2230/0091; A61F 2250/0006; A61F 2250/001; A61F 2/2442
See application file for complete search history.

(56) References Cited

U.S. PATENT DOCUMENTS

| | | | | |
|---|---|---|---|---|
| 10,226,342 | B2* | 3/2019 | Kutzik | A61F 2/2445 |
| 10,258,466 | B2* | 4/2019 | Lashinski | A61F 2/2418 |
| 10,335,275 | B2* | 7/2019 | Lashinski | A61B 17/068 |
| 10,548,731 | B2* | 2/2020 | Lashinski | A61F 2/2442 |
| 10,555,813 | B2* | 2/2020 | Lashinski | A61F 2/2436 |
| 10,939,997 | B2* | 3/2021 | Lashinski | A61F 2/2445 |
| 2008/0262609 | A1* | 10/2008 | Gross | A61F 2/2445 |
| | | | | 623/2.38 |
| 2011/0106247 | A1* | 5/2011 | Miller | A61B 17/0401 |
| | | | | 623/2.17 |
| 2011/0166649 | A1* | 7/2011 | Gross | A61F 2/2466 |
| | | | | 623/2.36 |
| 2014/0277563 | A1* | 9/2014 | White | A61F 2/243 |
| | | | | 623/23.7 |
| 2016/0235526 | A1 | 8/2016 | Lashinski et al. | |

\* cited by examiner

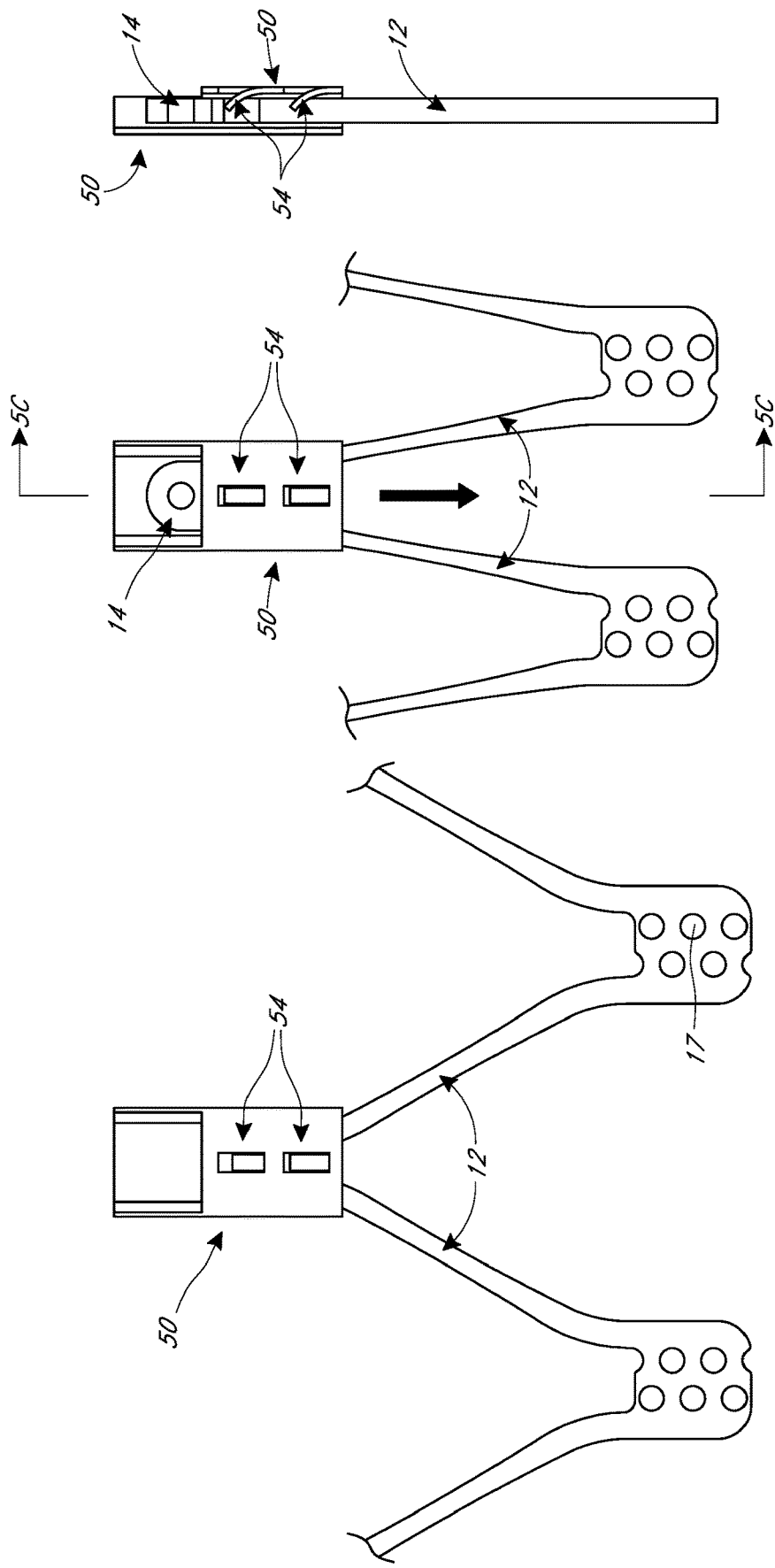

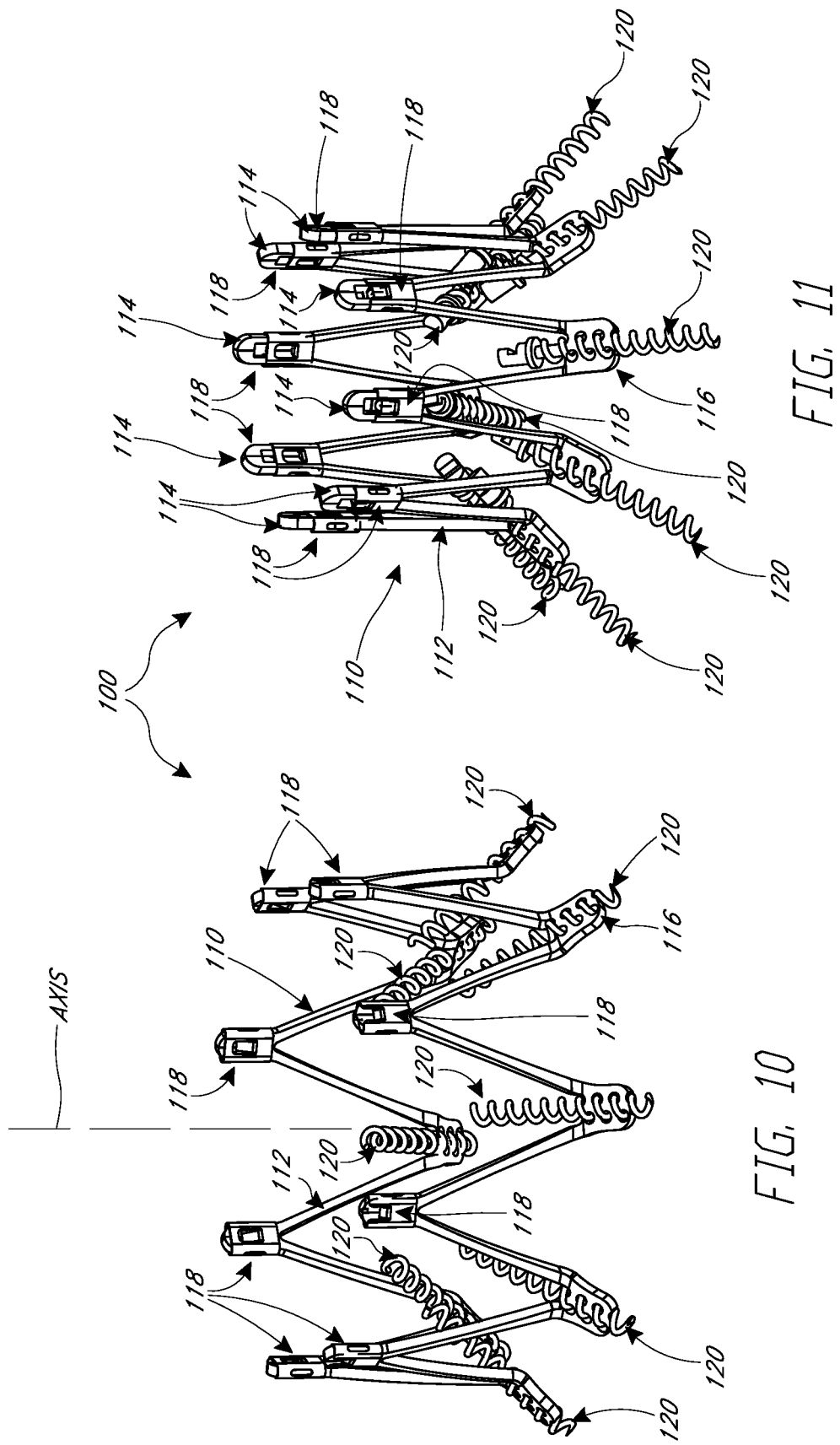

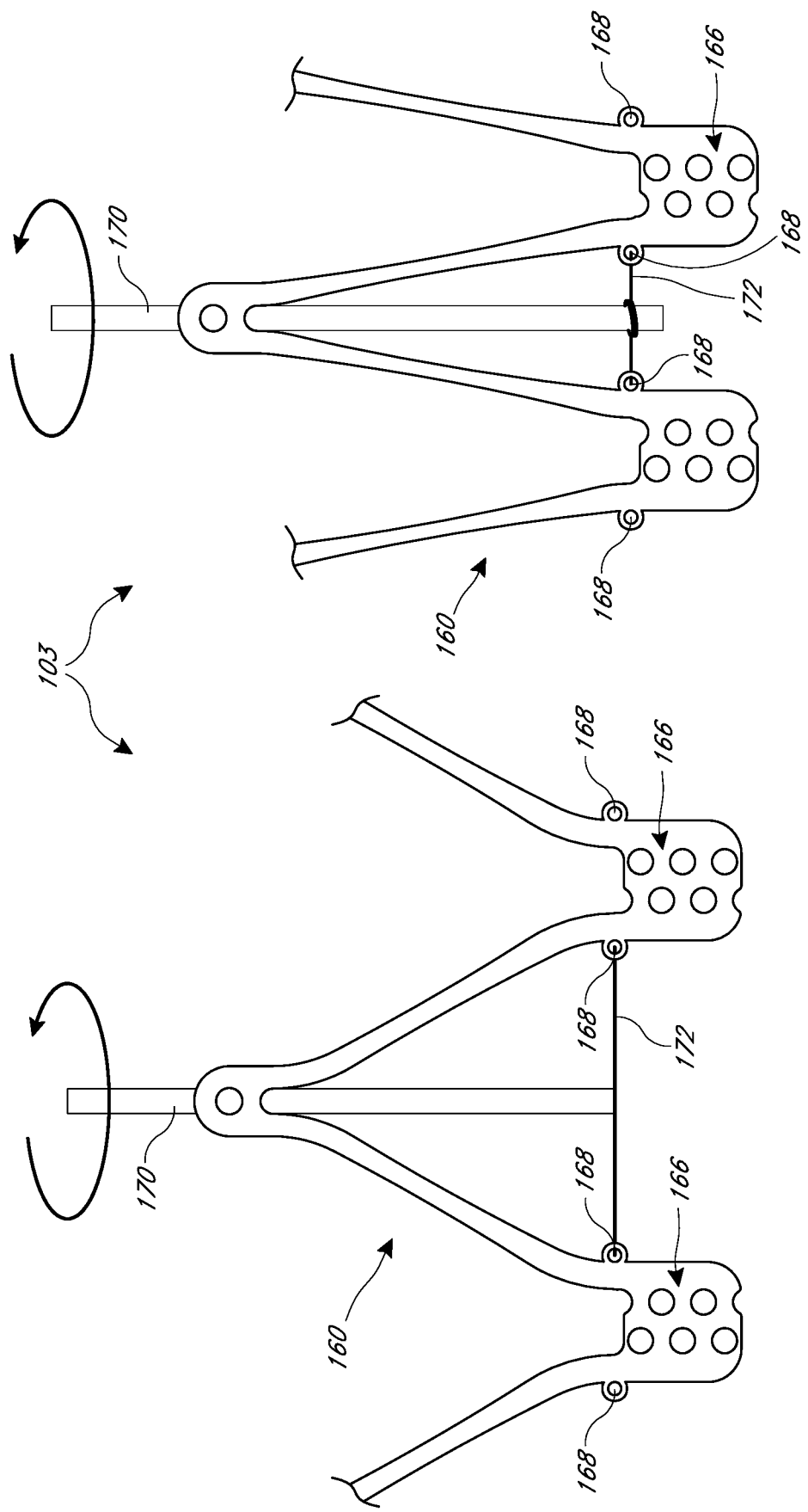

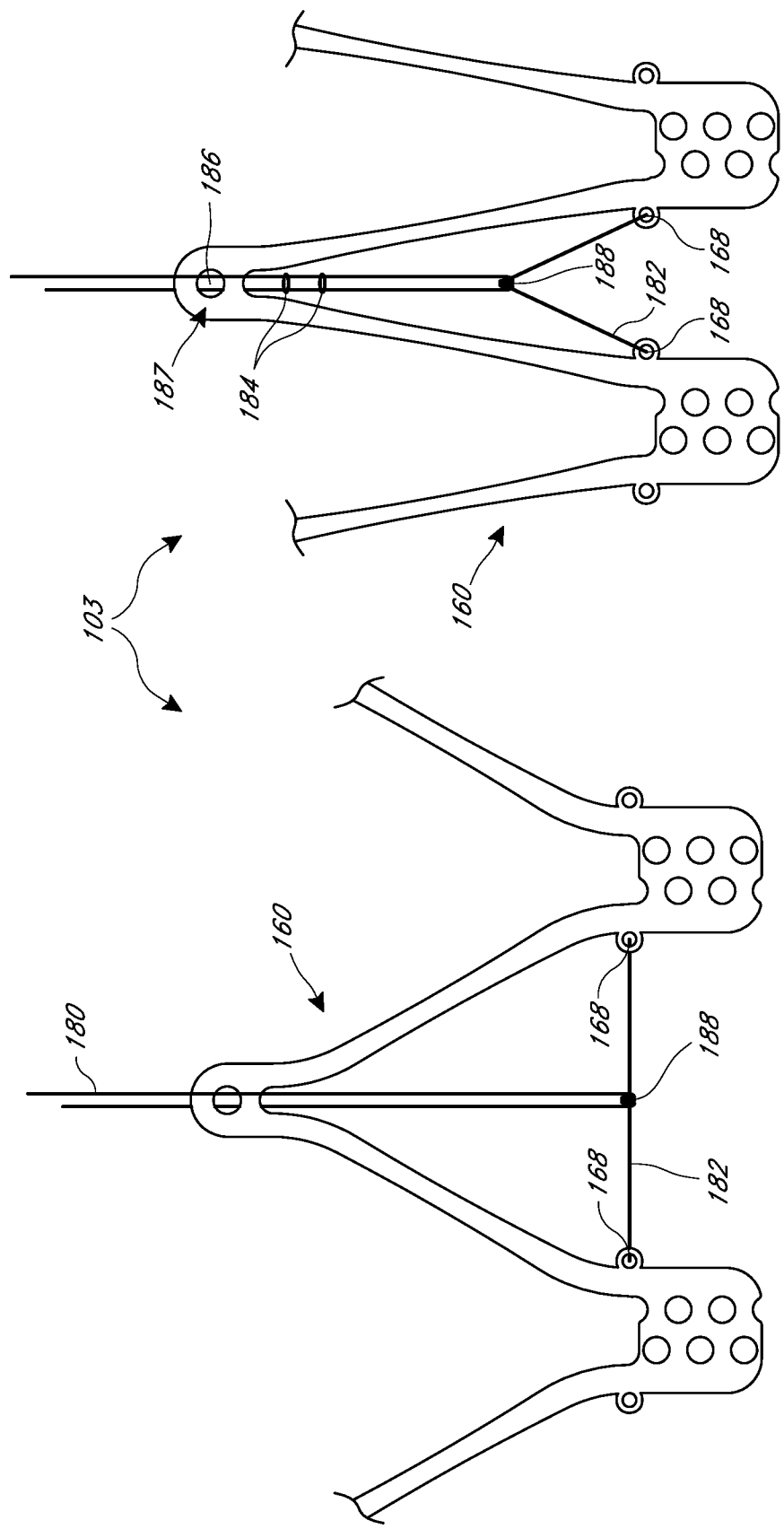

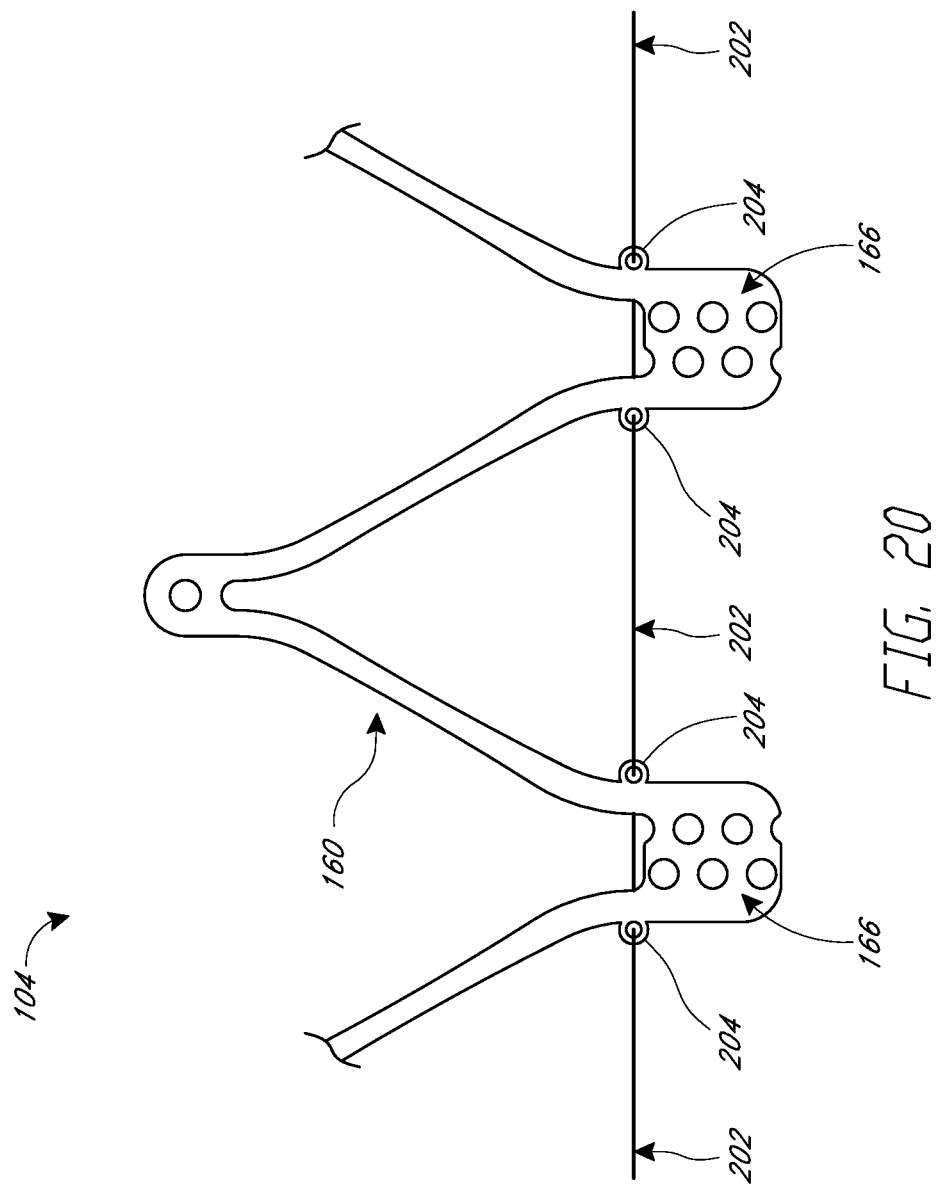

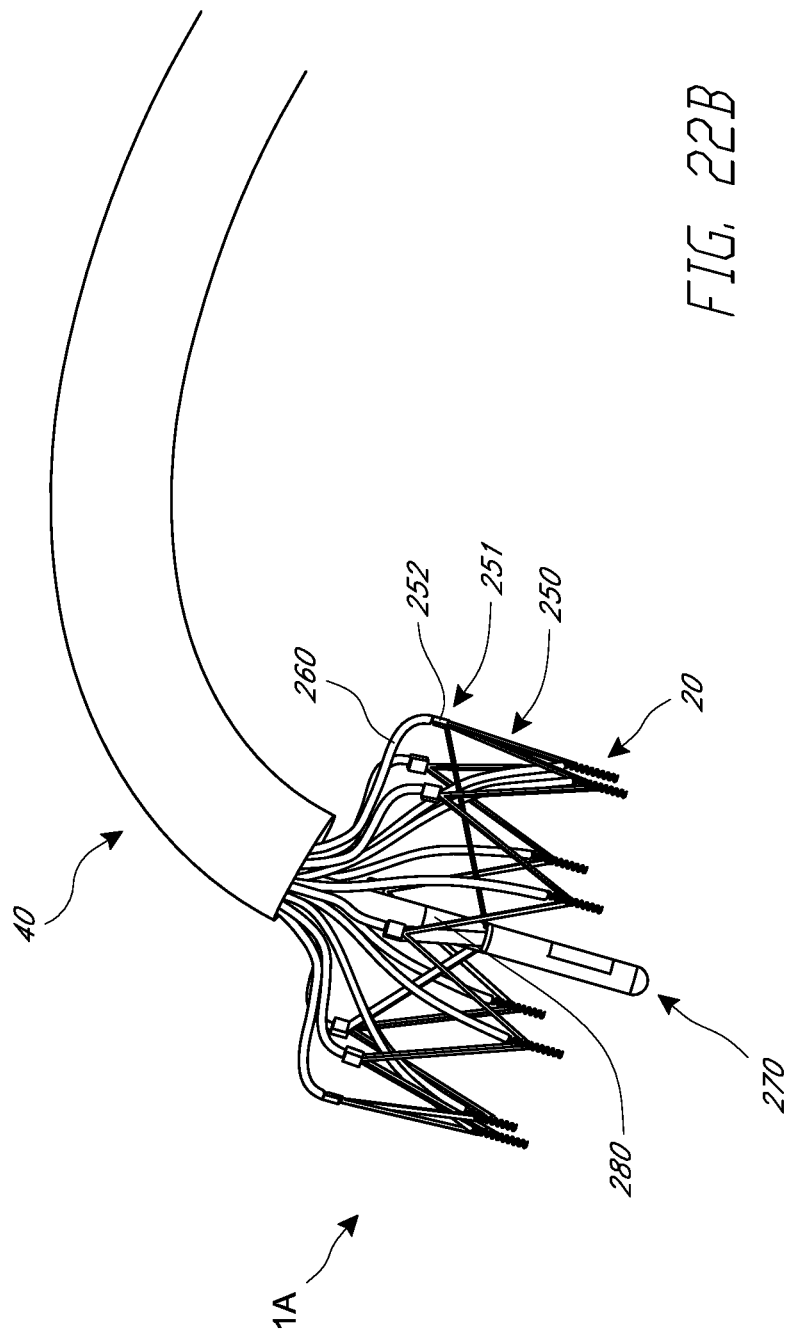

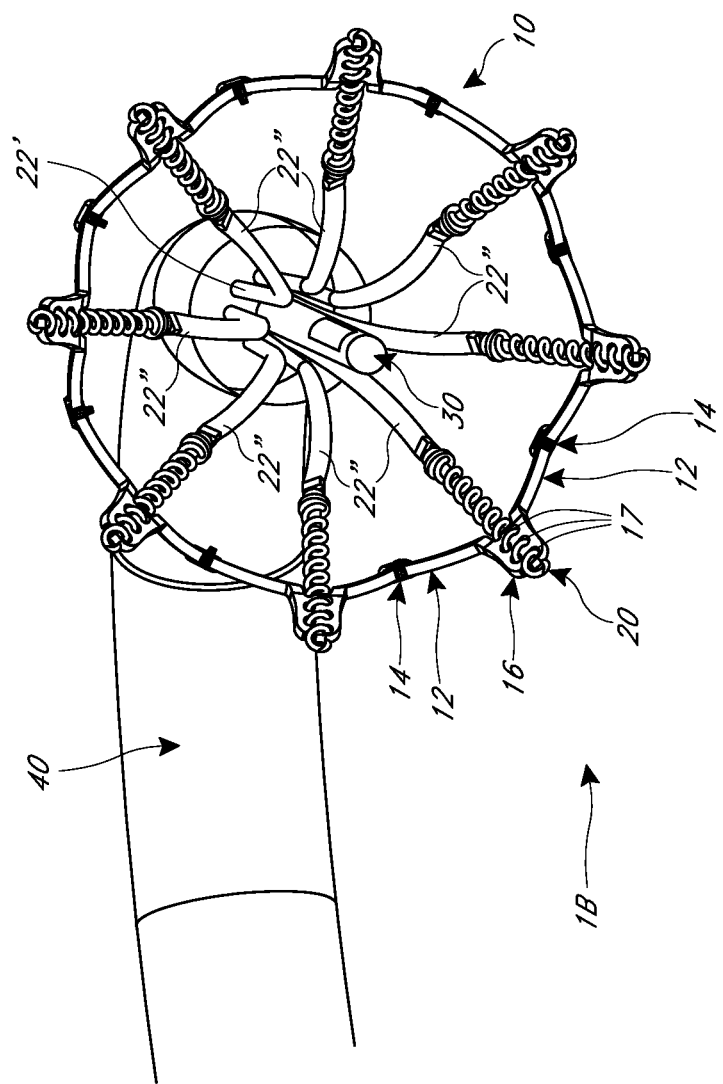

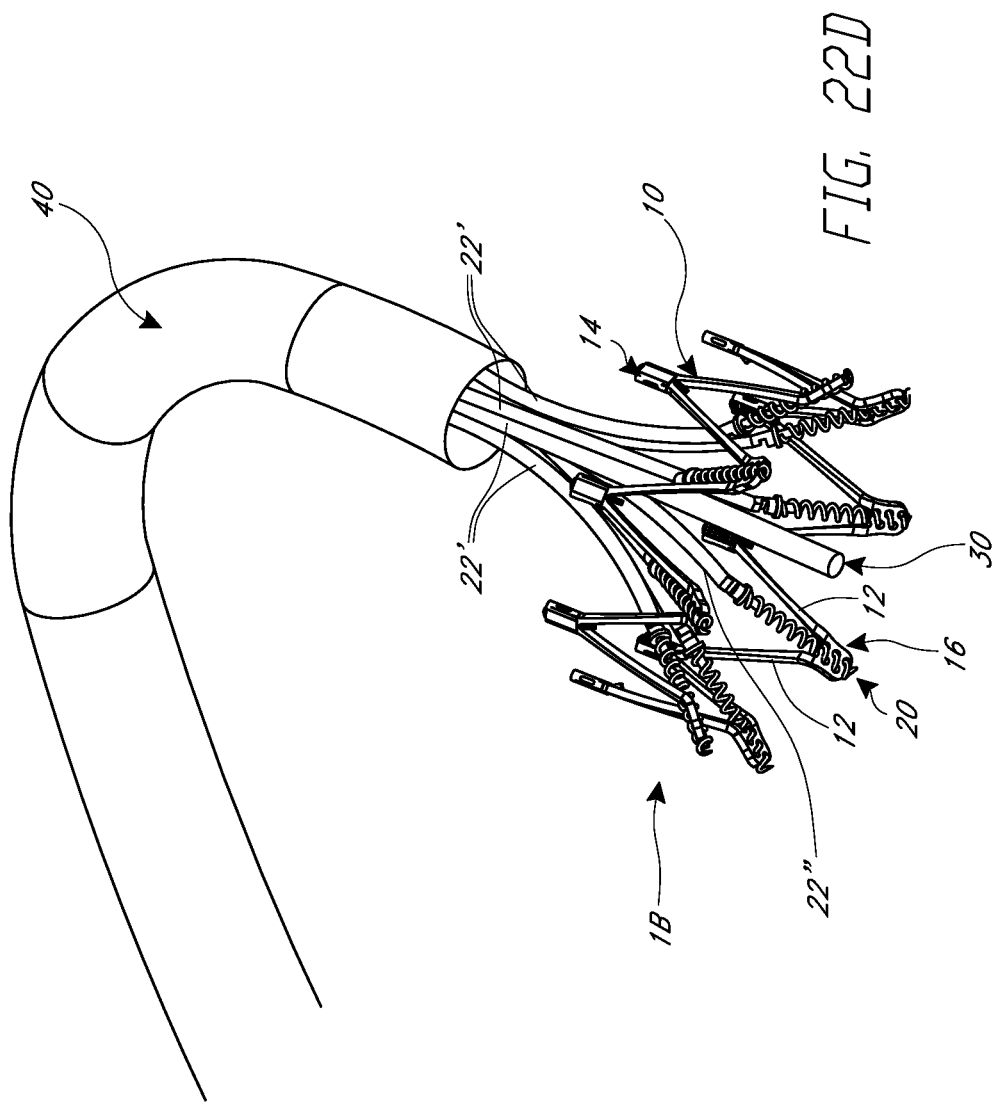

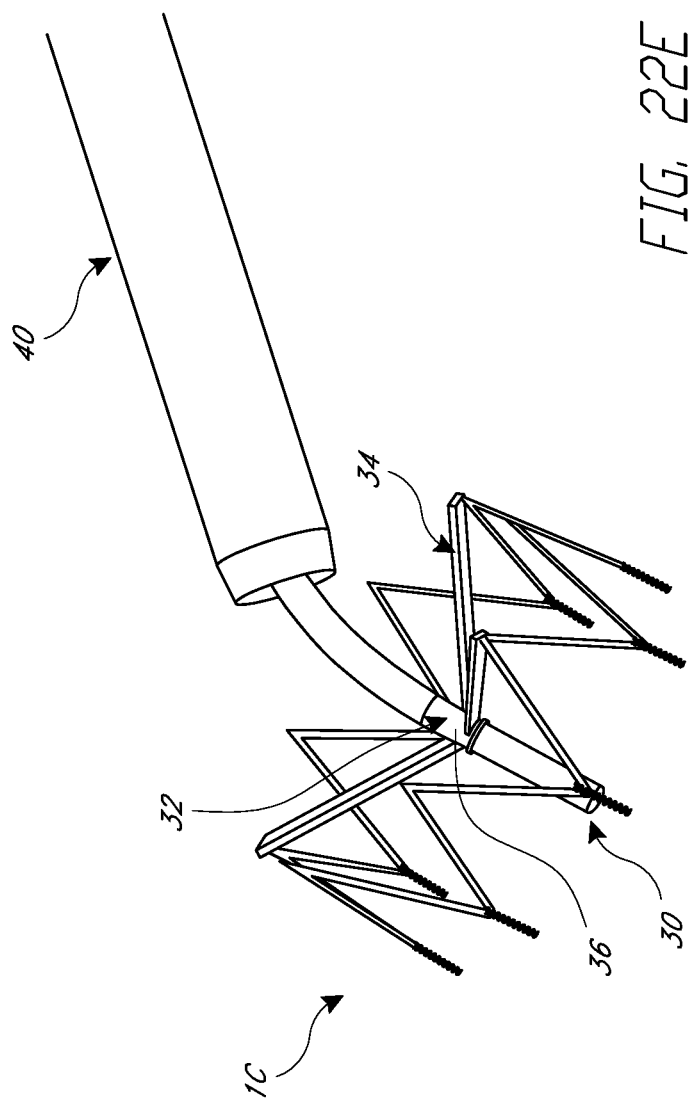

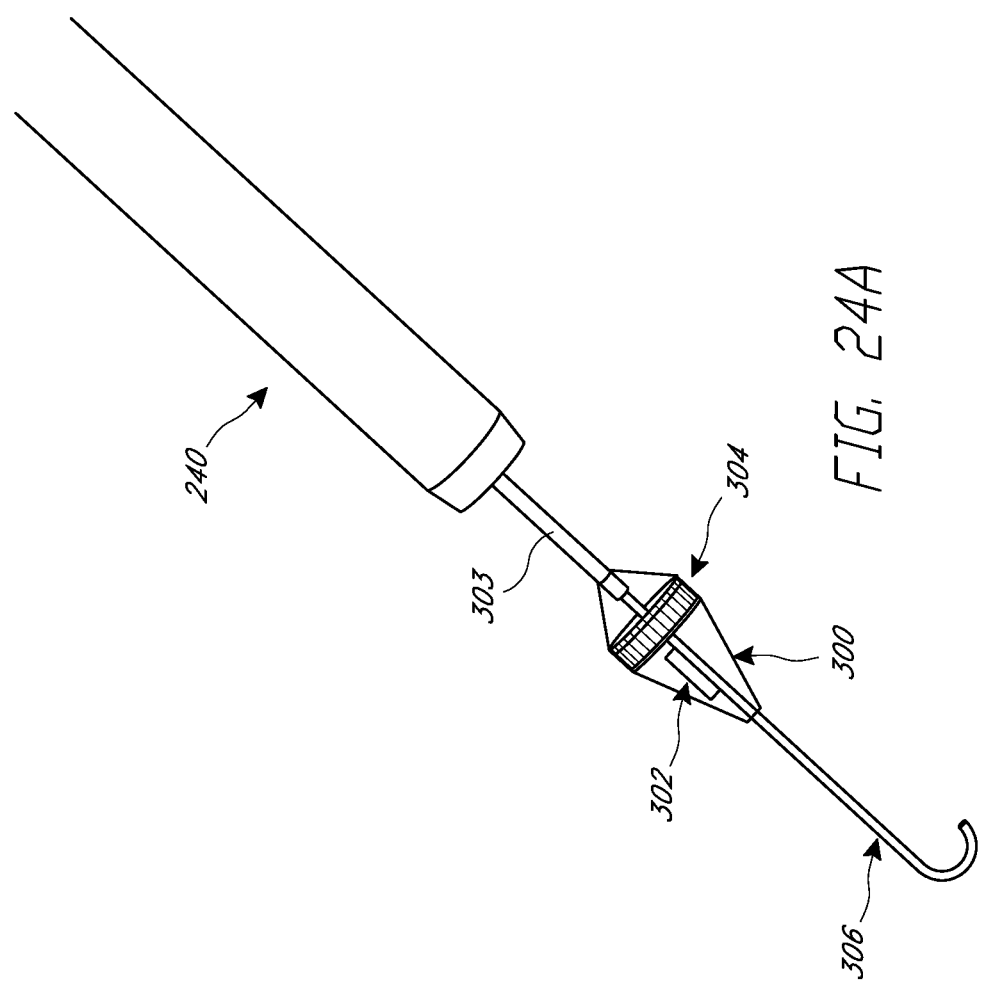

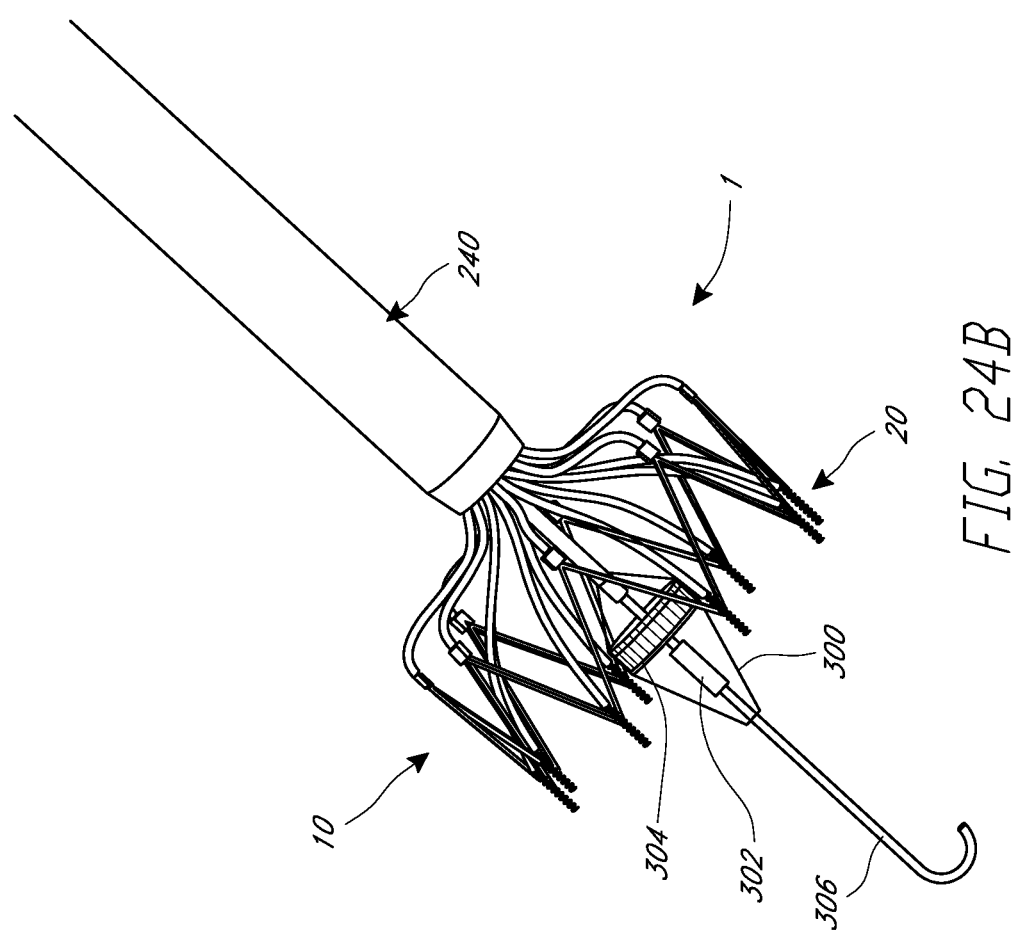

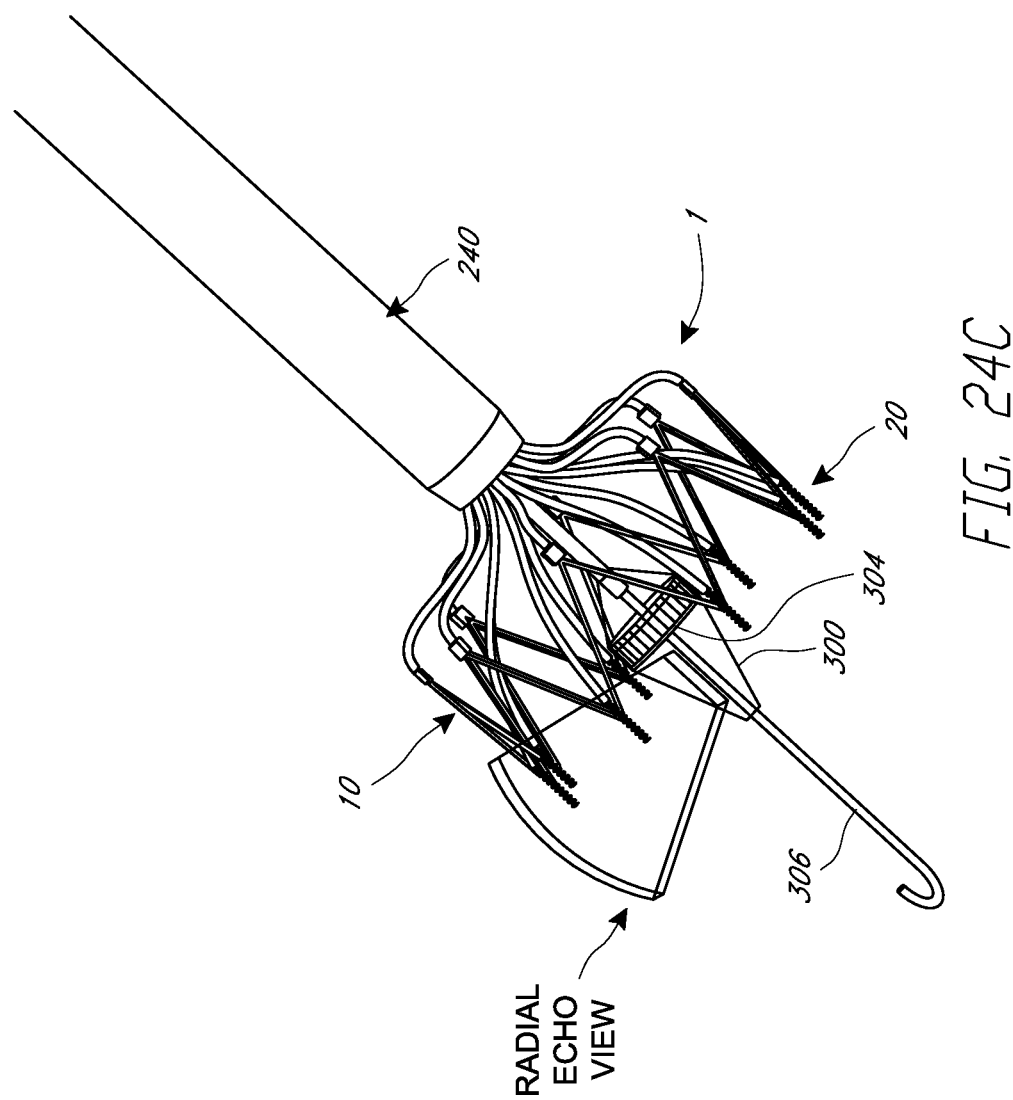

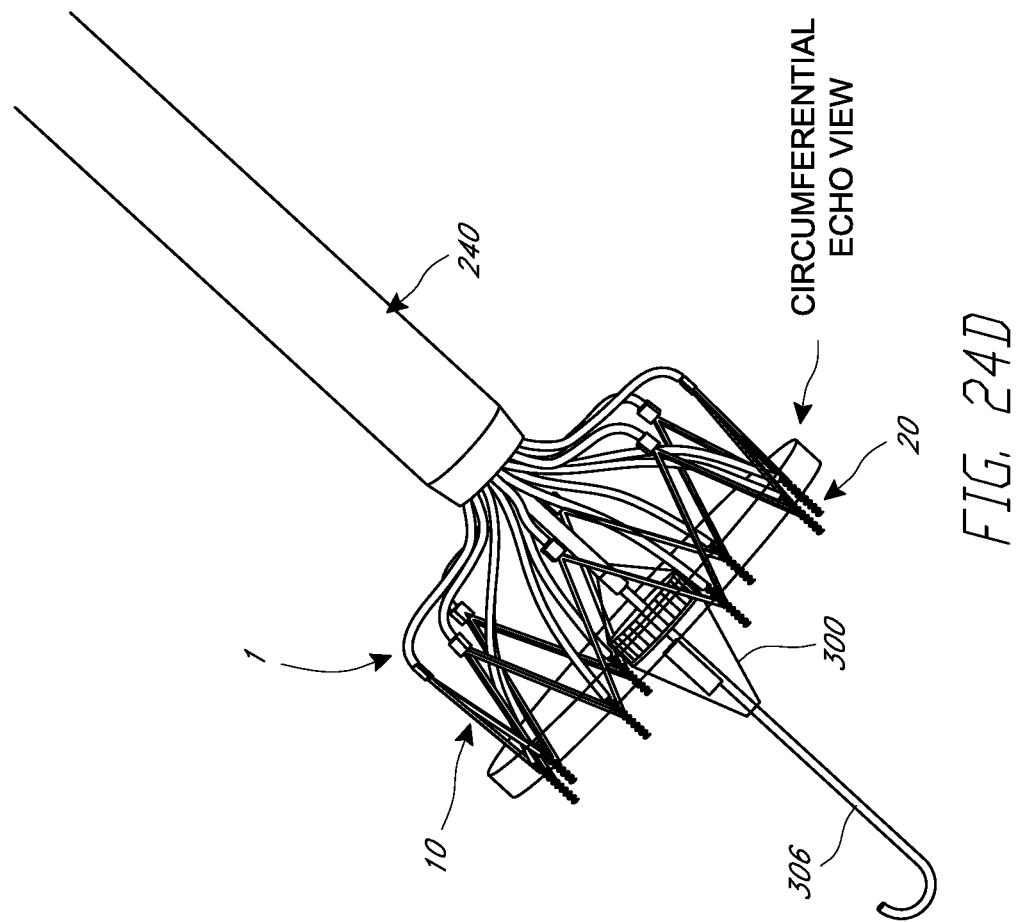

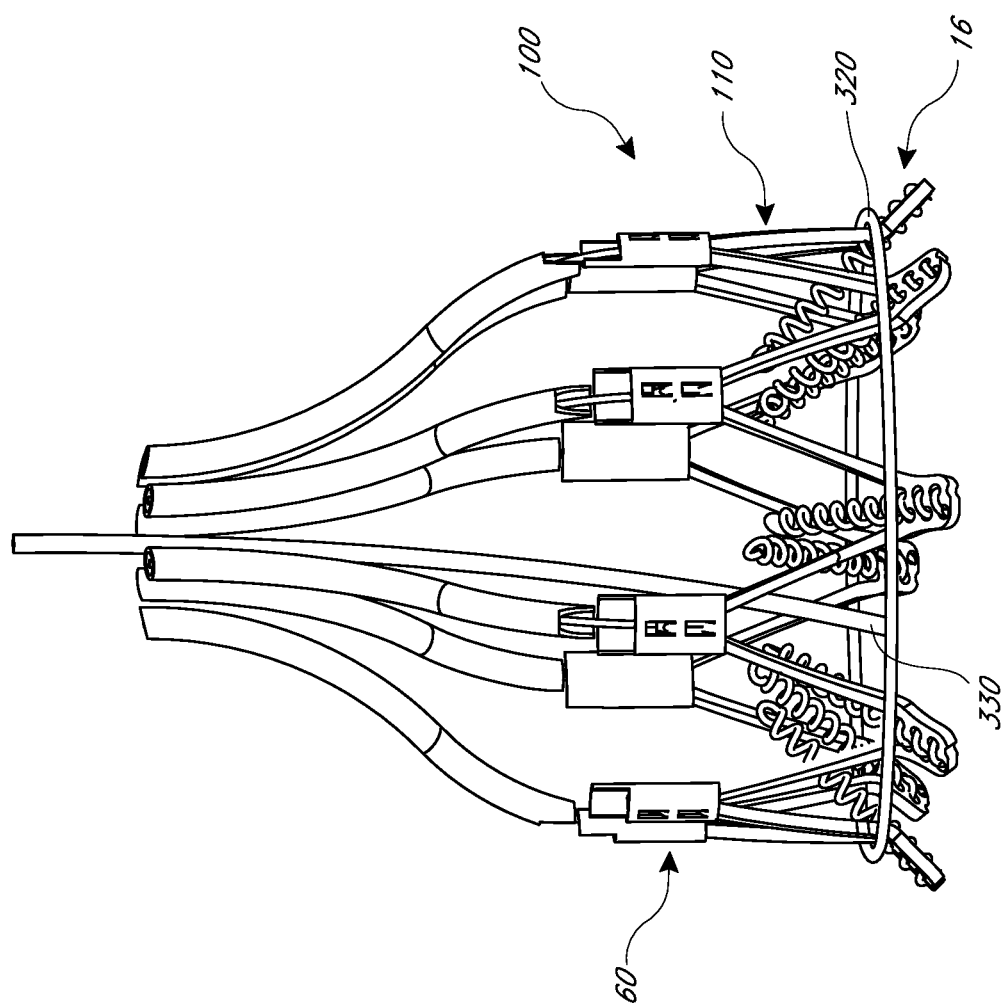

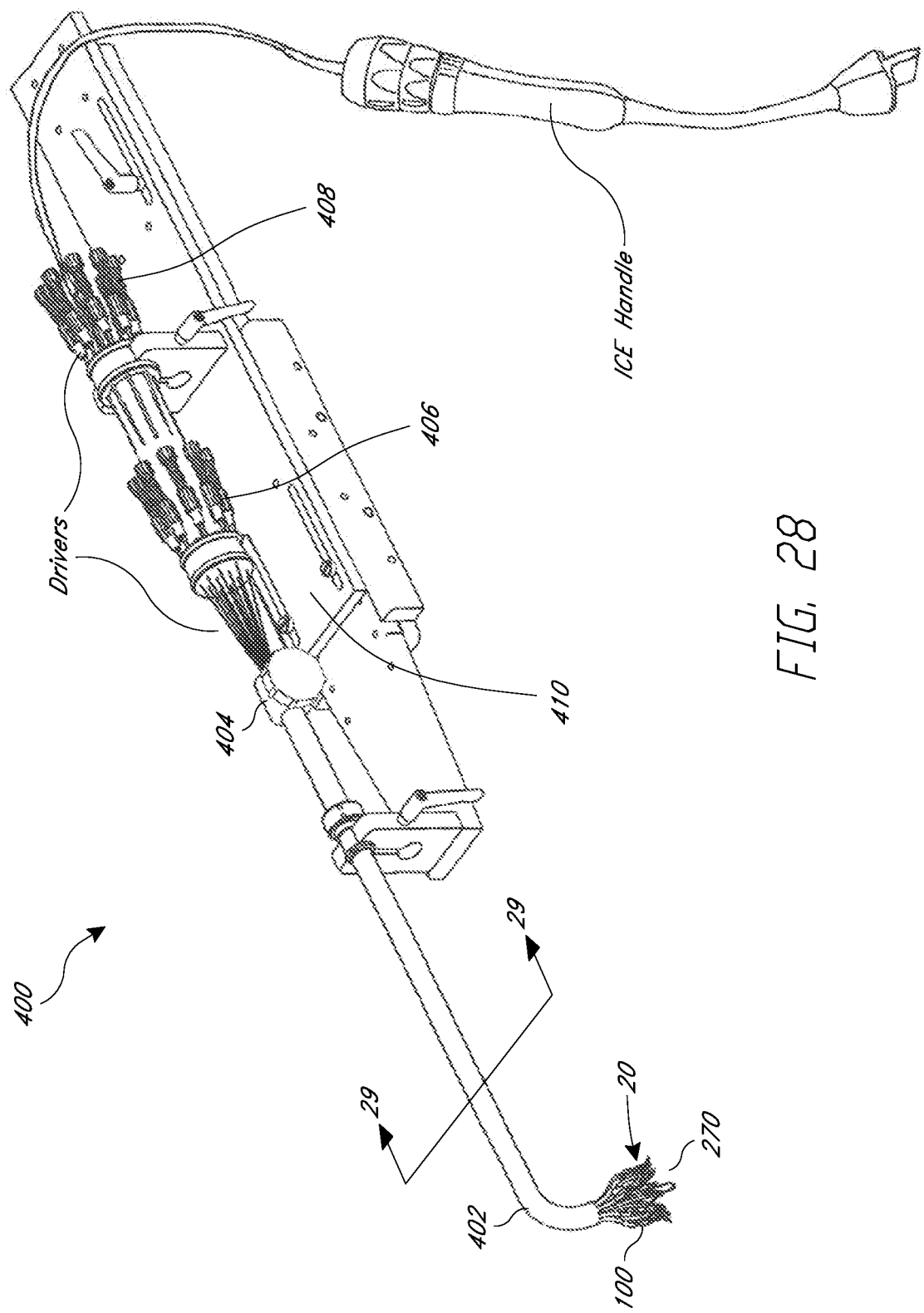

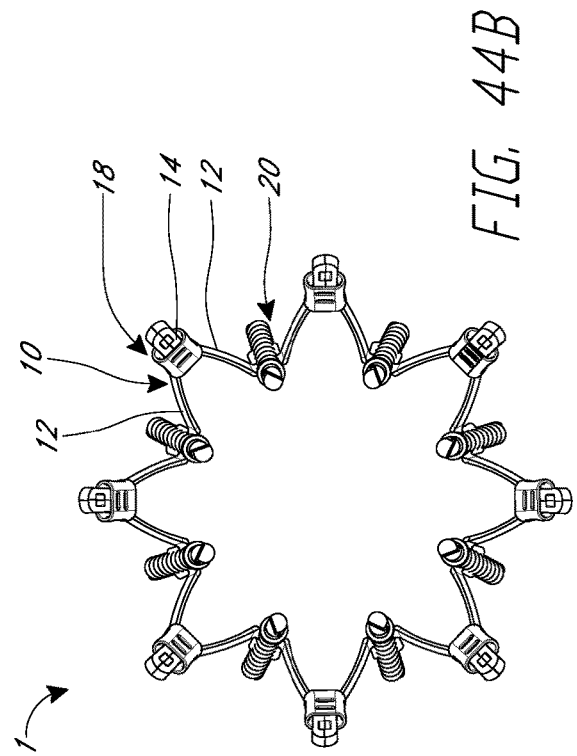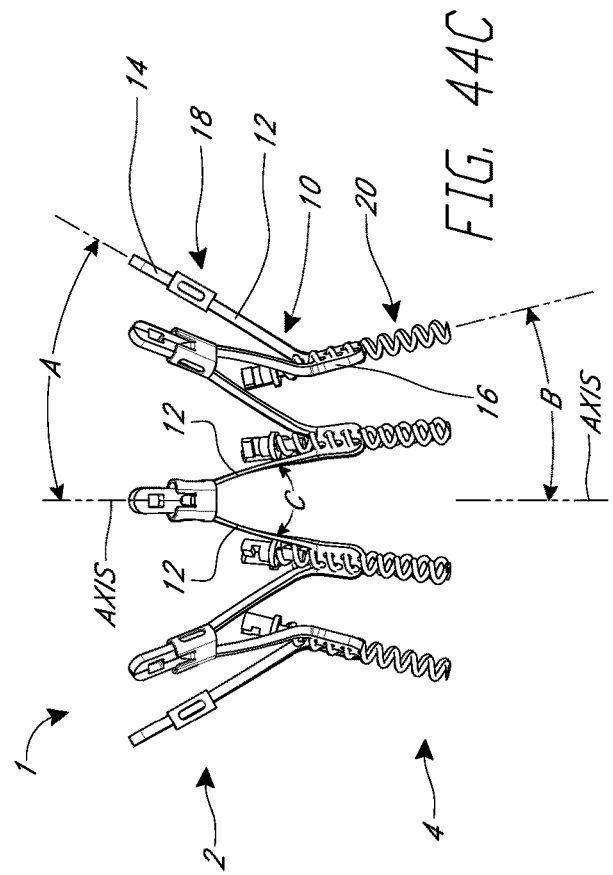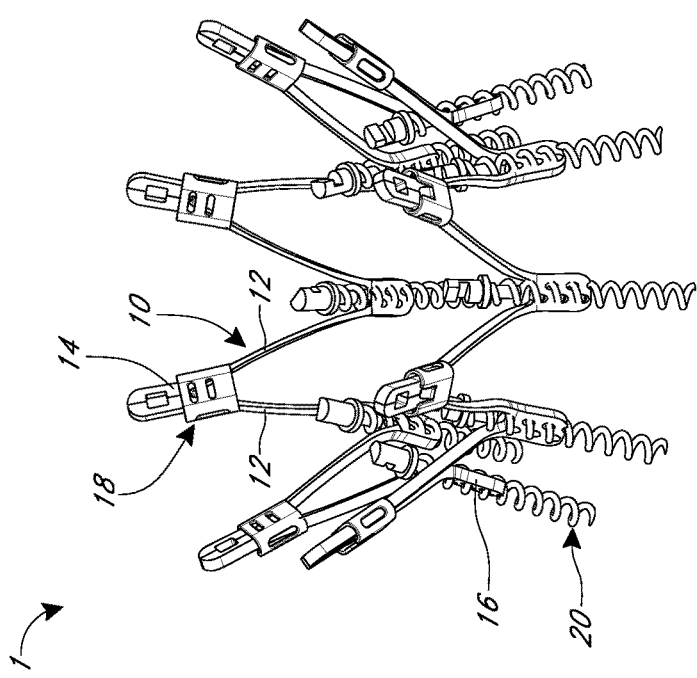

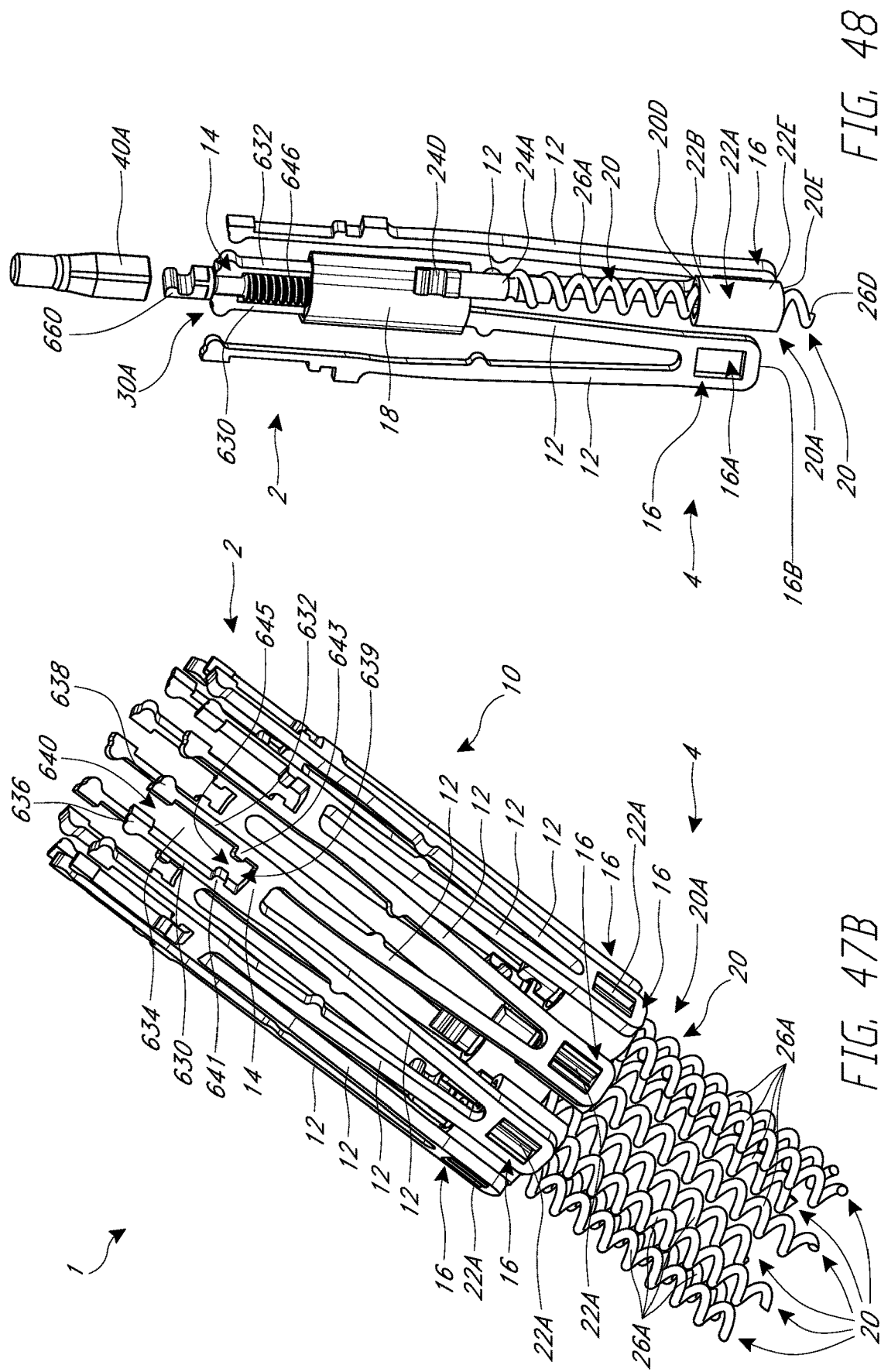

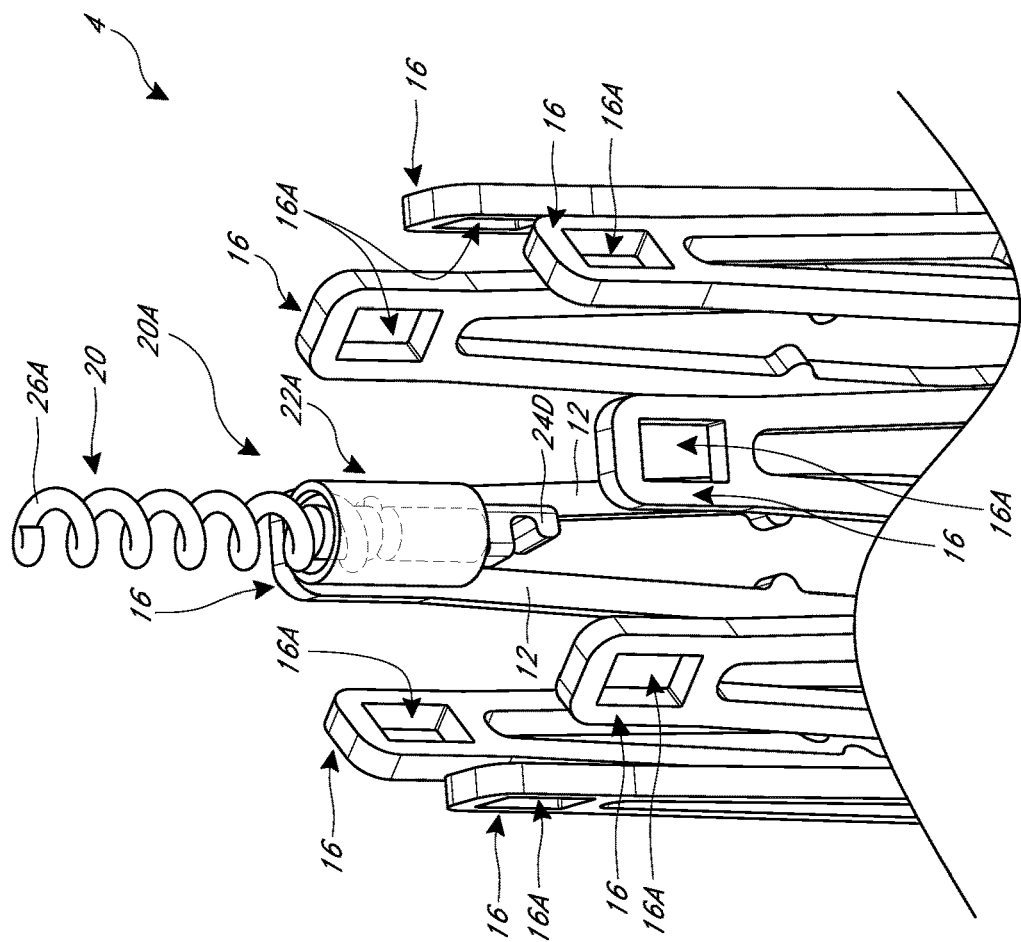
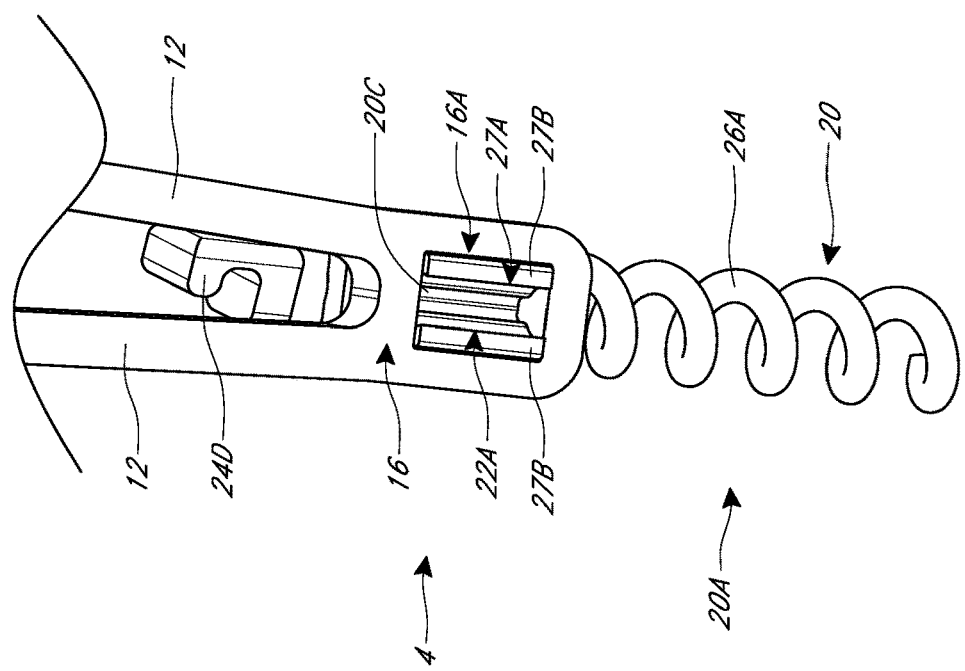
FIG. 49B
FIG. 49A

IMPLANTABLE DEVICE AND DELIVERY SYSTEM FOR RESHAPING A HEART VALVE ANNULUS

INCORPORATION BY REFERENCE TO ANY RELATED APPLICATIONS

Any and all applications for which a foreign or domestic priority claim is identified in the Application Data Sheet as filed with the present application are hereby incorporated by reference in their entirety under 37 CFR 1.57.

This application is a continuation of U.S. patent application Ser. No. 15/893,122, filed Feb. 9, 2018, which claims the benefit of priority to U.S. provisional patent application No. 62/457,441, entitled IMPLANTABLE DEVICE AND DELIVERY SYSTEM FOR RESHAPING A HEART VALVE ANNULUS and filed Feb. 10, 2017, and to U.S. provisional patent application No. 62/552,896, entitled IMPLANTABLE DEVICE AND DELIVERY SYSTEM FOR RESHAPING A HEART VALVE ANNULUS and filed Aug. 31, 2017, the disclosure of each which is hereby incorporated by reference herein in its entirety for all purposes and forms a part of this specification.

BACKGROUND

Field

In general, features related to implantable medical devices are described. In particular, devices for reshaping a valve annulus and associated transcatheter delivery and positioning systems for implanting the various devices are described.

Description of the Related Art

Heart valve incompetency is a serious problem. For example, heart disease can cause the chambers of the heart to expand and weaken. With specific reference to the mitral valve, as a result of aging or disease, the left ventricle dilates and the papillary muscles are displaced. Consequently, the annulus of the mitral heart valve dilates excessively. In this state of dilation, valve leaflets no longer effectively close, or coapt, during systolic contraction. Consequently, regurgitation (i.e. retrograde flow back across the valve that should be closed) of blood occurs during ventricular contraction. Cardiac output is thus decreased.

This condition is typically addressed by the surgical implantation of an annuloplasty ring. A surgeon positions the annuloplasty ring proximate the valve annulus and sutures it in place thereby restoring the valve annulus to approximately its native configuration. The valve leaflets can now function normally again.

This procedure is invasive as it is performed open chest and is also time consuming. In open heart surgery, the patient is put on cardiopulmonary bypass with its associated risks of morbidity and mortality due to stroke, thrombosis, heart attack and extended recovery time.

There is, therefore, a need for less invasive and more efficient solutions to these problems that avoid the aforementioned drawbacks.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

Systems, devices and methods for a heart valve implant and related delivery systems are described. The implant is intended to be delivered in a minimally invasive percutaneous manner, such as transfemorally, transeptally, or transapically. The implant may instead be implanted surgically, in that it should reduce the duration of the procedure and, more particularly, the duration that the patient is on bypass. The development can be directed to mitral valve or tricuspid valve procedures.

The development relates to the implant and delivery systems, and associated methods of use of each. The implant contracts to a first configuration, such as a delivery configuration, having a first diameter for delivery via a delivery catheter. The implant is capable of expanding out to a second configuration, such as a tissue engaging configuration (and/or anchored configuration), having a second diameter larger than the first diameter to match the shape, e.g. width, of a dilated annulus of a heart valve. The implant engages the tissue of the heart valve annulus with anchors and then contracts to a third configuration, such as an annulus remodeling diameter, having a third diameter that is smaller than the second diameter, thus gathering and cinching in the dilated annulus to decrease the width of the dilated annulus.

The implant includes a tubular frame with moveable struts, where pairs of adjacent struts form proximal apices or crowns and define an angle between each pair of adjacent struts. The apices each have a moveable restraint, for example a slider or collar, at least partially surrounding a corresponding pair of adjacent struts. A threaded shaft mechanically communicates with each moveable restraint. After engaging heart valve annulus tissue with the implant, such as with any of the various the anchors described herein, the collars can be moved in a generally axial direction, e.g. downward or distally, along the apex and/or struts, by rotating the threaded shaft. The shaft may extend through an opening in the collar such that rotation of the shaft causes translation of the collar. The shaft may be rotatable about a local central axis and be axially stationary relative to a respective apex. The collar may be rotationally stationary and axially moveable relative to the respective apex. The collar may be moved distally to decrease the angle between the adjacent struts, causing the tubular frame to contract in width. This pulls the tissue of the heart valve annulus closer together. The implant thus reconfigures the valve annulus down to a smaller width or diameter, reducing and/or eliminating problems associated with the valve, such as regurgitation or backflow of blood. For adjustment, the collars can be moved upward or proximally to increase the angle between the adjacent struts, causing or allowing the frame to expand. The collars are independently moveable to adjust individual pairs of struts for localized geometric control or repositioning of the implant. The implant may be retrieved by disengaging the anchors from the tissue and contracting the implant to a sufficiently small width for transcatheter removal from the patient.

A delivery system and associated methods are also disclosed that comprise a catheter and imaging and positioning features to maneuver the distal end of the catheter and the device into the desired position above and proximate the heart valve annulus. Transeptal delivery may be used, for example, with procedures involving the mitral valve. The delivery system can be used with the implant described herein as well as other implantable devices.

Moreover, the development also provides an artificial heart valve with a modified ring-like structure that not only provides for reduction of the heart valve annulus, but also displaces or replaces one or more defective heart valve leaflets. The artificial valve may include the various implant devices described herein having the one or more leaflets attached thereto.

Also described are distal anchoring features. The anchors may be helical anchors engaged with openings in distal apexes of the implant. The anchors may be part of anchor assemblies that include the anchor having a helical distal portion and a proximal head where the anchor is received in an anchor housing or mount at the distal apex. These and other anchoring features, among other advantages, address reliability of the distal ends of the ring-like implant frame to secure with and to fully contact the target annulus tissue after the anchors have been advanced. This contact may affect the effectiveness of the ring-like member to appropriately reduce the size of the dilated annulus. In addition, such contact ensures that more than only a portion of the anchor embeds into the heart tissue, which among other advantages will prevent pull out during the step of re-sizing the valve annulus. Moreover, for example, with the distal end(s) in contact with the valve tissue, the risk of fatigue failure of the anchor is decreased.

Thus, some embodiments of the anchor assembly described herein are designed to achieve more complete contact of the distal ends of the prosthesis with the tissue of the valve annulus and reduce, if not eliminate, gaps between the lower ends of the ring-like member and the valve tissue. Such contact, among other things, allows the ring-like member to effectively and appropriately re-size the dilated annulus, reduces the possibility of anchor withdrawal during re-sizing, and reduces the risk of fatigue on the anchors, among other benefits. These are merely some of the features described herein.

In one aspect, an implant for reshaping a mitral valve annulus is described. The implant comprises a tubular frame, a shaft and a collar. The tubular frame has a proximal end, a distal end and a central lumen extending therethrough. The frame has a first pair of adjacent struts joined at a proximal apex. The shaft is carried by the proximal apex and has an outer thread. The shaft is configured to rotate about a rotation axis. The collar is carried by the frame and at least partially surrounds the first pair of adjacent struts. The collar has an inner thread engaged with the outer thread of the shaft. Rotation of the shaft about the rotation axis causes the collar to advance along the first pair of adjacent struts to change an angle between the first pair of adjacent struts.

Various embodiments of the various aspects are also described. For example, rotation of the shaft about the rotation axis in a first direction may cause the collar to advance along the first pair of adjacent struts toward the distal end to decrease the angle between the first pair of adjacent struts, thereby contracting the implant. Rotation of the shaft about the rotation axis in a second direction that is opposite the first direction may cause the collar to advance along the first pair of adjacent struts toward the proximal end to allow an increase in the angle between the first pair of adjacent struts, thereby allowing the implant to expand. The frame further may comprise a first support and a second support extending from the proximal apex toward the proximal end of the frame and at least partially defining a window configured to at least partially retain the shaft therein. The collar may further comprise a first channel and a second channel configured to receive respectively the first support and the second support. The implant may further comprise a coupling attached to a proximal end of the shaft, the coupling configured to be rotated by a driver to rotate the shaft. The tubular frame may define a central longitudinal axis, and the adjacent pair of struts may be configured to incline radially outward relative to the central longitudinal axis. The pair of adjacent struts may be configured to incline radially outward relative to the central longitudinal axis in response to decreasing the angle between the first pair of adjacent struts.

The implant may further comprise an anchor coupled with the frame, the anchor configured to engage tissue of the mitral valve annulus. The frame may further comprise a second pair of adjacent struts joined at a distal apex, with the anchor coupled with the distal apex. The anchor may be a helical anchor. The distal apex may include a series of openings configured to rotatably receive the anchor therethrough.

The frame may comprise a second pair of adjacent struts joined at a distal apex, with the distal apex including an anchor housing configured to rotatably receive the anchor therethrough. The housing may have an opening extending axially therethrough, and the anchor may be configured to engage the tissue of the heart valve annulus by rotating within the housing while maintaining an axial position relative to the housing. The opening may have a proximal engagement structure and a distal chamber, with a maximum width of the distal chamber being greater than a minimum width of the proximal engagement structure.

The implant may further comprise a plurality of the first pair of adjacent struts, with each pair joined at a respective proximal apex, a plurality of the shafts each carried by the respective proximal apex, and a plurality of the collars each configured to engage a respective shaft. There may be eight pairs of adjacent struts, eight proximal apices, eight shafts, and eight collars. There may be eight anchors.

In another aspect, an implant for reshaping a mitral valve annulus is described. The implant comprises a tubular frame, a rotatable shaft and a collar. The tubular frame has a first pair of adjacent struts joined at a proximal apex. The rotatable shaft is located at the proximal apex. The collar at least partially surrounds the first pair of adjacent struts and the shaft. Rotation of the rotatable shaft causes the collar to advance along the first pair of adjacent struts to decrease an angle between the first pair of adjacent struts, thereby contracting the implant.

Various embodiments of the various aspects are also described. For example, the implant may further comprise an anchor coupled with the frame, the anchor configured to engage tissue of the mitral valve annulus. The implant may further comprise a window at the proximal apex that axially restrains the rotatable shaft.

In another aspect, a method of reshaping a mitral valve annulus is described. The method comprises positioning an implant adjacent a mitral valve annulus. The implant comprises a tubular frame having a pair of struts, a rotatable shaft carried by the frame, a translatable collar engaged with the rotatable shaft and at least partially surrounding the pair of struts, and an anchor coupled with the frame. The method further comprises securing the anchor to tissue of the mitral valve annulus, rotating the shaft to cause the collar to translate along the first pair of struts, and decreasing an angle between the first pair of struts due to translation of the collar.

In another aspect, an implant for reshaping a heart valve annulus having a "reach anchor" is described. The implant comprises a tubular frame, a housing and an anchor. The tubular frame has a proximal end, a distal end and a central lumen extending therethrough. The housing is coupled with the distal end of the frame. The housing has a proximal portion, a distal portion and an opening extending axially therethrough. The anchor is received in the opening of the housing. The anchor is configured to advance distally to engage tissue of the heart valve annulus by rotating within the housing while maintaining an axial position relative to the housing. In some embodiments, the anchor is configured to advance distally to engage tissue of the heart valve annulus by rotating within the housing while maintaining a constant or substantially constant axial position relative to the housing. In some embodiments, the housing further comprises an inner threaded portion in the proximal portion, and a chamber in the distal portion, and the anchor is configured to rotate within the chamber in the distal portion of the housing while maintaining an axial position relative to the distal portion of the housing. In some embodiments, the anchor further comprises a proximal cylindrical head having a coupling configured to be engaged by a driver to rotate the anchor, and a distal helical portion coupled with the proximal head extending distally therefrom and configured to engage the tissue.

In another aspect, an anchor assembly for an implant for reshaping a mitral valve annulus is described. The anchor assembly comprises a housing and an anchor. The housing has a proximal portion, a distal portion and an opening extending axially therethrough. The anchor is received in the opening of the housing. The anchor is configured to advance distally to engage tissue of the heart valve annulus by rotating within the housing while maintaining an axial position relative to the housing. In some embodiments, the opening has a proximal engagement structure and a distal chamber, with a maximum width of the distal chamber being greater than a minimum width of the proximal engagement structure, and the anchor is configured to rotate within the distal chamber while maintaining an axial position relative to the distal chamber. In some embodiments, the proximal engagement structure comprises a helical groove.

In another aspect, a method of securing an implant to a heart valve annulus is described. The implant comprises an anchor and an anchor housing. The method comprises simultaneously i) rotating the anchor within the housing, ii) advancing the anchor distally and axially into tissue of the heart valve annulus, and iii) maintaining an axial position of the anchor relative to the housing.

In another aspect, an implant for reshaping a mitral valve annulus having flared aspects is described. The implant comprises a tubular frame having a proximal end, a distal end and a central lumen extending therethrough. The frame comprises a pair of adjacent struts joined at an apex. The adjacent pair of struts are configured to incline radially outward relative to a central longitudinal axis in response to changing an angle between the pair of adjacent struts.

In another aspect, a coupling for an implant for reshaping a heart valve annulus is described. The coupling comprises a distal base coupled with a proximal lateral projection by a recess surface, with the recess surface defining an opening between the distal base and the proximal lateral projection, and with the opening configured to receive therein a rotatable driver for rotating the coupling.

In another aspect, a restraint for an implant for reshaping a heart valve annulus is described. The implant comprises a pair of adjacent struts joined at an apex and defining an angle therebetween. The restraint comprises a body extending axially, a central opening extending axially through the body, and an internal engagement structure on an inner surface of the central opening. The restraint is configured to at least partially surround the pair of adjacent struts at the apex and to engage the internal engagement structure with an actuator such that actuation of the actuator advances the restraint along the pair of adjacent struts to change the angle therebetween. In some embodiments, the restraint further comprises a first and second channel extending axially through the body on either side of the central opening, with the first and second channels configured to receive respective supports of the implant therethrough.

In another aspect, a rotatable shaft for an implant for reshaping a heart valve annulus is described. The implant comprises a pair of adjacent struts joined at an apex and defining an angle therebetween. The rotatable shaft comprises an elongated body having an external thread along an outer surface of the body, and a proximal coupling having a distal base coupled with a proximal lateral projection by a recess surface, with the recess surface defining an opening between the distal base and the proximal lateral projection, and with the opening configured to receive therein a rotatable driver for rotating the shaft.

In another aspect, a method of repositioning an implant for reshaping a heart valve annulus is described. The implant comprises a shaft, a collar, a pair of struts, and an anchor. The method comprises rotating the shaft in a first direction, translating the collar proximally along the pair of struts, increasing an angle between the pair of struts, disengaging the anchor from a first location of tissue of the heart valve annulus, engaging the anchor with a second location of the tissue of the heart valve annulus, rotating the shaft in a second direction, translating the collar distally along the pair of struts, and decreasing the angle between the pair of struts. In some embodiments, disengaging the anchor from the first location comprises rotating the anchor in a third direction, and engaging the anchor with the second location comprises rotating the anchor in a fourth direction.

In another aspect, a method of retrieving an implant secured with a heart valve annulus of a patient is described. The implant comprises a shaft, a collar, a pair of struts, and an anchor. The method comprises rotating the shaft in a first direction, translating the collar proximally along the pair of struts, increasing an angle between the pair of struts, disengaging the anchor from tissue of the heart valve annulus, rotating the shaft in a second direction, translating the collar distally along the pair of struts, decreasing the angle between the pair of struts, receiving the implant in a delivery catheter, and removing the implant from the patient.

In another aspect, an implant for dynamic post implantation constriction of an annulus surrounding a heart valve is described. The implant comprises an implant body, a plurality of tissue anchors, and a moveable restraint. The implant body comprises a proximal end, a distal end, a central lumen extending therethrough and at least one pair of adjacent struts joined at an apex and having an angle there between. The plurality of tissue anchors are on the implant body, and the anchors are configured to embed into tissue surrounding the heart valve. The moveable restraint is at least partially surrounding the pair of adjacent struts and can be moved along the pair of adjacent struts away from the apex to reduce the angle between the pair of adjacent struts, thereby causing the implant body to contract the annulus from a first diameter to a second, smaller diameter with at least one strut initially elastically deflected by resistance to movement imposed by the annulus when in the second diameter. The implant is configured to contract post implantation from the second diameter to a third, smaller diameter as elastic tension in the strut relaxes and overcomes resistance to movement imposed by the annulus. In some embodiments, the elastic tension is stored in the struts in between the movable restraint and a tissue anchor.

In another aspect, a method of dynamic post implantation constriction of an annulus surrounding a heart valve is described. The method comprises the steps of securing an implant to the wall of the atrium surrounding a mitral valve annulus having a first diameter, actively adjusting the implant with an adjustment catheter to reduce the annulus from the first diameter to a second, smaller diameter, removing the adjustment catheter, and continuing to reduce the diameter to a third diameter, smaller than the second diameter following removal of the catheter, in response to potential energy stored in the implant.

Various embodiments of the various aspects are described. For example, the second diameter may be no more than about 27 mm and the third diameter may be at least 1 mm smaller than the second diameter. The second diameter may be no more than about 27 mm and the third diameter may be at least 2 mm smaller than the second diameter. The implant may be configured to contract post implantation from the second diameter to a third, smaller diameter within about 30 days from the removing the adjustment catheter step. Mitral leaflet coaptation may increase by at least about 25% in response to reduction of the annulus from the second diameter to the third diameter. Mitral leaflet coaptation may increase by at least about 50% in response to reduction of the annulus from the second diameter to the third diameter. The diameter may continue to reduce for at least about five days following the removing the adjustment catheter step. The diameter may continue to reduce for at least about 10 days following the removing the adjustment catheter step.

In another aspect, a method of increasing mitral valve leaflet coaptation following implantation of a dynamic mitral valve annulus constriction device is described. The method comprises the steps of securing an implant to the wall of the atrium surrounding a mitral valve annulus having a first diameter, actively adjusting the implant with an adjustment catheter to reduce the annulus from the first diameter to a second, smaller diameter, and removing the adjustment catheter. Following the removing the catheter step, the dynamic implant increases leaflet coaptation by at least about 25% from the coaptation corresponding to the second diameter. In some embodiments, following the removing the catheter step the dynamic implant increases leaflet coaptation by at least about 50% from the coaptation corresponding to the second diameter. In some embodiments, following the removing the catheter step, the dynamic implant increases leaflet coaptation by at least about 2 mm. In some embodiments, following the removing the catheter step the dynamic implant increases leaflet coaptation by at least about 4 mm.

In another aspect, a method of remodeling a mitral valve annulus, after implantation of an implant for reshaping the annulus, is described. The method comprises positioning an implant adjacent a mitral valve annulus. The implant comprises a tubular frame having a pair of struts, a rotatable shaft carried by the frame, a translatable collar engaged with the rotatable shaft and at least partially surrounding the pair of struts, and an anchor coupled with the frame. The method further comprises securing the anchor to tissue of the mitral valve annulus, rotating the shaft to cause the collar to translate along the first pair of struts, decreasing an angle between the first pair of struts due to translation of the collar, contracting a width of the heart valve annulus to a first reduced width for a period of time longer than twenty four hours, and subsequent to the period of time, further contracting the width of the heart valve annulus to a second reduced width that is less than the first reduced width.

In another aspect, an implant for reducing heart valve regurgitation is described. The implant comprises a frame, a plurality of anchoring members and a plurality of collars. The frame has upper crowns, lower crowns and struts between the upper and lower crowns. The frame has a tissue engaging configuration having a tissue engaging diameter, and an annulus remodeling configuration where the frame has an annulus remodeling diameter that is less than the tissue engaging diameter. The plurality of anchoring members are coupled with the lower crowns of the frame for engaging cardiac tissue proximate the heart valve annulus. The plurality of collars are coupled with the upper crowns of the frame, wherein when force is applied to the collars, the collars slide along the upper crowns and the struts to move the frame from the tissue engaging configuration towards the annulus remodeling configuration.

In some embodiments, the plurality of anchoring members are helically wound anchoring members and the lower crowns of the frame are adapted to threadingly receive the helically wound anchoring members. The helically wound anchoring members may further include anchoring heads for engagement with actuators to rotationally advance the helically wound anchoring members in the cardiac tissue to anchor the frame into the cardiac tissue. The implant may further comprise abutments on each of the anchor heads to engage with the struts and the lower crowns to limit travel of the helically wound anchoring members. The helically wound anchoring members may have sharpened tips to facilitate penetration of the helically wound anchor members into the cardiac tissue.

The implant may further comprise at least one tab on each of the collars, with the tabs inwardly biased to engage with the upper crowns when the collars are slid over the upper crowns and struts. The implant may further comprise a groove formed on an outwardly facing side of the upper crowns and at least one tab on each of the collars with the tabs inwardly biased to engage with the groove. Each of the collars may comprise a plurality of the tabs, and the plurality of tabs can be advanced over the upper crowns and struts to selectively vary the annulus remodeling diameter of the frame. The plurality of tabs may be vertically disposed on an outwardly facing portion of the collars and comprise a lowermost tab, with the lowermost tab initially disposed and engaged with an underside of the upper crown.

The implant may further comprise a plurality of pusher members that engage with the plurality of collars to forcibly advance the collars over the upper crowns and struts to reduce the diameter of the frame.

The implant may further comprise flex sections on the collars to facilitate advancement of the collars over the upper crowns and struts.

The frame may define a longitudinal axis, and the lower crowns and anchoring members received in the lower crowns may be inclined outwardly in a distal direction at an angle between about 30° to about 60° with respect to a portion of the axis that extends distally below the implant.

In another aspect, a delivery system for delivering an implant for reducing heart valve regurgitation is described. The delivery system comprises the implant, a delivery catheter, and an imaging catheter. The implant comprises a frame, a plurality of anchoring members and a plurality of collars. The frame has upper crowns, lower crowns and struts between the upper and lower crowns, and a tissue engaging configuration with a tissue engaging diameter and an annulus remodeling configuration where the frame has an annulus remodeling diameter less than the tissue engaging diameter. The plurality of anchoring members are coupled with the lower crowns of the frame for engaging cardiac tissue proximate the heart valve annulus. The plurality of collars are coupled with the upper crowns of the frame, and when force is applied to the collars, the collars slide on the upper crowns and the struts to move the frame from the tissue engaging configuration towards the annulus remodeling configuration. The delivery catheter is releasably attached to the implant and is configured to deliver the implant to a position proximate the heart valve annulus. The imaging catheter comprises a distal end configured to extend proximate the heart valve annulus and to capture one or more images therein of the position of the implant relative to the heart valve annulus.

In some embodiments, the delivery system further comprises a plurality of actuating members for engaging corresponding anchoring members of the implant to cause the anchoring members to penetrate and advance into the cardiac tissue to anchor the frame in position proximate the heart valve annulus. The delivery system may further comprise a plurality of pusher members for engaging corresponding collars of the implant to forcibly advance each collar over its respective upper crown and struts thereby reducing the diameter of the frame and the valve annulus. The delivery system may further comprise means for centering the imaging catheter with respect to the implant. The distal end of the imaging catheter may comprise longitudinally disposed and circumferentially disposed ultrasound transducers. The frame may define a longitudinal axis, and the lower crowns and anchoring members received in the lower crowns may be inclined outwardly in a distal direction at an angle of approximately 45° with respect to a portion of the axis that extends distally below the implant.

In some embodiments, the delivery system may further comprise a loop encircling the frame proximate its lower crowns, and a constricting actuator to constrict the loop to facilitate collapse and loading of the implant into the delivery system. Each of the collars may comprise a plurality of tabs that are inwardly biased to engage with corresponding undersides of the upper crowns when the collars are slid over the upper crowns and struts by the pusher members. After the frame has been anchored into the cardiac tissue, the loop may be constricted to determine the desired reduction in diameter of the frame prior to advancing the collars and tabs over the respective upper crowns and struts.

In another aspect, a method of reducing the size of an enlarged heart valve annulus is described. The method comprises the steps of delivering an implant in a delivery system to a site above and proximate the enlarged heart valve annulus, the implant having a proximal end and a distal end; releasing the implant from the delivery system to allow the implant to take on a tissue engaging diameter; anchoring the distal end of the implant into cardiac tissue proximate and above the enlarged heart valve annulus; translating a plurality of collars over corresponding upper crowns of the proximal end of the implant to reduce the tissue engaging diameter to an annulus remodeling diameter, thereby reducing the size of the enlarged heart valve annulus; and disengaging the anchored and reduced diameter implant from the delivery system.

In another aspect, a heart valve replacement implant is described. The heart valve replacement implant comprises a replacement valve, a tubular valve housing, a cinch frame, a plurality of anchoring members and a plurality of collars. The replacement valve has a plurality of replacement valve leaflets. The tubular valve housing is fixedly attached to the replacement valve leaflets. The cinch frame is connected to and circumferentially surrounds the tubular valve housing. The cinch frame has upper crowns, lower crowns and struts between the upper and lower crowns, and is configurable between a tissue engaging configuration with opposing upper crowns separated by a tissue engaging diameter and an annulus remodeling configuration with opposing upper crowns separated by an annulus remodeling diameter that is less than the tissue engaging diameter. The plurality of anchoring members are coupled with the upper crowns of the cinch frame for engaging cardiac tissue proximate the heart valve annulus. The plurality of collars are coupled with the lower crowns of the cinch frame. When force is applied to the collars, the collars slide on the lower crowns and the struts to reconfigure the cinch frame from the tissue engaging configuration towards the annulus remodeling configuration.

In some embodiments, the heart valve replacement implant further comprises a sealing flange on the cinch frame that is disposed on the atrial side of the heart valve when the heart valve replacement system is implanted.

In another aspect, a heart valve replacement implant is described. The heart valve replacement implant comprises a replacement valve, a tubular valve, a cinch frame, a plurality of anchoring members and a plurality of collars. The replacement valve has a plurality of replacement valve leaflets. The tubular valve housing is fixedly attached to the replacement valve leaflets. The cinch frame is connected to and circumferentially surrounds the tubular valve housing. The cinch frame has upper crowns, lower crowns and struts between the upper and lower crowns, and is configurable between a tissue engaging configuration with opposing lower crowns separated by a tissue engaging diameter and an annulus remodeling configuration with opposing lower crowns separated by an annulus remodeling diameter that is less than the tissue engaging diameter. The plurality of anchoring members are coupled with the lower crowns of the cinch frame for engaging cardiac tissue proximate the heart valve annulus. The plurality of collars are coupled with the upper crowns of the cinch frame. When force is applied to the collars, the collars slide on the upper crowns and the struts to reconfigure the cinch frame from the tissue engaging configuration towards the annulus remodeling configuration.

In some embodiments, the tubular valve housing has a proximal end and a distal end, and the upper crowns of the cinch frame have extensions adapted to be received in openings in the proximal end of the valve housing such that the upper crowns and the cinch frame pivot about the proximal end of the valve housing.

In another aspect, an implant for reshaping a mitral valve annulus is described. The implant comprises a tubular frame, a shaft and a collar. The tubular frame has a proximal end, a distal end and a central lumen extending therethrough. The frame comprises a first pair of adjacent struts joined at a proximal apex. The shaft is carried by the proximal apex. The shaft extends along a rotation axis and has an external thread. The shaft is configured to rotate about the rotation axis. The collar is carried by the frame and has an opening extending axially therethrough in which to receive the shaft. The collar has a complementary surface structure for engaging the threads of the shaft. The collar is configured to at least partially surround the first pair of adjacent struts. Rotation of the shaft about the rotation axis in a first rotation direction causes the collar to advance along the first pair of struts toward the distal end of the frame to decrease an angle between the first pair of adjacent struts.

In some embodiments, rotation of the shaft about the rotation axis in a second rotation direction that is opposite the first rotation direction causes the collar to advance along the first pair of struts toward the distal end to allow an increase in the angle between the first pair of adjacent struts.

In some embodiments, the implant may further comprise an anchor coupled with the frame, with the anchor configured to engage tissue of the mitral valve annulus. The frame may comprise a second pair of adjacent struts joined at a distal apex, and the anchor is coupled with the distal apex. The anchor may be a helical anchor. The distal apex may include a series of openings configured to rotatably receive the anchor therethrough.

In some embodiments, the frame may further comprise a window at the proximal apex, the window configured to at least partially retain the shaft therein. The frame may further comprise a first support and a second support, with the first and second supports extending from the apex toward the proximal end and at least partially defining the window on opposite sides of the shaft.

In some embodiments, the complementary surface structure of the collar may comprise an internal thread disposed along at least a portion of one or more inner surfaces of the collar. The internal thread may be a centrally threaded bore of the collar. The internal thread may be disposed along first and second inner surfaces from a proximal end to a distal end of the collar. The complementary surface structure of the collar may comprise a series of teeth extending along one or more inner surfaces of the collar. The opening of the collar may further comprise a first channel and a second channel, and the first pair of adjacent struts may include a first strut and a second strut, with the first channel configured to receive the first strut, and the second channel configured to receive the second strut.

In some embodiments, the implant of claim 1, further comprising a coupling attached to a proximal end of the shaft, the coupling configured to be rotated by a driver coupling to rotate the shaft. The coupling may comprise a lateral projection having a proximally facing recess surface for engaging the driver coupling.

In some embodiments, the tubular frame defines a central longitudinal axis, and the adjacent pair of struts are configured to incline radially outward relative to the central longitudinal axis. The adjacent pair of struts may be configured to incline radially outward relative to the central longitudinal axis in response to decreasing the angle between the first pair of adjacent struts.

In some embodiments, the implant may further comprise a plurality of the first pair of adjacent struts with each pair joined at a respective proximal apex, a plurality of the shafts each carried by the respective proximal apex, and a plurality of the collars each configured to engage a respective shaft.

In another aspect, an implant for reshaping a mitral valve annulus is described. The implant comprises a tubular frame, a shaft and a collar. The tubular frame comprises a first pair of adjacent struts joined at an apex. The shaft is carried by the frame and extends along a rotation axis, the shaft having a radial engagement structure. The collar is carried by the frame and at least partially surrounds the first pair of adjacent struts, the collar having an internal complementary surface structure for engaging the radial engagement structure of the shaft. Rotation of the shaft about the rotation axis causes the collar to advance along the first pair of struts to change an angle between the first pair of adjacent struts.

In another aspect, a method of reshaping a mitral valve annulus is described. The method comprises positioning an implant adjacent a mitral valve annulus. The implant comprises a tubular frame having a pair of struts, a rotatable shaft carried by the frame, a translatable collar engaged with the rotatable shaft and at least partially surrounding the pair of struts, and an anchor coupled with the frame. The method further comprises securing the anchor to tissue of the mitral valve annulus, rotating the shaft to cause the collar to translate along the first pair of struts, and decreasing an angle between the first pair of struts due to translation of the collar.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIGS. 5A-5E are various views of embodiments of a collar and frame that may be used with the implant of FIG. 1.

FIGS. 10 and 11 are perspective views of an embodiment of an implant having collars with locking tabs shown, respectively, in an expanded and a cinched state.

FIGS. 16 and 17 are partial side views of an embodiment of an implant having a rotational member and filament for cinching adjacent struts of the implant.

FIGS. 18 and 19 are partial side views of an embodiment of an implant having two strings for cinching adjacent struts of the implant.

FIG. 20 is a partial side of an embodiment of an implant having an axially displaceable circumferential filament for cinching the frame of the implant.

FIGS. 22A through 22E are perspective views of various embodiments of delivery systems having positioning and imaging capabilities that may be used to deliver the various implants described herein.

FIGS. 24A through 24D are perspective views of another embodiment of an ICE catheter and delivery system for delivering, e.g. aligning and positioning, the various implants described herein and having a circular array of sensors at the tip of the catheter, e.g. for radial and/or circumferential echo views.

FIG. 26 is a side view of an embodiment of an implant having a constricting loop and is shown interacting with a delivery system for advancing the collars.

FIG. 28 is a perspective view of an embodiment of a delivery system having an implant attached thereto for delivery and securement of the implant to a heart valve annulus.

FIGS. 44A-44C depict various views of an embodiment of an implant having flared proximal ends, for example after anchoring the implant to heart tissue.

FIG. 47B is a perspective view of the implant of FIG. 47A having anchor assemblies with anchor housings at distal apexes and with certain features at the proximal apexes removed for purposes of illustration.

FIG. 48 is a partial perspective view of the interior of the implant of FIG. 47A, showing an embodiment of a cinching assembly at the proximal end of the frame having a rotatable threaded shaft and an axially translatable collar shown in a distal position along a pair of adjacent struts, and an anchor assembly at the distal end of the frame having a housing and a corresponding anchor in a retracted proximal position.

FIG. 49A is a detailed perspective view of the exterior of the implant of FIG. 47A showing an anchor assembly at a distal apex of the frame with the anchor housing engaged with the distal apex.

FIG. 49B is a partial perspective view of the distal end of the implant of FIG. 47A showing an interior view of an anchor assembly attached at a distal apex of the frame with the anchor housing engaged with the distal apex.

DETAILED DESCRIPTION

Figure 1:
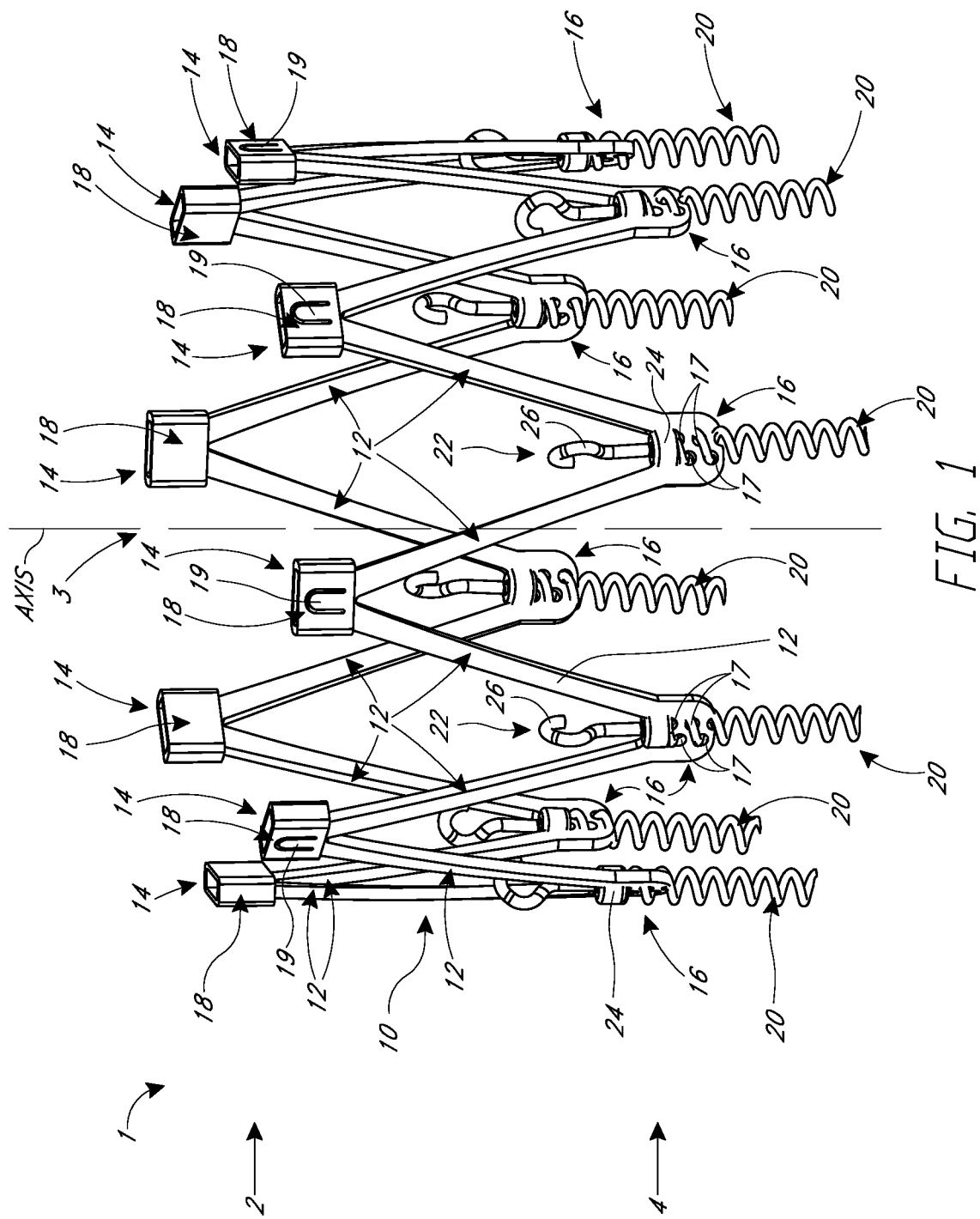
FIG. 1 is a perspective view of an embodiment of an implant, having a frame, collars and anchors, for reshaping a heart valve annulus.

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

The implants, delivery systems, methods, and features thereof that are shown in and described with respect to FIGS. 1-37 may have the same or similar features and/or functionalities as other implants, delivery systems, methods, and features thereof described herein, such as the implant 1 described with respect to FIGS. 38A-59, and vice versa. Thus, any of the implants described herein may have rotatable shafts 646 that engage axially translatable collars 18, and/or anchor assemblies 20A with helical anchors 20 and anchor housings 22A, as further described herein.

FIGS. 1-4 are perspective views of an embodiment of an implant 1. The implant 1 is intended to be delivered proximate to, above and/or or within, the cardiac valve annulus. Unless otherwise stated, "valve" as used herein may refer to any of a variety of valves, including the tricuspid or mitral valve of the heart. The implant 1 may be subsequently implanted in the annular cardiac tissue just above the plane of the valve orifice. In some embodiments, the implant may be a heart valve replacement including valve leaflets, which can be implanted in annular cardiac tissue and extend into the valve annulus, as further described herein.

Particular features for various embodiments of an implant, of a delivery system, and of related systems and methods of use of the implant and delivery system (either together or separately), are described herein. The implant, delivery system, and related systems and methods of use may have the same or similar features and/or functionalities as other implants, delivery systems, and related systems and methods of use as described, for example, in U.S. patent application Ser. No. 14/861,877 entitled "ADJUSTABLE ENDOLUMENAL IMPLANT FOR RESHAPING MITRAL VALVE ANNULUS and filed on Sep. 22, 2015 (issued on Apr. 11, 2017, as U.S. Pat. No. 9,615,926), as described, for example, in U.S. Provisional Application No. 62/234,592 entitled "HEART VALVE DELIVERY SYSTEM WITH INTRAVASCULAR ULTRASOUND IMAGING CAPABILITY" and filed on Sep. 29, 2015, as described, for example, in U.S. patent application Ser. No. 15/280,004 entitled "METHODS FOR DELIVERY OF HEART VALVE DEVICES USING INTRAVASCULAR ULTRASOUND IMAGING" and filed on Sep. 29, 2016, as described, for example, in U.S. patent application Ser. No. 15/043,301 entitled "VALVE REPLACEMENT USING ROTATIONAL ANCHORS" and filed on Feb. 12, 2016 (issued on Dec. 26, 2017, as U.S. Pat. No. 9,848,983), as described, for example, in U.S. patent application Ser. No. 15/352,288 entitled "IMPLANTABLE DEVICE AND DELIVERY SYSTEM FOR RESHAPING A HEART VALVE ANNULUS" and filed on Nov. 15, 2016, as described, for example, in U.S. Provisional Patent Application No. 62/457,441 entitled "IMPLANTABLE DEVICE AND DELIVERY SYSTEM FOR RESHAPING A HEART VALVE ANNULUS" and filed on Feb. 10, 2017, as described, for example, in U.S. Provisional Patent Application No. 62/552,896 entitled "IMPLANTABLE DEVICE AND DELIVERY SYSTEM FOR RESHAPING A HEART VALVE ANNULUS" and filed on Aug. 31, 2017, as described, for example, in U.S. patent application Ser. No. 12/794,235 entitled "DEVICE FOR TRANSLUMENAL RESHAPING OF A MITRAL VALVE ANNULUS" and filed on Jun. 4, 2010, as described, for example, in U.S.

patent application Ser. No. 14/567,872 entitled "RECONFIGURING TISSUE FEATURES OF A HEART ANNULUS" and filed on Jun. 4, 2010 (issued on Oct. 24, 2017, as U.S. Pat. No. 9,795,480), as described, for example, in U.S. patent application Ser. No. 14/427,909 entitled "MITRAL VALVE INVERSION PROSTHESES" and filed on Mar. 12, 2015 (issued on Apr. 4, 2017, as U.S. Pat. No. 9,610,156), and/or as described, for example, in U.S. patent application Ser. No. 14/774,656 entitled "SYSTEMS AND METHODS FOR RESHAPING A HEART VALVE" and filed on Sep. 10, 2015, the entire disclosure of each of which is incorporated herein by reference for all purposes and forms a part of this specification. Thus, the description of particular features and functionalities herein is not meant to exclude other features and functionalities, such as those described in the references incorporated herein by reference or others within the scope of the development.

With reference to FIG. 1, the implant 1 is an implantable device. The implant 1 forms a lumen or opening 3 extending through the implant 1. For sake of description, a geometric reference longitudinal axis is indicated. The implant 1 may be described with reference to the axis. An "axial" direction refers to movement generally parallel to the axis in either an upward or downward direction, unless otherwise indicated. The opening 3 extends axially between an upper portion 2 of the implant 1 and a lower portion 4 of the implant 1. The upper and lower portions 2, 4 may include various features of the implant 1. The terms "upper," "upward," and the like refer to directions generally toward the upper portion or proximal end 2, and the terms "lower," "downward," and the like refer to directions generally toward the lower portion or distal end 4, unless otherwise indicated. "Proximal" refers to a direction in the upward direction, and "distal" refers to a direction in the downward direction. The terms "inner," "inward," and the like refer to directions generally toward the axis, and terms "outer," "outward," and the like refer to directions generally away from the axis. These geometric references generally apply unless otherwise indicated, either explicitly or by context.

The implant 1 includes a frame 10. The frame 10 extends circumferentially around and partially axially along the axis. The axis may be defined by the frame 10. The frame 10 is generally symmetric with respect to the axis. However, the frame 10 need not be symmetric with respect to the axis. The frame 10 has a generally tubular shape. "Tubular" includes circular as well as other rounded or otherwise closed shapes. The frame 10 is generally circular about the axis. The frame 10 may be circular, rounded, ellipsoidal, segmented, other shapes, or combinations thereof. The frame 10 may change shape, size, configuration, etc. The frame 10 may have various shapes, sizes, configurations etc. at various phases of use, e.g. pre-delivery, during delivery, after engagement with tissue, after contracting the annulus, post-contraction, during the lifetime of use while implanted, etc.

The implant 1 includes one or more struts 12. The struts 12 may form all or part of the frame 10. The struts 12 are elongated structural members. The struts 12 and/or other parts of the frame 10 are formed of a metal alloy. The struts 12 and/or other parts of the frame 10 may be formed of an alloy of nickel titanium. In some embodiments, the struts 12 and/or other parts of the frame 10 are formed of other metals, metal alloys, plastics, polymers, composites, other suitable materials, or combinations thereof. There are sixteen struts 12. In some embodiments, there may be fewer or more than sixteen struts 12. In some embodiments, there may be at least two, four, six, eight, ten, twelve, fourteen, eighteen, twenty, twenty-two, twenty-four, twenty-six, twenty-eight, thirty, or more struts 12.

The struts 12 may be part of the same, monolithic piece of material (e.g. tube stock). Thus the struts 12 may refer to different portions of the same, extensive component. The struts 12 may be formed from the same piece of material. The struts 12 may be formed separately and attached permanently together, e.g. by welding, etc. In some embodiments, the struts 12 may be separate components that are detachably coupled together by other components of the implant 1. For example, the struts 12 may be held together via various components described herein, such as collars 18, anchors 20, other features, or combinations thereof. In some embodiments, separate strut units may include two or more struts permanently attached together such as at an apex, and the separate units may each be coupled together, either permanently or detachably, to form the frame 10. In some embodiments, the struts 12 may be attached by hinges, pins, or other suitable means.

The elongated, middle portions of the struts 12 have a generally rectangular cross-section but can vary in circumferential width and radial thickness to allow for different beam characteristics and forces applied as the collars are advanced. This may facilitate for example post implantation constriction or remodeling of the annulus, as further described. The long ends of the rectangular cross-section of the struts 12 extend along the circumference of the frame 10. "Circumference" as used herein generally refers to a perimeter or boundary and can refer to a circular or other rounded or non-rounded path lying in a plane substantially transverse to the axis, unless otherwise stated. The short ends of the rectangular cross-section of the struts 12 extend transversely to the circumference of the frame 10. In some embodiments, other configurations and/or cross-sectional shapes of the struts 12 may be implemented. The cross-section may be rounded, circular, other shapes, or combinations thereof.

The struts 12 extend around the axis to form the various shapes of the frame 10. The struts 12 are arranged such that the wall pattern of the frame 10 may be approximately sinusoidally or zig-zag shaped. In some embodiments, the wall pattern may have other suitable shapes, sinusoidal or otherwise. The vertices of the sinusoidal shaped frame 10 may be pointed or rounded.

Pairs of adjacent struts 12 meet at an apex. At least a first pair of adjacent struts 12 meets at an upper apex or crown 14 at the upper portion 2 of the implant 1. At least a second pair of adjacent struts 12 meets at a lower apex or crown 16 at the lower portion 4 of the implant 1. The terms "apex," apices," and the like may be used interchangeably with terms "crown," "crowns," and the like, as used herein and as used in any reference incorporated by reference herein, unless otherwise stated. The upper and lower crowns 14, 16 are spaced sequentially along the circumference of the frame 10, with one of the upper crowns 14 followed by one of the lower crowns 16, followed by another one of the upper crowns 14, etc. In the illustrated embodiment, there are eight upper crowns 14 and eight lower crowns 16. In some embodiments, there may be no more than about six or four or fewer or more than eight or ten or twelve upper and lower crowns 14, 16, depending on the number of struts 12 and the resulting number of apices.

The upper crowns 14 are each configured to have a restraint such as a collar 18 fitted over and/or around the upper crown 14. Thus, the upper crowns 14 may include various features, dimensions, etc. as described herein for coupling with the collar 18, as further described. The upper crowns 14 are shown partially covered by the collars 18 in FIG. 1. The upper ends of the upper crowns 14 are more clearly seen in FIG. 4, where the collars 18 have been moved distally toward the lower portion 4 of the implant 1 relative to their position in FIG. 1. In some embodiments, one or more of the upper crowns 14 may not have the collar 18. In some embodiments, fewer than all of the upper crowns 14 are configured to receive the collar 18. In some embodiments, all of the upper crowns 14 may be configured to receive the collar 18 but when implanted only some of the upper crowns 14 may actually include the collar 18.

At least two and optimally at least four or six or all of the lower crowns 16 are configured for coupling with an anchor 20. The anchor 20 is moveably coupled with the lower crown 16. The anchor 20 engages with tissue of the heart, for example the annulus, to secure the implant 1 to the tissue, as further described herein. Movement of the anchor 20 relative to the lower crowns 16 causes the anchor 20 to penetrate the tissue. The lower crowns 16 may include a variety of engagement features to allow such movement of the anchors 20, such as flanges and/or the openings 17. The lower crowns 16 each include a series of the openings 17 extending through the lower crowns 16. The openings 17 extend in two spaced columns in the axial direction along the lower crown 16. The openings 17 in each column are alternately located in the axial direction, as shown, to accommodate receipt of the anchor 20 therein. Other configurations and/or spacings of the openings 17 may be implemented. For clarity, only some of the openings 17 are labeled in FIG. 1. The openings 17 are shown as circular holes. Other shaped openings 17 may be implemented.

The openings 17 of the lower crown 16 are configured to rotatably receive a helical segment of the corresponding anchor 20 such that the anchor extends sequentially through the openings 17, both while the anchor 20 moves relative to the struts 12 and while the anchor 20 is stationary relative to the struts 12, as further described herein. In some embodiments, features alternative to or in addition to the openings 17 may be used to couple the anchor 20 with the corresponding lower crown 16. In some embodiments, fewer than all of the lower crowns 16 may be configured for coupling with the anchor 20. Thus one or more of the lower crowns 16 may not have the openings 17 and/or other features for coupling with the anchor 20. In some embodiments, all of the lower crowns 16 may be configured for coupling with the anchor 20, but when implanted only some of the lower crowns 16 may actually include the anchor 20.

The struts 12 are reconfigurable about the upper and lower crowns 14, 16. Pairs of adjacent struts 12 that meet at the upper and lower crowns 14, 16 can move angularly relative to each other. Such movement may be described as a rotation or pivot of the adjacent struts 12 about the corresponding upper or lower crown 14, 16. For example, two adjacent struts 12 forming the upper crown 14 may be moved such that the struts 12 effectively rotate relative to each other about the upper crown 14. For example, two adjacent struts 12 forming the lower crown 16 may be moved such that the struts 12 effectively rotate relative to each other about the lower crown 16. "Rotation" of the struts 12 as described includes pinching together of the struts 12, for example with the collar 18 as described herein. Thus, adjacent struts 12 may not include an actual rotatable hinge, pin, or other rotation features. Movement of the struts 12 closer together to decrease the angle therebetween is described as a "closing" of the struts 12. Movement of the struts 12 farther apart to increase the angle therebetween is described as an "opening" of the struts 12.

The struts 12 may be biased to an enlarged cross-sectional configuration in the absence of an external force applied to the struts 12. Application of an external circumferentially compressive force to the struts 12, for example with the collar 18, causes the struts 12 to move angularly, for example to close. Movement of the struts 12 in this closing manner also causes the implant 1 to decrease its circumference (e.g. diameter) in the case of a circular implant 1. In its free, unconstrained state, the frame 10 may be in an enlarged configuration. Application of the compressive circumferential force causes the circumference of the frame 10 to reduce. Removal or lessening of the circumferential force allows the frame 10 to open. The circumferential force may be increased or decreased by moving the collar 18 farther downward or upward, respectively, in the axial direction, as further described herein. The collar 18 may lock in place after translating axially down the upper crown 14 to secure the implant 1 at a particular width.

The implant 1 includes one or more restraints such as the sliders or collars 18. The terms "collar," collars," and the like may be used interchangeably with the terms "slider," "sliders," "sliding members," and the like, as used herein and as used in any reference incorporated by reference herein, unless otherwise stated. As shown in FIGS. 1-4, the implant 1 includes eight collars 18. In some embodiments, there may be fewer or more than eight collars 18. The number of collars 18 may correspond to the number of upper crowns 14. In some embodiments, there may be fewer collars 18 than upper crowns 14. Thus, in some embodiments, some upper crowns 14 of the frame 10 may not include the collar 18. The collars 18 may translate axially due to axial applied force. The collars 18 may translate axially due to engagement with a central rotating shaft 646, as further described herein, for example with respect to FIGS. 38A-48.

The collar 18 couples with the corresponding upper crown 14. The collar 18 may be fitted over the upper crown 14. The collar 18 forms an inner opening at least partially therethrough and into which the upper crown 14 is received as the collar 18 fits over the upper crown 14. The collar 18 may have a rectangular profile as shown. In some embodiments, the collar 18 may have other profiles, e.g. rounded, segmented, polygonal, other suitable shapes, or combinations thereof. The profile of the collar 18 may be a closed shape, as shown, or it may be an open shape such as a "C" shape. The collar 18 thus at least partially surrounds the corresponding upper crown 14. As shown, the collar 18 completely surrounds the corresponding upper crown 14. In some embodiments the collar 18 may not completely surround the upper crown 14. The collar 18 engages with the upper crown 14.

The collar 18 may engage with circumferentially opposed sides of the upper crown 14 and/or adjacent struts 12. The collar 18 engages with and may be advanced downward over the upper crown 14 to angularly move the corresponding pair of adjacent struts 12 towards each other. The collar 18 may apply a compressive circumferential force to the struts 12 to cause the struts 12 to decrease the angle between the struts 12. The circumferential force may be applied inwardly to the struts 12 and towards the upper crown 14. Thus, a vertical force applied to the collars 18 may be translated into a circumferential force on the struts 12. By "circumferential" it is meant that the direction of the forces is along the outer perimeter or boundary of the frame 10 as viewed from the top or bottom of the frame 10, and is not meant to limit the shape of the frame 10 to a circle. Movement of the collar 18 over the struts 12 moves, e.g. rotates, the struts 12 such that the angle between the adjacent struts 12 decreases. A first circumferential force may be applied to one of the struts 12 by the collar 18 and a second circumferential force that is opposite in direction to the first circumferential force may be applied to the adjacent strut 12 by that same collar 18. The farther the collar 18 is moved down over the struts 12, the more the struts 12 move and the more the angle decreases, causing the frame 10 to decrease in width, e.g. diameter. The struts 12 thus move relative to each other about the upper crown 14 due to movement of the collar 18. The collar 18 may lock in place, for example with a locking tab 19.

The collar 18 may include the locking tab 19. The locking tab 19 provides an engagement feature for the collar 18 to engage with the struts 12. The locking tab 19 locks the collar 18 in place on the upper crown 14 after movement of the collar 18 over the upper crown 14. The locking tab 19 is biased toward the inner opening formed by the collar 18. The locking tab 19 may be shape set to take on an inwardly oriented bias. The collar 18 and/or features thereof such as the locking tab 19 are formed of a nickel titanium alloy such as Nitinol. In some embodiments, the collar 18 and/or features thereof such as the locking tab 19 are formed of other materials, such as metals, other metal alloys, plastics, polymers, composites, other suitable materials, or combinations thereof. Further details of various embodiments of the collar 18, and features thereof such as the locking tab 19, are described herein.

The collars 18 may thus provide one or more functions for the implant 1. In some embodiments, the collars 18 may cinch the frame 10, as described. In some embodiments, the frame 10 may be cinched by features in addition to or alternatively to the collars 18, and the collars 18 may restrain the frame 10 in the cinched state. In some embodiments, the collars 18 may thus not cinch the frame 10 but only restrain the frame 10 in the cinched state. In some embodiments, the collars 18 may cinch the frame 10 as well as restrain the frame 10 in the cinched state.

The implant 1 includes one or more anchors 20. In some embodiments, the anchors 20 may be part of anchor assemblies 20A, may include distal helical portions 26A and proximal anchor heads 24A, and/or may include proximal coupling 24D, as further described herein, for example with respect to FIGS. 38A-59. Referring to FIG. 1, the anchors 20 have anchor heads 22 attached at their upper or proximal ends. The anchor head 22 may have the same or similar features and/or functionalities as the anchor head 24D further described herein, and vice versa. As shown in FIG. 1, each anchor head 22 may comprise an abutment 24 and an engagement structure such as a hook 26. The abutment 24 may be a cap portion on an upper end of the anchor 20. The abutment may be cylindrical. The abutment 24 may have a width sized to limit axial advance of the anchor 20, as described herein. The hooks 26 are elongated, over-hanging members. The hooks 26 may provide an engagement for a delivery tool. The hooks 26 may interact with a delivery tool to rotate and axially advance the anchors 20, as described herein. In some embodiments, features other than the hooks 26 may be used, for example eye bolts.

The anchors 20 are made of a suitable biocompatible metal alloy such as stainless steel, cobalt chromium, platinum iridium, nickel titanium, other suitable materials, or combinations thereof. Each anchor 20 is sharpened at its distal point, or leading turn, so as to facilitate penetration into the cardiac tissue. Each anchor 20 may be from about ten to about fifteen millimeters (mm) in total axial length. In some embodiments, the anchors 20 may be shorter or longer than ten to fifteen millimeters (mm) in total axial length. By "total" axial length it is meant the axial length of the anchor 20 from the end of the distal penetrating tip to the opposite, proximal end of the head 22. The helical portion of the anchor 20 may be from about six to about twelve millimeters (mm) in axial length, i.e. in an axial direction. In some embodiments, the helical portion of the anchor 20 may be shorter or longer than six to twelve millimeters (mm) in axial length. The anchor head 22 and/or other non-helical portions of the anchor 20 may be from about three to about four millimeters (mm) in axial length. In some embodiments, the anchor head 22 and/or other non-helical portions may be shorter or longer than three to four millimeters (mm) in axial length. The anchors 20 are capable of extending from about four to about seven millimeters (mm) axially beyond the corresponding lower crown 16. For example, the helical portions of the anchors 20 may extend from four to seven millimeters (mm) into the cardiac tissue. As mentioned, the frame 10 is shown with eight upper crowns 14 and eight lower crowns 16 and anchors 20, but this number of apices is shown for illustration purposes and may be varied, for example four upper and lower apices, sixteen upper and lower apices, etc. In some embodiments, regardless of the number of apices, each upper crown 14 is fitted with a collar 18 and each lower crown 16 has a respective anchor 20 threadingly received through the openings 17 of the anchor 20.

The anchors 20 couple with the lower crowns 16. The anchors 20 may be in the general shape of a helix. As shown, the openings 17 receive helically wound anchors 20. The openings 17 are spaced to accommodate the pitch of the helical anchors 20, for example the spacing between the turns in the helix of the anchor 20. There may be a gap between the inner diameter of the openings 17 and the outer diameter of the anchor 20 to allow for free movement of the anchor 20 through the openings 17. There may be a small gap between the inner diameter of the openings 17 and the outer diameter of the anchor 20. In some embodiments, there may be an interference fit between the openings 17 and the anchor 20 or a varying pitch to provide interference between the anchor and frame. In some embodiments, the anchors 20 may instead engage anchor housings 22A at the distal apexes 16, as further described herein.

Figure 2:
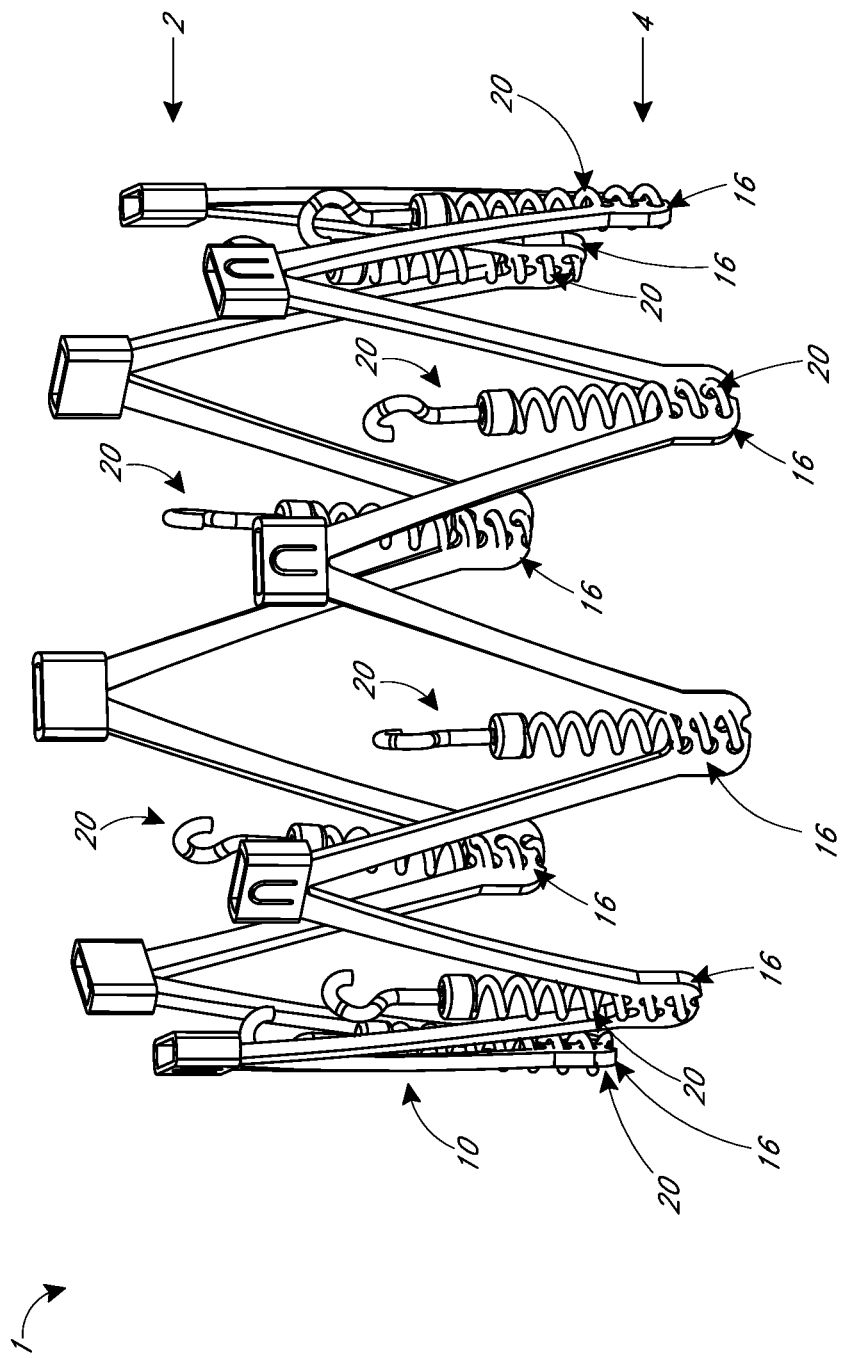
FIG. 2 is a perspective view of the implant of FIG. 1 shown in an unconstrained state.
Figure 3:
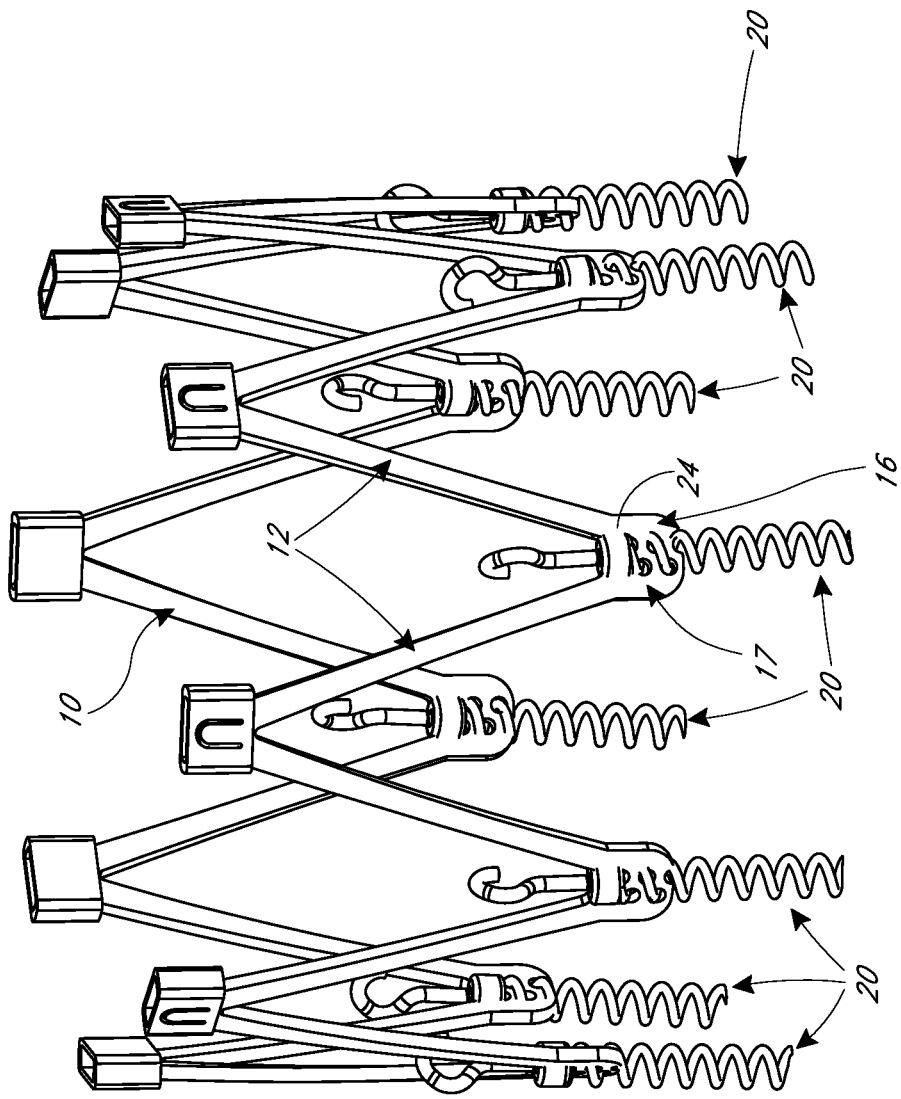
FIG. 3 is a perspective view of the implant of FIG. 1 shown in an anchored state.
Figure 4:
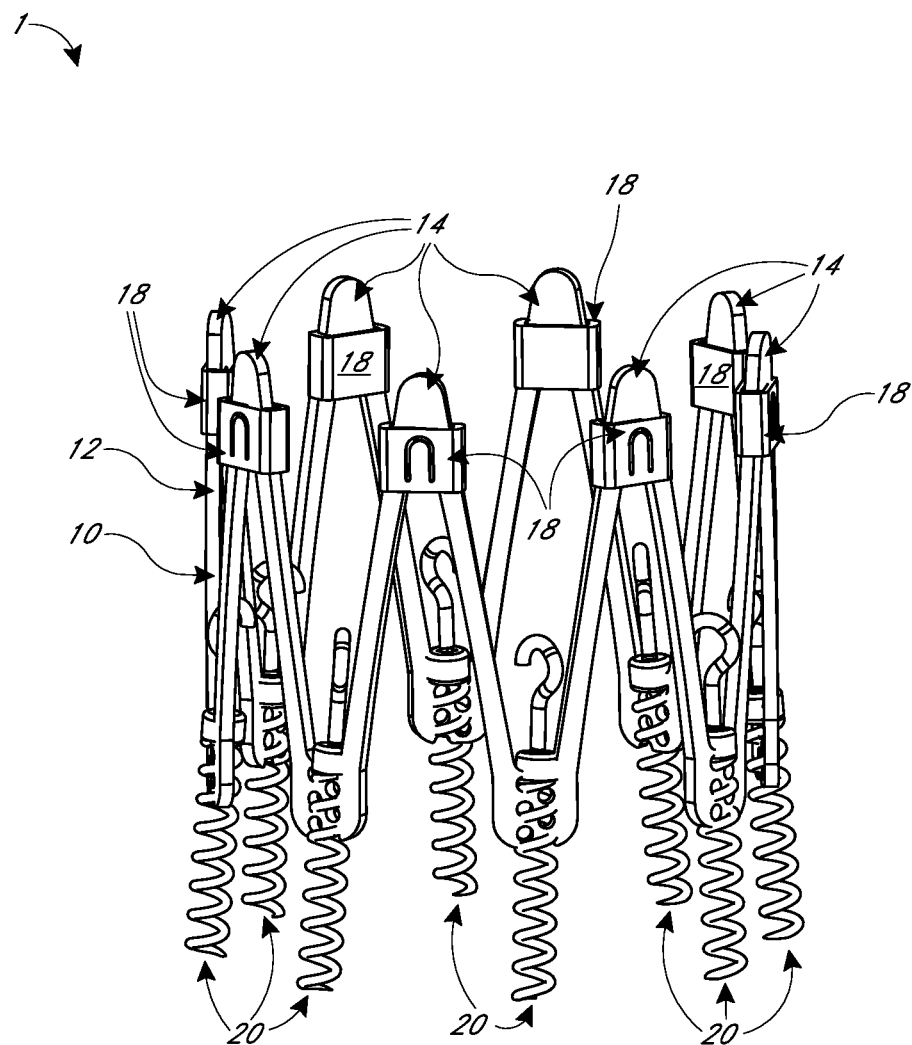
FIG. 4 is a perspective view of the implant of FIG. 1 shown in a cinched state.

FIGS. 2 through 4 illustrate the implant 1 in various stages of delivery and deployment. In FIG. 2, the implant has been expelled from a delivery catheter and is in its unconstrained state above and proximate the cardiac valve annulus. This unconstrained state may be a tissue engaging configuration of the implant 1 having a tissue engaging diameter and a tissue engaging height. In this unconstrained state, the frame 10 may have an overall axial height in the range of 15 to 20 millimeters (mm). This height or range of height will vary even further from this 15 to 20 mm range, depending on the number of apices and anchors 20. More specifically, the height is smaller with more apices and anchors 20 and is greater with fewer apices and anchors 20. In the embodiment shown in FIG. 2, the frame has a height of approximately 17 millimeters. Other heights in the unconstrained state are possible, and this particular embodiment is not limiting of the scope of the present disclosure.

FIG. 3 depicts the implant after it has been anchored into the cardiac tissue. This anchored state may be an anchored configuration, which may or may not be similar to the tissue engaging configuration, of the implant 1 having an anchored diameter and an anchored height. The anchored diameter of the implant 1 may be less than, equal to, or greater than the tissue engaging diameter of the implant 1 in the tissue engaging configuration. The anchored height of the implant 1 may be less than, equal to, or greater than the tissue engaging height of the implant 1 in the first configuration. Thus, the implant 1 when engaged with and anchored into the tissue may be in the tissue engaging configuration. The anchors 20 have been rotationally advanced through the lower crowns 16 and the tissue piercing end has rotationally advanced into the cardiac tissue. The abutments 24 function as a depth control for the anchors 20, limiting the extent of axial travel of the helical anchors 20 into the cardiac tissue as the abutments 24 seat in the valley bounded by the lower ends of the adjacent struts 12.

FIG. 4 shows the implant 1 in its contracted or cinched state. This cinched state may be an annulus remodeling configuration of the implant 1 having an annulus remodeling diameter and an annulus remodeling height. The annulus remodeling diameter of the implant 1 is less than the tissue engaging diameter of the implant 1 in the tissue engaging configuration. The annulus remodeling height of the implant 1 may be greater than the tissue engaging height of the implant 1 in the tissue engaging configuration. In the cinched state, the collars 18 have been moved downwardly over the upper crowns 14 until inwardly biased locking tabs 19 engage with the gap or valley bounded by the upper portions of adjacent struts 12, below the underside of the upper crowns 14. This engagement of the locking tabs 19 to the valley under the upper crowns 14 locks the implant into its cinched position. In an alternate embodiment, cut-outs may be formed on the upper crowns 14 to accept the locking tabs 19.

The implant 1 in it cinched state has a reduced circumference. Thus the cinched implant 1 has a reduced length perimeter or boundary relative to the unconstrained state. The reduction in circumference need not result in the same general shape of the implant as before the cinching. For example, before cinching, the implant 1 may be in a generally elliptical, oval or other shape, and after cinching the implant 1 may be in a general "D" shape or other shape (and with a relatively reduced circumference). Thus, the implant 1 may be in a variety of shapes before or after cinching, as well as during cinching. For instance, restraints such as the collars 18 may be advanced individually, i.e. not simultaneously. The implant 1 may thus have an irregular shape while being cinched. In some embodiments, even in the cinched state not all of the collars 18 are advanced, and/or are not all advanced the same amount, such that in the cinched state the angular displacements among different pairs of adjacent struts may not be the same. The implant 1 may thus be cinched in a custom manner depending on the particular patient's needs. In some embodiments, about half of the implant 1 may be cinched, for example to bring the anterior native leaflet closer to the posterior native leaflet, or vice versa. Thus, the "cinched" state of the implant 1 is not limited to only those particular shapes shown and described herein, but includes a multitude of possible shapes, sizes, etc. and which may be chosen based on needs of the patient.

Figure 5D:
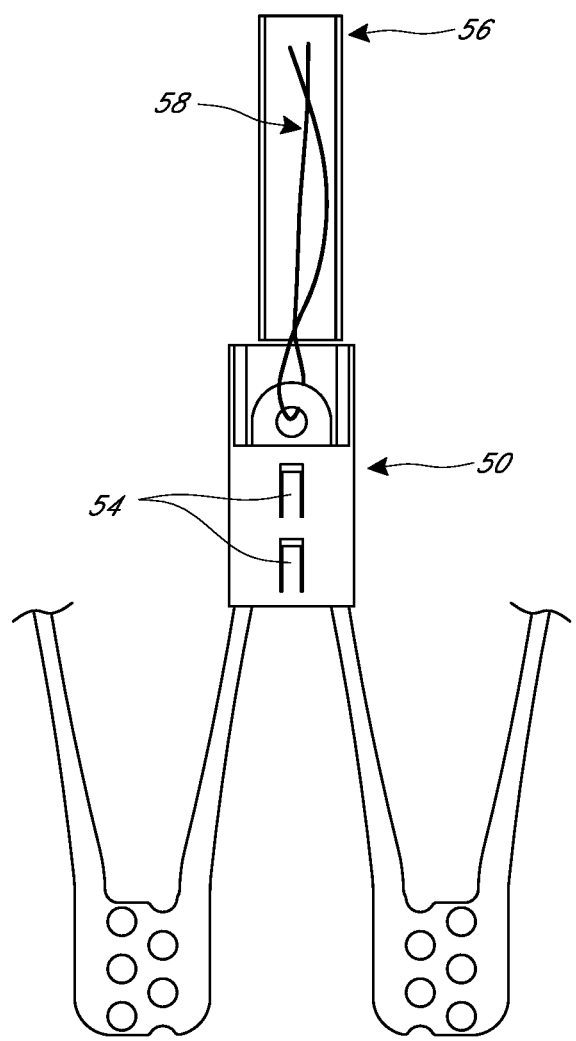

FIGS. 5A through 5D are various views of an embodiment of a collar 50 that may be used with the implant 1. The collar 50 is shown coupled with the struts 12 at the upper crown 14. FIGS. 5A and 5B are front views of a portion of the implant 1, showing the collar 50 coupled with the upper crown 14 at different axial locations. FIG. 5A shows the implant 1 in a unconstrained state. FIG. 5B shows the collar 50 advanced distally relative to the position of the collar 50 shown in FIG. 5A to reconfigure the implant 1 in a cinched state. FIG. 5C is a cross section view of the implant 1 taken along line 5C-5C of FIG. 5B. FIG. 5D is a front view of the implant 1 showing a portion of a delivery tool engaging the implant 1.

The collar 50 has multiple locking tabs 54. The locking tabs 54 may have the same or similar features and/or functionalities as other locking tabs described herein, for example the locking tabs 19, and vice versa. The locking tabs 54 may be projections or cutouts of the collar 50. The locking tabs 54 are biased toward the upper crown 14. The locking tabs 54 may therefore contact the upper crown 14. The upper crown 14 may include openings which can receive the ends of the locking tabs 54 therein. The upper crown 14 may define a gap in between adjacent struts 12 at a valley, as described, which may receive the end of the locking tabs 54 therein. While two such locking tabs 54 are shown, it should be understood that three or more locking tabs 54 could be employed. The plurality of locking tabs 54 allows the physician/user of the implant 1 to adjust the degree of cinch of the implant 1. Increased cinch, resulting in a smaller width of the implant 1 due to contraction, will tend to further reduce the width of the heart valve annulus.

FIGS. 5B and 5C depict the collar 50 advanced distally. The collar 50 as shown may be in its fully advanced state, thus reconfiguring the implant 1 to a state of maximum cinch. The uppermost locking tab 54 is engaging the underside of the upper crown 14. As stated with reference to FIGS. 1-4, rather than engaging the underside or upper crown 14, cut-outs in the upper crown 14 itself can provide the locking engagement with tabs 54. Additionally, as best seen in FIG. 5D, the collar 50 has a modified or cut out upper section to more readily receive a driver tube 56. A string member 58, which could take the form of a wire, cable, thread, suture or the like, is used to apply tension to the upper crown 14 as the driver tube 56 advances the collar 50. The driver tube 56 may be an elongated tube configured to contact and the collar 50 and to apply a downward pressure to the collar 50 to advance the collar 50 along the frame 10. The string member 58 extends through an opening in the upper crown 14 to counteract the downward force applied by the driver tube 56. This allows the frame 10 to remain stationary axially while the collar 50 advances distally to reconfigure the struts 12 and cinch the implant 1.

Figure 5E:
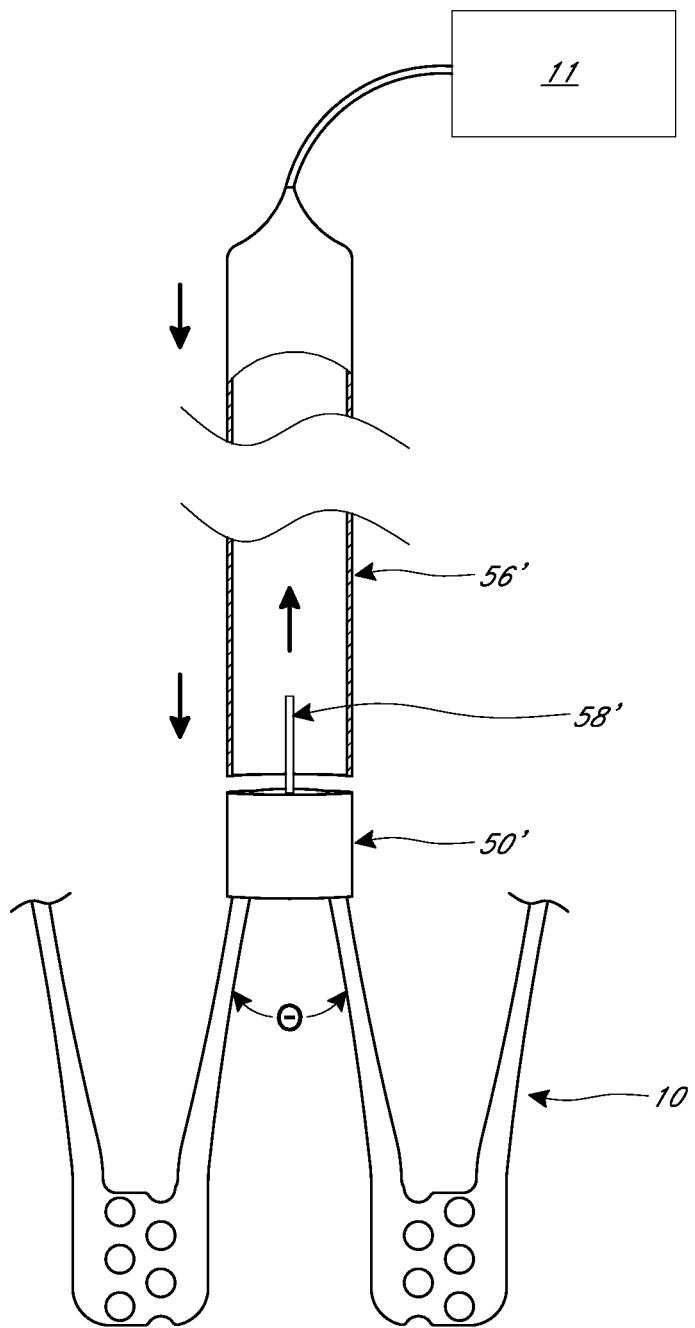

FIG. 5E is a partial side view of the frame 10 coupled with a frequency generator 11. The frequency generator 11 may be used with the various implants described herein, for example the implant 1, etc. The frame 10 is shown with a slider or collar 50', a pull wire 58' and a pusher tube 56'. The collar 50', pull wire 58' and/or pusher tube 56' may be analogous to the collar 50, the pull wire 58 and/or the driver tube 56, respectively. To advance the collar 50' over the frame 10 a high-frequency vibration can be added by the frequency generator 11 to assist the movement of the collar 50'. For example, relative vibrational movement between the collar 50' and the frame 10 may produce dynamic movement that facilitates overcoming a static friction between the collar 50' and the frame 10. The vibration could be transmitted through the pull-wire 58' and/or the pusher tube 56'. Vibration of either or both the pull-wire 58' or the pusher tube 56' will transmit the force to the frame 10 and collar 50' vibrating the frame 10 and collar 50' at a frequency to allow an easier movement between the frame 10 and collar 50'. An additional tensioning of the pull-wire 58' during the advancement will provide a force to the frame 10, changing the frame 10 upper apex shape from a wide angle to a more acute angle thus lessening the force required to advance the collar 50'. This combination of pull-force and vibration will lower the push-pull forces required to advance the collar 50' over the frame 10. The frequency transmitted through the tensioning wire and/or pusher tube 56' will lower these forces and could be coupled through each connection. A variety of suitable frequency generator tools could be used as the frequency generator 11 to transmit these vibrational frequencies, such as a CUSA system (Integra® CUSA® EXcel+ Ultrasonic Tissue Ablation System). The frequency may be, for example, from 1 to 100 KHz. The frequency can be varied during the procedure, tailored during the procedure or provided at a fixed defined frequency.

Figure 6B:
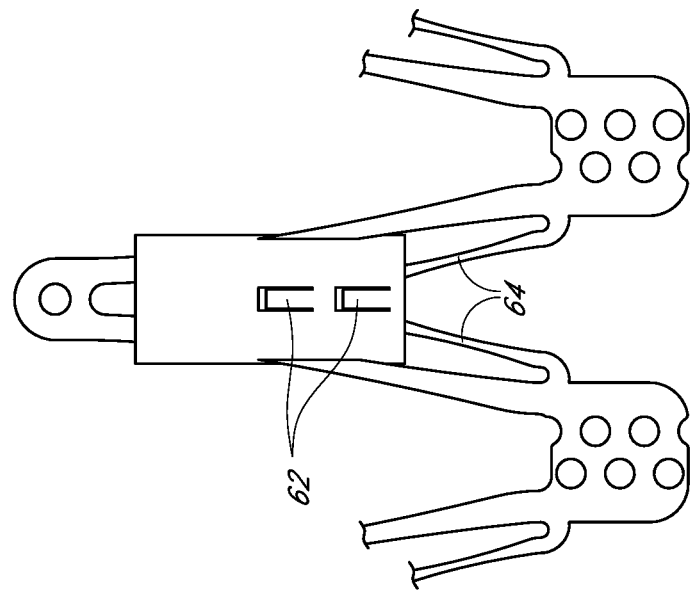
FIGS. 6A and 6B are side views of embodiments of a collar and frame that may be used with the implant of FIG. 1 shown, respectively, in an expanded and a cinched state.
Figure 6A:
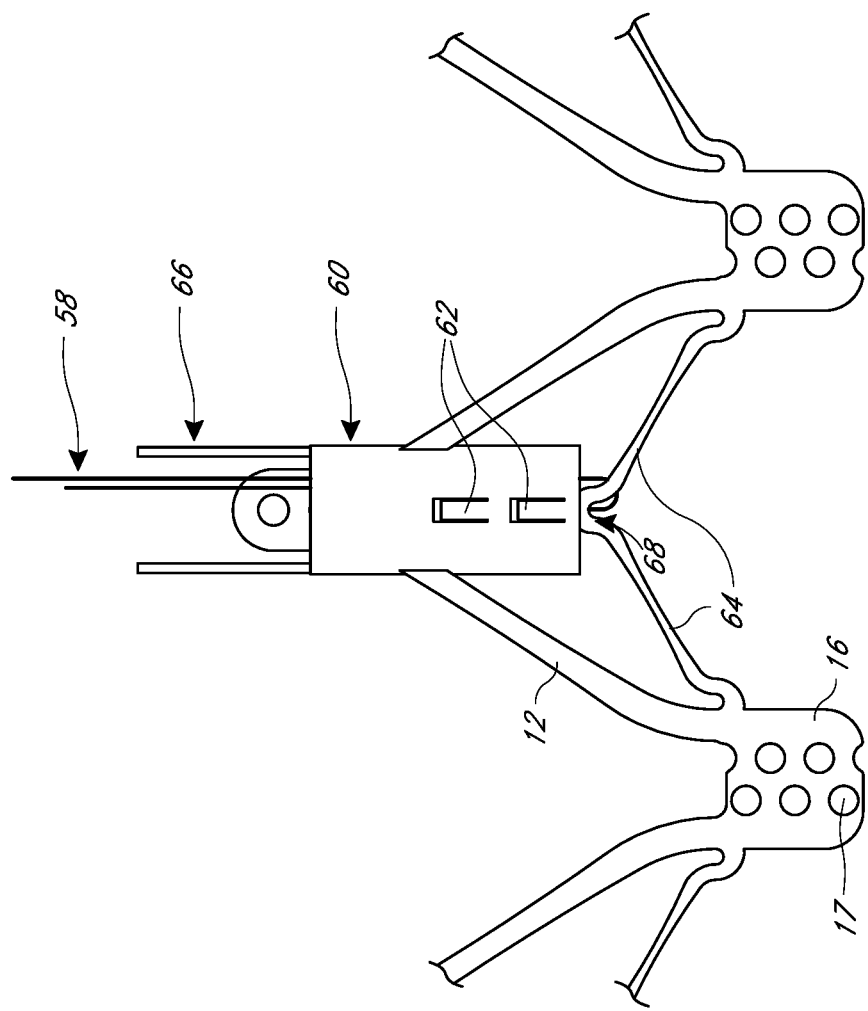
Figure 7D:
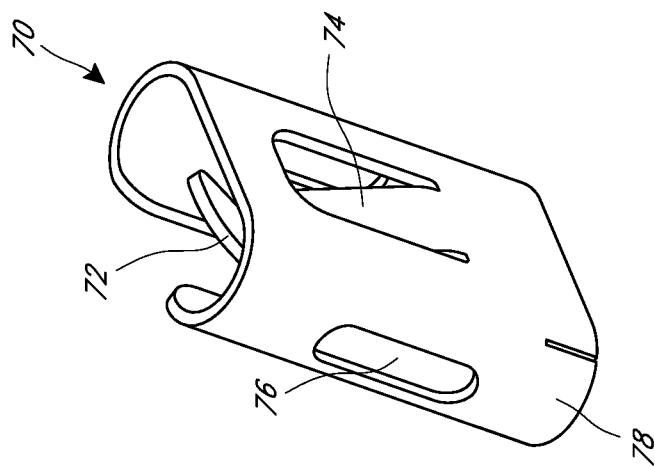
FIGS. 7A through 7D show, respectively, a circumferentially outward facing view, a side view, a circumferentially inward facing view, and a perspective view of an embodiment of a collar having locking tabs.
Figure 7C:
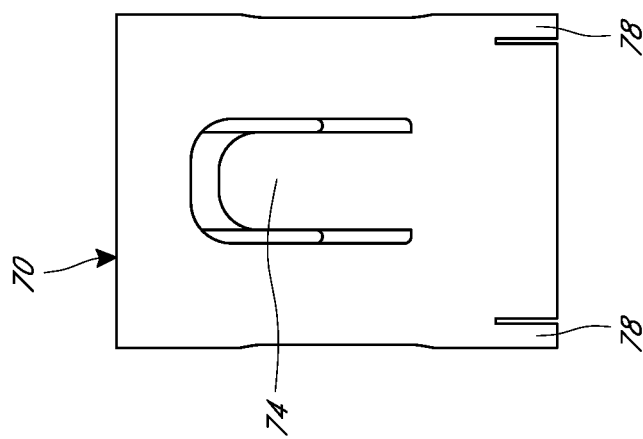
Figure 7B:
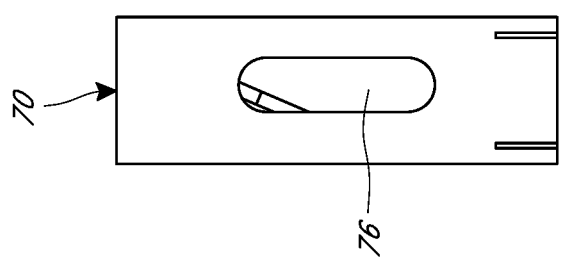
Figure 7A:
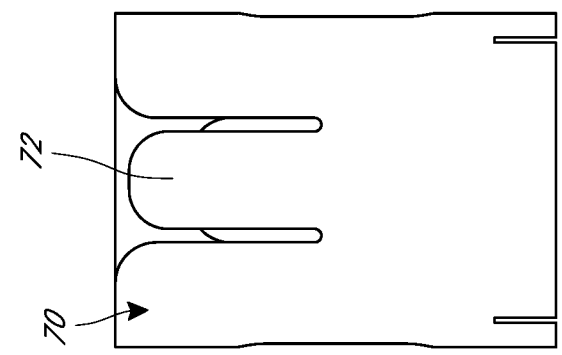

FIGS. 6A and 6B depict an alternate embodiment of the frame 10 and the frame/collar interaction. In addition to the struts 12, the frame 10 is further provided with mid-struts 64. The mid-struts 64 have crowns 68 and bridge the gap between lower apices 16. Locking tabs 62, of collars 60, engage with mid-strut crown 68 as collar 60 is advanced by operations of wire 58 and driver tube 66. The mid-strut crown 68 may be pulled proximally by the wire 58 to engage the locking tabs 62. The locking tabs 62 engage with the underside of mid-strut crowns 68 reducing the diameter of the frame 10 and cinching and locking the implant as shown in FIG. 6B. The collars 60 have sections removed along their sides from proximate mid collar to the collar distal end to accommodate movement of struts 12 as the collar is advanced over the mid-strut crown 68. Also, it is understood that rather than engaging with the underside of mid-strut crown 68, cut-outs could be provided in the surface of the mid-strut crowns 68. A driver tube 66 may act to drive the collar 60. The collar 60, locking tabs 62 and driver tube 66 may have the same or similar features and/or functionalities as, respectively, the collar 50, the locking tabs 54, and the driver tube 56, and vice versa.

FIGS. 7A through 7D are various views of another embodiment of a collar 70 that may be used with the various devices, systems and methods described herein. The collar 70 may have the same or similar features and/or functionalities as the other collars described herein, and vice versa. FIGS. 7A, 7B, 7C and 7D show, respectively, a circumferentially outward facing view, a side view, a circumferentially inward facing view, and a perspective view of the collar 70. The collar 70 includes locking tabs 72, 74. Here the locking tabs 72, 74 are on opposing sides of the collar 70. Two cut-outs 76 are located proximate the midsection of the sides of the collar 70. There may be only one or more than two cut-outs 76. Flex sections 78 are provided on either of the lower sides of the collar 70. There are numerous advantages of these features on the collar 70. For example, the lower tab 74 acts as a safety tab. As part of the assembly process, the lower tab 74 is positioned into engagement with a cut out in the upper crown 14, or, alternatively, the underside of the upper crown 14, of the implant 1. This may, for example, keep the collar 70 engaged with the upper crown 14 during the rigors of packaging and shipping and during the surgical procedure itself. As further example, both tabs 72, 74 can act as safety tabs by having multiple cut outs on either side of the upper crowns 14. In some embodiments, the cut outs 76 are created for preferential forming of the collar 70. For example, a starting material of a round hypotube may be crushed or swaged into an oval shape to slide the collar 70 over the upper crowns 14. Further, the flex sections 78 may reduce friction when the collar 70 is being advanced over the struts 12. The flex sections 78 may also minimize scraping of the collar 70 against the struts 12 of the frame 10 when the collar 70 is advanced. Additionally, as best seen with reference to FIG. 7D, when the collar 70 is advanced such that the upper locking tab 72 is engaged with the underside of an upper crown 14, the lower, inwardly biased tab 74 will help support upper tab 72 when it is advanced into locking engagement with the upper crown 14.

Figure 8C:
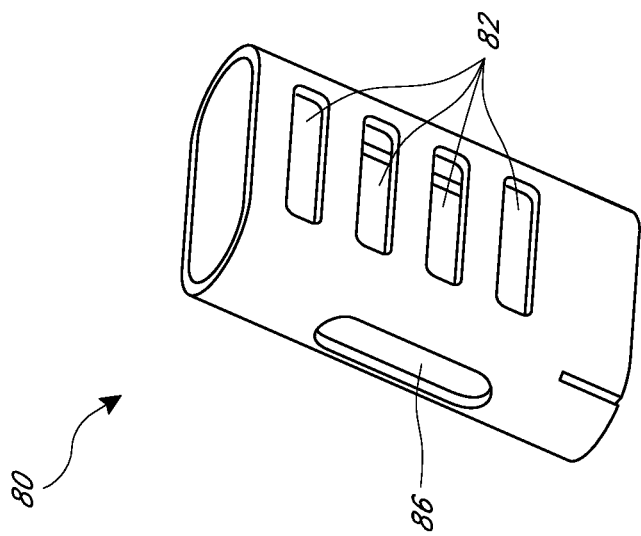
FIGS. 8A through 8C are various views of an embodiment of a collar having cutouts that may be used with the implant of FIG. 1.
Figure 8B:
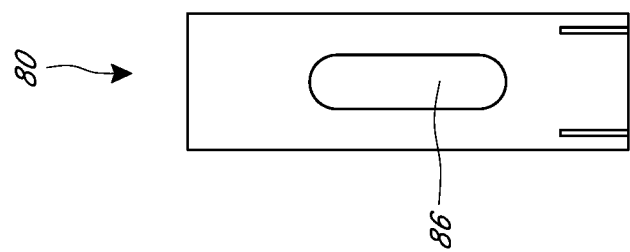
Figure 8A:
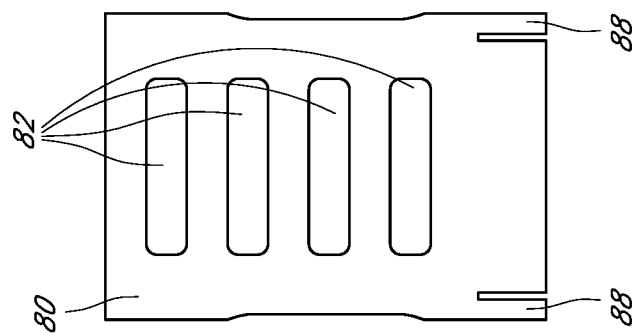

FIGS. 8A through 8C illustrate another embodiment of a collar 80 that may be used with the various devices, systems and methods described herein. The collar 80, also referred to as a "slider," may have the same or similar features and/or functionalities as the other collars described herein, and vice versa. FIG. 8A is a front view of the slider or collar 80, FIG. 8B is a side view of the collar 80, and FIG. 8C is a perspective view of the collar 80. This variation of the collar 80 is also provided with preferential forming cut outs 86 and flex sections 88, which may be similar or the same as the cutouts 76 and flex sections 78 as described with reference to the collar 70 in FIGS. 7A through 7D. In this embodiment, however, locking tabs are not provided on the collar 80. Rather, tabs are instead provided on the upper crown 14 (not shown) for locking engagement with cut outs 82 on the collar 80. These tabs would extend outwardly from the upper crown 14 and be downwardly biased.

Figure 9:
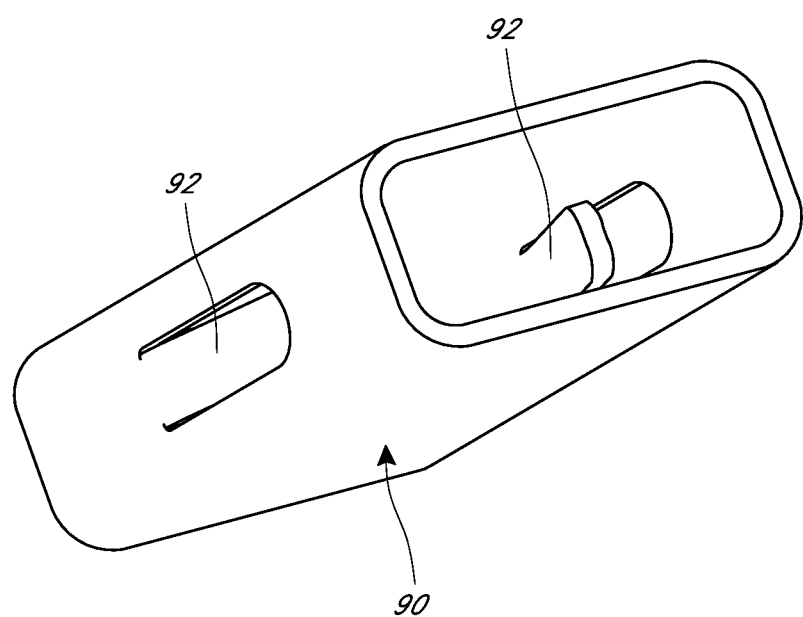
FIG. 9 is a perspective view of an embodiment of a collar with locking tabs.

FIG. 9 is a perspective view of another embodiment of a slider or collar 90. The collar 90 is provided with radial locking tabs 92. Locking tabs 92 are located on the sides of the collar 90 and are inwardly biased to engage with grooves (not shown) on the sides of the upper crowns 14 of the frame 10. Multiple levels of such grooves may be formed on the upper crown 14, and in addition or alternatively can be provided on the upper portions of the struts 12. Such grooves in either or both locations allow for more varied degrees of cinching of the implant 1.

FIGS. 10 through 15 are perspective views of various embodiments of implants that may be used with the various systems and methods described herein. In FIGS. 10 through 15, only some of the same features may be labeled for clarity. For example, only some of the struts 12 may be labeled in the figures, etc. FIGS. 10 and 11 are perspective views of an embodiment of an implant 100. The implant 100 may have the same or similar features and/or functionalities as other implants described herein, for example the implant 1, and vice versa. In particular, the implant 100 may have the same or similar features and/or functionalities as the implant 1 shown in and described with respect to FIGS. 38A-59, and vice versa.

In FIG. 10, the implant 100 is shown in an embodiment of an unconstrained state. The implant 100 is shown in an embodiment of an anchored, cinched and locked state in FIG. 11. The implant 100 includes a frame 100 having struts 112, upper crowns 114, lower crowns 116 and anchors 120. These may be analogous to, for example, the frame 10, the struts 12, the upper crowns 14, the lower crowns 16, and the anchors 20, respectively. By "analogous" it is meant these features may have the same or similar features and/or functionalities as each other. The implant 100 has lower crowns 116 that are inclined at an angle with respect to the struts 112. The lower crowns 116 may be inclined downward and outward, or distally and outward, relative to the struts 112 and/or relative to the axis (shown in FIG. 10). In this manner, the anchors 120 may be directed more in a direction into the annular tissue above and proximate the heart valve, and less in a downward direction toward the valve leaflets. The angle may be measured between the direction the lower crowns 116 extend and a portion of the axis extending underneath the implant 100. The angle may also be measured between the direction the lower crowns 116 extend and the direction that the struts 112 extend downward. This angle may be between thirty to sixty degrees. In some embodiments, this angle is approximately forty-five degrees. The anchors 120 are formed as one piece. A variety of different types of anchors may be used with the implant 100. For example, other anchors described herein may be used, for example the anchor 20 having the anchor head 22 and anchor abutment 24, as described with respect to FIGS. 1 through 4. The implant 100 in FIGS. 10 and 11 includes opposing tab sliders or collars 118. The collars 118 may be analogous to the collars 70, described with respect to FIGS. 7A through 7D. In some embodiments, the collars 18 may be used that engage with a central rotating shaft 646, as further described for example with respect to FIGS. 38A-59.

Figure 13:
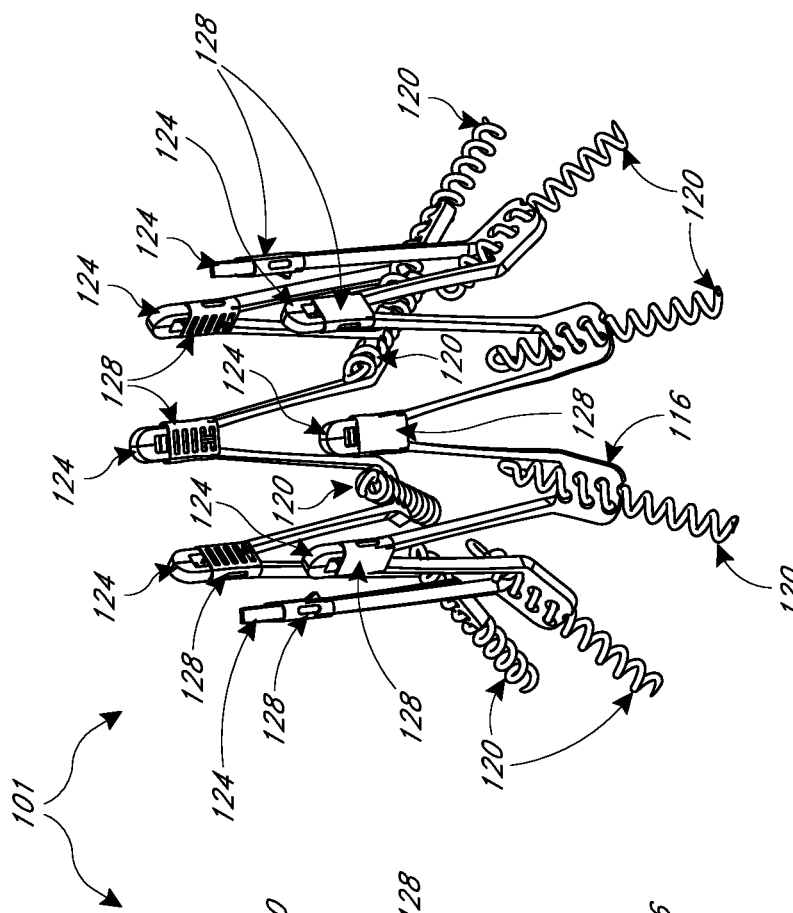
FIGS. 12 and 13 are perspective views of an embodiment of an implant having collars with cutouts shown, respectively, in an expanded and a cinched state.
Figure 12:
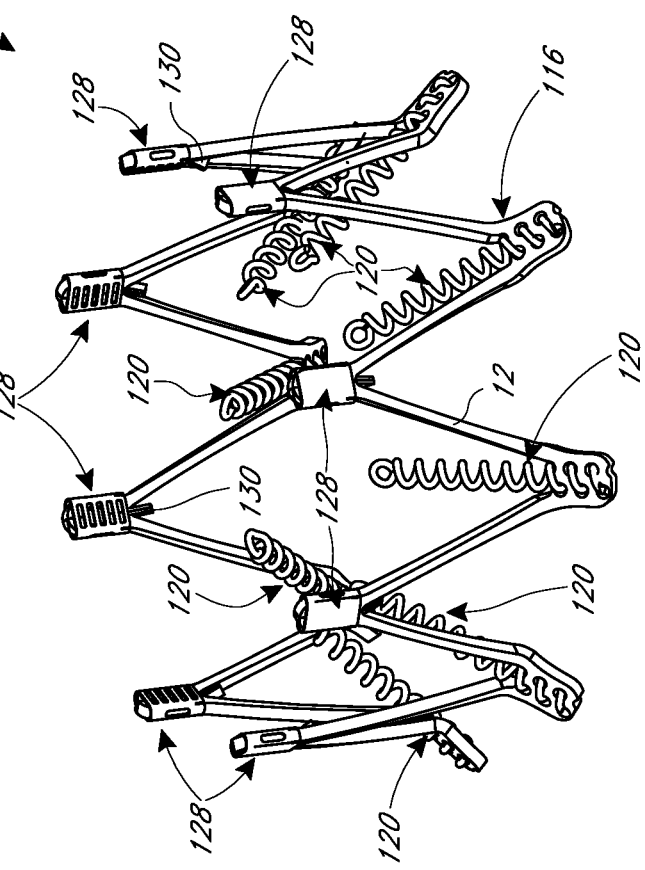

FIGS. 12 and 13 are perspective views of an embodiment of an implant 101. The implant 101 may have the same or similar features and/or functionalities as the implant 100, and vice versa. In particular, the implant 101 may have the same or similar features and/or functionalities as the implant 1 shown in and described with respect to FIGS. 38A-59, and vice versa. In FIG. 12, the implant 101 is shown in an embodiment of an unconstrained state. The implant 101 is shown in an embodiment of an anchored, cinched and locked state in FIG. 13. The implant 101 has upper crowns 124 having locking tabs 130. The implant 101 also includes indexed sliders or collars 128. The collars 128 may be analogous to the collars 80 described with respect to FIGS. 8A through 8C. The tabs 130 are provided on the upper crowns 124 for locking engagement with the grooves formed in the collar 128. Such grooves may be similar to the grooves 82 of the collar 80.

Figure 15:
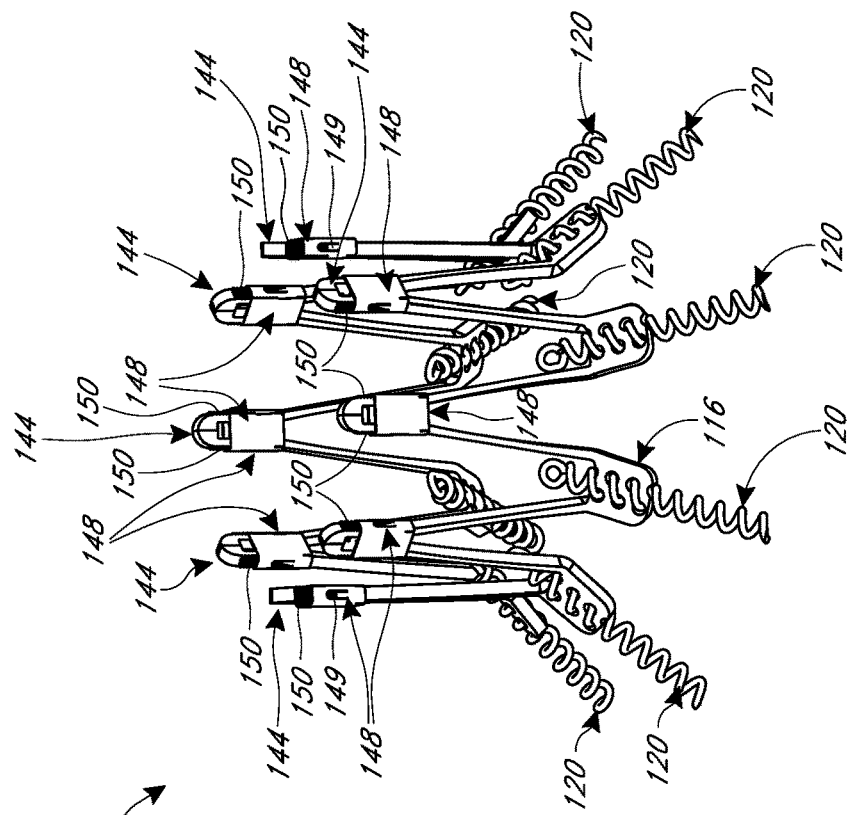
FIGS. 14 and 15 are perspective views of an embodiment of an implant having collars with locking tabs shown, respectively, in an expanded and a cinched state.
Figure 14:
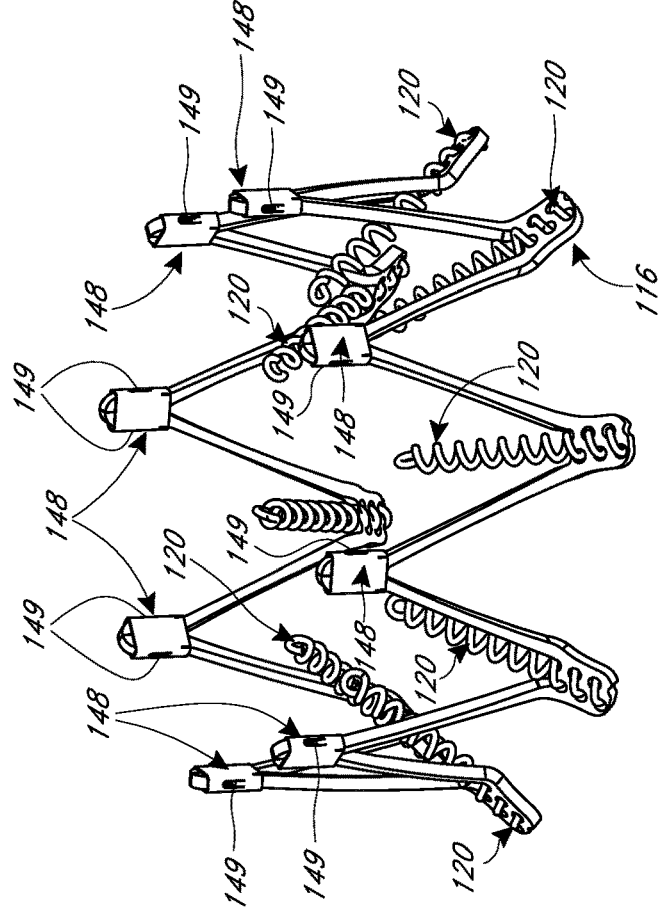

FIGS. 14 and 15 are perspective views of an embodiment of an implant 102. The implant 102 may have the same or similar features and/or functionalities as the implant 100 and/or 101, and vice versa. In particular, the implant 102 may have the same or similar features and/or functionalities as the implant 1 shown in and described with respect to FIGS. 38A-59, and vice versa. In FIG. 14, the implant 102 is shown in an embodiment of an unconstrained state. The implant 102 is shown in an embodiment of an anchored, cinched and locked state in FIG. 15. The implant 102 includes radial locking collars 148. The collars 148 may be analogous to the collars 90, described with respect to FIG. 9. Radially inwardly biased locking tabs 149 on the collars 148 engage with grooves 150 cut into the outer sides of the upper crowns 144. The pitch of the helically wound anchors 120 can be varied. The pitch of the last turn of the anchors 120 may also be varied, for example to self-lock the anchors 120 into the lower crowns 116. Moreover, the last or most distal turn of the helical anchors 120 may be swaged from a circular cross section to a more oval cross section to prevent backing out of the anchors 120 from the lower crown 116, for example to prevent backing out after engagement or anchoring in the heart tissue. Rather than swaging, pitch of the most distal turn of the helical anchors could be varied to prevent backing out.

FIGS. 16 and 17 are side views of a portion of an implant 103 in an uncinched and cinched state, respectively. The views indicate an embodiment of a method for cinching the implant 103 after anchoring. The implant 103 may be analogous to the various implants described herein, for example the implant 1, etc. The implant 103 includes a frame 160. The frame 160 may be analogous to other frames described herein, for example the frame 10, etc. The frame 160 has lower apices 166 which include eyelets 168. A string 172 is attached to or fed through the eyelets 168. Alternatively, the string 172 can carry enlargements, knots, and the like at its ends to prevent the ends from passing through the eyelets 168 as the frame 160 is cinched. String 172 can be made of wire, cable, suture, thread, or the like. Rotational member 170 is either fixedly attached to string 172 or string 172 is passed through a tunnel formed in the end of rotational member 170. FIG. 16 shows frame 160 in an unconstrained state. FIG. 17 shows the frame in its implanted state. After anchoring, the rotational member 170 is rotated thereby winding string 172 about the member 170. This action causes the gap between lower apices 166 to shorten thereby cinching, or reducing the diameter, of the frame 160.

FIGS. 18 and 19 show a variation of the implant 103 of FIGS. 16 and 17. In FIGS. 18 and 19, rather than have a rotational member cause the cinching, a string 180 is provided. The string 180 can take the form of a thread, suture, or the like. The string 180 is attached to a string 182 by way of loop or knot 188. The string 182 is similar to the string 172 shown in FIGS. 16 and 17. FIG. 18 shows the frame 160 in an unconstrained state, while FIG. 19 shows the frame 160 being brought towards a cinched state. As the proximal end of the string 180 is pulled by the operator to cause cinching of the frame 160, the knots 184 will click, one by one, through an eyelet 186 in the upper crowns 187. The knots 184 are sized so to be able to be pulled through the eyelet 186, but cannot reverse back through the eyelet 186. In this manner, the knots 184 provide a locking function and multiple degrees of cinch of the frame 160. After the desired degree of cinching has been achieved, the proximal ends of the string 180 are secured to maintain tension and then cut and the ends removed from the system.

FIG. 20 is a partial side view of another embodiment of an implant 104. The implant 104 may be analogous to the other implants described herein, for example the implant 1, etc. The implant 104 includes features for cinching the frame 160. A string-like member 202 is passed through multiple eyelets 204 disposed on the lower apices 166. The string-like member 202 extends circumferentially about the lower section of the frame 160. A driver unit (not shown) can be used to grab and gather the string-like member 202 until the desired amount of reduction in the diameter of the frame 160, or cinching, is achieved. In some embodiments, other features described herein may be used with the string-like member 202 to cinch the string-like member 202, for example the string 180 or the rotational member 170.

Figure 21B:
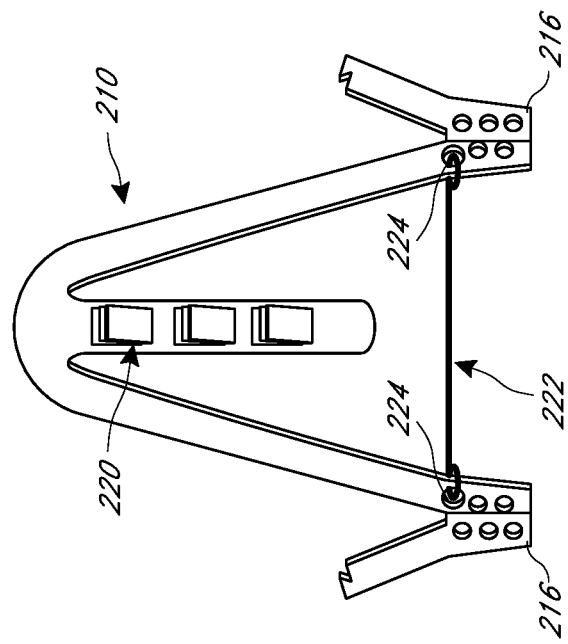
FIGS. 21A through 21D are partial sequential side views of an embodiment of a frame showing sequential cinching of adjacent struts using a string member and tabs.
Figure 21A:
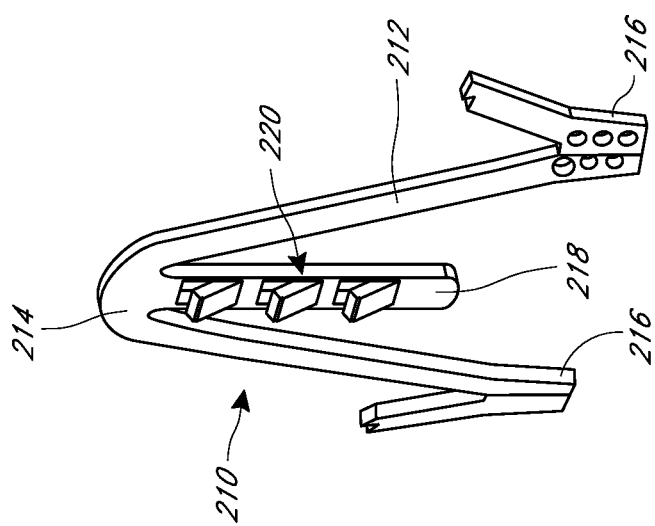
Figure 21D:
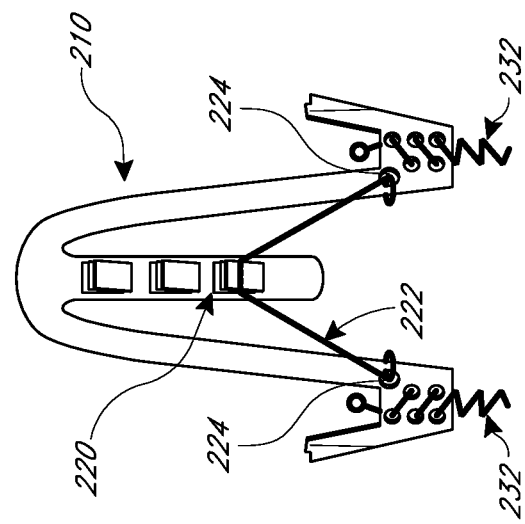
Figure 21C:
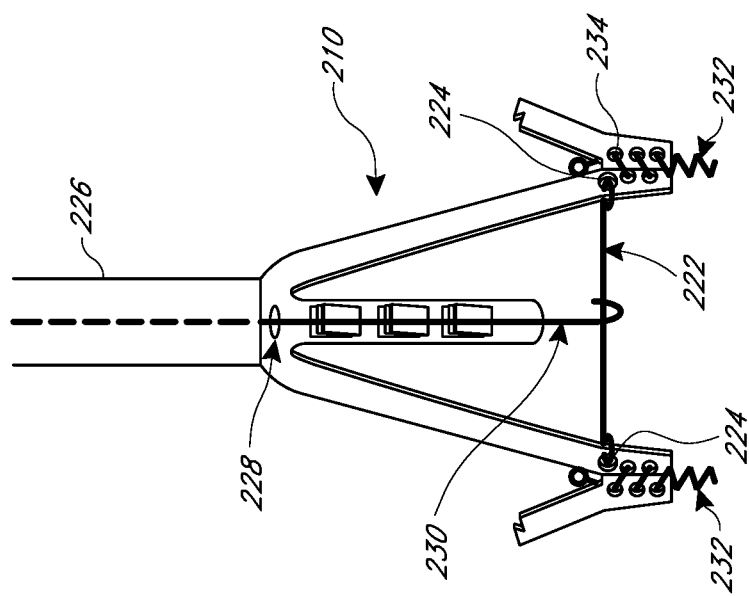

FIGS. 21A through 21D are partial side views of an embodiment of a frame 210 that may be used with the various implants described herein, for example the implant 1, etc. The views sequentially show a technique for cinching the frame 210. As shown in FIG. 21A, the frame 210 has struts 212, upper crowns 214 and lower crowns 216, which may be analogous, respectively, to other struts, upper crowns and lower crowns described herein. A central projection 218 extends downwardly from the upper crown 214 into the gap or valley bounded by adjacent struts 212. The central projection 218 includes three tabs 220. There may be fewer or greater than three tabs 220. The tabs 220 extend in an upwardly oriented and angled direction, e.g. outward, from the central projection 218. With reference to FIG. 21B, a string member 222 spans the distance between adjacent lower apices 216. The string member 222 may be between one, some or all distances between pairs of adjacent lower apices 216. The string member 222 can take the form of a wire, cable, suture, thread, or the like. The string member 222 is passed through one or more holes 224 in the lower crowns 216. The holes 224 are sized and positioned so as not to interfere with the rotation of helical anchors 232 as they are threadingly advanced through the holes 234 (see FIG. 21C). The anchors 232 may be analogous to other anchors described herein, for example the anchors 20, etc. The ends of the string members 222 may be knotted, for example for thread or suture string members 222. The ends of the string members 222 may be provided with a weld ball, collar, etc.

crimped onto its ends, for example if the string members 222 are wire or cable. Such end features may prevent the ends of the string members 222 from being pulled through the holes 224 when tension is applied. As shown in FIG. 21C, a driver tube 226 is operated to apply tension to pull wire 230. For ease of operation, an alignment feature 228 can be provided to align pull wire 230 with central projection 218 and its tabs 220. Either by pulling or rotating driver tube 226, the operator applies tension to pull wire 230 which is hooked around string member 222. The operator can then apply varying degrees of cinching to frame 210 by ratcheting string member 222 up and into engagement with tabs 220. FIG. 21D shows the frame in one particular state of cinch. The string member 222 may be engaged with any of the tabs 220 to provide more or less cinching to the frame 210.

Figure 22A:
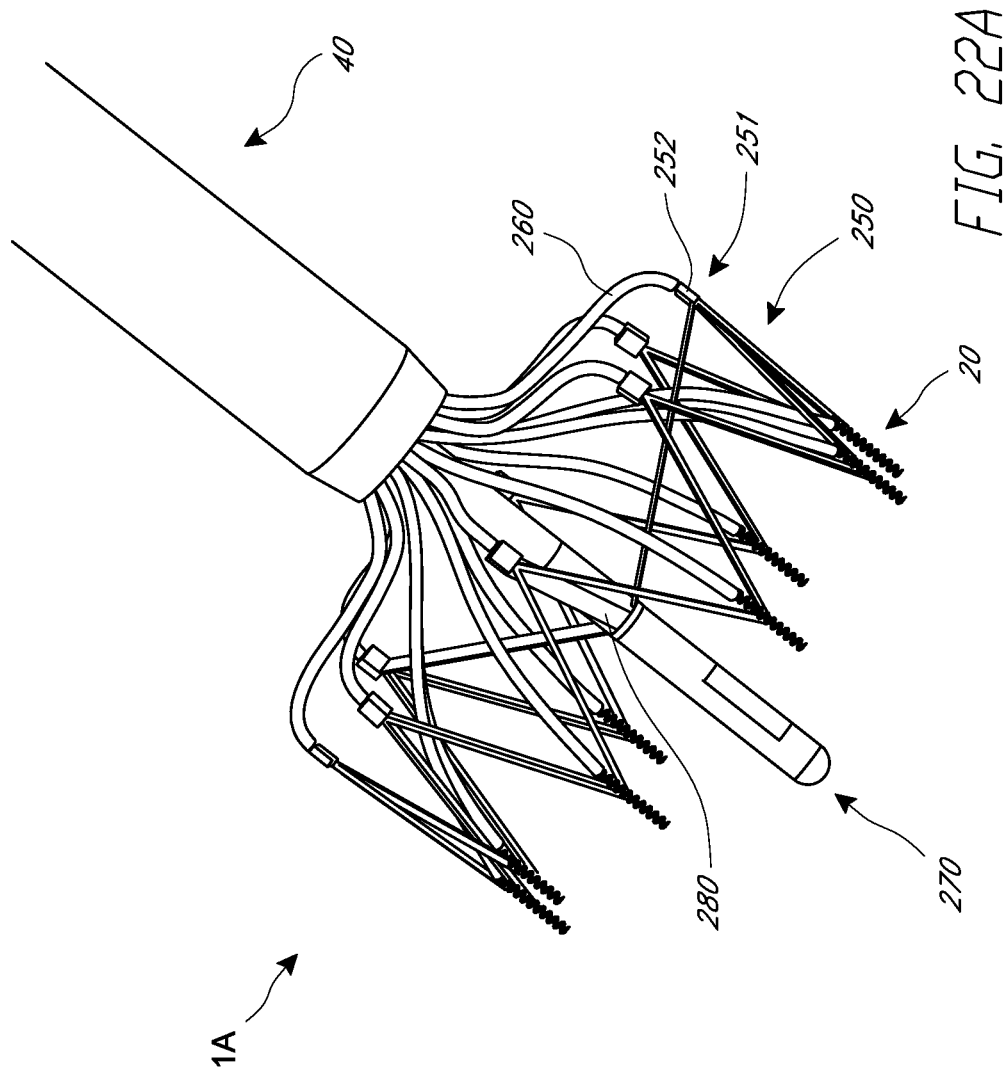

FIGS. 22A and 22B are perspective views of an embodiment of a distal end of a delivery catheter 40 being used to deliver an implant 1A. The delivery catheter 40 has various positioning and imaging capabilities. The distal end of the delivery catheter 40 is maneuvered into position above the heart valve annulus. The delivery catheter 40 may be used to deliver the various implants described herein, for example the implant 1, etc. In particular, the delivery catheter 40 may be used to deliver the implant 1 shown in and described with respect to FIGS. 38-59A. The implant 1A shown being delivered in FIGS. 22A-22B is for resizing the heart valve annulus. It is understood that a variety of different implants may be delivered with the delivery system and methods described herein. The implant 1A may be analogous to the other implants described herein, such as the implant 1. As shown, this particular implant 1A includes a frame 250. The frame 250 has anchors 20 attached to a lower or distal portion of the frame 250 and extending distally therefrom. The frame 250 has an upper or proximal portion with collars 252 extending over upper crowns 251 of the frame 250. Only some of the collars 252, upper crowns 251 and anchors 20 are labelled for clarity. The collars 252 may be moved, e.g. distally, along the frame 250 by driver tubes 260 to resize the frame 250. The frame 250, upper crowns 251 and collars 252 may be analogous to the various frames, upper crown and collars described herein, such as the frame 10, upper crowns 14 and collars 18, and vice versa. The collars 18 may be translated axially by engagement with the central rotating shaft 646, as further described. The anchors 20 may engage with anchor housings 22A at the distal apexes, as further described.

The frame 250, one or more driver tubes 260, and an intravascular cardiac echography (or "ICE") catheter 270 may be extended from the distal end of the delivery catheter 40. The frame 250 and driver tubes 260 may be analogous to the various frames and driver tubes described herein. The driver tubes 260 are shown engaging corresponding upper crowns 252 of the frame 250. A centering frame 280 maintains concentric positioning of the ICE catheter 270 relative to the frame 250 during deployment, alignment and positioning of the frame 250 above and proximate to the target heart valve annulus tissue. The centering frame 280 maintains a generally centered position of the catheter 270 relative to the frame 250. By centering the ICE catheter within the frame 250, the operator need only rotate the ICE catheter 270 to view each anchor 20 and placement of the anchors 20. Further, the ICE catheter 270 could be used to view various other individual features of the implant 1A, such as the collars 252, for instance to view the extent to which each collar 252 is advanced down and over upper crowns 251 of the frame 250, to more precisely adjust the size of the frame 250. The ICE catheter 270 could also provide significant benefit to an embodiment where a singular cinching mechanism or driver tube needs to be landed on each crown 251 of the frame 250 to adjust the sizing of the frame 250. An indexing feature (not shown) may also be provided on the ICE catheter 270, for example, such that actuation of the indexing feature by the operator causes the ICE catheter 270 to automatically move, or rotate, to the next anchor 20 position.

FIGS. 22C and 22D are perspective views of an embodiment of an implant 1B being delivered and implanted by the delivery catheter 40. The implant 1B may be analogous to the various implants described herein, such as the implants 100, 101, 102, and vice versa. As shown in FIGS. 1C and 1D, the implant 1B includes a frame 10 with struts 12 forming upper apices or crowns 14 and lower apices or crowns 16. The lower crowns 16 have openings 17, such as holes, aligned to receive the anchors 20 there through. For clarity, only some of the upper crowns 14, lower crowns 16, struts 12 and anchors 20 are labelled in FIGS. 1C and 1D. The anchors 20 may be rotated to move distally through the openings 17. The implant 1B is intended to be delivered proximate to and above a cardiac valve (tricuspid, mitral) annulus, and subsequently implanted in the annular cardiac tissue just above the plane of the valve orifice.

Driver tubes 22', having proximal portions 22" extending out of the delivery catheter 40, are provided for rotationally engaging the anchors 20. Manipulation, for example rotation, of the driver tubes 22' by the operator causes the anchors 20 to advance towards, engage with and penetrate cardiac tissue to secure frame 10 into the annulus approximate and above the valve. The anchors 20 may be advanced individually one at a time, some advanced together, or all advanced together. In some embodiments, the driver tube 22' may rotate relative to the proximal portion 22". In some embodiments, the driver tube 22' and proximal portion 22" are part of the same, continuous driver tube and/or the entire tube 22' and proximal portion 22" may rotate together.

An embodiment of an ultrasound catheter 30, such as the Acuson IPX8 AcuNav catheter, is shown contained within and advanced down a central lumen of the delivery catheter 40. The ultrasound catheter 30 may be analogous to the ICE catheter 270. In some embodiments, by rotating the ultrasound catheter 30 around the inside of the valve annulus, the relative position of the frame 10, and of any valve leaflets, will be seen for accurate positioning of the anchors 20 around and above the valve annulus.

In some embodiments, the ultrasound catheter 30 is contained within and advanced down an offset, non-central lumen of the delivery catheter 40. In this manner, the ultrasound catheter 30 would not interfere with the frame 10, its attachments or other features, and the driver components. In some embodiments, the ultrasound catheter 30 may be located and steered to the side of the annulus to image, allowing for less rotation to more quickly view the anchor points of the frame 10. An offset lumen could exit more proximally with regard to the distal end of the delivery catheter 40. This more proximal exit would reduce the overall profile or diameter of the distal end of the delivery catheter 40. In addition, this more proximal exit port would enable a view of the valve annulus from above. The offset lumen could also be compressible allowing for an even smaller profile until the ultrasound catheter 40 is advanced through the offset lumen.

While the ultrasound catheter 30 is shown integrated into the same delivery system as the delivery catheter 40, in some embodiments the ultrasound catheter 30 could otherwise be introduced secondarily through another entry site, such as through the aortic valve, and placed near or inside the implant for imaging and placement of the anchors 20.

FIG. 22E is a perspective view of an embodiment of a centering frame 32 coupled to the ultrasound catheter 30 and to an implant 1C. The implant 1C may be analogous to other implants described herein, such as the implants 1, 1A, 1B, and vice versa. The centering frame 32 has centering arms 34 connected to a centering hub 36 that is mounted on the ultrasound catheter 30. As the distal end of the delivery catheter 40 is maneuvered into position above the heart valve annulus, the centering frame 32 maintains concentric positioning of the ultrasound catheter 30 relative to the frame 10 during deployment, alignment and positioning of the frame 10 above and proximate to the target heart valve annulus tissue. The centering aspect is desirable, for example, because if the ultrasound catheter 30 remains centered within the frame 10, the operator such as a surgeon or technician need only rotate the ultrasound catheter 30 to view each anchor 20 and placement the of each anchor 20. There may also be an indexing feature (not shown) on the ultrasound catheter 30 such that actuation of the indexing feature by the operator causes the ultrasound catheter 30 to automatically move, or rotate, to the next anchor position. The centering frame 32 may be used with delivery of the various implants described herein, such as the annulus resizing implants and/or the heart valve replacement implants.

Figure 23:
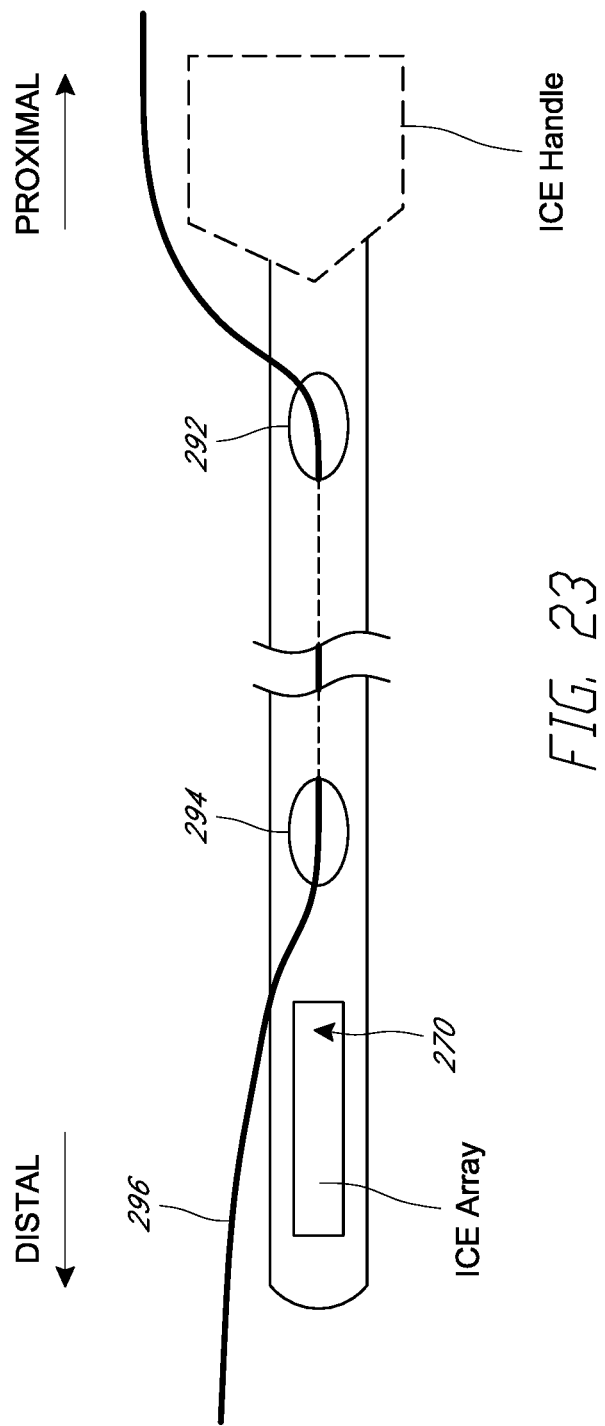
FIG. 23 is a side view of an embodiment of an intravascular cardiac echography (ICE) catheter for delivering, e.g. aligning and positioning, the various implants described herein, and having a guidewire entering and exiting the catheter.

FIG. 23 is a side view of an embodiment of an ICE catheter 270. The ICE catheter 270 as shown includes a guidewire entry port 292 and a guidewire exit port 294 which together accept the guidewire 296. This embodiment allows the ICE catheter 270 to be delivered separately from the frame 10 thereby reducing the overall diameter of the delivery catheter 40 (e.g. as shown in FIGS. 22A and 22B). An ICE handle may be located at a proximal end of the catheter 270. An ICE array may be located at the distal end of the catheter 270.

In some embodiments, a separately delivered ultrasound catheter 270 could be functionally linked to the distal end of the delivery catheter 40 and to the inside of the frame 10. The delivery catheter 40 could have mechanical docking and radiopaque features to aid in delivery and stability of the ultrasound catheter 270 relative to the delivery catheter 40.

FIGS. 24A, 24B, 24C and 24D depict an embodiment of an ICE catheter 300 that may be used with the various implants and delivery devices, systems and methods described herein. The ICE catheter 300 has radial ultrasonic transducers 302, circumferential ultrasonic transducers 304 and guidewire 306 passing centrally therethrough. A guidewire lumen 303 extends out from a delivery catheter 240. The delivery catheter 240 may be analogous to the delivery catheter 40. The ICE catheter 300 extends out through the guidewire lumen 303. FIGS. 24B and 24C show the implant 1 deployed with the ICE catheter 300 tip. The other implants described herein may be delivered with the ICE catheter 300, such as the implants 1, 1A, 1B, 1C, and the implants 500, 520, 530 described below, etc. In particular, the implant 1 shown in and described with respect to FIGS. 38A-59 may be delivered with the ICE catheter 300. FIG. 24C further shows the relationship of the ICE catheter 300 to the delivery catheter 240 while it is taking a radial echo view to properly position the anchor 20 for insertion into heart valve annulus tissue. FIG. 24C shows the ICE catheter 300 capturing a circumferential echo image for properly positioning the frame 10 in a plane above the heart valve and its leaflets. The features shown and described in FIGS. 24A-24D may be used to deliver various other implants, such as other resizing devices or heart valve replacement valves.

In some embodiments, software or electronic controls can be effective to cycle through the radial cross sectional images around the valve annulus perimeter, relieving the need to physically move, via rotation, translation or deflection, the ICE catheter 300. A larger circumferential transducer array could also be placed distal of the annulus to not interfere with space limitations of the delivery catheter 240, further decreasing the profile of the delivery catheter 240. In another embodiment, the transducers of the ICE catheter 300 could generate a three dimensional image of the annulus of frame 10. The user could then more readily see the relative alignment of the annulus, valve leaflets and the implant 1.

FIGS. 25A through 25E are sequential perspective views of an embodiment of a delivery system 401 with imaging capability showing an embodiment of a method for the delivery, positioning and anchoring of the various implants described herein for resizing the native valve annulus. While FIGS. 25A through 25E depict delivery of the implant 1 for resizing the annulus, it is understood that implants for replacing the valve may also be delivered with the system 401. The implant 1 may be delivered, positioned and anchored to reshape the valve annulus. The implant 1 may be inserted using the delivery system 401 via access to the vasculature of the leg, in particular the femoral vein or the iliac vein. The system 401 may include the various implants, catheters and other features described herein, for example the implant 1, the delivery catheter 240, the ICE catheter 300, the guidewire 306, etc. The system 401 may include any of the implants described herein, for example implants including valve annulus reshaping devices or valve replacements that include valve leaflets.

Figure 25A:
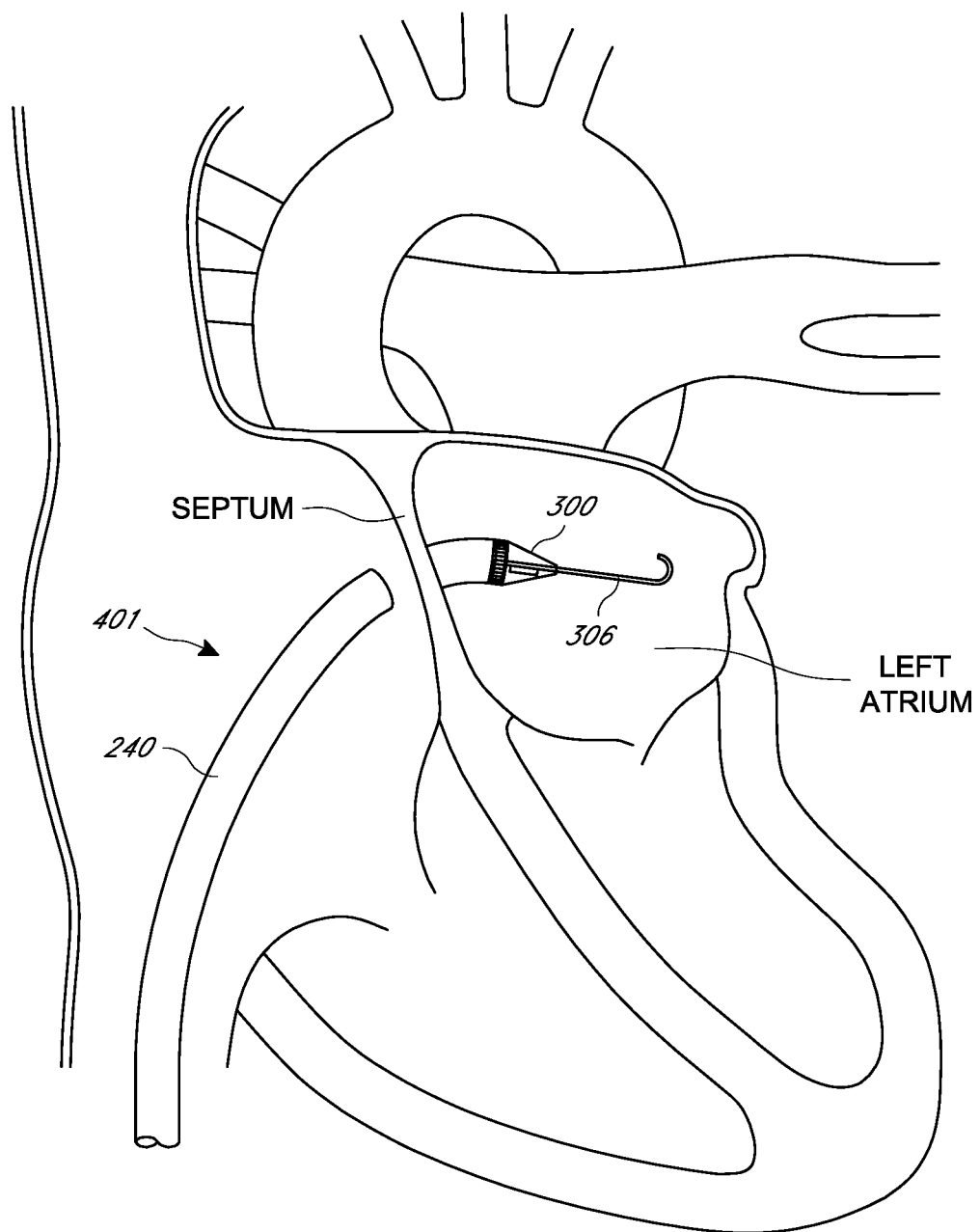
FIGS. 25A through 25E are sequential perspective views of an embodiment of a delivery system with imaging capability showing an embodiment of a method for the delivery, positioning and anchoring of the various implants described herein for resizing the native valve annulus.
Figure 25B:
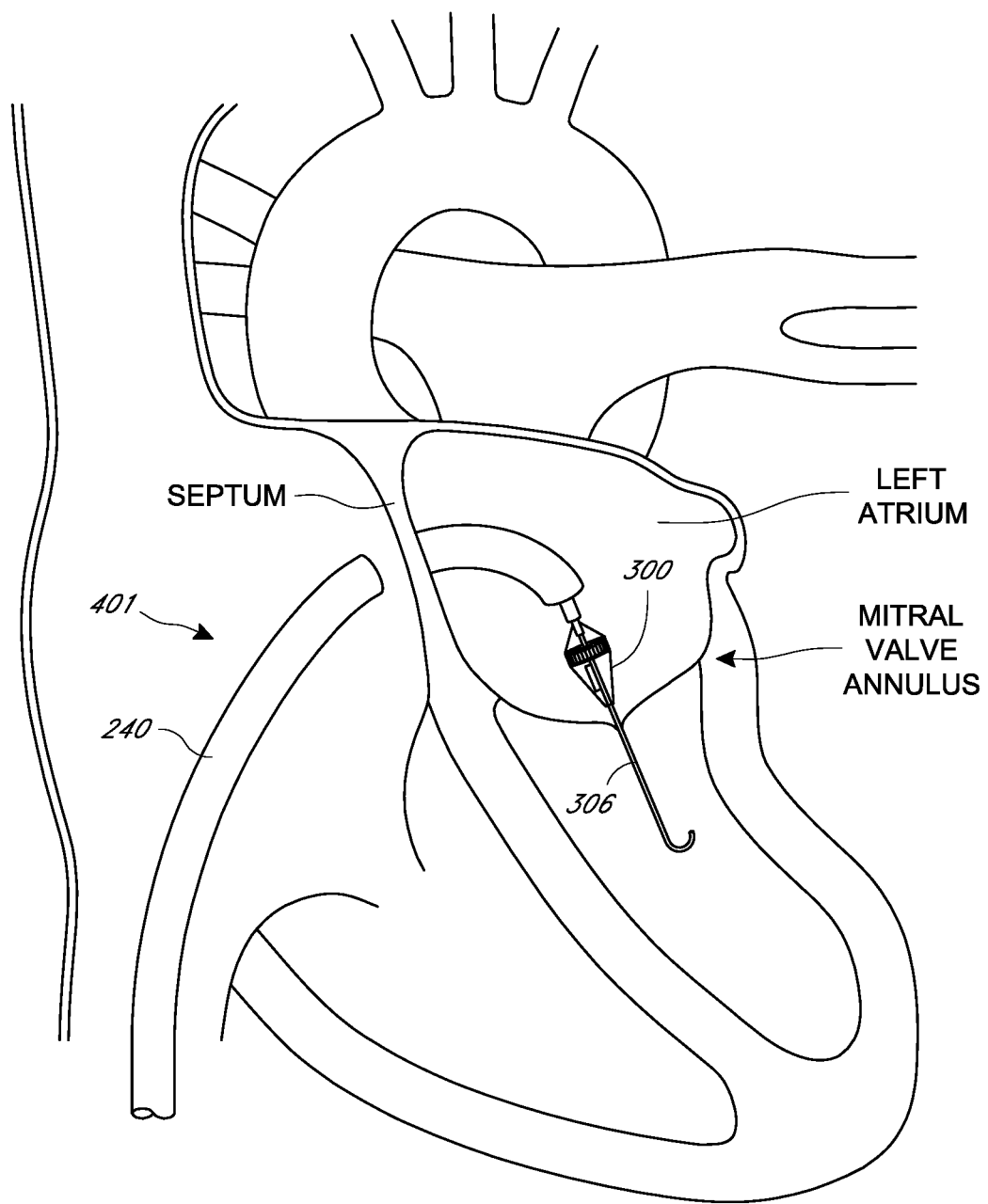
Figure 25C:
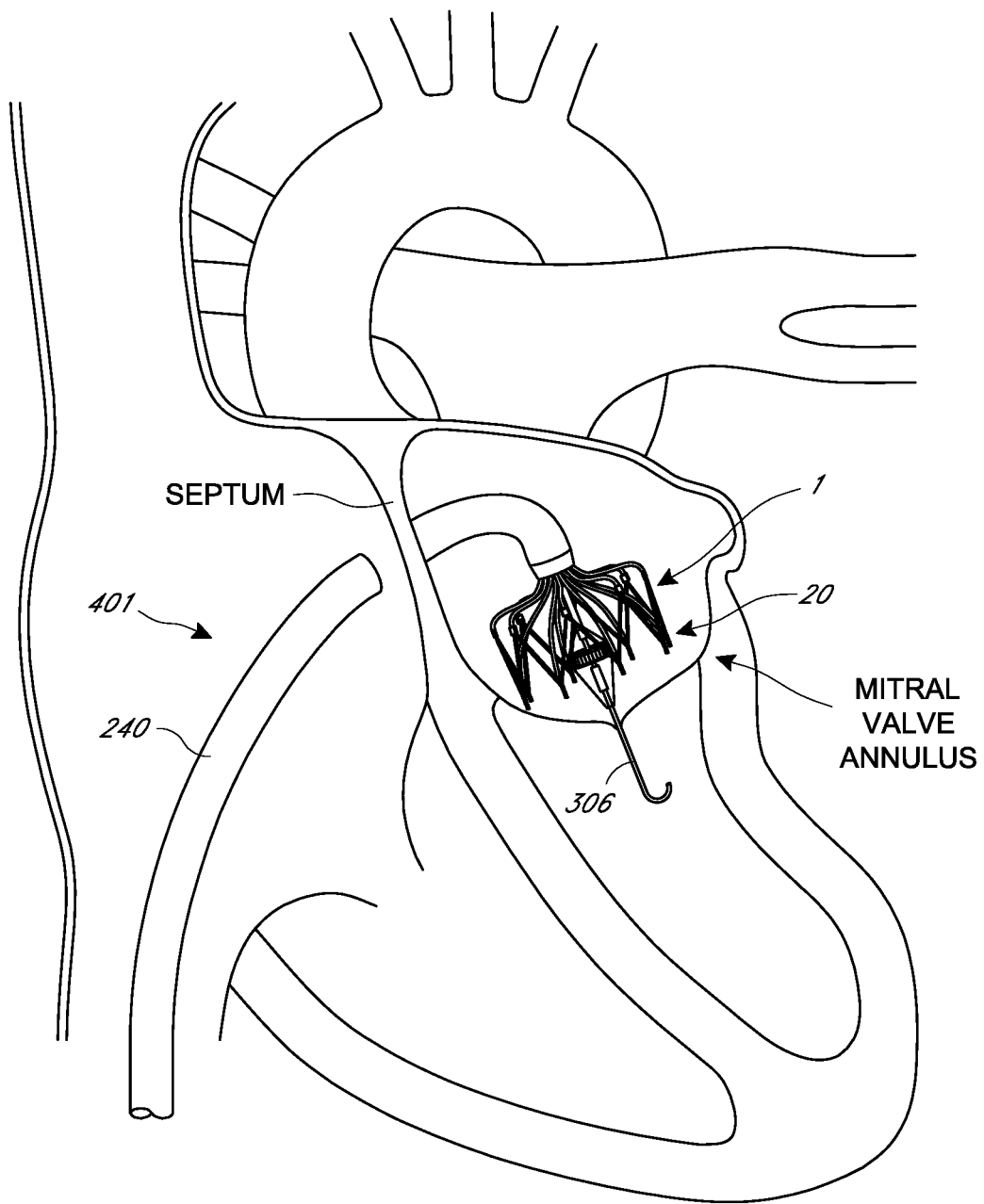
Figure 25D:
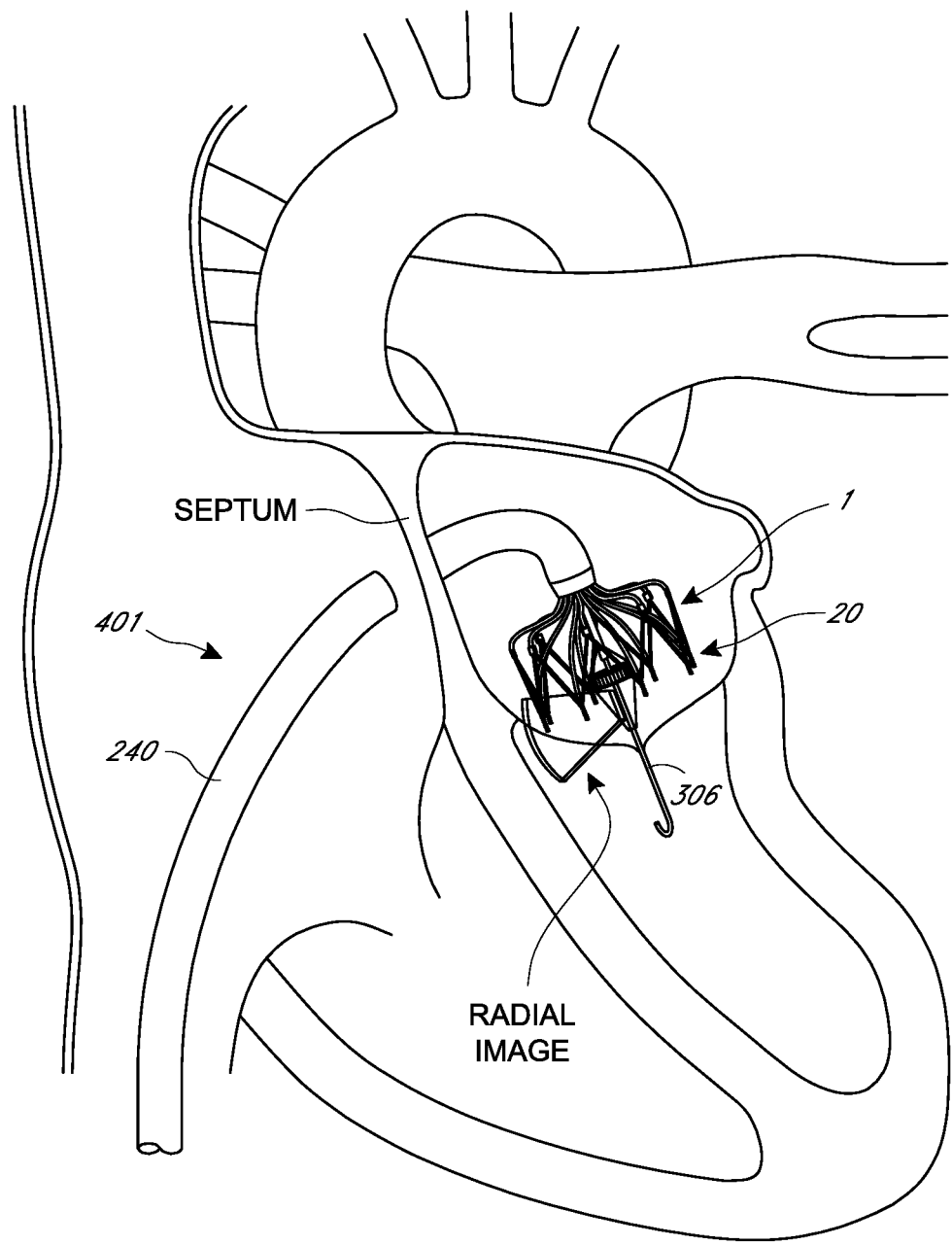
Figure 25E:
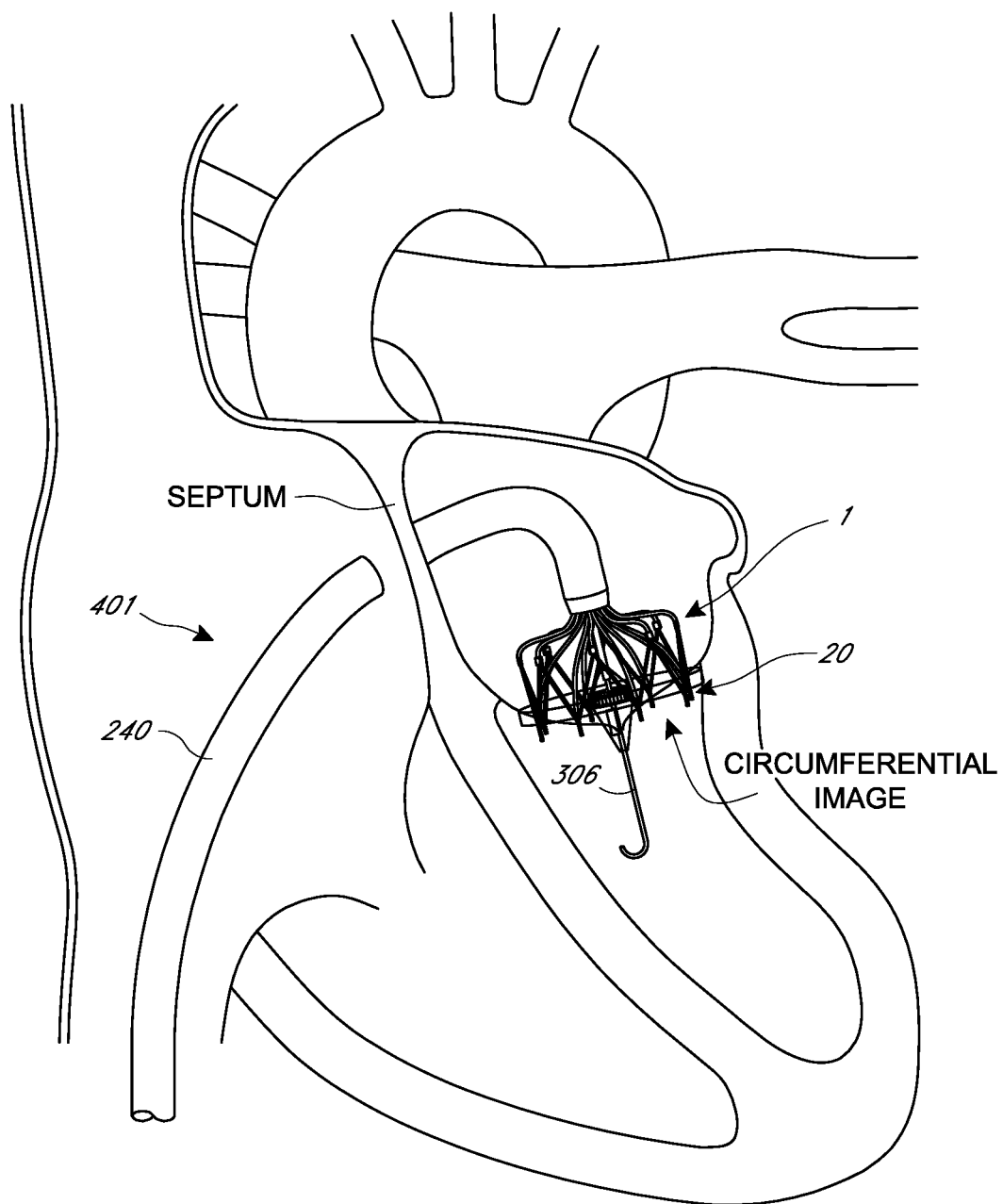

As shown in FIG. 25A, the system 401 is then advanced across the septum separating the upper chambers of the heart. The ICE catheter 300 is advanced to a position above the heart valve annulus, for example, the mitral valve annulus, as shown in FIG. 25B. FIG. 25C shows the implant 1 expelled from the distal end of the delivery system 401 above and proximate to the mitral valve annulus. A series of radial images are taken to properly position the anchors 20 for insertion into the mitral valve annulus tissue, as shown in FIG. 25D. Subsequently, a circumferential image is captured, as shown in FIG. 25E, to confirm that all anchors 20 are appropriately placed and anchored in the mitral valve annulus tissue above the mitral valve leaflets. If one or more anchors 20 are not positioned or anchored properly, they can be rotationally retracted, repositioned and re-anchored prior to removal of the driver tubes. In addition, a circumferential image can be taken prior to anchoring to confirm location of the lower crowns 16 of the frame 10 of the implant 1. It should also be understood that treatment of the tricuspid valve could involve insertion of the system 401 for access through the jugular vein whereby the system is then advanced down the superior vena cava and into the right atrium proximate and above the tricuspid valve annulus.

FIG. 26 is a perspective view of an embodiment of an implant 100 having a constricting loop 320. The implant 100 is shown interacting with a delivery system for advancing the collars 60. The constricting loop 320 may be used with other embodiments of the implant described herein, for example the implants 101, 102, etc. In particular, the constricting loop 320 may be used with the implant 1 shown in and described with respect to FIGS. 38A-59. As shown in FIG. 26, the constricting loop 320 is provided. The constricting loop 320 encircles the frame 110 proximate the lower crowns 16. The constricting loop may encircle upper portions of the lower crowns 16 as shown, or other portions. A constricting loop actuator 330 may be provided to act on and constrict the constricting loop 320. For example, the actuator 330 may include a wire with a loop through which the constricting loop 320 extends, and where pulling the wire proximally will constrict and tighten the constricting loop 320 about the frame 110. In operation, the constricting loop 320 may be actuated first, allowing the operator to first predetermine the desired diameter of the frame 110. The collars 60 may then be advanced, cinching the frame 110 and locking it in the desired diametric dimension. In some embodiments, other collars described herein may be implemented. The constricting loop 320 is then removed. Constricting the frame 110 also reduces resistance to advancement of the collars 60. Furthermore, the constricting loop 320 assists in collapsing the frame 110 into the distal portion of the delivery catheter. Moreover, the constricting loop 320 helps reduce friction between the flared lower crowns 16 and the inner diameter of the delivery catheter. Additionally, a proximal loop can be utilized to restrict the proximal portion of the frame 110 to change the angle at which the anchors address the valve annulus.

Figure 27A:
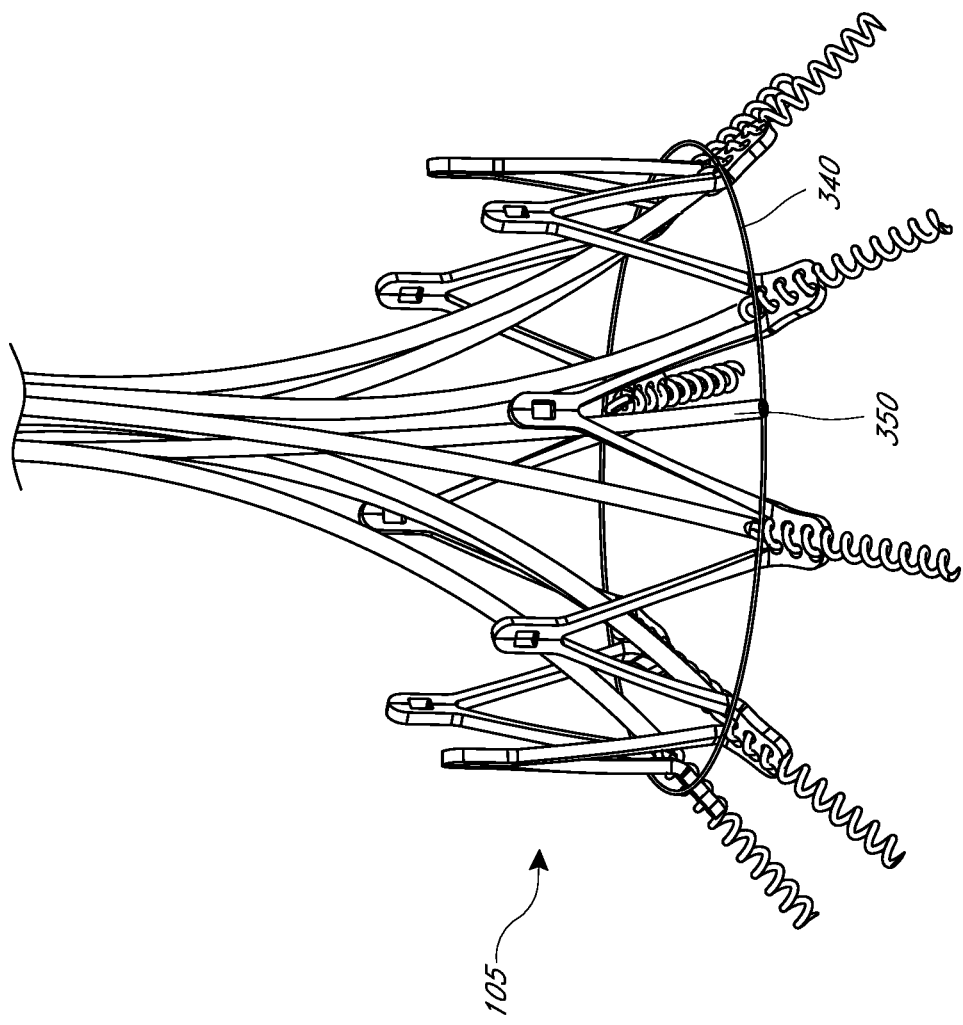
FIGS. 27A and 27B are side and detail views, respectively, of an embodiment of an implant having a cinch loop and is shown interacting with a delivery system for advancing the anchors.
Figure 27B:
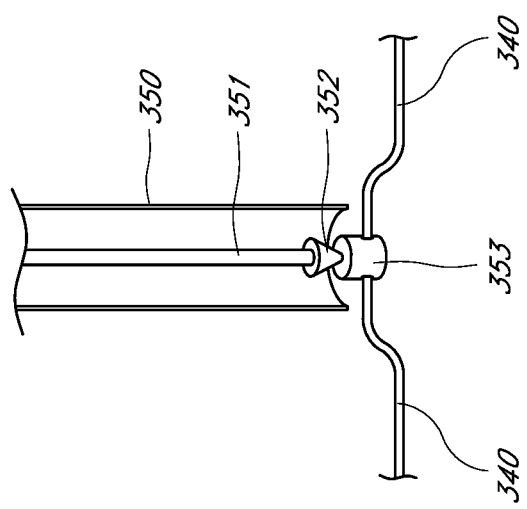

FIG. 27A is a perspective view of an embodiment of an implant 105 having a cinch loop 340. In this variation, the implant 105 does not include collars and the cinch loop 340 is provided to cinch and lock the frame of the implant 105 in the target heart valve annulus tissue. After anchoring, the cinch loop 340 is tightened down by operation of a cinch loop driver 350. FIG. 27B is a detail view showing a close up view of the driver 350 interacting with the loop 430. The driver 350 may include an inner tube or member 351 extending therethrough to or near a distal opening of the driver 350. A distal member 352, such as a wedge, may be attached to the distal end of the inner tube 351. The distal member 352 removably attaches to an element 353, for example by threaded engagement, friction fit, or other suitable engagement means. The loop 340 extends through or is otherwise attached to the element 353, locking the loop 340 in place. Pulling the element 353 in the proximal direction, for example by moving the driver 350 proximally, and/or pulling the inner tube 351 proximally, the loop 340 reduces in circumference around the implant 105, cinching the frame to a smaller diameter. The ends can then be snipped and driver 350 and inner tube 351 withdrawn. Once the operator has achieved the desired reduction in diameter of the anchored frame, the cinch loop 340 is locked in place and the cinch loop driver 350 is removed. In some embodiments, the cinch loop 340 may engage with the frame 110, for example with the lower crowns 16, to lock in place. Such engagement may be by friction fit, openings in the lower crowns 16 that allow for unidirectional movement of the loop 340, or other suitable means.

FIG. 28 is a perspective view of a delivery system 400 that may be used to deliver the various implants described herein. In particular, the delivery system 400 may be used to deliver the implant 1 shown in and described with respect to FIGS. 38A-59. As shown in FIG. 28, the delivery system 400 comprises a steerable sheath 402, a sheath steering knob 404, cinch knobs 406, anchor knobs 408, the implant 100 which may be any implant described herein, the ICE probe 270, all supported and secured to a base 410. The cinch knobs 406 and anchor knobs 408 are all spring loaded to maintain tension. Rotation of the anchor knobs 408 rotationally advance the helically wound anchors 20 into the annular tissue above the target heart valve. Cinch knobs 406 are manipulated by the operator to advance the collars and lock the frame of the implant 100 into a cinched position.

Figure 29:
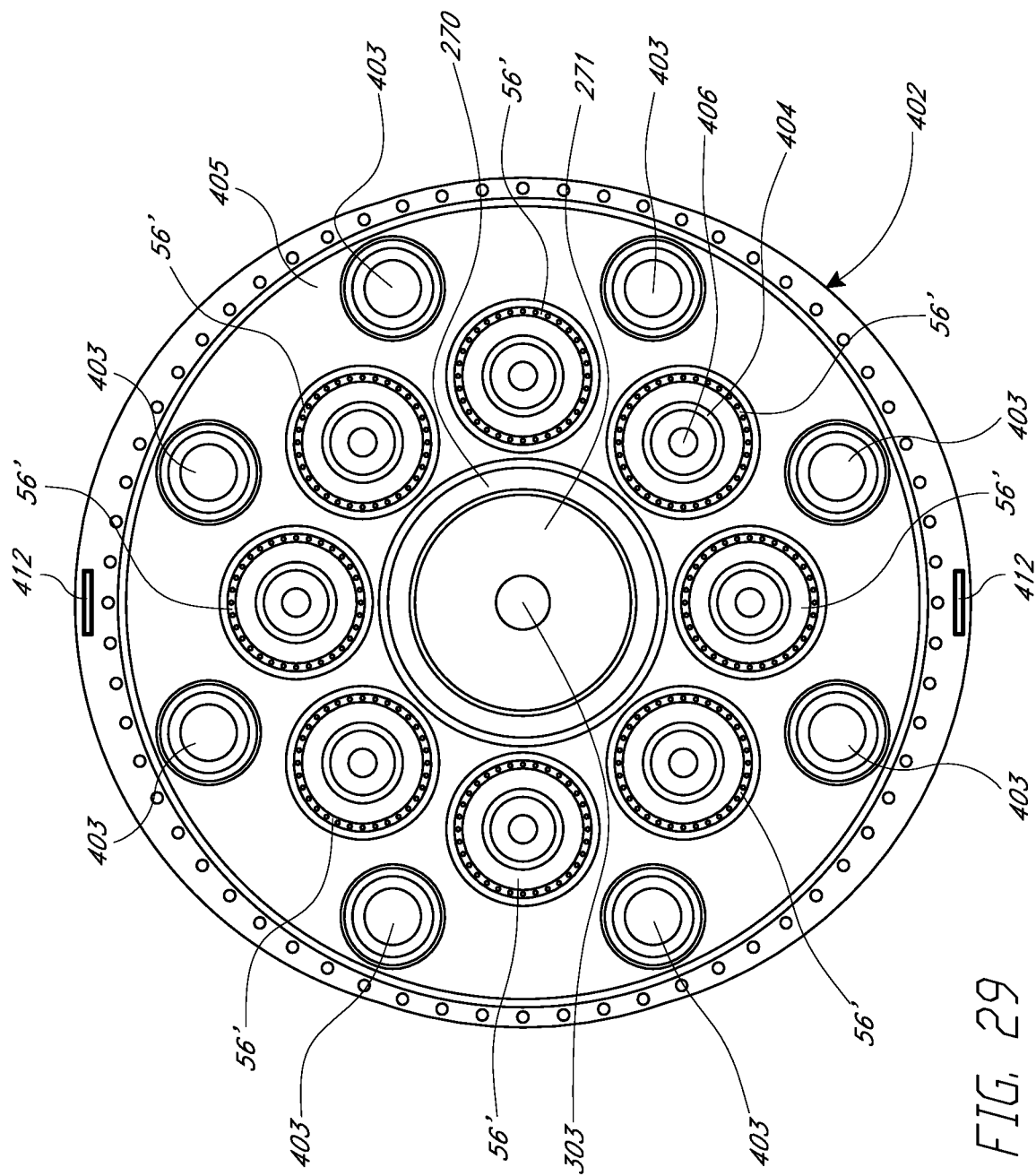
FIG. 29 is a cross section view taken along line 29-29 of FIG. 28 showing the internal features of a portion of the delivery system of FIG. 28.

FIG. 29 is a cross section taken along line 29-29 of FIG. 28. The pull wires 412 are attached to the sheath steering knob 404 to deflect the distal end of the sheath 402. The sheath 402 may be a steerable outer sheath 402, for example made of braided polymer or metal such as Nitinol or stainless steel. The ICE catheter shaft 270 may be centrally located with the guidewire lumen 303 located within the ICE catheter lumen 271. There are eight anchor driver wires 403, for example nitinol, circumferentially located within the sheath 402. The anchor driver wires 403 are located within anchor driver sheaths, for example laser cut hypotubes. There are eight pusher tubes 56', which may be braided, located around the ICE catheter shaft 270. The pusher tubes 56' may include a cinch retaining tube 404, for example a laser cut hypotube and a cinch retaining wire 407, for example nitinol.

Figure 30A:
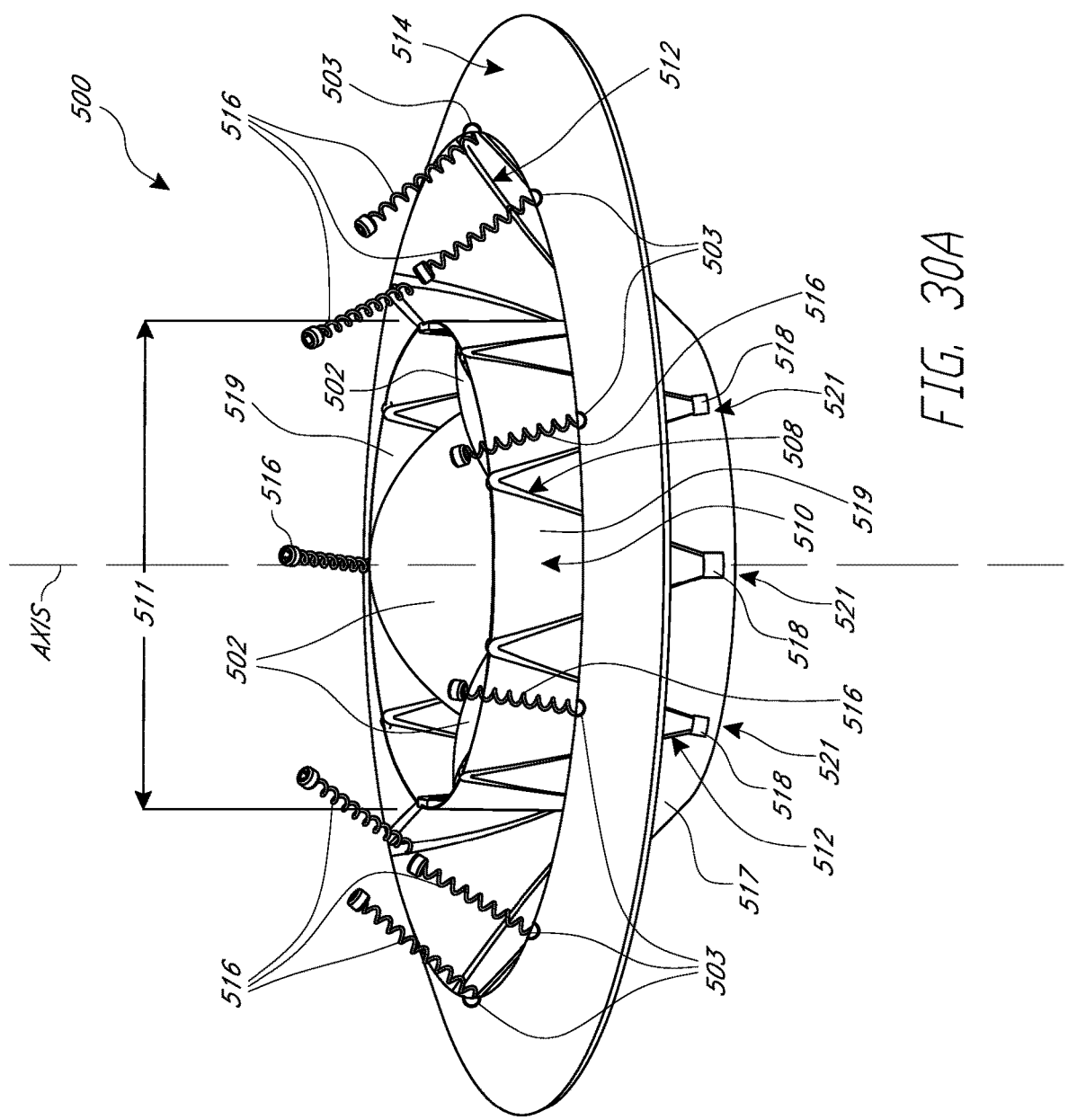
FIGS. 30A through 30C are perspective views of a replacement heart valve implant with anchors coupled to upper crowns and collars coupled with lower crowns and having a sealing atrial flange and shown, respectively, in an unconstrained state, an anchored state, and a cinched state.
Figure 30B:
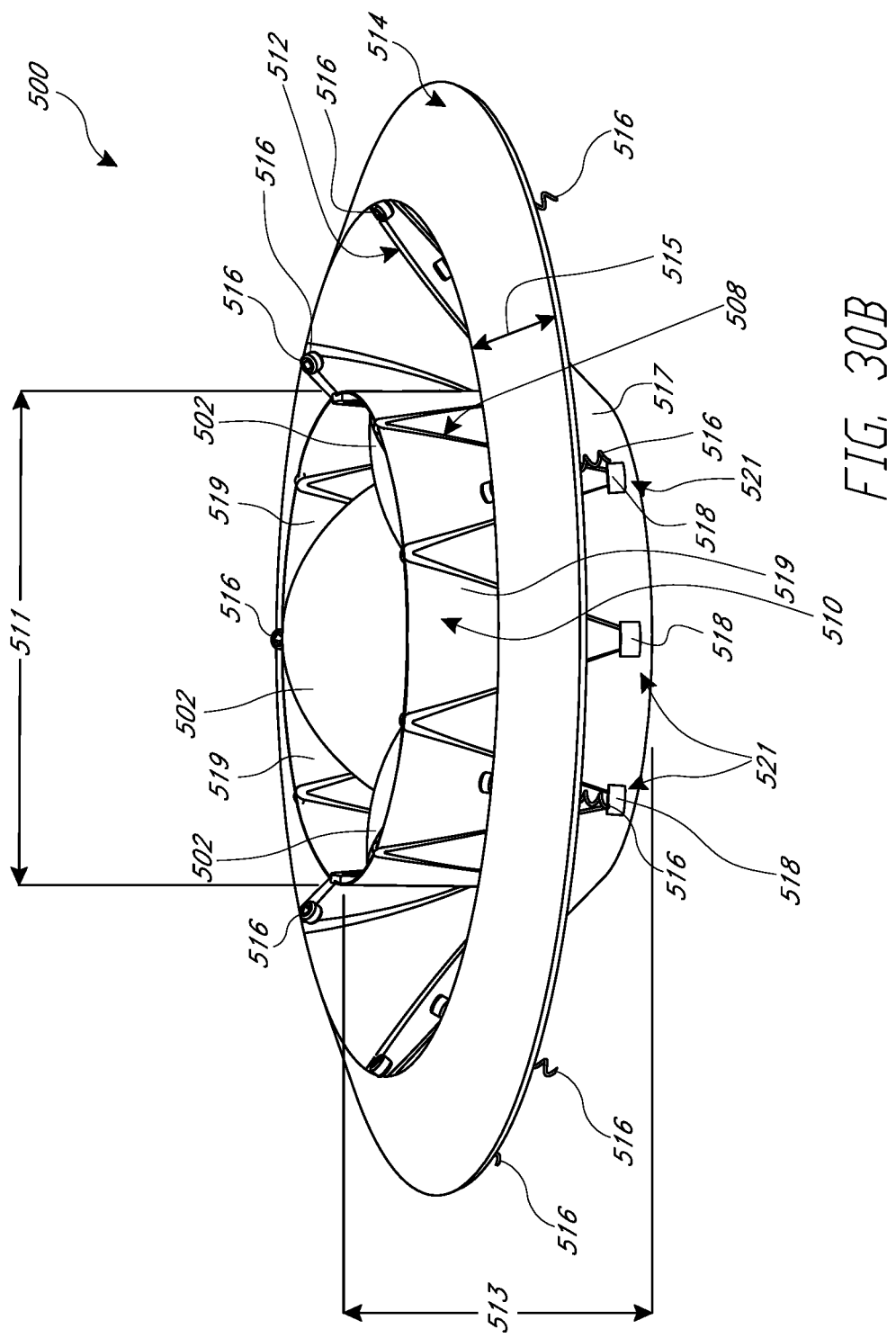
Figure 30C:
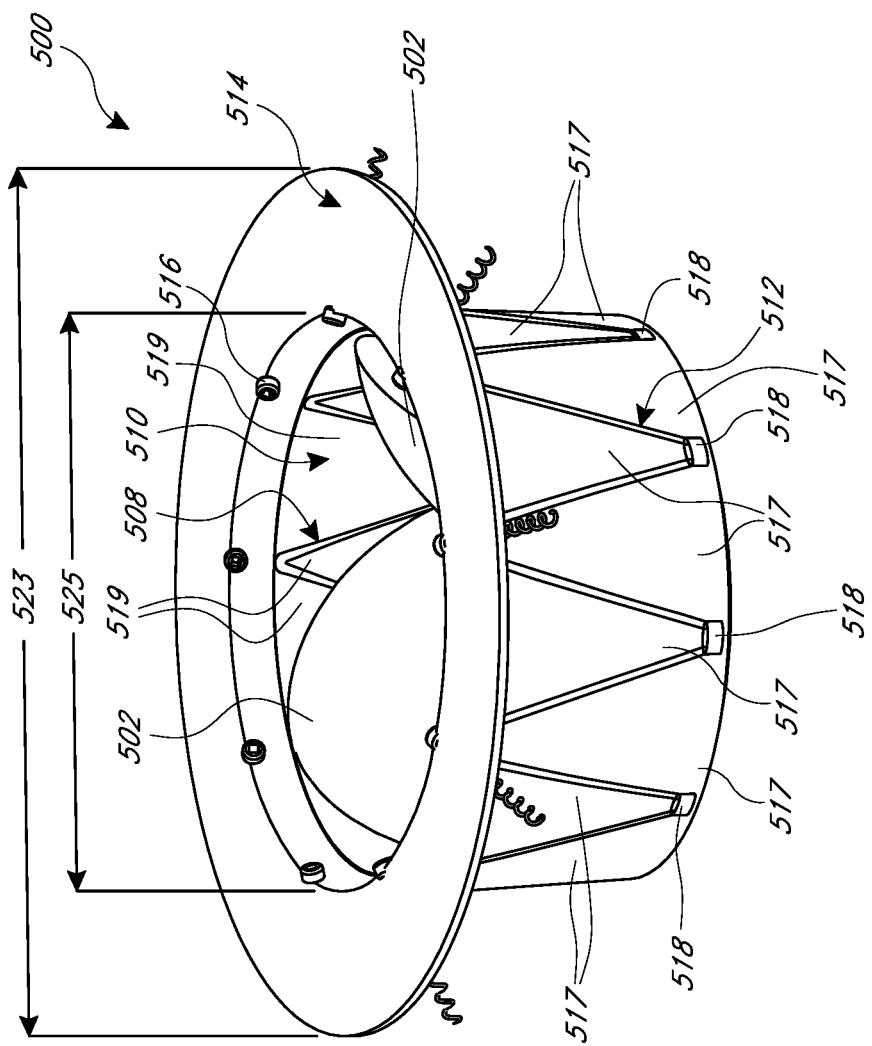

FIGS. 30A-30C are perspective views of an embodiment of an expandable replacement valve implant 500 shown in various states, i.e. configurations. FIG. 30A shows the replacement valve implant 500 in an unconstrained state. FIG. 30B shows the replacement valve implant 500 in a deployed and anchored state. FIG. 30C shows the replacement valve implant 500 in an anchored and cinched state. The implant 500 may have the same or similar features and/or functionalities as the various implants described herein, in particular the implant 1 shown in and described with respect to FIGS. 38A-59, and vice versa. Thus the implant 1 shown in and described with respect to FIGS. 38A-59 may also include a replacement valve such as with leaflets 502, etc.

The replacement valve implant 500 may be delivered with the various delivery systems and methods described herein. The replacement valve implant 500 may include an associated cinching structure. The replacement valve implant 500 is thus suited to treat multiple disease conditions. For example, the replacement valve implant 500 can treat mitral regurgitation developed as a consequence of cardiomyopathy and attendant dilation of the mitral valve annulus. Moreover, the replacement valve implant 500 and cinching structure can treat failed or defective heart valve leaflets by replacing the native valve apparatus. Additionally, the replacement valve implant 500 and cinching structure can treat both mitral regurgitation and those patients with concomitant defects in the valve leaflets themselves.

The replacement valve implant 500 includes one or more non-native valve leaflets 502. The leaflets 502 may be mechanical or tissue-based such as porcine or bovine. The leaflets 502 replace the function of the defective heart valves by providing normal or otherwise acceptable blood flow regulation. The leaflets 502 may be configured to mimic the natural configuration of native leaflets. As shown, there are three leaflets 502. In some embodiments, there may be one, two, three or more leaflets 502. The leaflets 502 are coupled with housing and/or other features of the replacement valve implant 500, as described herein. The replacement valve implant 500 includes an inner valve housing 510.

The valve housing 510 may be a support for various features of the implant 500, such as the leaflets 502, one or more frames, struts, etc. The valve housing 532 is configured to extend into the valve annulus and contain the leaflets 502 therein. The leaflets 502 may be mechanically attached to the inner valve housing 510 by a variety of suitable means, including sutures, fasteners, adhesives, crimping, other means, or combinations thereof. The valve housing 510 forms an inner portion of the replacement valve implant 500 that connects with an outer portion, as described herein. The valve housing 510 may include an inner frame 508 and/or an inner barrier 519, as described herein.

The inner frame 508 may be analogous to other frames described herein, such as the frame 10, and thus be a structural member, include a tubular shape, have sinusoidal struts, etc. The inner frame 508 may be a variety of suitable materials, such as metal, preferably nitinol. After deployment from a delivery catheter and expansion to the unconstrained shape, the inner frame 508 may or may not change shape, size, etc. The inner frame 508 may be coupled with an outer frame 512, as described herein. Lower apices of the inner frame 508 may be coupled with lower apices of an outer frame 512. The inner frame 508 may be a portion of the outer frame 512. For example, the inner frame 508 may be part of the same continuous structure as the frame 512 and form an inner portion thereof.

The inner frame 508 may be coupled to or otherwise carry the inner barrier 519 to form the valve housing 510. The inner barrier 519 is a membrane-like material extending around the circumference of the valvehousing 510. The inner barrier 519 is configured to extend into the valve annulus to contain the leaflets 502 within the annulus. The inner barrier 519 also acts to prevent leakage of blood flow around the replacement valve implant 500. The inner barrier 519 may comprise any of a variety of suitable materials, including ePTFE or a polyester material, such as Dacron. The inner barrier 519 may be coupled with the inner frame 508. The inner barrier 519 may be coupled with the inner frame 508 with a variety of suitable means, for example with sutures, mechanical attachments, embedding, other suitable features, or combinations thereof.

The inner barrier 519 may be carried by the radially inwardly or outwardly facing surfaces of the inner frame 508. As shown, separate segments of the inner barrier 519 may be coupled with the inner frame 508 in between struts of the inner frame 508. In some embodiments, the inner barrier 519 may be a single, continuous tubular membrane. For example, the inner barrier 519 may be provided entirely or mostly on the inside or internal diameter of the valve housing 510. In some embodiments, the inner barrier 519 may be provided entirely or mostly on the outside or external diameter of the valve housing 510. In some embodiments, there may be multiple barriers 519, such as an internal and an external inner barrier 519 each on opposite sides of the inner frame 508.

The illustrated replacement valve implant 500 includes an outer cinch frame 512. The outer frame 512 is coupled with one or more anchors 516 and one or more restraints such as collars 518. The outer frame 512, anchors 516 and collars 518 may be analogous to any of the other frames, anchors and collars described herein, for example the frame 10, anchors 20 and collars 18, respectively. In particular, the collar 18 may translate axially due to engagement by a rotating central shaft 646, and/or the anchors 20 may engage anchor housings 22A, as further described herein. The outer frame 512 may thus include a tubular shape, having a sidewall comprising sinusoidal or zigzag struts, with restraints, etc. The outer frame 512 may be coupled with the inner frame 508, for example at lower crowns 521 as shown. In some embodiments, the outer frame 512 may be coupled with the inner frame 508 in other manners, such as at upper crowns, etc. In some embodiments, the inner and outer frames 508, 512 may be part of the same monolithic material, for example different portions of a single, continuous wire or laser cut frame, etc. The outer frame 512 may compress for delivery within a delivery catheter, expand upon deployment from the catheter, and contract upon advancement of collars 518, as described herein. Contraction of the outer frame 512 may resize and/or re-shape the valve annulus. Activation of the restraints and/or manipulation of a control such as a pull wire advances the proximal end of the outer frame 512 radially inwardly toward the axis to reduce the inner diameter of the native valve annulus.

The anchors 516 may be located along a proximal end of the outer frame 512, as shown. In some embodiments, the anchors 516 may be in other locations along the circumference of the implant 500, for example located farther distally, located along the distal end of the implant 500, etc. The anchors 516 are inclined radially outward in the distal direction as deployed from the head of the anchors to the tissue-penetrating tips of the anchors. In some embodiments, the anchors 516 may have other orientations, for example substantially parallel to the axis, radially outward substantially transverse to the axis, inclined in the proximal or distal directions, or combinations thereof. The anchors 516 may engage either the inner frame 508 or the outer frame 512 of the implant 500, such as at a strut or apex of the outer frame 512. The anchors 516 act to secure the replacement valve implant 500 to tissue such that the replacement valve implant 500 extends through the native annulus and across the native valve. The anchors 516 may be helical as described herein and rotatably engage the tissue. The anchors 516 are shown retracted or pre-anchored in FIG. 30A. In FIG. 30B, the anchors 516 have been advanced into a tissue engagement orientation. In FIG. 30C, the outer frame 512 has been cinched such that the anchors 516 have now pulled the valve annulus inward to reduce the circumference of the annulus to conform to the implant 500 and reduce or eliminate the perivalvular space.

The collars 518 may be advanced along the outer frame 512 to adjust the circumference of the outer frame 512. The collars 518 may be advanced along upper or lower crowns of the outer frame 512. As shown, the collars 518 are coupled with the lower crowns 521. The collars 518 may be advanced along the lower crowns 521 similarly as described herein, for example, with respect to the implant 1 of FIGS. 1-4, etc.

The replacement valve implant 500 may include an outer barrier 517, which may be analogous to the inner barrier 519 of the valve housing 510. Thus, the outer barrier 517 of the frame 512 may be a material such as ePTFE or polyester, and may be selected to encourage or inhibit endothelial ingrowth. The outer barrier 517 may be elastic such that it can stretch and/or contract to reduce or prevent bunching or wrinkling of the material during and after delivery, deployment and cinching of the outer frame 512. The outer barrier 517 may be carried on the radially inwardly or outwardly surface of the outer frame 512. As shown, separate segments of the outer barrier 517 may be coupled with the frame 512 in between struts of the outer frame 512. In some embodiments, the outer barrier 517 may be a single, continuous membrane. For example, the outer barrier 517 may be provided on the inside or internal diameter of the outer frame 512. In some embodiments, the outer barrier 517 may be provided on the outside or external diameter of the outer frame 512. In some embodiments, there may be multiple barriers 517, such as an internal and external outer barrier 517. In some embodiments, there may not be any barrier 517.

The outer frame 512 and/or barrier 517 may form a generally frustoconical shape in the unconstrained state, as shown in FIG. 30A. Thus, the struts of the outer frame 512 and the barrier 517 are inclined outward in the proximal direction relative to the longitudinal axis of the replacement valve implant 500. The proximal edge of the barrier 517 is located radially farther outward relative to the distal edge of the barrier 517 in the unconstrained state. The outer frame 512 and/or outer barrier 517 may contact various portions of the native heart anatomy after deployment from the delivery catheter, such as the annulus wall. After the anchors 516 have engaged the tissue but before cinching the outer frame 512, the outer frame 512 and/or outer barrier 517 may still be in a generally frustoconical shape, as shown in FIG. 30B, leaving a perivalvular annular space but blocking perivalvular blood flow by the outer barrier 517 and/or inner barrier 519. After cinching the outer frame 512, the outer frame 512 and/or outer barrier 517 may form a generally cylindrical shape, as shown in FIG. 30C. In some embodiments, after cinching the outer frame 512, the outer frame 512 and/or outer barrier 517 may form other shapes, such as a generally frustoconical shape, other non-cylindrical shapes, etc.

The replacement valve implant 500 shown in FIGS. 30A-30B includes an annular atrial skirt or flange 514. The atrial flange 514 may be an extension of the barrier 517 in the radial or generally radial direction for at least about 2 mm, or about 5 mm, or more. The atrial flange 514 extends outward from a proximal edge of the outer frame 512. In some embodiments, the atrial flange 514 may instead extend outward from a distal edge of the outer frame 512, for example forming a "ventricular" flange situated inside the annulus and/or within the left ventricle (for a mitral valve implant). Such "ventricular" flange may be analogous to the atrial flange 514 as described herein. The atrial flange 514 and/or other flanges may further reduce and/or prevent of leakage of blood flow around the replacement valve implant 500, e.g. leakage in between the replacement valve implant 500 and the surrounding valve annulus. The atrial flange 514 may be a variety of suitable materials, such as ePTFE or a polyester material, for example Dacron. The atrial flange 514 may thus be a similar material as the outer barrier 517. In some embodiments, the atrial flange 514 may also include an extension of the outer frame 512 in the outward direction and providing support for the barrier material, such as the polyester material.

FIG. 30B shows the replacement valve implant 500 in its deployed and anchored state. As shown, the anchors 516 have been advanced through and engage the frame 508 and through the flange 514 and into tissue. Holes 503 are provided in or adjacent to the atrial flange 514 to allow the helically wound anchors 516 to pass therethrough and anchor into the annular tissue above the heart valve. The anchors 516 may also fixedly engage the flange 514. The anchors 516 may engage the atrial flange 514 such that a fixed connection is provided between the flange 514 and the respective anchor 516 before and/or after advancement of the anchors 516 therethrough. The flange 514 has a generally annular shape around the circumference of the implant 500. The flange 514 may be generally circular, or other rounded or non-rounded shapes. The flange 514 maybe symmetric or asymmetric with respect to the axis or with a plane that includes the axis The replacement valve implant 500 may have a variety of suitable dimensions. In the deployed and anchored state, and/or the deployed and unanchored state, and/or in the anchored and uncinched state, and/or in the anchored and cinched state, the valve housing 510 may have a height measured along the axis 513 in the range of about twenty millimeters to about thirty millimeters, although such height can vary. In some embodiments, in these various states the valve housing 510 may have a height in the range of about ten millimeters to about fifty millimeters. Referring to FIGS. 30A-30B, the inner diameter 511 of the valve housing 510 may be within the range of about twenty-five millimeters to about thirty millimeters, although such diameter can be varied. In some embodiments, the inner diameter 511 of the valve housing 510 may be within the range of about fifteen millimeters to about sixty millimeters. Referring to FIG. 30B, the atrial flange 514 may have a radial width 515 between about five millimeters and about thirty millimeters. In some embodiments, the atrial flange 514 may have a width 515 between about ten millimeters and about twenty millimeters wide. Referring to FIG. 30C, depending on the disease state(s), the cinch frame 512 can have an outer diameter 523 from about forty millimeters to about eighty millimeters. Larger diameters may be implemented, for example, if the disease state is or includes a dilated heart valve annulus as incidence of the patient's cardiomyopathy. The inner diameter 525 of the cinch frame 512, which may be measured in some embodiments from anchor 516 head to opposite anchor 516 head, may range from about thirty millimeters to about sixty millimeters, or in some embodiments from about fifteen millimeters to about one hundred millimeters, in the cinched orientation.

After the replacement valve implant 500 is anchored in place, it is cinched as shown in FIG. 30C. Cinching may be accomplished by a cinching mechanism on the deployment catheter, followed by advancing the collars 518 to achieve retention. Alternatively, cinching may be accomplished by manipulation and movement of collars 518. The various cinching techniques described herein may be employed. The replacement valve implant 500 may encourage tissue ingrowth after implantation. For example, the inner our outer frame 508, 512, the inner barrier 519, the outer barrier 517, other features of the implant 500, or combinations thereof, may be configured to facilitate tissue ingrowth and further securement of the implant 500 within the heart.

Figure 31:
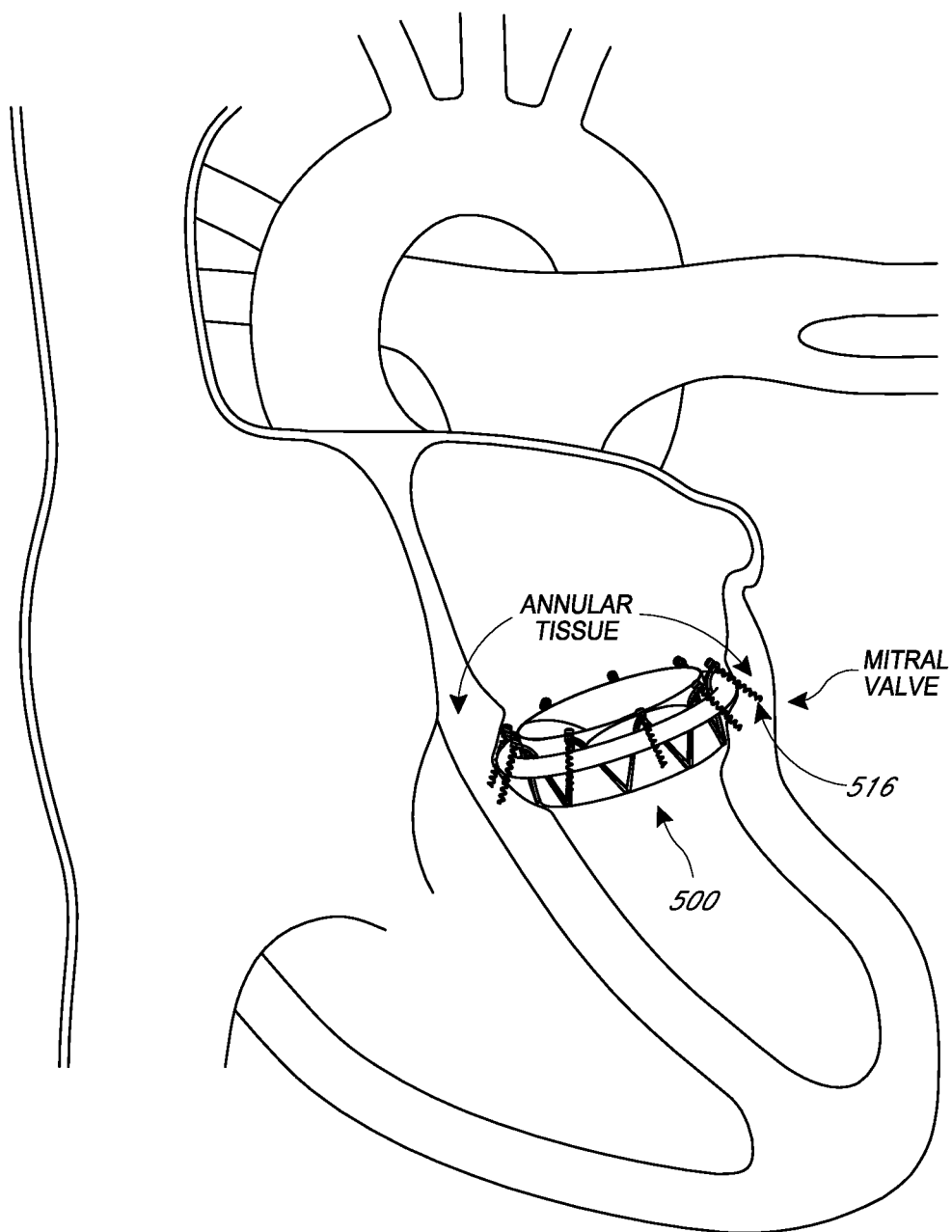
FIG. 31 is a cross-section view of a heart showing the replacement heart valve implant of FIGS. 30A through 30C deployed across a native mitral valve of the heart.

FIG. 31 illustrates the replacement valve implant 500 positioned, anchored, cinched and implanted in the annular tissue above and proximate the target heart valve. For illustration purposes, the replacement valve implant 500 has been deployed across the native mitral valve, with the atrial flange 514 blocking or at least substantially blocking paravalvular leakage around the replacement valve implant 500. The replacement valve implant 500 is in sealing engagement with the atrial wall surrounding the native valve, which in some embodiments may be due in part to atrial blood pressure.

Figure 32A:
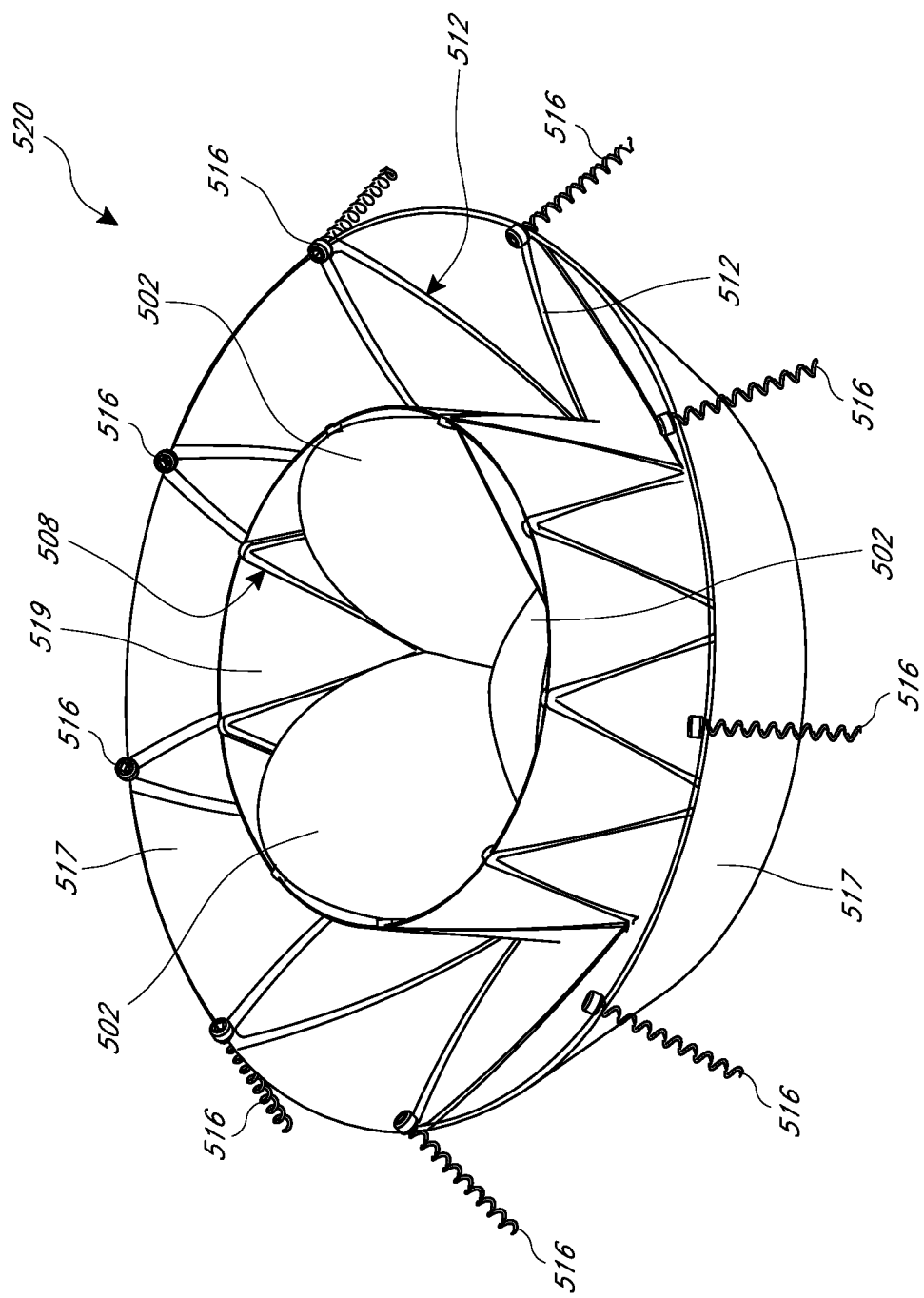
FIGS. 32A and 32B are perspective views of an embodiment of a replacement heart valve implant with anchors coupled to upper crowns and shown, respectively, in an anchored state and a cinched state.
Figure 32B:
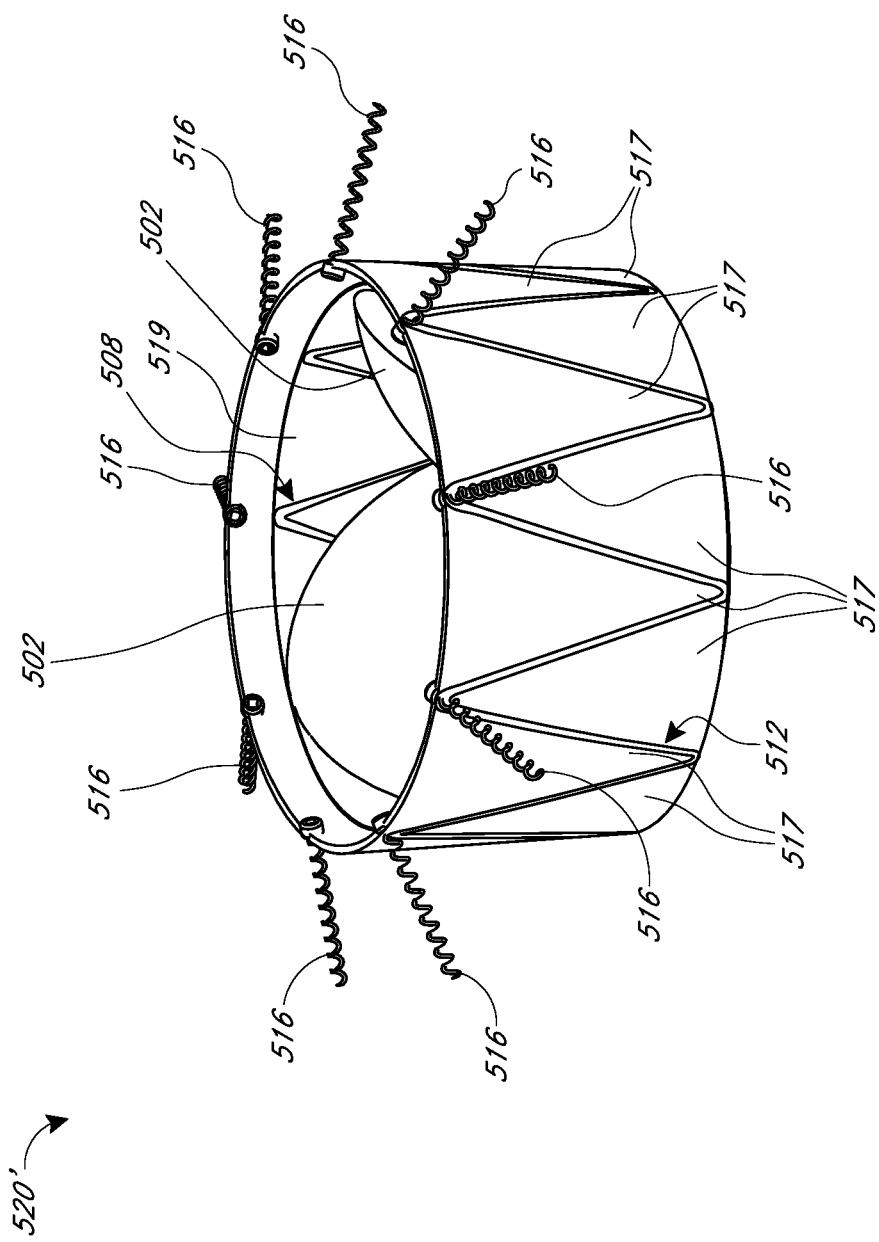

While the atrial flange 514 provides additional sealing in the atrium, in some embodiments such additional sealing may not be included. FIGS. 32A and 32B are perspective views of embodiments of heart valve replacements 520 and 520' without the additional sealing or atrial flange 514 and shown, respectively, in an unconstrained state and in a cinched state. Further, the heart valve replacement 520 includes the outer barrier 517 located on the outside of the outer frame 512, while the heart valve replacement 520' includes the outer barrier 517 located on the inside of the outer frame 512. The heart valve replacements 520 and 520' may otherwise be analogous to the heart valve replacement 500. Like reference numerals with respect to FIGS. 30A through 30C thus represent like elements in FIGS. 32A and 32B. After being anchored in position as shown in FIG. 32A, the collars are actuated, in a manner similar to that of FIG. 30C, to cinch the replacement valve 520 as shown in FIG. 32B. While nine anchors 516 have been shown with respect to the replacement valve embodiments of FIGS. 30 through 32, it is understood that the number of such anchors 516 can be varied. In some embodiments, such variance of the number of anchors 516 can range from three to eighteen. In some embodiments, the number of anchors 516 can vary in multiples of three.

Figure 33A:
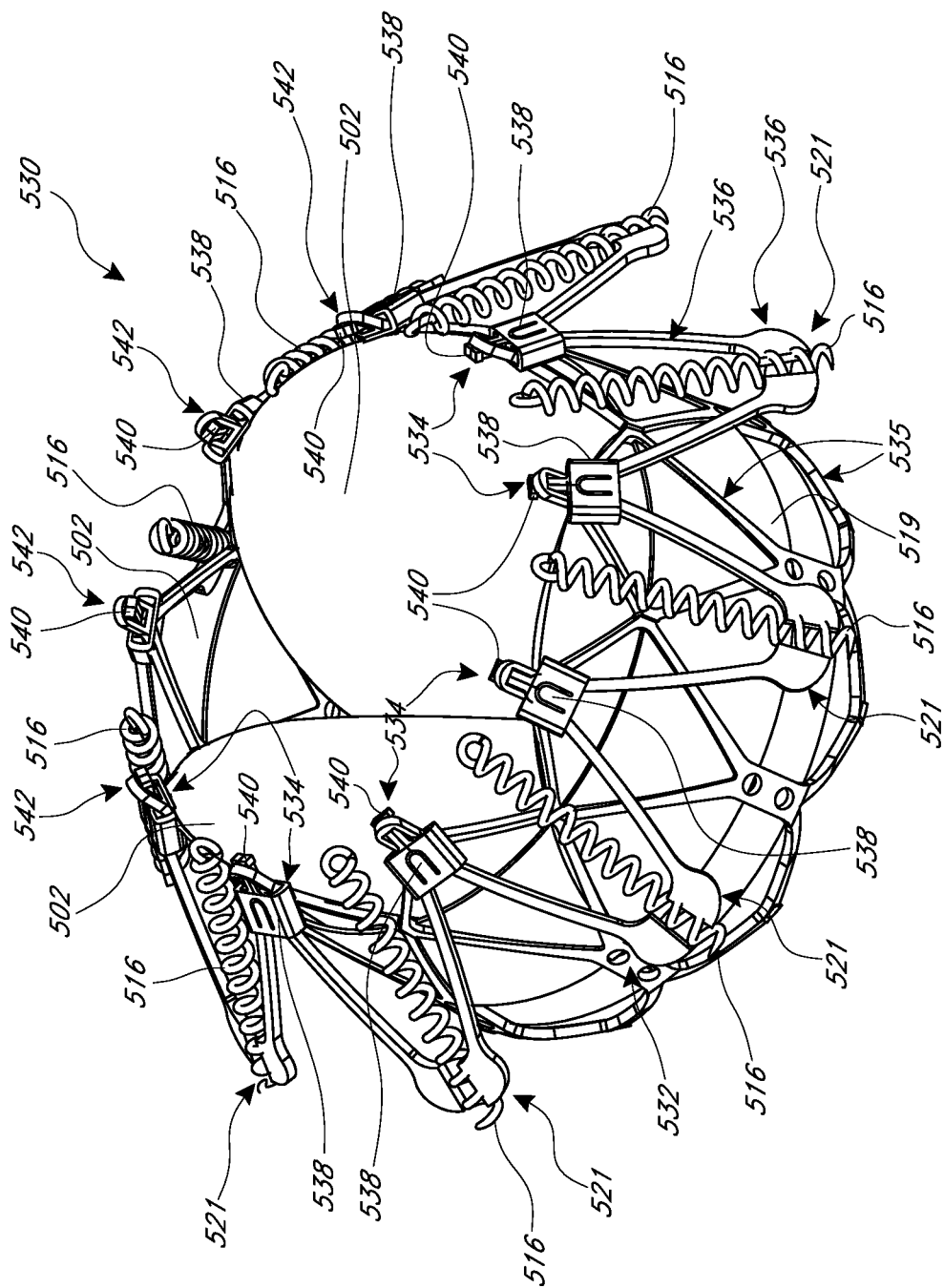
FIGS. 33A and 33B are perspective and side views of an embodiment of a replacement heart valve implant having a cinch frame and a housing and shown, respectively, in a deployed, unconstrained state and in an anchored, cinched and locked state.
Figure 33B:
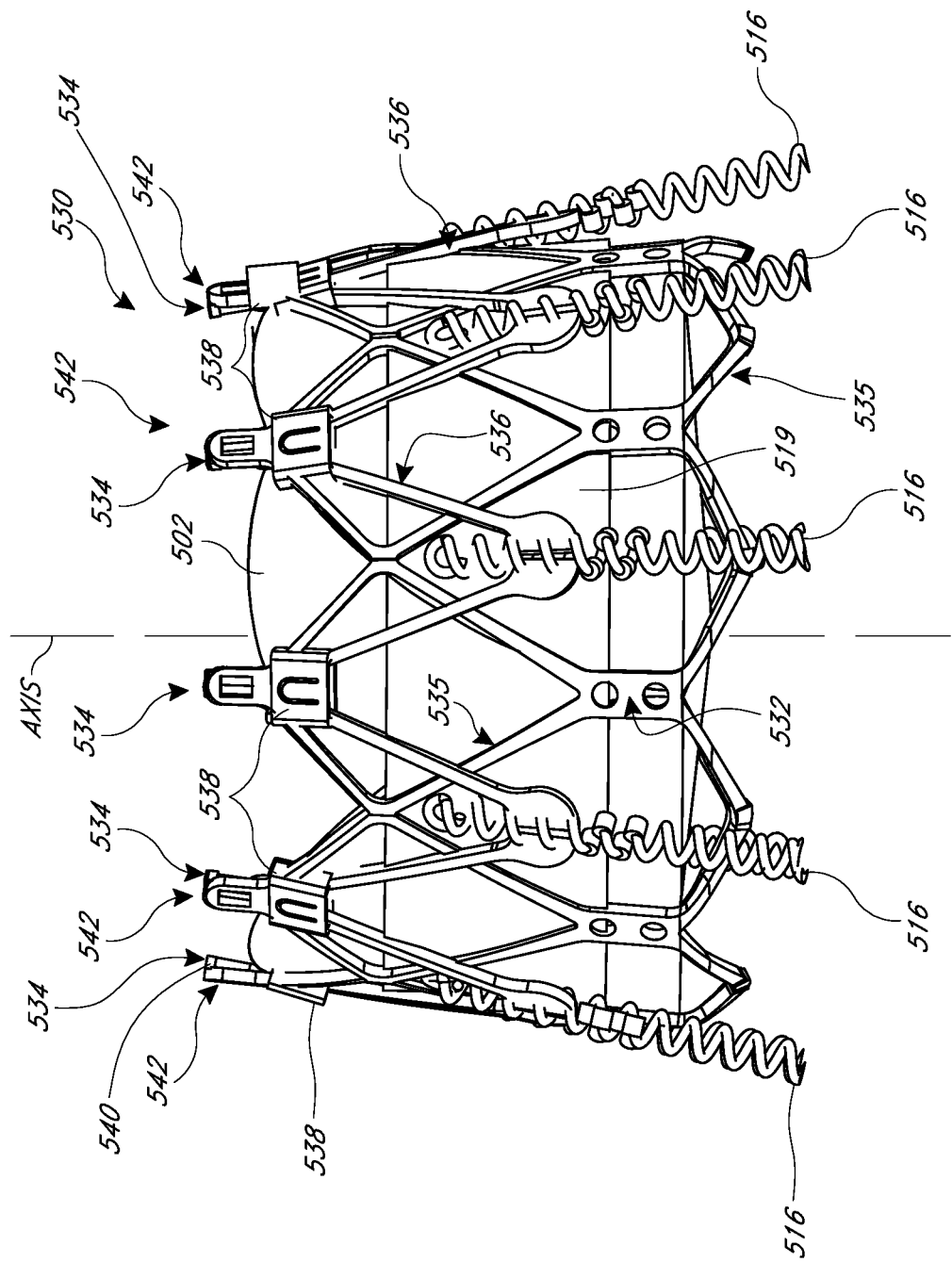

Another embodiment of a replacement valve implant 530 is depicted in FIGS. 33A and 33B. FIG. 33A shows the replacement valve implant 530 in an unconstrained and unanchored state and FIG. 33B shows the replacement valve implant 530 in an anchored, cinched and locked state. The replacement valve implant 530 may include features analogous to features described with respect to other implants herein, for example the implant 1, 500, 520, 520', etc., and vice versa. In particular, the replacement valve implant 530 may include features analogous to features described with respect to the implant 1 shown in and described with respect to FIGS. 38A-59, and vice versa.

The replacement valve implant 530 includes an inner valve housing 532 and an outer frame 536. The valve housing 532 may be analogous to the valve housing 510. The valve housing 532 may include one or more leaflets 502, which may be analogous to the leaflets 502 as described with respect to the replacement valve implant 500. The valve housing 532 may include an inner frame 535 as shown, which may be formed of nitinol. The inner frame 535 may thus have proximal, generally diamond-shaped segments that are adjacent distal, irregular hexagonal-shaped segments extending circumferentially in a generally tubular shape about an axis, as indicated in FIG. 33B. The valve housing 532 has a series of upper crowns 542 with openings therethrough. The openings may be circular or other shapes. The openings in the upper crowns 542 may engage with one or more features of an outer cinch frame 536, such as extensions 540 that extend from upper crowns of the outer frame 536.

The outer frame 536 may be analogous to other frames or outer frames described herein, for example, the frames 10, 512, etc. The outer frame 536 is coupled with one or more anchors 516 and one or more restraints such as collars 518. The outer frame 536 may be coupled with the valve housing 532, for example the inner frame 535, at the upper (proximal) crowns 542, as described. In some embodiments, the outer frame 536 may be coupled with the inner frame 535 in other manners, such as at lower crowns, etc. In some embodiments, the inner and outer frames 535, 536 may be part of the same monolithic material, for example different portions of a single, continuous frame, etc.

The outer frame 536 may compress for delivery within a delivery catheter, expand upon deployment from the catheter, and contract upon advancement of collars 518, as described herein. The outer frame 536 in an unconstrained state, as shown in FIG. 33A, inclines radially outward in a distal direction from a proximal end of the valve housing 532. Contraction of the outer frame 536 to a cinched state, as shown in FIG. 33B, may resize and/or re-shape the native valve annulus. The outer frame 536 may advance radially inwardly toward the axis to reduce the inner diameter of the native valve annulus into conformance with the inner frame 535. The outer frame 536 may include collars 538 at the upper crowns 534. The collars 538 may be advanced distally to cinch the implant 530 to cause the outer frame 536 to advance radially inward. The collars 538 may interact with the outer frame 536 to cinch the outer frame 536 as described herein with respect to other collars and frames, such as the collars 18 and the frame 10, etc.

The extensions 540 include perpendicularly disposed tabs generally forming T-Bar extensions on the upper crowns 534 of the outer frame 536. The extensions 540 engage with the openings in the upper crowns 542 of the valve housing 532 to pivotally secure the outer frame 536 to the valve housing 532. The extensions 540 may be inserted into the openings during assembly of the replacement valve implant 530. The anchors 516 are moveably engaged with lower crowns 521 that are located in between upper crowns 542 of the valve housing 532. The anchors 516 may engage with the lower crowns as described herein with respect to other anchors and crowns, such as the anchors 20 and lower crowns 16, etc. After the anchors 516 have been rotationally advanced into the annular heart valve tissue, cinching of the outer frame 536 as shown in FIG. 33B will draw the annular tissue or portions thereof toward the valve housing 532. Further, in the cinched state shown in FIG. 33B, portions of the native annulus tissue may be drawn radially inward and/or upward (proximally) in between the outer frame 536 and the valve housing 532. This action will reduce the potential for paravalvular leaking and migration of the replacement valve implant 530. In some embodiments, the valve housing 532 may be tapered, for example having a smaller diameter on the atrial side of the valve orifice and a larger diameter on the ventricular side to facilitate blood flow through and across the replacement heart valve 530.

Relatively large diameter catheter shafts are described herein that may be used to deliver the re-sizing implants, such as the implant 1 and others, or valve replacements, such as the valve 500 and others, as described herein. These large diameter catheter shafts may include features that mitigate or eliminate the tendency to kink, wrinkle or tear when attempting a sharp bend radius. FIGS. 34A through 37 show various embodiments of sections of steerable catheters that may be used with the various implants described herein. The features of the steerable catheters improve the catheter's ability to maneuver tight bends to a position above and proximate and/or into the mitral valve annulus or tricuspid valve annulus.

Figure 34B:
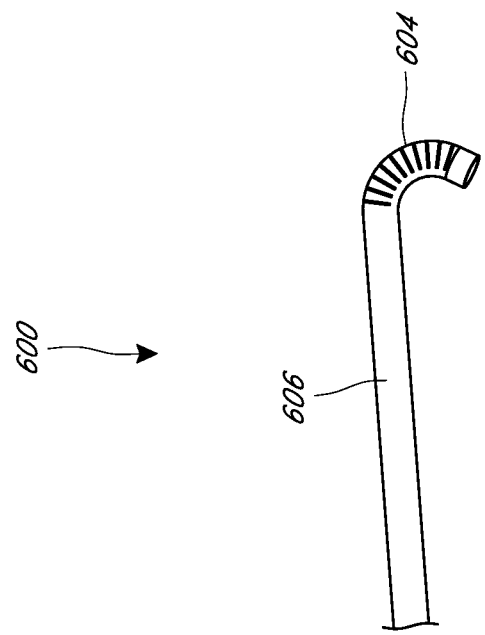
FIGS. 34A and 34B are side views of an embodiment of a distal section of a steerable catheter shown in straight and flexed states, respectively, that may be used to deliver the various implants described herein.
Figure 34A:
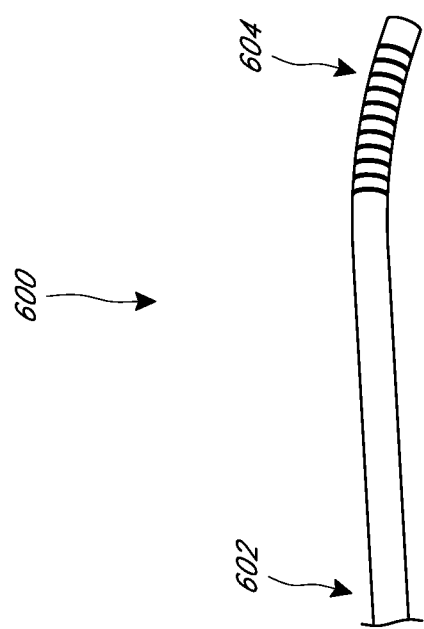

FIGS. 34A and 34B are side views of an embodiment of a distal section 600 of a steerable catheter 602 shown in straight and flexed states, respectively, that may be used to deliver the various implants described herein. In particular, the steerable catheter 602 may be used to deliver the implant 1 shown in and described with respect to FIGS. 38A-59. The steerable catheter 602 may be used in the various delivery systems and methods described herein. As shown in FIGS. 34A-34B, the steerable catheter 602 may have a distal end 604 and intermediate section 606. The distal end 604 may be a deflectable section, as described herein. The distal end 604 may include a length of the catheter 602 extending from the distal tip. For example, the deflectable section of the distal end 604 may include a length of five or ten or fifteen centimeters, or more or less, of the catheter 602 as measured from the distal tip in a proximal direction. The intermediate section 606 may take the form of a shaft section reinforced with a braid or slotted tubing. The catheter 602 may include a proximal end opposite the distal end 604. Only a portion of the catheter 602 is shown for clarity. The proximal end of the catheter 602 may be coupled with a proximal manifold having a deflection control. The catheter 602 and/or features thereof may be implemented with the various catheters and delivery systems described herein, for example those shown in and/or described with respect to FIGS. 22A-25E, or others.

Figure 35A:
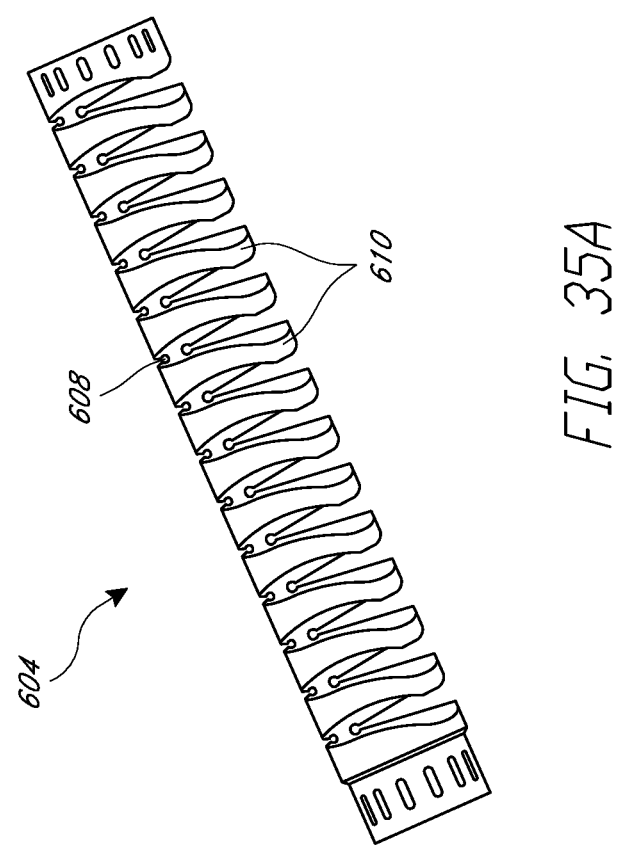
FIGS. 35A and 35B are side views of an embodiment of a distal section of a steerable catheter having a spine that may be used to deliver the various implants described herein.
Figure 35B:
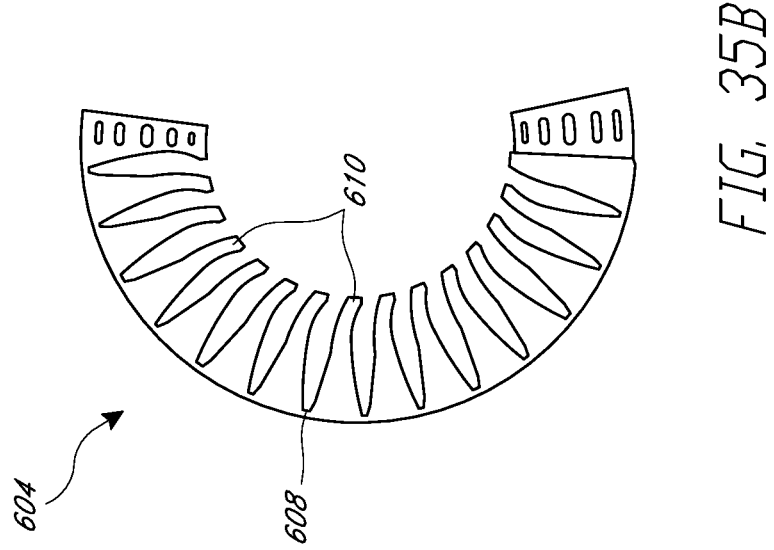

FIGS. 35A and 35B depict an embodiment of the distal section 604 that may be used with the steerable catheter 602, shown in straight and flexed states, respectively. The distal section 604 has a single spine 608 running along its outer curve, and a series of support ribs 610 formed or cut into the inner curve. The distal section 604 may be formed of a flexible metal tube, such as nitinol. The distal section 604 may incorporate pull wires for control of the delivery system. Alternatively, the pull wire may be looped around the distal section's distal tip and back toward the proximal part of the catheter 602. The support ribs 610, with voids therebetween, allow the distal section 604 to achieve a tight bend radius. This flexed state of the distal section 604 is realized with minimal protrusion of the support ribs 610 into the inner diameter or outer diameter of the distal section 604. Moreover, the spine 608 provides a smooth surface on the outer curve of the distal section 604 minimizing friction or interference with heart tissue during delivery and positioning of the catheter and implant.

Figure 36B:
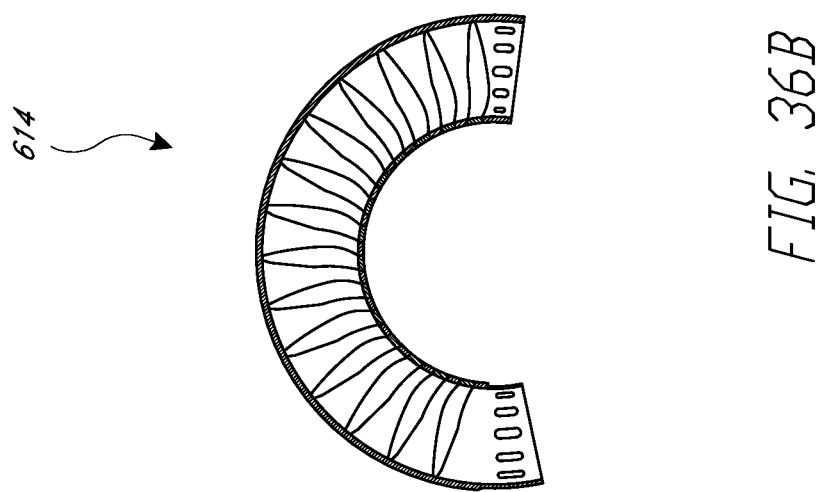
FIGS. 36A and 36B are side views of another embodiment of a distal section of a steerable catheter having a thin film that may be to deliver the various implants described herein.
Figure 36A:
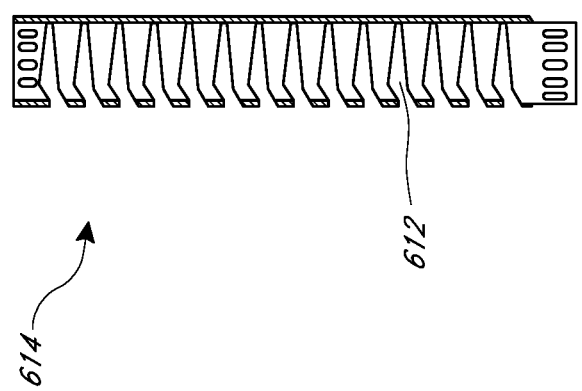

FIGS. 36A and 36B illustrate another embodiment of a distal section 614 that may be used with the steerable catheter 602. Here, the distal section 614 may be a flexible metal tube that is wrapped or encased in a thin film 612 or polymeric material such as Teflon, pTfe, nylon or other thin material. This thin film 612 encapsulation does not restrict the flexibility of the distal section 614 but does provide for smoother delivery and transition into and out of a guide catheter. The thin film 612 may be stretchable or designed to fold in on itself, somewhat similar to an accordion, when flexed as shown in FIG. 36B.

Figure 37:
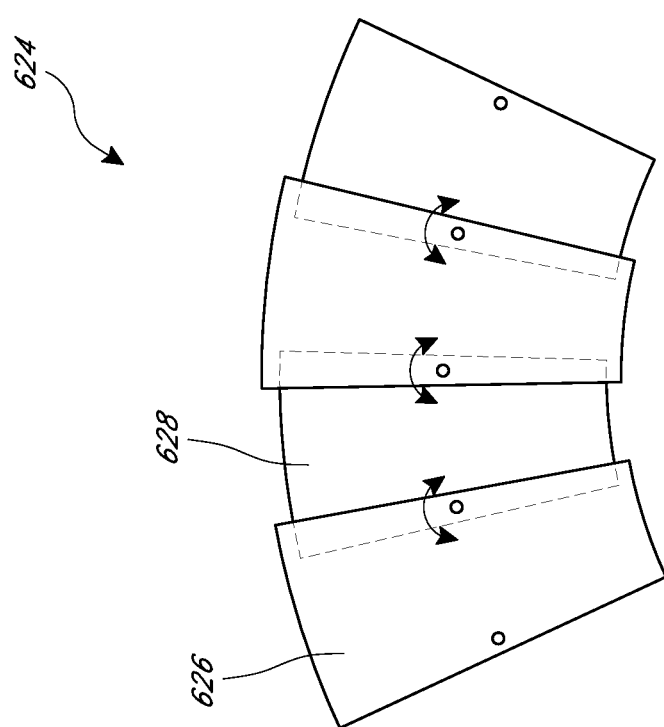
FIG. 37 is a side view of another embodiment of a distal section of a steerable catheter having nesting elements that may be used to deliver the various implants described herein.

FIG. 37 shows another embodiment of a distal section 624 that may be used with the steerable catheter 602. Here, distal section 624 comprises a series of larger elements 626 and smaller elements 628. The smaller elements 628 nest within the larger elements 626. All elements may slide over one another. When the distal section 624 is in a straight state, the metal elements are most overlapped. As the distal section 624 is actuated towards the flexed state, as shown for example in FIG. 37, there may be progressively less overlap of the elements particularly on the outer curve of the distal section 624.

The embodiments of the distal and intermediate sections of the catheter 602 are intended for use in the delivery and implant of both the ring-like embodiments and the replacement valve embodiments described herein. In treating the mitral valve, for example, once the catheter is passed through the septum separating the right and left atria, it is guided slightly upwardly towards the upper reaches of the left atrial chamber. It is then bent significantly in a direction downward towards the mitral annulus, aligning the distal end and the implant with the mitral annulus. The devices, systems and methods described herein allow such bending to occur without kinking or wrinkling which would otherwise impede delivery of the implant.

FIGS. 38A-59 show embodiments of implants having features for advancing, for example driving, translating or otherwise moving, a retention slider or collar 18 over a corresponding pair of adjacent struts 12. The features described with respect to FIGS. 38A-59 may be used with other implants, delivery systems, etc. as described herein, and vice versa. The various embodiments of the implant 1 described with respect to FIGS. 38A-59 may have the same or similar features and/or functionalities as other embodiments of the implant 1 or other implants described herein, such as the implants 1A, 1B, 1C, 100, 101, 102, 103, 104, 105, 500, 520, 520', 530, and vice versa. The implant 1 of FIGS. 38A-59 may operatively couple with, or be configured to operatively couple with, a valve or valve leaflets for complete valve replacement. Such valve replacement may also include annulus reshaping.

Figure 38A:
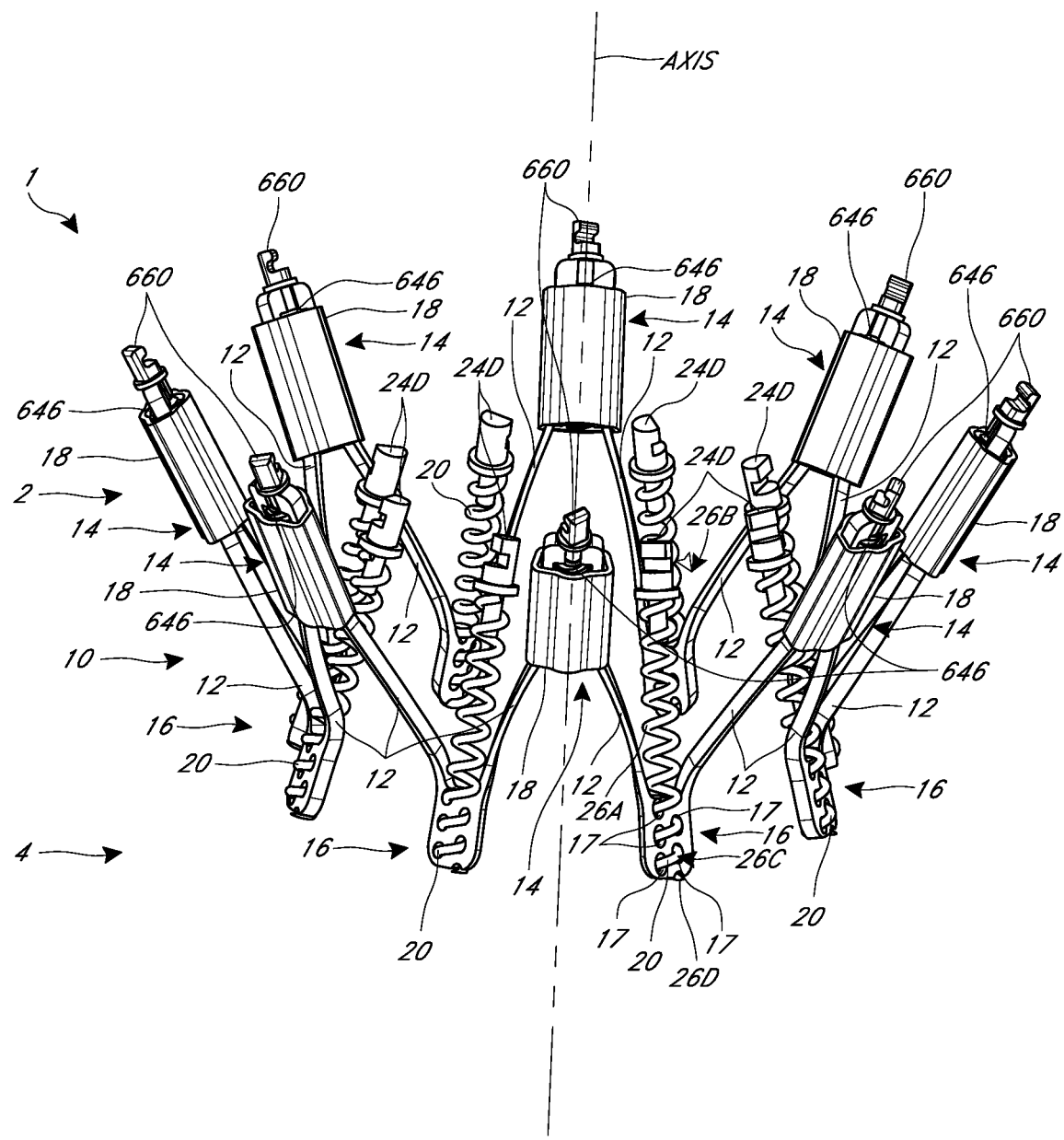
FIG. 38A is a perspective view of another embodiment of an implant having a rotatable threaded shaft nested within the frame and located internally to an axially translatable collar at the proximal apexes, with helical anchors engaged with openings in the distal apexes.

FIG. 38A is a perspective view of an embodiment of the implant 1 having a proximal end 2 and a distal end 4 with a central lumen extending therethrough along the axis as indicated. The implant 1 may be configured for catheter-based delivery. In treating the mitral valve, for example, a delivery catheter is inserted via a puncture in the femoral vein, after which it traverses the inferior vena cava, into the right atrium and passes through the septum separating the right and left atria. It is then directed distally towards the mitral annulus, aligning the distal end of the catheter and the implant 1 with the mitral annulus.

The implant 1 is shown having the frame 10 with rotatable shafts 646 and axially translatable collars 18 at the proximal apexes 14. The proximal end of the rotatable shafts 646 each include a coupling 660 for engagement and rotation by a driver or adjustment catheter to rotate the shaft 646. As further describe herein, rotation of the shaft 646 causes the collar 18 to advance along the struts 12 to change, e.g. increase or decrease, the angle between the struts 12 to radially contract or expand the implant 1. Each distal apex 16 includes the helical anchor 20 engaged with openings 17 of the corresponding distal apex 16. Each anchor 20 includes a proximal portion 26B and a distal portion 26C. On the proximal end of the proximal portion 26B is a coupling 24D. The coupling 24D may be engaged and rotated by a driver or adjustment catheter to rotate the anchor 20 through the openings 17 and into tissue. Each coupling 660 and 24D may be engaged and rotated by its own driver or adjustment catheter. Thus, there may be such a driver for each coupling 660, 24D. The collars 18 and anchors 20 are shown in a relative proximal position and may be adjusted proximally or distally therefrom to effect various changes in the frame 10. The implant 1 of FIG. 38A and its various features are described in further detail herein. The implant 1 of FIG. 38A may have any of the same or similar features and/or functionalities as any other implant described herein, including but not limited to the implant 1 of FIG. 47, and vice versa.

Figure 38B:
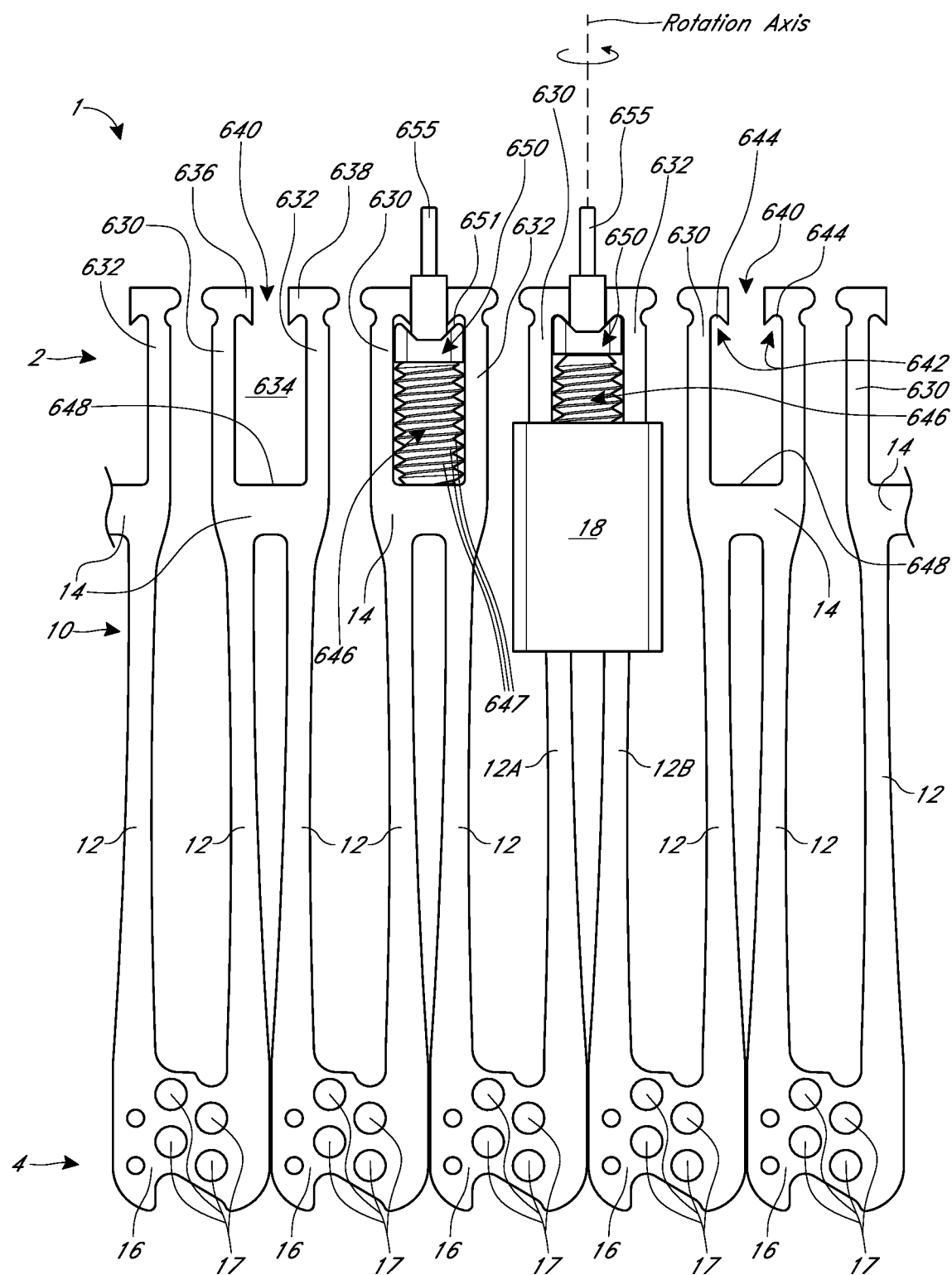
FIG. 38B is a flattened side view of a portion of the implant of FIG. 38A having certain features removed for purposes of illustration and the rotatable shafts shown with elongated proximal members instead of proximal couplings.

FIG. 38B depicts a partial flattened side view of the embodiment of the implant 1 shown in FIG. 38A. As shown in FIG. 38B, the implant 1 has an embodiment of the frame 10 with an axially translatable collar 18 and a rotatable threaded shaft 646. For clarity, only one collar 18 and two shafts 646 are shown. There may be more collars 18 and shafts 464, for example one collar 18 and one shaft 646 located at at least two or three or four or at each proximal apex of the frame 10. The threaded shaft 646 is located, for example nested, secured, retained, etc., within a portion of the frame 10 and located internally to the collar 18. In some embodiments for driving the collar 18 over an apex formed by a pair of adjacent struts 12, the threaded shaft 646 may be rotated internally to the collar 18. Rotational motion of the threaded shaft 646 is transmitted from external engagement features, such as threads, of the threaded shaft 646 to corresponding internal features, such as internal threads or teeth, of the collar 18, to result in axial movement of the collar 18. As the collar 18 moves distally, it causes adjacent struts 12 to move closer together, decreasing the angle C (as shown for example in FIG. 44C) between the struts 12, and causing the implant 1, for example the frame 10, to reduce in width, e.g. diameter. The collar 18 may remain or substantially remain rotationally stationary relative to the struts 12. Thus, for example, the threaded shaft 646 may be rotated while remaining axially stationary and the collar 18 may translate axially while remaining rotationally stationary or substantially rotationally stationery. By "substantially rotationally stationery" it is meant that the collar 18 may rotate some amount after which further rotational movement is prevented, for example due to play between the collar 18 and the struts, as further described.

These are general principles of the retention features for the implant 1 that are described in further detail herein. Various modifications may be implemented. For example, in some embodiments, the threaded shaft 646 may axially translate. In some embodiments, the collar 18 may rotate. In some embodiments, the collar 18 may be rotated and move axially, while the threaded shaft 646 remains rotationally and axially stationary. The mechanical communication between outer threads of the threaded shaft 646 and the inner features (such as threads) of the collar 18 may be direct communication, such as contact between the respective threads and features. In some embodiments, the mechanical communication may be indirect, for example with intervening structures such as bushings and the like, coatings, etc. in between the respective engagement features. These and other modifications to the implant 1 that are still within the scope of the disclosure will be apparent in light of the further details and description herein.

As further shown in FIG. 38B, there is illustrated a partial view of the frame 10 extending between a proximal end 2 and a distal end 4. The frame 10 may form a tubular shape, as described herein, for example with respect to FIG. 38A or FIG. 1. A plurality of the struts 12 extend between proximal apexes 14 and distal apexes 16, as has been discussed. The distal apex 16 may be provided with an anchor mount such as a plurality of apertures 17 for receiving helical anchors (such as the anchors 20, shown for example in FIGS. 44A-44C). In some embodiments, the distal apex 16 may include "reach" anchor features such as a housing, for example as described with respect to FIGS. 47A-59. One adjacent pair of struts 12A and 12B carry the collar 18. The collar 18 may be included on more than one or all of the proximal apexes 14 formed by corresponding pairs of adjacent struts 12. For clarity, some features are not shown on some of the proximal apexes 14.

In some embodiments, the proximal apex 14 may include features to carry the shaft 646 and/or collar 18. As shown, at least one proximal apex 14 is provided with at least a first support 630. The first support 630 may extend in a proximal direction from the corresponding strut 12. In the illustrated embodiment, a second support 632 is additionally provided, spaced apart from the first support 630. The first and second supports 630, 632 are structural members extending proximally from the apex 14. The first and second supports 630, 632 may have square or rectangular cross-sections, or other shapes. The first and second supports 630, 632 may be integral with the apex 14 or may be separate parts attached thereto. The first and second supports 630, 632 may have the same or similar radial thickness as the apex 14 and/or struts 12, and all may be laser cut from a single metal (e.g., stainless steel) tube. The first and second supports 630, 632 may at least partially form a window 634 therebetween. The window 634 is a space or opening between the supports 630, 632. The window 634 may have a generally rectangular shape as shown, or it may be square, rounded, or other shapes. The window 634 may be partially formed by other features of the frame 10, as further described.

The first support 630 is provided with a first medial flange 636 and the second support 632 is provided with a second medial flange 638. The first and second medial flanges 636, 638 may be integral with the first and second supports 630, 632, respectively, or may be separate parts attached thereto. The first and second medial flanges 636, 638 extend inwardly. The flanges 636, 638 extend towards a rotation axis of the threaded shaft 646. The flanges 636, 638 extend generally circumferentially.

The flanges 636, 638 are separated from each other by a central aperture 640. The aperture 640 is an opening or space located between the flanges 636, 638. In some embodiments, there may not be any flanges 636, 638, or the flanges 636, 638 may not extend inwardly toward the rotation axis, and the apertures 640 may thus be a space between the first and second supports 630, 632. The first and second medial flanges 636, 638 may partially form a proximal portion of a frame defining the window 634. The window 634 may be open to the aperture 640. A continuous space may be formed that extends from the window 634 to the aperture 640 and that opens to a proximal side of the frame 10.

In some embodiments, the flanges 636, 638 may be connected and form a continuous bridge along the proximal end of the window 634 that has the aperture 640 therethrough. For example, the proximal ends of the first and second supports 630, 632 may be connected by a circumferential cross member that includes the aperture 640 as a hole extending axially therethrough. In such embodiments, the shaft 646 may be radially inserted into the window 634 and a proximal post or coupling may be axially and distally inserted through the aperture 640 to attach to the shaft 646.

As shown, the first medial flange 636 provides a distally facing bearing surface 642, which may have an undercut 644, as will be discussed. The second medial flange 638 may also be provided with the bearing surface 642. For clarity, only some of the features at or around each proximal apex 14 shown in FIG. 38B are labelled, for example the medial flanges 636, 638, central aperture 640, bearing surface 642, undercut 644, etc. It is understood that the implant 1 may include these and other features in other locations, for example other apexes 14, even if not explicitly labelled in the figure. The bearing surface 642 may be a structure against which features of the shaft 646 may contact. The bearing surface 642 may have a topography that complements that of the shaft 646 or features thereof. The bearing surface 642 may be curved or rounded as shown. The bearing surface may be circumferentially rounded to accommodate, retain and guide an adjacent and complementary rotating surface of the shaft 646. The bearing surface 642 may be smooth or generally smooth. In some embodiments, the bearing surface 642 may include locking features, such as rough surface portions, proximally extending or angled tabs, or other features that prevent unwanted rotation by the shaft 646 and corresponding unwanted distal movement of the collar 18, for example after implantation. These various shapes and features may be formed or defined by the undercut 644 of the bearing surface 642.

The threaded shaft 646 may be an elongated structural member extending along an axis thereof. The threaded shaft 646 may be cylindrical. In some embodiments, the threaded shaft 646 may have other shapes, or be partially cylindrical, etc. The width of the threaded shaft 64 may be constant along all or a portion of the elongated length thereof. In some embodiments, the width may not be constant. The threaded shaft 646 may be solid, hollow, partially solid, or partially hollow. The threaded shaft 646 may be formed of stainless steel, cobalt-chromium, titanium, other implant grade materials, polymers, plastics, alloys, other suitable materials, or combinations thereof.

The threaded shaft 646 may have external engagement features such as outer threads 647. For clarity, only some of the threads 647 are labelled in FIG. 38B. The threads 647 may be one continuous thread extending helically around the shaft. In some embodiments, the threads 647 may be discontinuous. The threads 647 may be helical external ridges, for example wrapped around a central cylinder. The threads 647 may extend entirely or partially along the outside surface of the threaded shaft 646 from or between a distal end and a proximal end thereof. At one or both ends of the threads 647, the thread may be incomplete, for example a tab extending less than a full revolution about the shaft. The threaded shaft 646 may be similar to a screw or threaded fastener, such as an externally-threaded rotating screw member. The threads 647 may be cut, rolled, or formed by a variety of suitable techniques.

The threads 647 may have a variety of different pitches and inner/outer diameters. The threaded shaft 646 may have one or more portions having an external thread 647 measuring from about 0.010 to about 0.090 inches in diameter, from about 0.020 to about 0.080 inches in diameter, from about 0.030 to about 0.070 inches in diameter, or from about 0.040 to about 0.060 inches in diameter, or other amounts or ranges. This diameter may be an outer diameter as measured from peak to opposite peak of the threads 647. The threaded shaft 646 may have from about 10 to about 150 threads per inch, from about 20 to about 140 threads per inch, from about 30 to about 130 threads per inch, from about 40 to about 120 threads per inch, from about 50 to about 130 threads per inch, from about 60 to about 120 threads per inch, from about 70 to about 110 threads per inch, from about 80 to about 100 threads per inch, or other amounts or ranges. In some embodiments, the threaded shaft 646 has a portion having an external thread measuring from about 0.040 to about 0.060 inches in diameter and from about 60 to about 120 threads per inch. The pitch and inner/outer diameters of the threads 647 may complement that of corresponding internal engagement features, such as threads or teeth, of the collar 18.

The threaded shaft 646 may be located, for example carried or retained, at the proximal apex 14. The threaded shaft 464 may be retained at least partially in the corresponding window 634. The threaded shaft 646 may be mostly retained within such window 634. The threaded shaft 646 is freely or substantially freely rotatable about its rotation axis but is constrained or substantially constrained against axial and/or circumferential movement. The shaft 646 may extend circumferentially between the first and second supports 630, 632. The shaft 646 may extend, for example protrude, radially inward and/or outward beyond the first and second supports 630, 632.

In some embodiments, "axial" as applied to axial movement or restraint of the threaded shaft 646 or collar 18, or other features carried by an apex of the implant 1, includes directions that are at least partially in the proximal or distal direction and that are parallel or generally parallel to a plane containing a corresponding pair of adjacent struts 12, such as the struts 12A, 12B and/or a plane containing the apex 14. Thus axial may be in a proximal or distal direction along the apex 14 or along a plane defined by a pair of adjacent struts 12. This direction may or may not be parallel or generally parallel to the central axis of the implant 1. For instance, in some embodiments, the struts 12 may "flare" or incline radially inward or outward, as further described, such that the collar 18 may move in an "axial" direction that is not parallel to a central longitudinal axis of the implant 1 (for example, see the central longitudinal axis shown in FIG. 1). Thus, "axial" movement of the collar 18 may refer, in some configurations or during portions of the anchoring procedure, to a direction parallel to the longitudinal axis of the implant 1, and in other configurations or during other portions of the anchoring procedure to a direction that is not parallel to the longitudinal axis of the implant 1. The axial direction of movement of the collar 18 may change relative to the longitudinal axis of the implant 1 as the implant 1 changes configurations, for example cinches and reduces width. Further details of "flaring" of the implant 1 are provided herein, for example with respect to FIG. 44.

Referring to FIG. 38B, the threaded shaft 646 may interact with various features of the window 634, which may be formed by various features of the implant 1. The threaded shaft 646 extends between the bearing surface 642 and a distal bearing surface 648 carried by the proximal apex 14. The bearing surface or surfaces 642 and the distal bearing surface 648 may form, respectively, proximal and distal boundaries of the window 634. The threaded shaft 646 may be provided with a ridge 650. The ridge 650 may be an annular piece, and may be proximally facing. The ridge 650 may be integral with the threaded shaft 646, or a separate piece attached thereto. The ridge 650 is one option and other suitable proximal end features may be implemented, as described herein, for example with respect to FIG. 40A. As shown in FIG. 38B, the ridge 650 may have a proximal surface or surfaces 651. The surface 651 may be a complementary surface to the undercuts 644 of the corresponding medial flanges 636, 638. The surface 651 may contact the medial flanges 636, 638, for example the bearing surfaces 642 of the undercuts 644. In FIG. 38B, for clarity one of the ridges 650 (on the left as oriented in the figure) is shown backed off from the corresponding undercut 644, such that a gap exists. The surface 651 may help maintain centration of the shaft 646 during rotation of the threaded shaft 646. The surface 651 may maintain the axial location and/or alignment of a proximal end of the threaded shaft 646.

The distal end of the threaded shaft 646 may be provided with features to maintain alignment of the threaded shaft 646. In some embodiments, the threaded shaft 646 may be provided with a distally facing member such as a post, a proximally extending recess, etc. to engage a complimentary surface structure such as a post or recess on the apex 14, such as at or in the distal bearing surface 648, to enable rotational alignment between the threaded shaft 646 and the apex 14. An embodiment of additional example features for the distal end of the threaded shaft 646 is shown in and described with respect to FIG. 40A, which features may in addition or alternatively be included with the threaded shaft 646 as shown in FIG. 38B.

One or more coupling features may be located at a proximal region of the threaded shaft 646 to transmit rotational torque to the shaft 646, and in some embodiments transmit longitudinal push/pull forces to the shaft 646. In some embodiments, the threaded shaft 646 may be rotated by a proximal member 655, such as a post, protrusion, projection, etc. The feature may be a coupling 660 (see FIGS. 40A, 41-43) which may interact with a corresponding coupling 666 from a delivery system 680 (see FIG. 40B) that could be disconnected from the implant 1, e.g. from features of the threaded shaft 646 such as the coupling 660, for permanent implantation of the implant 1 in the body. In some embodiments, the proximal member 655 may be attached to the coupling 660 or other features for transmitting rotation. In some embodiments, the coupling 660 may attach to or replace the proximal member 655. The threaded shaft 646 may thus be nested internal to the frame 10 and may be rotated via the proximal member 655 and/or coupling 660 by a delivery system, for example by allowing a cut pattern to accept or otherwise couple with the proximal member 655 and/or coupling 660 of the threaded shaft 646, as further described. The proximal member 655 and/or coupling 660 may have a maximum width that is less than a maximum width of the threaded shaft 646, such that a moment arm for a required applied torque is minimized, as further described.

Thus, the threaded shaft 646 may be allowed to rotate within the window 634 and be driven from the proximal member 655 and/or coupling 660 proximal to the frame 10, through a rotating delivery system member coupled to the threaded shaft 646 via the proximal member 655 and/or coupling 660. The proximal member 655 and/or coupling 660 thus allow for rotational motion to be transmitted from external the implant 1, for example by the surgeon through a catheter, and also allow a translational motion for implant 1 positioning. The plurality of these connections would allow for an angulation of the implant 1 in the left atrium during anchor placement. Further detail of the coupling 660 and delivery and anchoring aspects are provided herein, for example with respect to FIGS. 40A-44.

Variable axial positioning of the collars 18 may be used for delivery and controlled radial expansion and/or contraction of the implant 1 during implantation and before anchoring to tissue. The collars 18 may be initially advanced in a position that is distal to a proximal-most position of the collar 18 along the struts, to restrain the implant 1 in a delivery configuration for delivery in a delivery catheter. Once the implant 1 is positioned in the atrium and exposed (e.g., a distal sheath over the implant 1 is removed), the collars 18 may be advanced proximally to allow radial expansion of the implant 1 to an anchoring configuration for anchoring to the annulus. Before or after the implant 1 is positioned adjacent to the annulus for anchoring, the collars 18 may be adjusted as needed to obtain the desired size and shape prior to anchoring to tissue. After the implant 1 is anchored, the collars 18 may then be advanced distally to radially contract the implant 1 and annulus. Thus, the collars 18 may also assist with achieving various delivery and anchoring configurations and adjustment of the implant 1. In some embodiments, alternatively or in addition to the collars, other features may provide such functions, such as features of the delivery system.

Figure 39:
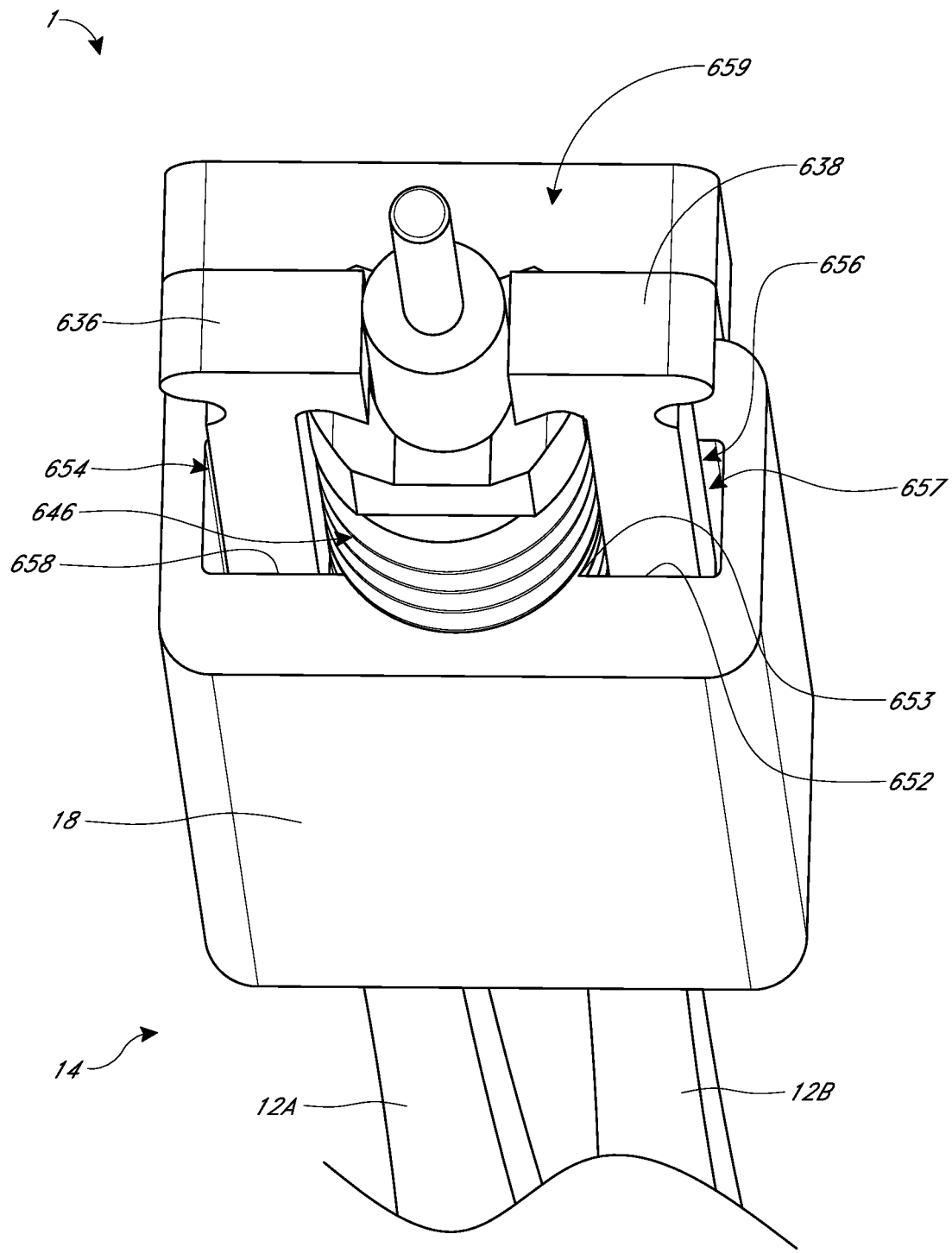
FIG. 39 is a partial perspective view of a proximal apex of the implant of FIG. 38A including an embodiment of an end cap for retaining the rotatable threaded shaft.

FIG. 39 is a partial perspective view of one of the proximal apexes 14 of the implant 1 showing one of the collars 18 interacting with the corresponding threaded shaft 646. One or more of the proximal apexes 14 may include one or more of the collars 18. In some embodiments, each proximal apex 14 includes one collar 18. There may be eight proximal apexes 14, each carrying a respective collar 18 and shaft 646 (i.e. eight collar 18 and eight shafts 646). In some embodiments, there may be less than or more than eight each of the proximal apexes 14, collars 18, and shafts 646. There may be one, two, three, four, five, six, seven, nine, ten, eleven, twelve, or more of each of the proximal apexes 14, collars 18, and shafts 646. In some embodiments, one or more of the distal apexes 16 may, in addition or alternatively, include one or more of the collars 18. For example, the various features described with respect to the threaded shaft 646 and collar 18, etc. located at the proximal apexes 14 may in some embodiments be located at distal apexes 17.

The collar 18 may have a generally rectangular shape. The cross-section may be rectangular. In some embodiments, the collar 18 may be square, rounded, contoured, other suitable shapes, or combinations thereof. The collar 18 may be constructed of an implant material such as stainless steel, cobalt chromium, titanium, nickel-titanium or polymers such as PEEK, plastics, other implant grade materials, or combinations thereof. The collar 18 may be formed by extrusion or other suitable techniques. The axial length may be from about 2 millimeters to about 16 millimeters, from about 3 millimeters to about 14 millimeters, from about 4 millimeters to about 12 millimeters, from about 5 millimeters to about 10 millimeters, from about 6 millimeters to about 8 millimeters, or other lengths or ranges of lengths.

The collar 18 includes a lumen or opening 657 extending axially therethrough. The opening 657 allows for receiving portions of the frame 10, such as the struts 12, proximal apex 14, and the threaded shaft 646, therein. There may be a single opening 657 extending through the collar 18 that surrounds all of the features therein. In some embodiments, the opening 657 may include one or more axial side channels, which may or may not be structurally separated from the opening 657, as further described. The opening 657 may extend from a proximal end to a distal end of the collar 18. The opening 657 may have a generally rectangular cross-section. In some embodiments, the opening 657 may have other cross-section shapes, such as a circular, rounded, partially rounded, or contoured shape to match complementary surface contours of the threaded shaft 646 and/or frame 10 such as the struts 12. The opening 657 may have a cross-sectional profile, for example perpendicular to the direction of axial extension of the body and opening 657 of the collar 18, that has a centrally wider portion compared to side portions, for respectively receiving and fitting around the shaft 646 and struts 12. The central portion may be rounded and the side portions may be square or rectangular, as generally shown in FIG. 39. The central portion may be part of the opening 657 and the side portions may be part of first and second axial channels 654, 656, as further described.

The collar 18 includes one or more inner surfaces 652. The inner surfaces 652 may extend along an inner side or sides of sidewalls of the collar 18 from a proximal end to a distal end thereof. The inner surfaces 652 may form inner boundaries of the opening or openings 657. The inner surface or surfaces 652 of the collar 18 are provided with a complementary engagement surface structure 653 for engaging the threaded shaft 646, such that rotation of the threaded shaft 646 interacts with the complementary surface structure 653 and causes the collar 18 to translate in a proximal or distal direction relative to the threaded shaft 646. Rotation of the threaded shaft 646 in a first rotational direction, such as clockwise, will cause movement of the collar 18 in a first translational direction, such as a distal direction. Rotation of the threaded shaft 646 in a second rotational direction opposite the first rotational direction, such as counter-clockwise, will cause movement of the collar 18 in a second translational direction opposite the first translational direction, such as a proximal direction.

The collar 18 may change the angles of adjacent struts 12 (the "angle C" between adjacent struts 12, as shown for example in FIG. 44C) by moving over the struts 12 to close or decrease the angle C between adjacent struts 12, or to open or increase the angle C, as described. The collar 18 may lock the struts 12 at a given angle due to moving over the struts 12. In some embodiments, the collar 18 may cause, for example push, a secondary slider located distally to the collar 18 to move over the struts 12 to decrease the angle C. A secondary slider may be used that also locks the angle of the struts 12 in place to account for any possible backing off of the collar 18, for example undesirable distal movement of the collar 18, after implantation.

The complementary surface structure 653 may be a complementary helical thread to slidably and/or rotatably engage some or all of the outer threads 674 of the threaded shaft 646. A mating internal thread pattern on the collar 18 (e.g. cut thread, rolled thread or alternative method) may mate with the threaded shaft 646. The collar 18 may translate, i.e. move linearly, due to a rotation of the threaded shaft 646, as described.

In some embodiments, features of a rack and pinion gear system may be incorporated. In some embodiments, the complementary surface structure 653 may be one or more tabs or teeth extending radially inwardly from the inner surface 652. The complementary surface structure 653, such as tabs or teeth, may be arranged in a ladder-like configuration along all or a portion of one or more of the inner surfaces 652.

The complementary surface structure 653 may extend in a proximal and/or distal direction. For example, radially inner and outer sides of the inner surface 652, as assembled with the frame 10, may include the complementary surface structure 653, such as portions of a threaded surface drilled into and through the collar 18, or a series of tabs, teeth, etc. in a ladder-like configuration, etc. The inner threads, tabs or other features of the complementary surface structure 653 may be located within the collar 18 and extend along the proximal and/or distal directions. The complementary surface structure 653 may extend along this length, or it may be broken into separate sub-structures that are located along this length. The complementary surface structure 653 may extend entirely or partially along the axial length of the inner surface 652. The complementary surface structure 653 may be located centrally relative to the opening 657. Further details of the internal engagement features of the collar 18 are described herein, for example with respect to FIGS. 45A-45B.

In some embodiments, various locking features may be incorporated into the threads 647 of the threaded shaft 646 and/or into the complementary surface structure 653. For example, features related to self-locking fasteners or nuts, modified male or female threads, etc. may be incorporated to produce a self-locking engagement that is resistant to loosening due to cyclic loading, vibrations and other environmental disturbances.

The lumen or opening 657 of the collar 18 may include one or more axially extending channels. The collar 18 may include a first channel 654. The first channel 654 may be a portion of the opening 657, such as a side portion thereof. The first channel 654 may slidably receive the first strut 12A. The collar 18 may include a second channel 656. The second channel 656 may be a portion of the opening 657, such as a side portion thereof that is opposite the first channel 656. The second channel 656 may slidably receive the second strut 12B. The opening 657 may form a central portion that surrounds the shaft 646. In some embodiments, the first and/or second channels 654, 656 may be structurally separated from the opening 657. For example, the first and/or second channels 654, 656 may be separated, entirely or partially, by a wall or other divider that separates and prevents contact between the struts 12A, 12B and the threaded shaft 646.

Each of the first and second channels 654, 656 may comprise at least one first surface 658. The first surface 658 may engage, for example slidably engage, the respective strut 12A, 12B. Engagement of the first surface 658 with the struts 12A, 12B may prevent and/or limit rotation of the collar 18 about its axis. As the threaded shaft 646 is rotated, rotational forces may be imparted to the collar 18. The collar 18 may thus rotate until the one or more first surfaces 658 contacts the strut 12A. The first surface 658 may be a region of the inner surface 652. In some embodiments, the first surface 658 may be a part coupled with or built integrally into the inner surface 652. There may be multiple first surfaces 658, for example corresponding to opposite sides of corresponding struts 12A, 12B. For clarity, only one of the first surfaces 658 is labelled in FIG. 39. There may be four first surfaces 658, with two first surfaces 658 on radially inward and radially outward sides of the strut 12A, and two first surfaces 658 on radially inward and radially outward sides of the strut 12B. One, some or all of the first surfaces 658 may contact corresponding side surfaces of the respective struts 12A, 12B to prevent or limit rotation of the collar 18. In some embodiments, rotation of the collar 18 in a first rotational direction will cause diagonally opposite first surfaces 658 to contact the struts 12A, 12B, and rotation of the collar 18 in a second opposite rotational direction will cause the other of diagonally opposite first surfaces 658 to contact the struts 12A, 12B.

As further shown in FIG. 39, in some embodiments, the implant 1 may include an end cap 659. The end cap 659 may be a structural member coupled with the apex 14, such as with the medial flanges 636 and/or 638. The end cap 659 can be placed on the struts 12 that make up the window 634 to capture, or otherwise prevent dislodgment of, the theaded shaft 646. The end cap 659 may extend from a proximal end of the first and second supports 630, 632 in a generally radially inward or outward direction, i.e. toward or away from the central longitudinal axis of the frame 10. The end cap 659 may be integral with the frame 10 or may be a separate part attached thereto. The end cap 659 may thus facilitate retention, for example radial retention, of the threaded shaft 646. For example, after driving the collar 18 distally to angle the struts 12A, 12B, the end cap 659 may provide a retaining feature to assist with radially retaining the proximal end of the threaded shaft 646.

The positioning of the collar 18 over the threaded shaft 646 may also prevent the threaded shaft 646 from falling out of the window 634 in the frame 10 and dislodging from the implant 1. In some embodiments, the window 634 may have an open proximal side as shown. As described above, in some embodiments, the window 634 may be an enclosed region. For example, the open proximal side may be closed, such as with a bridge or with connected flanges 636, 638, but have an axial opening such as a hole therethrough, with the threaded shaft 646 and/or other features extending therethrough into the window 634 and engaging with the collar 18.

Figure 40A:
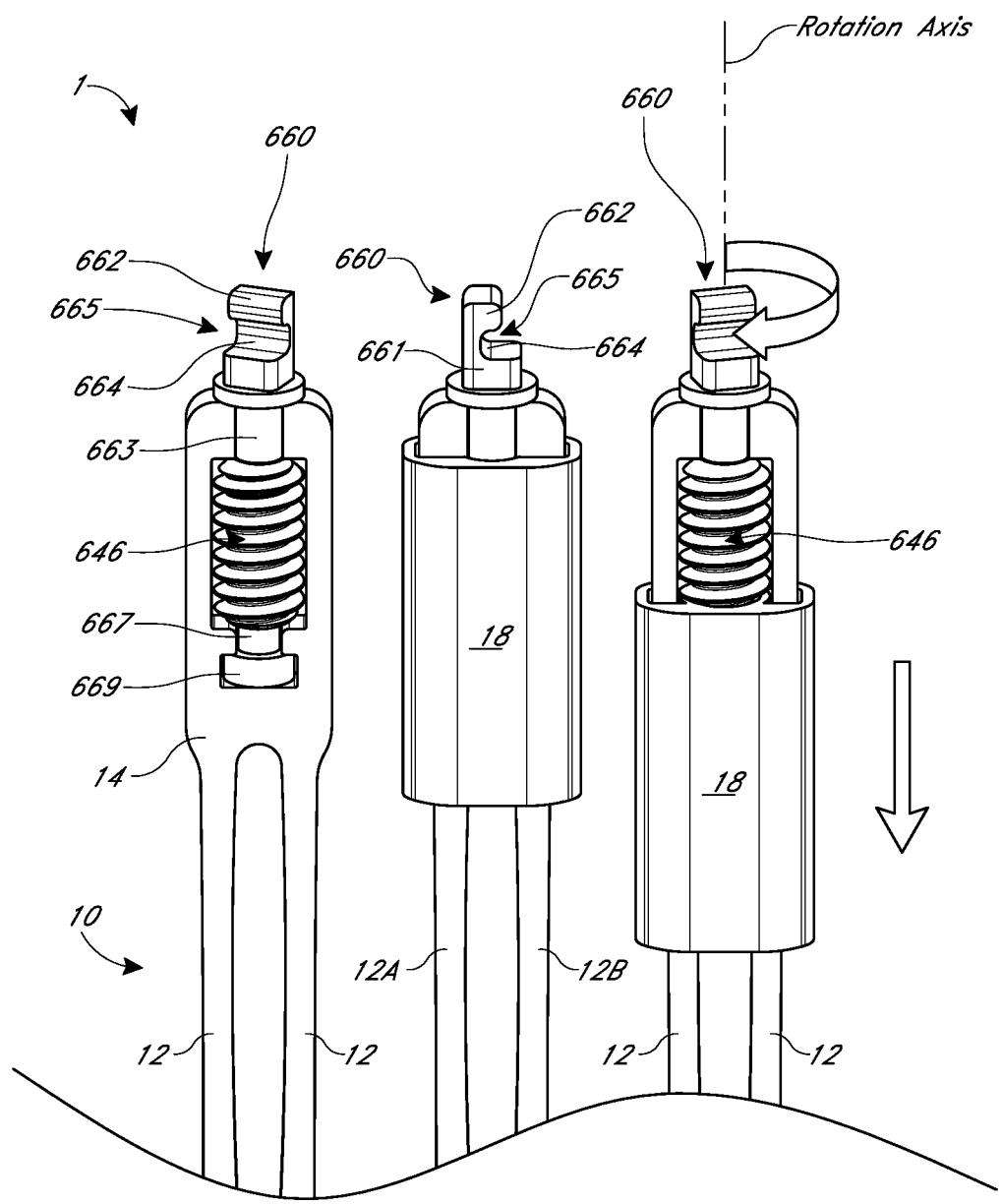
FIG. 40A is a partial perspective view of another embodiment of an implant having an axially translatable collar and a rotatable threaded shaft nested within the frame and located internally to the collar and with a coupling for engagement by a driver coupling for rotating the threaded shaft to cause axial movement of the collar.
Figure 40B:
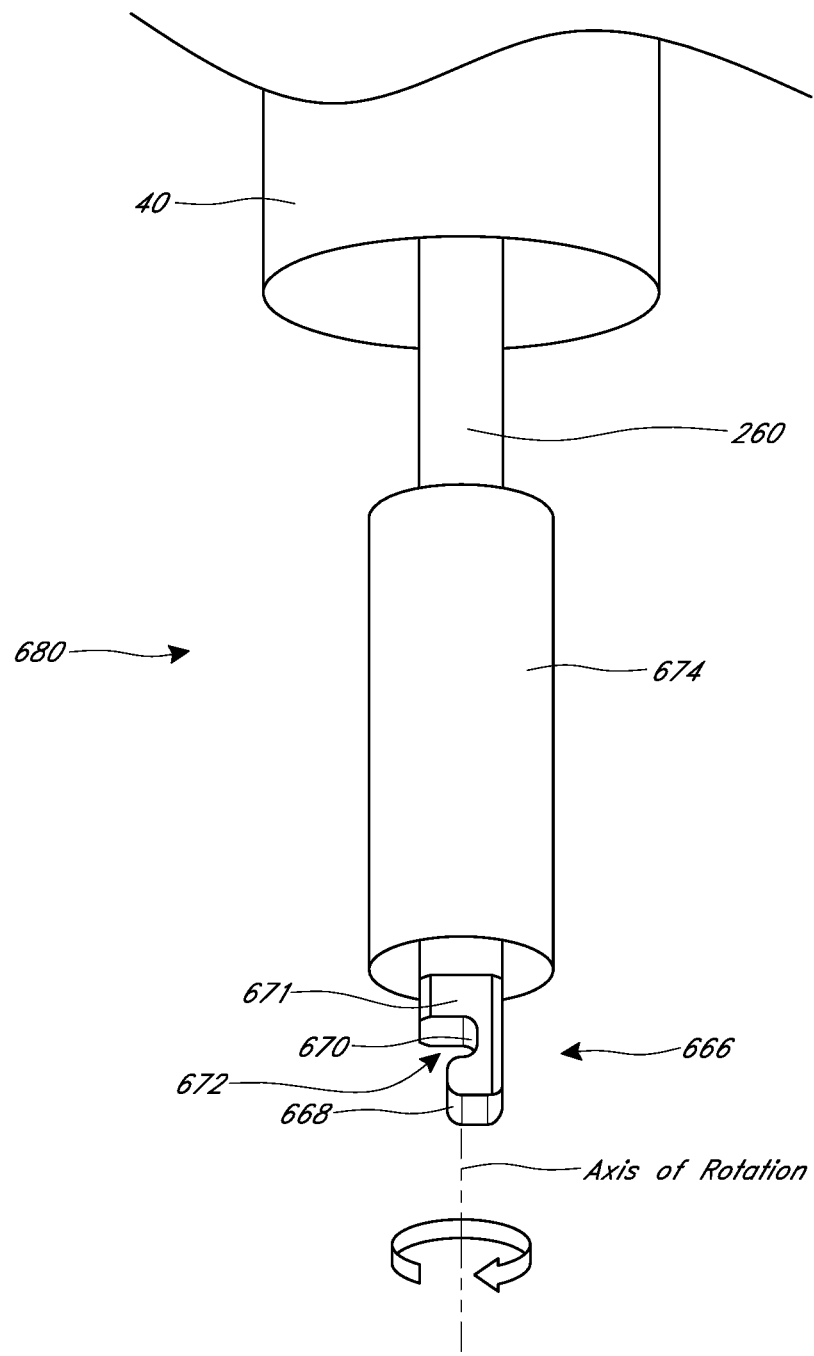
FIG. 40B is a partial perspective view of an embodiment of a driver coupling that may be used with the implant coupling of FIG. 40A.

FIGS. 40A and 40B depict embodiments of coupling features that may be used with the implant 1 and a delivery system to rotate the threaded shafts 646. FIG. 40A is a partial perspective view of an embodiment of the implant 1. The implant 1 is shown as having an axially translatable collar 18 and a rotatable threaded shaft 646 nested within the frame 10 and located internally to the collar 18. The implant 1 includes a coupling 660 for engagement by a driver coupling 666 for rotating the threaded shaft 646 to cause axial movement of the collar 18. FIG. 40B is a partial perspective view of an embodiment of the driver coupling 666 that may be used with the implant coupling 660.

The threaded shaft 646 may be driven with one or more coupling features. Any of a variety of complementary couplings may be utilized, between the threaded shaft 646 and the driver coupling 666. As shown in FIG. 40A, the proximal end of the threaded shaft 646 may be provided with the coupling 660. The coupling 660 may allow for releasable engagement of the coupling 660 with the driver coupling 666. The proximal end of the threaded shaft 646 may be provided with the coupling 660, either directly or indirectly coupled thereto. The coupling 660 may couple with the proximal member 655, such as a post, as described with respect to FIG. 38B. In some embodiments, there is no proximal member 655 such as a post and there is only the coupling 660. The coupling 660 may be integral with the proximal end of the threaded shaft 646. The coupling 660 may be a separate part that is attached, for example welded, bonded, fastened, etc. to the threaded shaft 646. The coupling may be made of the same or similar materials as the threaded shaft 646, or other suitable materials.

Referring to FIG. 40A, an example axis of rotation of the coupling 660 on the right, as oriented in the figure, is shown. The corresponding distal axial movement of the corresponding collar 18 is indicated by the distal pointing arrow next to the collar 18. The axis of rotation 660 of the coupling 660 may align with the axis of rotation of the threaded shaft 646, as shown. In some embodiments, the axis of rotation of the coupling 660 may be parallel but not coincident with the axis of rotation of the threaded shaft 646. In some embodiments, the axis of rotation of the coupling 660 may not be parallel with the axis of rotation of the threaded shaft 646. For example, the coupling 660 may be coupled with the threaded shaft 646 using an angled or rotatable fitting whereby rotation of the coupling 660 about a first axis transmits rotation to the threaded shaft 646 about a second axis that is angled relative to the first axis.

The coupling 660 may comprise a lateral projection 662. The lateral projection 662 may extend perpendicularly or generally perpendicularly to the axis of rotation of the coupling 660. The lateral projection 662 may extend in a variety of directions, including at angles other than ninety degrees relative to the axis of rotation. In some rotational orientations of the coupling 660, the lateral projection 662 may extend tangentially or generally tangentially to a circumferential direction relative to the rounded frame 10 of the implant 1. However, the coupling 660 may be rotated such that the lateral projection may extend in a variety of directions relative to the frame 10.

The lateral projection 662 may extend over a base 661 of the coupling 660. The lateral projection 662 may extend for a portion of the width of the base 661. The base 661 may be coupled with (i.e. attached directly or indirectly with) the threaded shaft 646 in any of the manners described above. In some embodiments, the lateral projection 662 may extend for a quarter of, half of, three quarters of, the entire, or more than the entire width of the base 661, or other amounts.

The lateral projection 662 may overhang a recess surface 664. The recess surface 664 may be located distally to the lateral projection 662. The recess surface 664 may be an inner surface or surfaces of the coupling 660 extending at or near a proximal region of the base 661 and to or near a distal region of the lateral projection 662, and anywhere in between. The recess surface 664 may follow a generally rounded contour as shown. In some embodiments, the recess surface 664 may be straight, rounded, segmented, polygonal, other suitable shapes or contours, or combinations thereof.

The lateral projection 662 and recess surface 664 may form or define a laterally opening recess 665. The laterally opening recess 665 may define an opening or window configured to be coupled with a corresponding driver or delivery system feature for engagement of the coupling 660, as further described. The laterally opening recess 665 may open perpendicularly or generally perpendicularly to the axis of rotation of the threaded shaft 646. In some embodiments, the laterally opening recess 665 may open at angles other than ninety degrees or about ninety degrees relative to the axis of rotation. In some embodiments, the coupling 660 may be rotated such that the laterally opening recess 665 faces a different direction. For example, in FIG. 40A as oriented, the couplings 660 on the left and right are rotated and the corresponding laterally opening recesses 665 each faces in a different lateral direction. Therefore "lateral" is not restricted to circumferential, but may be any direction that is generally perpendicular (or at other angles) to the axis of rotation of the coupling 18. For instance, the coupling 660 on the right as oriented is shown rotating about the rotation axis as indicated. The laterally opening recess 665 may face in any direction that is generally perpendicular to this axis. In some embodiments, the laterally opening recess 665 may be angled with respect to such perpendicular direction. For example, the laterally opening recess 665 may open in a proximal or distal direction at an angle relative to such perpendicular direction.

Also shown in FIG. 40A is one of the proximal apexes 14 (on the left as oriented in the figure) without the collar 18 to show various possible features of the threaded shaft 646. For example, the threaded shaft 646 may have a proximal connector 663 and a distal connector 667, as shown in FIG. 40A. The proximal connector 663 may extend proximally from a proximal end of the threaded portion of the threaded shaft 646. The proximal connector 663 may connect the threaded portion of the threaded shaft 646 with the coupling 660. The proximal connector 663 may be integral with the threaded portion and/or the coupling 660. The distal connector 667 may extend distally from a distal end of the threaded portion of the threaded shaft 646. The distal connector 667 may connect to a base 669 of the threaded shaft 646. The distal connector 667 may be integral with the threaded portion and/or the base 669. Thus, in some embodiments, the coupling 660, the proximal connector 663, the threaded portion of the threaded shaft 646, the distal connector 667 and the base 669 may be an integral, monolithic piece. The various parts or portions of the threaded shaft 646 may complement openings or other features of the frame 10, as further described herein, for example with respect to FIG. 41.

Referring to FIG. 40B, a portion of an embodiment of a driver system 680 for use with the various implants described herein, such as the implant 1, is shown. The driver system 680 may be used with the various driver and delivery systems described herein, for example the driver tube 260 and delivery catheter 40 as shown, and described above. For clarity only a portion of the delivery catheter 40 and one driver tube 260 are shown. There may be additional driver tubes 260 extending from the distal end of the delivery catheter 40, as described above. In addition or alternatively, in some embodiments, the driver system 680 may be used with other delivery and driver features and/or implants described herein, such as the driver tubes 22', the delivery catheter 240, the delivery system 400, the steerable sheath 402, the steerable catheter 602, the implants 1A, 1B, 1C, 100, 101, 102, 103, 104, 105, 500, 520, 520', 530, etc.

The driver system 680 may include a driver coupling 666. The driver coupling 666 may releasably engage with and drive, for example rotate, the coupling 660 of the implant 1. A surface structure or structures of the driver coupling 666 complementary to a surface or surfaces of the implant coupling 660 may be provided on a distal end of the driver system 680. As shown, the driver coupling 666 may include a lateral projection 668, a recess surface 670, a base 671, and an opening recess 672, which may have the same or similar features and/or functionalities as, respectively, the lateral projection 662, the recess surface 664, the base 661, and the opening recess 665 of the implant coupling 660. The driver coupling 666 may thus complement the implant coupling 660 to allow for engagement of the couplings 660, 666.

The driver coupling 666 may be engaged with the implant coupling 660 by extending the driver coupling 666 to a position adjacent the implant coupling 660. The lateral projection 668 of the driver coupling 666 may then be inserted into the opening recess 665 of the implant coupling 660, and the lateral projection 662 of the implant coupling 660 may be inserted into the opening recess 672 of the driver coupling 666. The two lateral projections 662, 668 may be inserted to respective opening recesses 672, 665 simultaneously. The various complementary surfaces of the two couplings 660, 660 may contact or otherwise engage with each other, either completely or partially, for example the recess surfaces 664 and 670, etc.

When engaged, the couplings 660, 666 may be restrained from translating in one or more directions but free to translate in one or more other directions. For example, the couplings 660, 666 when engaged may be free to move in a first direction that is perpendicular to directions of extension of the lateral projections 662, 668, but the couplings 660, 666 may be restrained from movement in the remaining two directions that are perpendicular to this first direction. Thus, the engagement may restrain movement in two dimensions but allow for movement in one dimension, with respect to a three-dimensional or three-axis system. Similarly, the couplings 660, 666 when engaged may be free to rotate about the rotation axis but restrained from rotation about axes perpendicular to the rotation axis. Rotation of the driver coupling 666 transmits forces to the implant coupling 660, for example to the recess surface 664, to cause rotation of the implant coupling 660. Thus, the driver coupling 666 and the implant coupling 600 may rotate together as a unit, with the driver coupling 666 controlling the rotation and the implant coupling 660 passively rotating in response to the forces imparted from the rotating driver coupling 666.

The driver coupling 666 may be held in engagement with the coupling 660 on the threaded shaft 646 by an outer tubular sleeve 674. The sleeve 674 may be axially retractable to expose the driver coupling 666. After engagement of the coupling 660 with the driver coupling 666, the sleeve 674 may then be axially advanced in a distal direction to cover the engaged couplings 660, 666. The sleeve 674 may completely or partially surround the couplings 660, 666. The sleeve 674 may ensure the couplings 660, 666 remain engaged, for example by preventing uncoupling in a direction that is perpendicular to the direction of extension of the lateral projections 6682, 668. The sleeve 674 may be rounded as shown, or have other shapes. In some embodiments, the sleeve 674 may comprise two prongs extending in a distal direction that cover sides of the lateral projections 662, 668 to prevent de-coupling of the lateral projections 662, 668 in directions perpendicular to the direction of extension of the lateral projections 6682, 668.

The driver coupling 666 may be coupled with a distal end of the driver tube 260. Actuation, for example rotation, of the driver tube 260 may transmit rotation to the driver coupling 666. The driver coupling 666 may engage with and rotate the coupling 660, as described, with the sleeve 674 extended distally about the engaged couplings 660, 666. In some embodiments, the driver coupling 666 may be driven in the reverse rotational direction to cause proximal axial advancement of the collar 18, for example to allow for or cause an increase in the angle between adjacent struts 12. The driver coupling 666 may be driven in the reverse rotational direction with the sleeve 674 extended distally about the engaged couplings 660, 666.

After the desired distal or proximal advancement of the collar 18, the sleeve 674 may be retracted proximally to expose the engaged couplings 660, 666. Proximal retraction of the sleeve 674 exposes the interlocked couplings 660, 666 thus allowing the driver coupling 666 to be released from the implant coupling 660. The driver coupling 666 may thus be disengaged or released from the implant coupling 660. For example, the driver coupling 666 may be moved perpendicular to the direction of extension of the lateral projection 668 to disengage the respective lateral projections 662, 668. The driver coupling 666 may then be retracted from the heart by the delivery system 680 and removed from the body. Similar engagement, covering, driving, uncovering, disengagement and removal methods and techniques may be performed for each coupling 660 of the implant 1. A separate driver coupling 666 and corresponding driver tube 260 may be used for rotating each implant coupling 660.

A variety of advantages result from the features described herein. For example, by having the threaded shaft 646 located internally to the collar 18, a smaller torque or rotational force is required to be exerted to move the collar 18. Because the moment arm for the threaded shaft 646 located internally to the collar 18 is much smaller relative to the moment arm of an externally located member that would surround the collar 18, such as a socket, the torque required to be transmitted by the surgeon is much smaller. The rotational force or torque (T) applied to an object or required to be overcome is equal to the moment arm or distance (D) from the rotational center times the force (F) applied at that distance, or T=F×D. Thus, the rotation of an internal member, i.e. a member located internally of the collar 18, requires a small torque T due to the small distance from the location of the center of rotation, i.e. a small "D". The resulting torque that must be overcome to turn the shaft is thus much smaller. This enhances reliability and ease of use of the driver system 680, as the torque in a transcatheter delivery system must be transmitted along the entire length of the driver through the catheter 40. By requiring a smaller torque to be transmitted, the implant 1 is more easily and simply cinched. Further, this eases requirements of other parts of the system. For example, the material and geometry of the length of the driver tube 260 that must transmit the torque over the long distance through the catheter 40 lumen need not sustain large torques, simplifying design and construction, and enhancing the reliability and robustness of the driver system 680.

Figure 41:
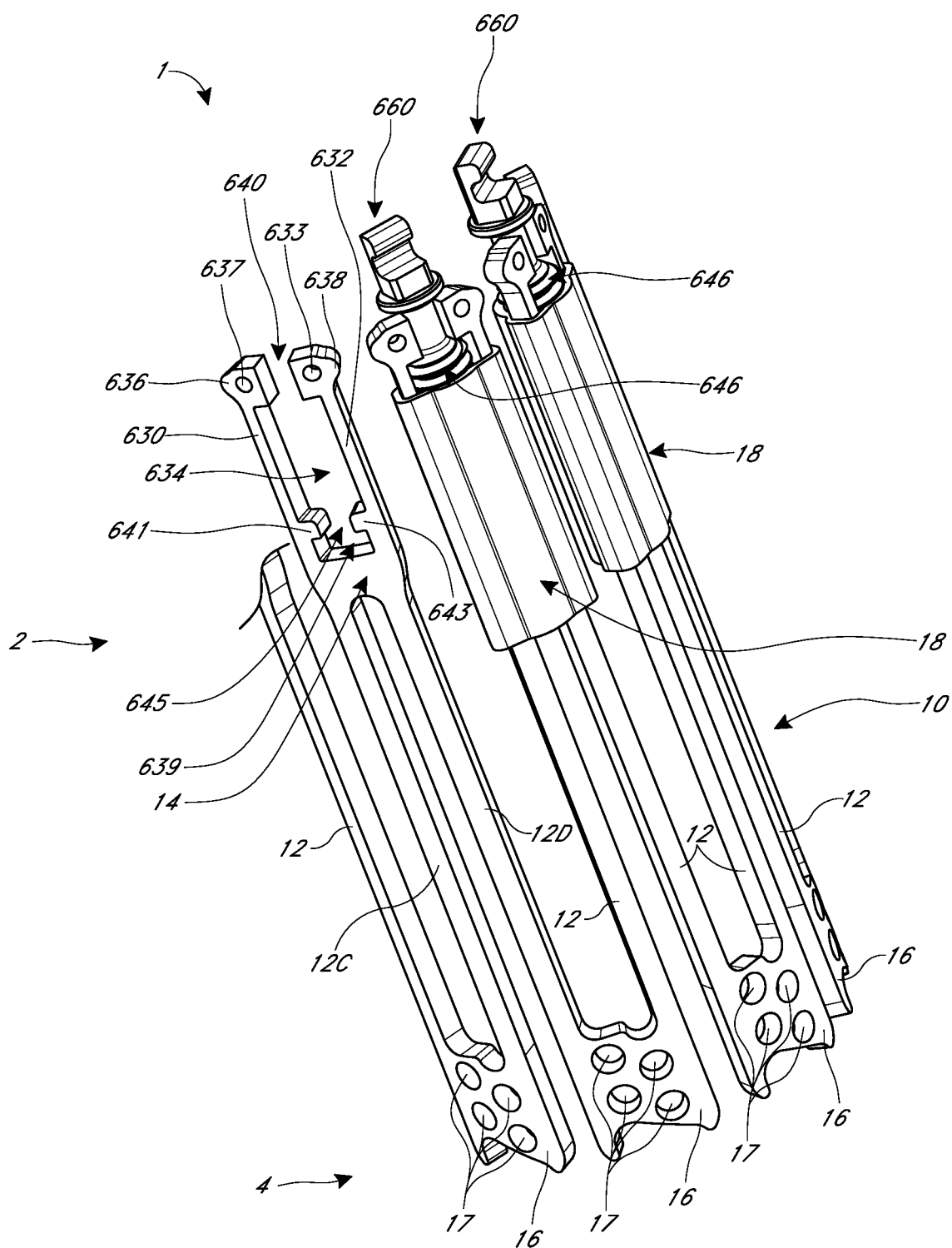
FIG. 41 is a partial perspective view of another embodiment of an implant having an axially translatable collar that is contoured and a rotatable threaded shaft nested within the frame and located internally to the collar and with a coupling for engagement by a driver for rotating the threaded shaft to cause axial movement of the collar.

FIG. 41 is a partial perspective view of an embodiment of the implant 1 having a contoured collar 18 and with various features at or near the proximal apex 14 removed for clarity. The implant 1 has an axially translatable collar 18 that is contoured. The collar 18 has contoured sidewalls to match the contours of the struts 12 and the threaded shaft 646. Thus a central bulge protrudes along radially inward and outward sides of the collar 18. The collar 18 may be contoured for a reduced crossing profile design, which may for example prevent excess rotation of the collar 18 before engaging with the struts 12 to prevent further rotation of the collar 18, provide a smaller delivery configuration of the implant 1, etc.

As shown in FIG. 41, on one of the apexes 14 (to the left of the figure as oriented), the collar 18, threaded shaft 646 and coupling 660 have been removed for purposes of illustration. The exposed proximal apex 14 is at the proximal end of the struts 12C, 12D. First and second supports 630, 632 extend proximally therefrom and terminate at medial flanges 636, 638, as described herein. Additionally, the medial flanges 636, 628 have openings 637, 633 respectively. The openings 637, 633, for example holes, extend through the flanges 636, 628. The openings 637, 633 may be used to attach various features to the frame 10, such as the end caps 659 as described herein.

The frame 10 includes the window 634, as described. Additionally, the frame 10 may include a lower window 639 as shown. The lower window 639 is separated from the window 634 by first and second projections 641, 643. The first projection 641 extends from the first support 630 toward the second support 632, and the second projection 643 extends from the second support 632 toward the first support 630, at a distal end of the window 634. A gap 645 is formed in between the two projections 641, 643. The gap 645 separates the window 634 from the lower window 639. Further, the frame 10 may include the central aperture 640, as described, for example in between the medial flanges 636, 638.

The threaded shaft 646 may have complementary features for insertion into the central aperture 640, window 634, gap 645, and/or lower window 639. The threaded shaft 646 may have the coupling 660, proximal connector 663, the distal connector 667, and/or the base 669, as described with respect to FIG. 40A. When the threaded shaft 646 is assembled with the frame 10, the coupling 660 may be proximal to the medial flanges 636, 638, the proximal connector 663 may be located within the central aperture 640, the threaded portion of the threaded shaft 646 may be located within the window 634, the distal connector 667 may be located within the gap 645, and/or the base 669 may be located within the lower window 639. The threaded shaft 646 may thus be retained at or near the apex 14 of the frame 10 by the corresponding structural features of the frame 10. In addition or alternatively, other suitable features may be used to retain the threaded shaft 646 with the frame 10, as further described.

Figure 42:
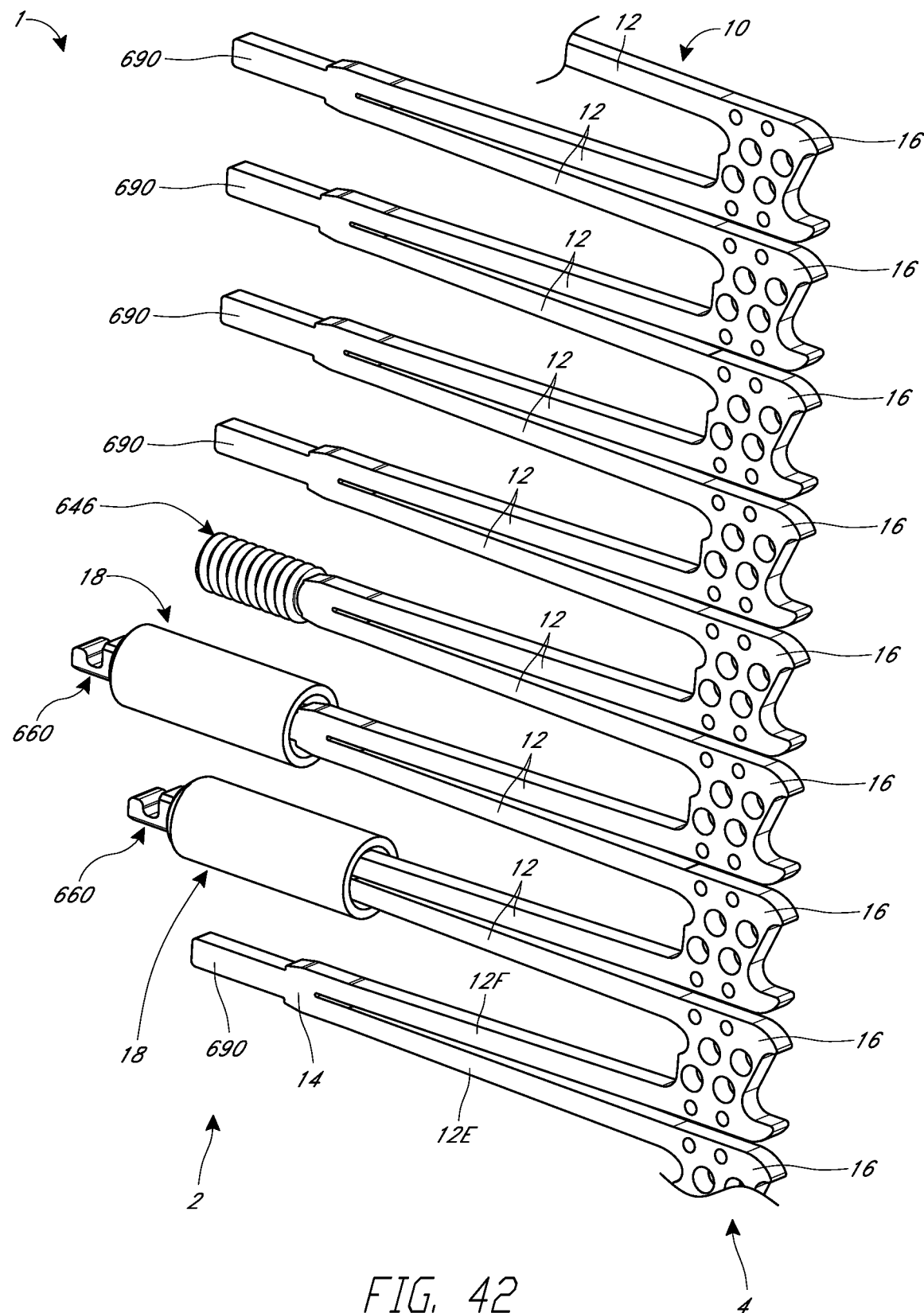
FIG. 42 is a flattened perspective view of another embodiment of an implant having an axially translatable collar and a rotatable threaded shaft surrounding a proximal post of the frame and located internally of a rounded collar.

FIG. 42 is a flattened perspective view of another embodiment of the implant 1 with a frame 10 having a proximal post 690 and a rounded collar 18. The implant 1 has the axially translatable collar 18 and the rotatable threaded shaft 646 surrounding the proximal post 690 of the frame 10 and located internally to the collar 18. The collar 18 has a generally cylindrical shape. The collar 18 may have an internal engagement structure such as internal threads, as described, that engages with the external engagement feature, such as external threads, of the threaded shaft 646 to axially translate the collar 18.

The post 690 may extend proximally from the proximal apex 14. As an example, the proximal apex 14 may be at the proximal end of the struts 12E, 12F, with the proximal post 690 extending therefrom. Each proximal apex 14 may have the proximal post 690. The threaded cannulated shaft 646 may extend over the proximal post 690, such that the proximal post 690 extends through or into an opening or recess of the threaded shaft 646. In some embodiments, the driver system 680 may utilize the proximal post 690 where the threaded shaft 646 is allowed to rotate on or over the proximal post 690 while trapped or pinned onto the proximal post 690 thereby preventing or substantially preventing axial movement of the threaded shaft 646. The threaded shaft 646 may bottom out at the proximal apex 14. In some embodiments, an internal proximal end of a central opening through the threaded shaft 646 may bottom out on the proximal end of the proximal post 690. The proximal post 690 may have a cylindrical shape to accommodate a rotating shaft 646. In some embodiments, there may be a bushing in between the post 690 and the shaft 646 to facilitate rotation of the shaft 646.

Figure 43:
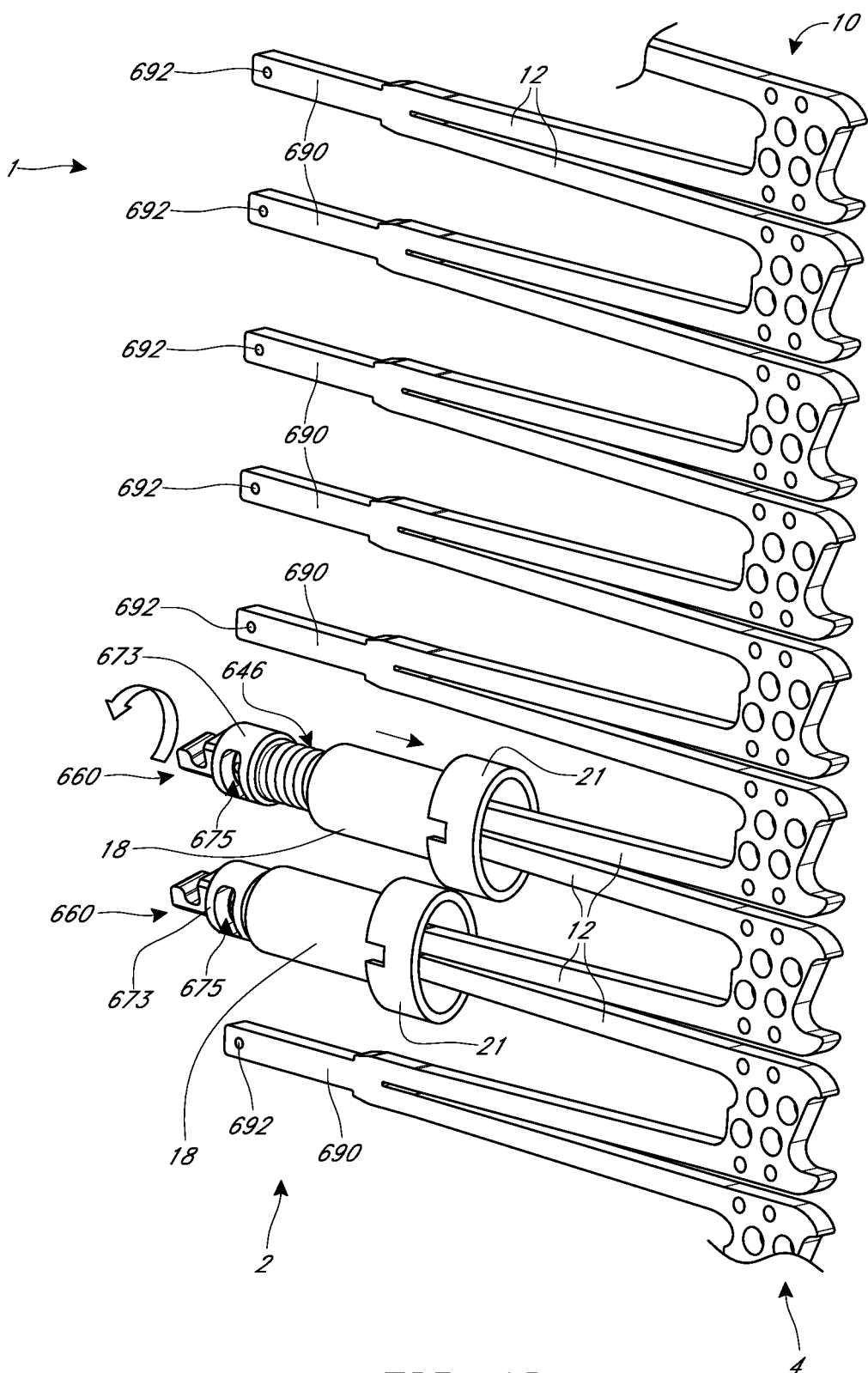
FIG. 43 is a flattened perspective view of another embodiment of an implant having an axially translatable collar and a rotatable threaded shaft surrounding a proximal post and pin of the frame and located internally to the collar.

FIG. 43 is a flattened perspective view of another embodiment of the implant 1. As shown the implant 1 may include the frame 10 having the proximal post 690 and a proximal stop 692. As further shown, the implant 1 may have a rounded collar 18 having an expanded distal portion 21. The proximal stop 692 may mechanically communicate with the threaded shaft 646. The proximal stop 692 may provide features for engaging complementary features of the threaded shaft 646. In some embodiments, the proximal stop 692 may be an elongated member, such as a cylinder or other shape, extending through the proximal post 690 from one side to another thereof. In some embodiments, the proximal stop 692 may protrude outward from one or more side surfaces of the proximal post 690. For example the proximal stop 692 may extend outward from two opposite sides of the proximal post 690 and be received into an annular groove on an internal surface of the threaded shaft 646 to prevent axial movement of the threaded shaft 646 relative to the proximal stop 692 while allowing for rotation of the threaded shaft 646 about the proximal post 690. In some embodiments, the proximal stop 692 may be a recess or hole in the post 690. Such stop 692 may receive a complementary inward protrusion from the shaft 646 or coupling 660, for example to limit or prevent rotation.

The threaded shaft 646 may have a complementary opening in a sidewall or a recess along an inner wall thereof near a proximal end of the threaded shaft 646. For example, the threaded shaft 646 may be a hollow cylinder with an inner wall having a radial opening therethrough or an annular recess along an inner surface thereof at a proximal end. The threaded shaft 646 may be slid over the proximal post 690 such that the proximal pin 692 extends into the complementary features within the threaded shaft 646, such as through the opening or within the annular recess. The engagement of the proximal pin 692 with the threaded shaft 646 may restrain movement of the threaded shaft 646 in the axial directions proximally and distally while allowing for rotation of the threaded shaft 646 about the proximal post 690. In some embodiments, the proximal pin 692 may be retractable such that the threaded shaft 646 may be slid over the pin 692 until the complementary features within the threaded shaft 646 allow the pin 692 to pop back out and engage the threaded shaft 646. In some embodiments, there may be a friction fit between the proximal pin 692 and the threaded shaft 646. The rotation of the threaded shaft 646 may drive the collar 18 over the struts 12 changing the angle C (see FIG. 44C) between the adjacent struts 12 as the collar 18 travels up and down the frame 10. Thus, the threaded shaft 646 may rotate about the proximal post 690. In some embodiments, the collar 18 may be rotated over the threaded shaft 646. For example, the threaded shaft 646 may be rotationally stationary and the collar 18 may be rotated over the threaded shaft to translate the collar 18 axially.

The collar 18 may include the expanded distal portion 21 having an expanded width, e.g. diameter, relative to other portions of the collar 18. As shown, the expanded distal portion 21 may be circular and have a cutout at a proximal end thereof.

Further shown in FIG. 43 is an embodiment of the coupling 660 having a cap 673. The cap 673 may be a rounded, for example cylindrical, member with a distal opening configured to receive therein a proximal portion of the threaded shaft 646. The cap 673 may include a side window 675. The side window 675 may be an opening in the sidewall of the cap 673. In some embodiments, the proximal pin 692 may extend into the side window 675 to engage the cap 673. Rotation of the cap 675 via the coupling 673 will cause the proximal pin 692 to contact portions of the cap 675 adjacent the side window 675, thus transmitting rotation of the coupling 660 to the threaded shaft 646.

FIGS. 44A-44C depicts various views of an embodiment of the implant 1 having flared proximal ends 2, for example after anchoring the implant 1 to heart tissue. FIG. 44A is a perspective view, FIG. 44B is a top (proximal end) view, and FIG. 44C is a side view. The features and functionalities of the implant 1 shown in and described with respect to FIGS. 44A-44C may apply to any other implants described herein, for example the implants 1A, 1B, 1C, 100, 101, 102, 103, 104, 105, 500, 520, 520', 530, including embodiments of the implant 1 shown in and described with respect to FIGS. 38A-43, and vice versa.

As shown in FIGS. 44A-44C, the implant 1 is shown having the frame 10 with the proximal end 2 and the distal end 4. A series of struts are connected to form a series of the proximal apexes 14 and a series of the distal apexes 16. The proximal apexes each have an embodiment of the collar 18, here shown as a slidable collar 18. It is understood that any of the collars described herein may be incorporated, including but not limited to the collar 18 shown in and described with respect to FIGS. 38A-43 that is driven axially by the internally rotating threaded shaft 646, as described. For clarity, only some of the features in FIGS. 44A-44C are labelled.

As shown, the implant has a "flared" proximal end 2. The proximal end 2 of the implant 1, for example the portion of the implant 1 above the distal apexes 16, inclines radially outward in the proximal direction relative to a central longitudinal axis of the implant 1 to give it the flared shape. The struts 12 may extend proximally and radially outward to form a generally frustoconical shape. In some embodiments, the implant 1 may not be circular and so the flared shape may not be exactly frustoconical. The implant 1 may have the flared shape before, during, and/or after anchoring the implant 1 to the heart tissue. As shown, the anchors 20 are extended distally and may be anchored into heart tissue (not shown). In some embodiments, the implant 1 may not be flared before anchoring and may take the flared shape after engaging the helical anchors 20 with tissue. The engagement of the anchors 20 may cause the implant 1 to have the proximally flared shape. In some embodiments, the implant 1 may assume the flared shape after removal of the drivers connected to the rotatable shafts 646. For example, each proximal apex 14 may flare outward upon removal of a corresponding driver or adjustment catheter from the corresponding shaft 646 or coupling for that particular apex 14.

The proximal end 2 of the implant 1 may be inclined varying amounts. As shown, the struts 12 may be inclined radially outward relative to the central longitudinal axis of the implant 1 by an angle A. The angle A may be from about five degrees to about seventy-five degrees, from about five to about sixty degrees, from about ten degrees to about seventy degrees, from about fifteen degrees to about sixty-five degrees, from about fifteen to about thirty degrees, from about twenty degrees to about sixty degrees, from about twenty-five degrees to about fifty degrees, from about thirty degrees to about forty-five degrees, or any other amounts or ranges. In some embodiments, the angle A may be zero or near zero such that the proximal apex 14 does not incline or only inclines slightly radially outward. In some embodiments, the angle A may be negative such that the proximal apex 14 inclines radially inward.

The angle A may change based on the stage of delivery and anchoring. In some embodiments, the angle A may change based on the number and/or amount of advancement of each of the collars 18 distally along corresponding pairs of struts 12. For example, the angle A may change a given angular amount based on amount of displacement or advancement of the collar 18 and/or rotational movement of the threaded shaft 646. In some embodiments, the angle A may increase or decrease by at least about 5 degrees or 15 degrees or 25 degrees or more degrees given axial advancement of the collar 18 by about 1 or 2 or 3 or more millimeters. In some embodiments of the implant 1 with the rotatable threaded shaft 646, two turns of the threaded shaft 646 produces about 5 millimeters of outward anchor 20 displacement. In some embodiments of the implant 1 with the slidable collar 18, a two millimeter advancement of the slidable collar 18 provides an outward anchor 20 movement of about 7.5 millimeters at the anchors 20.

In some embodiments, the angle A may increase by a factor of at least about 5× relative to the movement of the collar 18. For instance, each one millimeter of travel of the collar 18 may result in at least about three degrees or at least about five degrees radially outward swing or "flare" of the corresponding proximal apex 14. In some embodiments, the angle A may change based on other factors, such as the number and/or amount of insertion of each of the anchors 20 into tissue. Further, the angle A may not be uniform for all of the proximal apexes 14. For instance, a first proximal apex 14 may be inclined radially outward at a first angle, and a second proximal apex 14 may be inclined radially outward at a second angle, where the first angle is greater than the second angle. Therefore, none, some or all of the proximal apexes 14 may be inclined at the same angle A.

In some embodiments, the distal end 4 of the implant 1 may also be flared outward. For example, the anchors 20 may incline radially outward in the distal direction as shown, which may be before, during, and/or after engagement of the anchors 20 with tissue. The distal end 4 of the implant 1 may be inclined varying amounts. As shown, the anchors 20 and/or distal apexes 16 may be inclined radially outward relative to the central longitudinal axis of the implant 1 by an angle B. The angle B may be from about five degrees to about seventy-five degrees, from about five to about sixty degrees, from about ten degrees to about seventy degrees, from about fifteen degrees to about sixty-five degrees, from about fifteen to about thirty degrees, from about twenty degrees to about sixty degrees, from about twenty-five degrees to about fifty degrees, from about thirty degrees to about forty-five degrees, or any other amounts or ranges. In some embodiments, the angle B may be zero or near zero such that the distal apex 16 does not incline or only inclines slightly radially outward. In some embodiments, the angle B may be negative such that the distal apex 16 inclines radially inward.

The angle B may change based on the stage of delivery and anchoring, for example as described with respect to the angle A above. Further, the angle B may not be uniform for all of the anchors 20 or distal apexes 16. For instance, a first anchor 20 may be inclined radially outward at a first angle, and a second anchor 20 may be inclined radially outward at a second angle, where the first angle is greater than the second angle. Therefore, none, some or all of the anchors 20 or distal apexes 16 may be inclined at the same angle B.

Further, the angles A and/or B may change based on the amount of insertion of the anchors 20 and/or the number of anchors 20 inserted into tissue. In some embodiments, the angles A and/or B may change by one, two, three, four, five, or more degrees for each millimeter of advancement of either the anchors 20 or the collars 18. In some embodiments, the angles A and/or B may change by two, five, ten, fifteen, or twenty percent for each millimeter of advancement of either the anchors 20 or the collars 18. The distances and percentages may change, for example be greater or smaller, based on the particular geometry of the implant 1 and the frame 10, as well as particular anatomical features of the patient.

The flared shapes of the various portions of the implant 1 may enhance securement and functioning of the implant 1. For example, the flared distal end 4 may provide a more secure engagement as removal of the anchors 20 requires movement of the anchors 20 along non-parallel lines, thus reducing the chances that forces acting on the implant 1 will cause it to dislodge. As further example, the flared proximal end 2 may provide a greater opening to facilitate blood flow through the implant 1 and heart valve annulus. The flared configurations shown are merely examples and other variations of the flared aspects may be implemented.

Figures 45A, 45B:
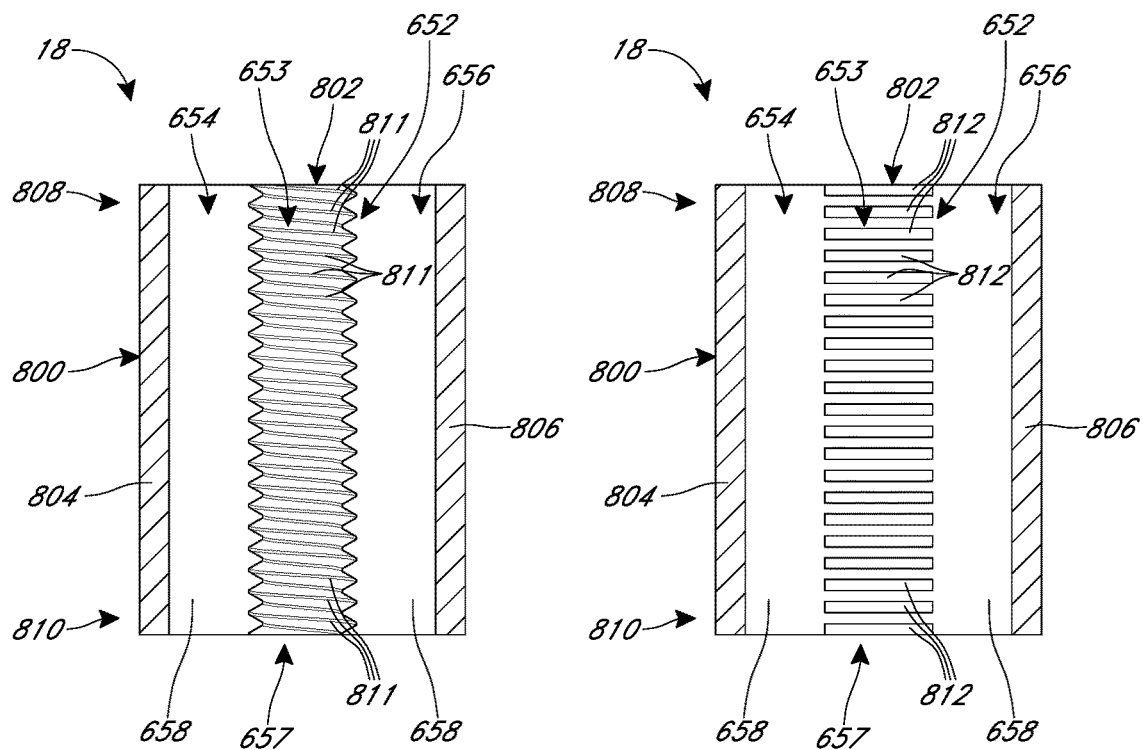
FIGS. 45A-45B are cross-section views of various embodiments of a collar that may be used with the various implants described herein.

FIGS. 45A and 45B are cross-sections views of embodiments of the collar 18 having various complementary surface structures 653. As shown, the collar 18 has a body 800 that includes sidewalls 802, 804, 806. The radially inward sidewall 802 may be located on a radially-inward side of the collar 18 as oriented when assembled with the implant 1. Thus "radially inward" here refers to a side relatively nearer the central longitudinal axis of the implant 1. A radially outward sidewall (not shown) may be located opposite the radially inward sidewall 802. "Radially inward" here refers to a side relatively farther from the central longitudinal axis of the implant 1. Sidewalls 804 and 806 may connect the radially inward sidewall 802 to the radially outward sidewall. The body 800, for example the sidewalls, may extend from a proximal end 808 to a distal end 810 of the collar 18.

The cross-section views of the collar 18 show a portion of the inner surface 652. The inner surface 652 extends from the proximal end 808 to the distal end 810 along interior sides of the sidewalls. The opening 657 is also shown extending from the proximal end 808 to the distal end 810. The channels 654, 656, which are shown as part of the opening 675 but which may be separated as described, extend from the proximal end 808 to the distal end 810 along the radially inward sidewall 802. The channels 654, 656 may also extend extend from the proximal end 808 to the distal end 810 along the radially outward sidewall. The first surfaces 658, as described, are shown extending from the proximal end 808 to the distal end 810 along the radially inward sidewall 802. The first surfaces 658, may also extend from the proximal end 808 to the distal end 810 along the radially outward sidewall.

Further shown in FIGS. 45A and 54B are embodiments of the complementary surface structures 653. FIG. 45A shows an embodiment of the complementary surface structure 653 including internal threads 811. For clarity, only some of the threads 811 are labelled in the figure. The threads 811 may extend axially from the proximal end 808 to the distal end 810 along the inner surface 652, or along any portion or portions therebetween. The threads 811 are incomplete, meaning less than a full revolution of the threads 811 are present. In some embodiments, the threads 811 may be complete, for example where a divider separates the opening 657 form the channels 654, 656, as described. The threads 811 are located on the radially inward sidewall 802. The threads 811 may also be located on the readily outward sidewall (not shown). In addition or alternatively, in some embodiments, the threads 811 may be located along inner surfaces 652 of the sidewalls 804, 806. The threads 811 may interrupt or separate the first surfaces 658 as shown.

FIG. 45B shows an embodiment of the complementary surface structure 653 including a series of teeth 812. For clarity, only some of the teeth 812 are labelled in the figure. The teeth 812 may extend axially from the proximal end 808 to the distal end 810 along the inner surface 652, or along any portion or portions therebetween. Each of the teeth 812 as shown may extend perpendicularly to a longitudinal axis of the collar 18, or the teeth 812 may be angled relative to the axis. Each of the teeth 812 may extend along a sidewall for a portion thereof in a lateral direction. The teeth 812 are located on the radially inward sidewall 802. The teeth 812 may also be located on the readily outward sidewall (not shown). In addition or alternatively, in some embodiments, the teeth 812 may be located along inner surfaces 652 of the sidewalls 804, 806. The teeth 812 may interrupt or separate the first surfaces 658 as shown.

Figure 46:
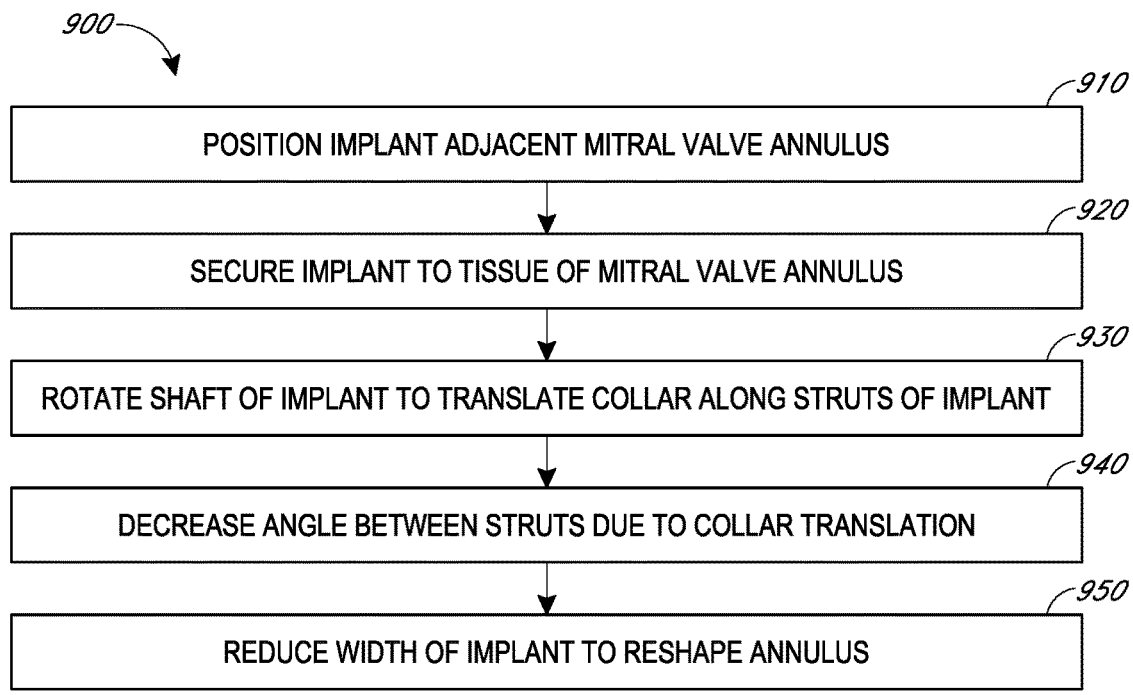
FIG. 46 is a flowchart showing an embodiment of a method for reshaping a mitral valve annulus using the various implants described herein.

FIG. 46 is a flowchart showing an embodiment of a method 900 for reshaping a mitral valve annulus. The method 900 may be performed with a variety of the implants described herein, including but not limited to the various embodiments of the implant 1 described with respect to FIGS. 38A-45B.

The method 900 begins with step 910 wherein an implant is positioned adjacent a mitral valve annulus. The implant may be the implant 1, and it may be positioned using the transcatheter delivery systems described herein or other delivery systems, including but not limited to the delivery system 400. The implant may have a tubular frame having a pair of struts, a rotatable shaft carried by the frame, a translatable collar engaged with the rotatable shaft and at least partially surrounding the pair of struts, and an anchor coupled with the frame. In some embodiments, the implant 1 includes the frame 10, struts 12, shaft 646, collar 18 and anchors 20, including but not limited to those described with respect to FIGS. 38A-44B.

The method 900 next moves to step 920 wherein the anchor is secured to tissue of the mitral valve annulus. In step 920, the anchor may be the anchor 20, or other anchors. Thus, step 920 may include rotating a helical anchor through a distal end of the frame to rotatably engage the tissue. In step 920, the anchors may be secured at an angle with respect to a central longitudinal axis of the implant, for example flared or inclined radially outward in a distal direction.

The method 900 next moves to step 930 wherein the shaft is rotated to cause the collar to translate along the first pair of struts. Step 930 may include rotating the threaded shaft 646 to cause the collar 18 to translate along the struts 12 in a distal direction. In step 930, the shaft may be rotated using the various drivers described herein, including but not limited to the delivery system 680 and the driver coupling 666, etc.

The method 900 next moves to step 940 wherein an angle between the first pair of struts is decreased due to translation of the collar. Step 940 may include decreasing the angle between the struts 12A, 12B due to axial movement of the collar 18 along the struts 12A, 12B.

The method 900 next moves to step 950 wherein the width of the implant is reduced or otherwise altered to reshape the mitral valve annulus. In step 950, the width of the implant 1 may be altered due to decreasing the angles between respective pairs of adjacent struts 12 from movement of respective collars 18 along the struts 12. The annulus may be reshaped due to the anchors 20 that secure the implant 1 to the tissue, thus bringing in the tissue with the reduced width implant 1.

The various features and functionalities may be combined in various aspects. In one aspect, an implant such as a heart valve support or mitral valve annulus reconfiguration device may have a frame comprising a plurality of struts, with adjacent pairs of struts joined or integrally formed to form an apex which may point in an axial direction. The direction may be proximal and/or distal. A restraint such as a collar (or slider) may be advanced axially in a direction away from the apex (either proximally or distally) and over the struts, reducing the angle between struts at the apex and drawing or allowing the pair of struts to incline closer together. Movement of the collar towards the apex allows or causes an increase in the angle at the apex between adjacent struts and allows or causes the pair of struts to incline farther apart. For example, the struts may self-expand to increase the angle therebetween upon movement of the collar toward the apex, and/or the collar may positively cause the struts to move apart to increase such angle. A shaft, including but not limited to the threaded shaft described herein, having at least one radial engagement structure such as a tab, a recess or a helical thread, has an axis of rotation extending in an axial direction. At least a first end and optionally a second end of the shaft is rotatably connected to or with respect to the apex to permit rotation of the shaft with respect to the apex but prevent axial displacement of the shaft with respect to the apex. The collar is provided with a complementary engagement structure such as at least one tab, recess or complimentary helical thread for rotatably or slidably engaging or otherwise engaging the engagement structure on the shaft such that rotation of the shaft produces axial displacement of the collar.

In one implementation of this aspect, the collar has a first axially extending channel for receiving a first strut and a second axially extending channel for receiving a second strut. The collar may instead have a single axially extending opening or channel for receiving both the first and second struts. The collar is also provided with a central threaded bore or other complementary features for engaging a threaded shaft carried by the apex. Rotation of the shaft drives the collar axially along the pair of struts. A coupling or connector may be provided for releasably coupling the shaft to a driver. The coupling may be a proximally facing surface structure having an engagement surface for engaging a complementary engagement surface on the distal end of the driver. Actuating the driver, for example rotating the driver, will transmit rotation to the coupling and shaft and axial translation to the collar, cinching or otherwise reducing the width of the implant, as described.

FIGS. 47A-59 describe various embodiments of the implant 1, which may include any of the features for the various implants described herein, such as the axially translatable collar 18 with rotatable shaft 646. Further, the implant 1 may include "reach" anchor features. These anchor features may be used with any of the embodiments of the implant described herein, including but not limited to the implants 1, 1A, 1B, 1C, 100, 101, 102, 103, 104, 105, 500, 520, 520', 530, which includes any embodiments of the implant 1 shown in and described with respect to FIGS. 38A-46, and vice versa.

Figure 47A:
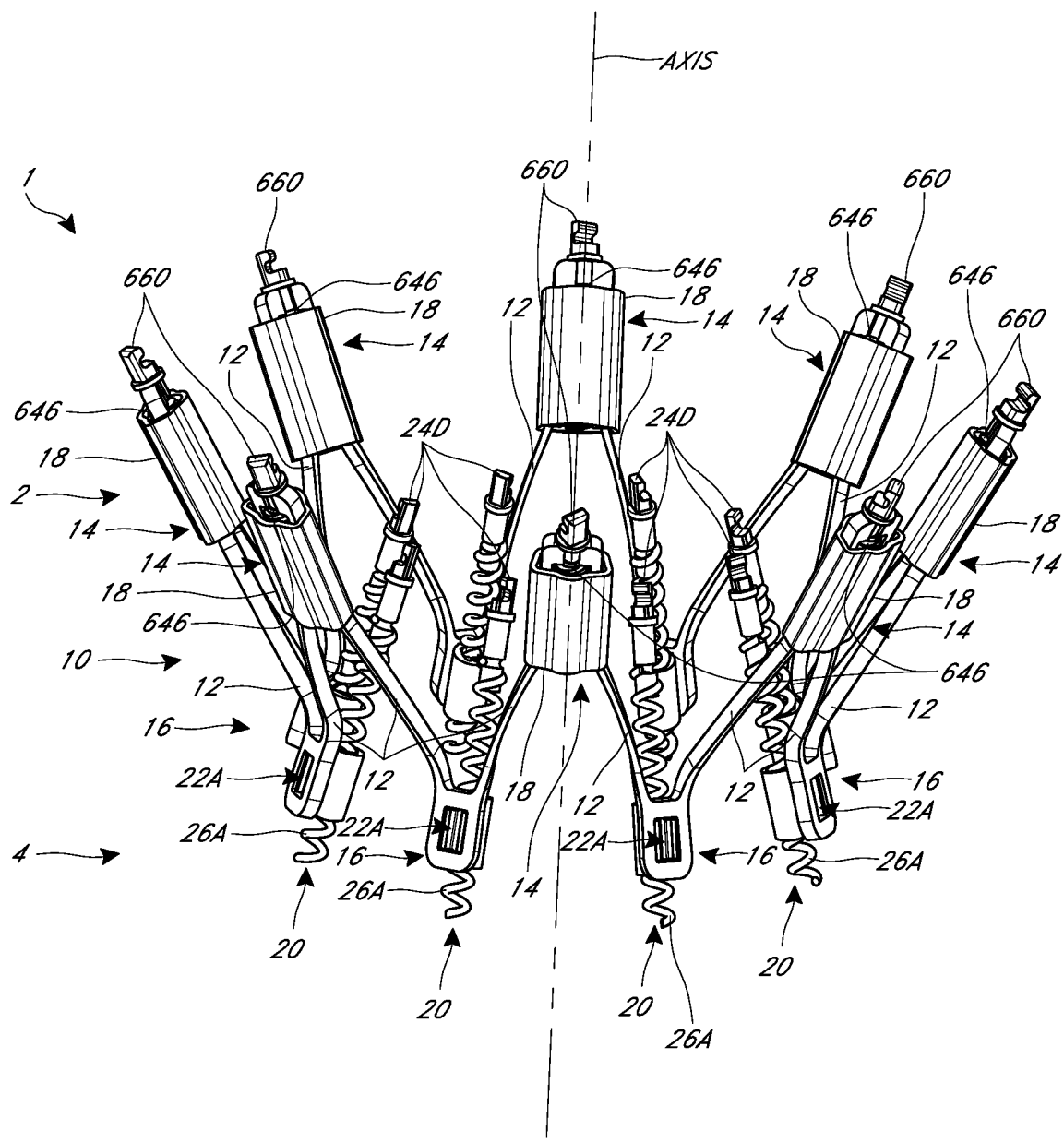
FIG. 47A is a perspective view of another embodiment of an implant having a rotatable threaded shaft nested within the frame and located internally to an axially translatable collar at the proximal apexes, and having anchor assemblies with anchor housings at distal apexes.

FIG. 47A is a perspective view of the implant 1 having anchor assemblies 20A at each distal apex 16. The implant 1 includes the frame 10 having the proximal end 2 and distal end 4. The proximal end 2 of the implant 1 includes the shafts 646 with proximal couplings 660 and collars 18 surrounding pairs of adjacent struts 12, as described. The distal end 4 includes the anchor assemblies 20A each having an anchor housing 22A and an embodiment of the anchor 20 having a distal helical portion 26A with a proximal coupling 24D. The housing 22A is coupled with the distal apexes 16 and receives the anchors 20 therethrough. The collars 18 and anchors 20 are shown in a relative proximal position and may be adjusted proximally or distally therefrom to effect various changes in the frame 10. The implant 1 of FIG. 47A and its various features are described in further detail herein. The implant 1 of FIG. 47A may have any of the same or similar features and/or functionalities as any other implant described herein, including but not limited to the implant 1 of FIG. 38A, and vice versa.

FIG. 47B is a perspective view of the implant 1 of FIG. 47A shown in a radially contracted configuration, for example a configuration suitable for delivery through a delivery catheter. In FIG. 47B, the proximal end 2 of the implant is shown without the cinching or contracting mechanism described herein (threaded shaft 646, collar 18, etc.) for purposes of illustration. The implant 1 may include the same or similar features as described herein. For example the implant 1 includes the frame 10 with struts 12 forming proximal apexes 14 and distal apexes 16, first and second proximal supports 630, 632 forming the window 634, medial flanges 636, 638 forming the aperture 640, first and second projections 641, 643 forming the gap 645, and the lower window 639. As described in further detail above, the struts 12 may be joined at the proximal and distal apexes 14, 16 and the frame 10 may be formed of a metal alloy, such as an alloy of nickel titanium.

In FIG. 47B, the implant 1 supports a plurality of anchor assemblies 20A. The implant 1 may have one or more of the anchor assemblies 20A. As shown there are eight anchor assemblies 20A. There may be one, two, three, four, five, six, seven, nine, ten, eleven, twelve, or more anchor assemblies 20A. There may be one of the anchor assemblies 20A for each distal apex 16. The anchor assemblies 20A are coupled with, for example attached to, the distal end 4 of the implant 1, such as with the corresponding distal apex 16.

The anchor assembly includes an anchor housing 22A and an anchor 20. The anchor housing 22A is coupled with, for example attached to, the distal end 4 of the implant 1. As shown, the housing 22A is attached to the frame 10 at the distal apex 16. The housing 22A may be a separate part that is attached to the frame 10, or the housing 22A maybe integral with the frame 10, such as with the distal apex 16. The housings 22A are located primarily on a radially inward side of the distal apexes 16. The housing 22A may be located entirely on a radially inward side. The housings 22A extend from the apex 16 toward the central longitudinal axis of the implant 1 (shown, for example, in FIG. 1). In some embodiments, the housings 22A may be located primarily or entirely on radially outer sides of the distal apexes 16.

FIG. 48 is a partial perspective view of a radially inward side of the implant 1 of FIG. 47A. The implant 1 in FIG. 48 includes an embodiment of a cinching or contracting mechanism 30A. The mechanism 30A may include any of the features described herein for any embodiment of the implant 1. As shown in FIG. 48, the mechanism 30A includes the threaded shaft 646 retained between the first and second supports 632, 634 at the proximal apex 14, with the coupling 660 on a proximal end of the shaft 646, and the collar 18 positioned at the proximal apex 14 and surrounding the proximal ends of the pair of adjacent struts 12. Rotation of the shaft 646 causes the collar 18 to advance distally or proximally along the struts 12 to decrease or increase the angle between the struts 12, as described herein.

An embodiment of a driver 40A is also depicted. The driver 40A is used to engage with and drive, for example rotate, the shaft 646 by engaging the coupling 660. The driver 40A may have the same or similar features and/or functionalities as any other drivers described herein, for example the driver tubes 22' shown in and described with respect to FIG. 22D. There may be multiple drivers 40A. There may be one of the drivers 40A for each of the shafts 646. The drivers 40A may be connected with a rotational force transmitting member, such as a wire, that extends through the delivery catheter and exits the patient at a proximal end for manipulation by a surgeon.

FIG. 48 also depicts the implant 1 having one of the anchor assemblies 20A. Other anchor assemblies 20A, which may be included, are not shown for purposes of illustration. The anchor assemblies 20A are preferably made of a suitable biocompatible metal alloy such as stainless steel, cobalt chromium, platinum iridium, or nickel titanium.

The anchor assembly 20A includes the anchor 20 having a distal helical portion 26A and a proximal anchor head 24A. The anchor 20 includes a proximal coupling 24D at a proximal end of the anchor head 24A. The anchor 20 is received within the anchor housing 22A. The anchor 20 is shown in a proximal position relative to the anchor housing 22A, such that a distal portion of the anchor 20 is located within the housing 22A in the orientation shown. The anchor 20 may be advanced, for example rotated, through the housing 22A to secure the helical portion 26A to tissue. The anchor 20 may be driven by a corresponding driver that engages the coupling 24D.

The helical portion 26A is connected to the proximal head 24. Each helical portion 26A is sharpened at its distal point 20B, or leading turn, so as to facilitate penetration into the cardiac tissue. Each helical portion 26A is preferably seven to ten millimeters long in axial length as measured along a central axis thereof. In some embodiments, the axial length of the helical portion 26A may be from about five millimeters to about fifteen millimeters, from about six millimeters to about thirteen millimeters, or other ranges or lengths. The helical portion 26A may be seven, eight, nine or ten millimeters long in axial length. The helical portion 26A is capable of extending from about four to about seven millimeters beyond the distal edge 16B of the distal apex 16. In some embodiments, the helical portion 26A may be capable of extending from about two to about nine millimeters beyond the distal edge 16B of the distal apex 16, or other ranges or distances. The helical portion 26A may be capable of extending four, five, six, or seven millimeters beyond the distal edge 16B of the distal apex 16.

The anchor assembly 20A includes the housing 22A facing radially inward. The housing 22A is coupled with the distal apex 16 at the window 16A. An attachment 27A, as further described herein for example with respect to FIGS. 49A and 53A-53B, may attach to the distal apex 16 at the window 16A. The window 16A may be a cutout of the distal apex 16. The window 16A may therefore be an opening or space extending through the distal apex 16.

The housing 22A includes a proximal portion 22B and a distal portion 22E. The proximal and distal portions 22B, 22E may include various features for engaging and/or guiding the anchor 20 to secure the anchor 20 to tissue of the valve annulus. The proximal portion 22B includes a proximal end 20D. The distal portion 22E includes a distal end 20E. The proximal and distal ends 20D, 20E may be used in the securement process. The proximal end 20D may provide a surface upon which a driver may bear while advancing the anchor 20. The distal end 20E may provide a surface that contacts the tissue. The distal end 20E may be located distally of a distal edge 16B of the distal apex 16. The distal edge 16B is a distal-most end or surface of the distal end 4 of the frame 10. The distal edge 16B of the anchor housing 22A may be located even with or proximal to the distal edge 16B of the distal apex 16. Further details of the housing 22A are described herein, for example with respect to FIGS. 51-55.

FIGS. 49A and 49B are partial perspective views of the distal end 4 of the implant 1. FIG. 49A depicts one of the distal apexes 16. FIG. 49B depicts eight of the distal apexes 16 with only one anchor assembly 20A, for purposes of illustration.

As shown in FIG. 49A, the anchor housing 22A includes the attachment 27A that engages with the window 16A of the distal apex 16. The attachment 27A may include two sidewalls 27B, such as radial extensions of the anchor housing 22A, that form an interference or friction fit inside the window 16A for securement therein. The housing 22A may be attached to the distal apex 16 using interference or friction fit, mechanical attachments, welding, adhesives, other suitable means, or combinations thereof. The housing 22A may be integral with the distal apex 16.

As shown in FIG. 49B, the implant 1 is inverted relative to the orientation in FIG. 49A. The anchor 20 is advanced in a relative distal direction compared with FIG. 48. The coupling 24D is located adjacent the proximal end of the housing 22A. Portions of the anchor 20 located inside the housing 22a are shown in dotted line. Further details of the anchor assembly 20A are described herein, for example with respect to FIGS. 50A-55.

Figure 50A:
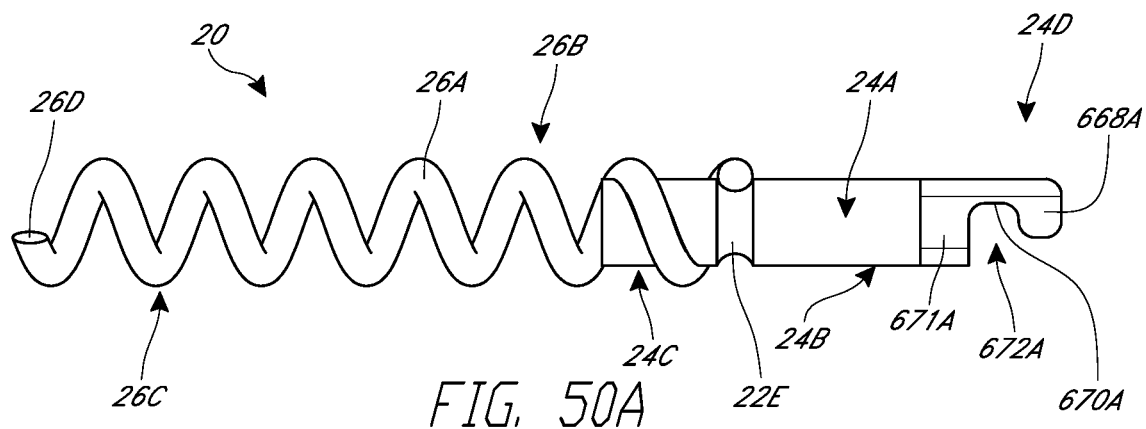
FIG. 50A is a side view of an embodiment of an anchor having a distal helical tissue engagement portion and a proximal head, that may be used with the various implants.

FIG. 50A depicts a side view of the anchor 20 having the distal helical portion 26A and proximal head 24A. The helical portion 26A includes a distal portion 26C and a proximal portion 26B. The distal portion 26C may end at a tip 26D. The tip 26D may be a sharpened point configured to pierce the cardiac tissue. The proximal head 24A extends from a distal end 24C to a proximal end 24B. The proximal head 24A may be solid or hollow. The head 24A may be formed from the same or similar materials as the helical portion 26A. In some embodiments, the head 24A and helical portion 26A may be different materials. The proximal head 24A may be cylindrical in shape. In some embodiments, the proximal head 24A may be partly cylindrical, rounded, segmented, other shapes, or combinations thereof.

All or a portion of the proximal portion 26B of the helical portion 26A may be coupled with the proximal head 24A. The helical portion 26A may be wrapped around a distal end 24C of the proximal head 24A. The helical portion 26A may be a separate portion attached to the proximal head 24A. The helical portion 26A may be received by a radially outer groove 24E formed in the outer surface of the proximal head 24A. The groove 24E may be partially or entirely helical in shape. The groove 24E may extend radially inward into the head 24A for a distance of about half the thickness of the extended member, for example wire, that forms the helical portion 26A. The groove 24E may include a circumferential or annular portion as shown at or near a proximal end of the helical portion 26A. In some embodiments, the helical portion 26A may be mechanically attached to the proximal head 24A, such as by interference or friction fit, with fasteners, adhesives, bands, other suitable means, or combinations thereof. In some embodiments, the helical portion 26A may be integral with the proximal head 24A, for example formed from the same monolithic piece of material.

The anchor head 24A includes a proximal end 24B having the coupling 24D. The coupling 24D may be integral with the proximal head 24A or a separate part attached thereto. The coupling 24D may have the same or similar features and/or functionalities as other couplings described herein, such as the coupling 660. As shown, the coupling 24D includes a proximal lateral projection 668A, a recess surface 670A, a distal base 671A, and an opening 672A. These may be analogous to, respectively, the lateral projection 668, recess surface 670, a distal base 671, and opening 672 described with respect to the coupling 660. A corresponding driver may engage and actuate, for example rotate, the coupling 660 to distally advance or proximally retract the anchor 20, as further described herein, for example with respect to FIG. 54.

Figure 50B:
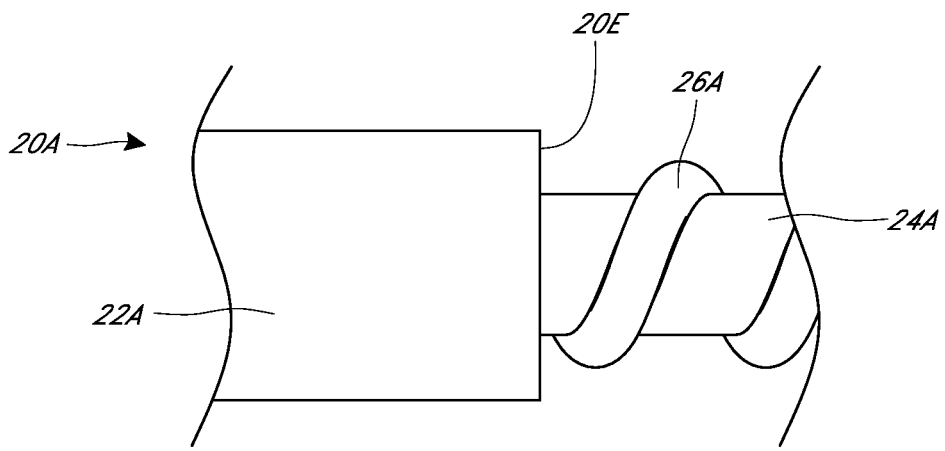
FIG. 50B is a detail view of the anchor assembly of the implant of FIG. 47A showing an interface between the anchor and a proximal end of the anchor housing.

FIG. 50B is a detail side view of the anchor assembly 20 showing an interface between the anchor housing 22A and the anchor 20. The proximal head 24A and helical portion 26A are received into the housing 22A. The entire helical portion 26A may be advanced distally of the proximal end 20E of the housing 22A. The proximal head 24A may be advanced distally of the proximal end 20E of the housing 22A.

Figure 51:
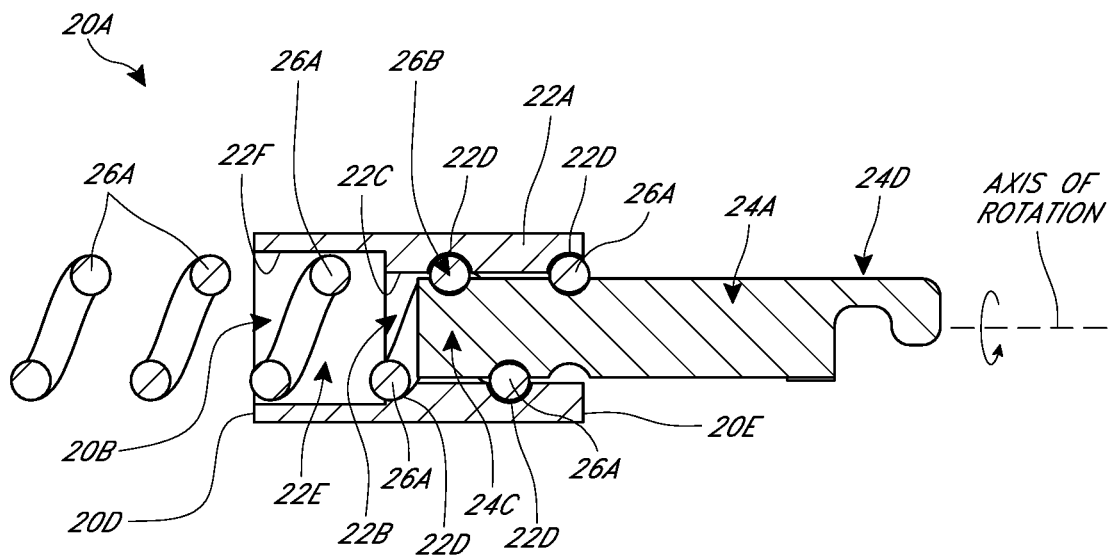
FIG. 51 is a partial cross-section view of an interface between the anchor and a proximal end of the anchor housing of FIG. 47A, showing the distal helical tissue engagement portion engaging internal grooves in the anchor housing.

FIG. 51 is a partial cross-section view of the anchor assembly 20A. Only part of the helical portion 26A of the anchor 20 is shown for purposes of illustration. The helical portion 26A appears as separate parts due to the cross-section view. An axis of rotation is indicated. The anchor 20 may be rotated about the axis to proximally or distally advance the anchor 20 relative to the housing 22A.

The housing 22A includes a lumen or opening 20B extending through the housing 22A. The opening 20B is a space axially extending along the axis of rotation through the housing 22A. The opening 20B provides a space through which the anchor 20 may be advanced. The opening 20B extends through the proximal portion 22B of the housing 22A. The proximal portion 22B of the opening 20B includes a groove 22D configured to guide the helical portion 26A therealong. The groove 22D may be an internal thread of the proximal portion 22B. The helical portion 26A is received partially into the groove 22D and prevents axial translation of the anchor 20 until the anchor 20 is rotated so that the helical portion 26A can slide circumferentially along the groove 22D. The groove 22D may have a corresponding helical shape and extend from a proximal end of the proximal portion 22B, such as from the proximal end 20E, to a distal end of the proximal portion 22B.

The housing 22A includes a proximal inner surface 22C located at the proximal portion 22B. The inner surface 22C defines a width, for example diameter, of a region of the opening 20B that extends through the proximal portion 22B. The inner surface 22C is located radially inward relative to an outer diameter of the groove 22D. The inner surface 22C may be defined by a proximal sidewall of the housing 22A that circumferentially surrounds the proximal region of the opening 22B and extends axially.

The housing 22A includes a distal portion 22E located distally of the proximal portion 22B. The opening 20B extends through the distal portion 22E to form a chamber. The distal portion 22E includes a distal inner surface 22F. The inner surface 22F defines a width, for example diameter, of a region of the opening 20B that extends through the distal portion 22E. The width of the opening 20B at the distal portion 22E is greater than a width of the opening 20B at the proximal portion 22B. For example, the diameter of the distal inner surface 22F is greater than the diameter of the proximal inner surface 22C. The distal inner surface 22F may have a width that is the same or greater than the outer radial dimension of the groove 22D of the proximal portion 22B. The inner surface 22F may be defined by a distal sidewall of the housing 22A that circumferentially surrounds the distal region of the opening 22B and extends axially. The inner surface 22F may be smooth, for example it may not include grooves or threads.

The anchor 20 may be introduced into the housing 22A by engaging the tip 26D of the helical portion 26A with the groove 22D and then rotating the anchor 20 through the proximal portion 22B of the housing 22A. As the anchor 20 is rotated, the helical portion 26A mechanically communicates with, for example slides through, the groove 22D to advance the anchor 20. Rotation of the anchor 20 in a first rotation direction will cause axial advancement of the anchor 20 in a first axial direction (for example distally), and rotation of the anchor 20 in a second rotation direction that is opposite the first rotation direction will cause axial advancement of the anchor 20 in a second axial direction (for example proximally) that is opposite the first axial direction.

In the configuration shown in FIG. 51, the helical portion 26A of the anchor 20 is engaged with the inner groove 22D of the housing 22A and extends into the distal portion 22E and exits the distal end of the housing 22A. The head 24A of the anchor extends out the proximal end of the housing 22A. The anchor 20 may be further rotated to advance the anchor 20 distally such that the helical portion 26A advances distally and entirely exits the proximal portion 22B. The helical portion 26A may then be located inside the distal portion 22E, for example as shown in FIG. 52.

Figure 52:
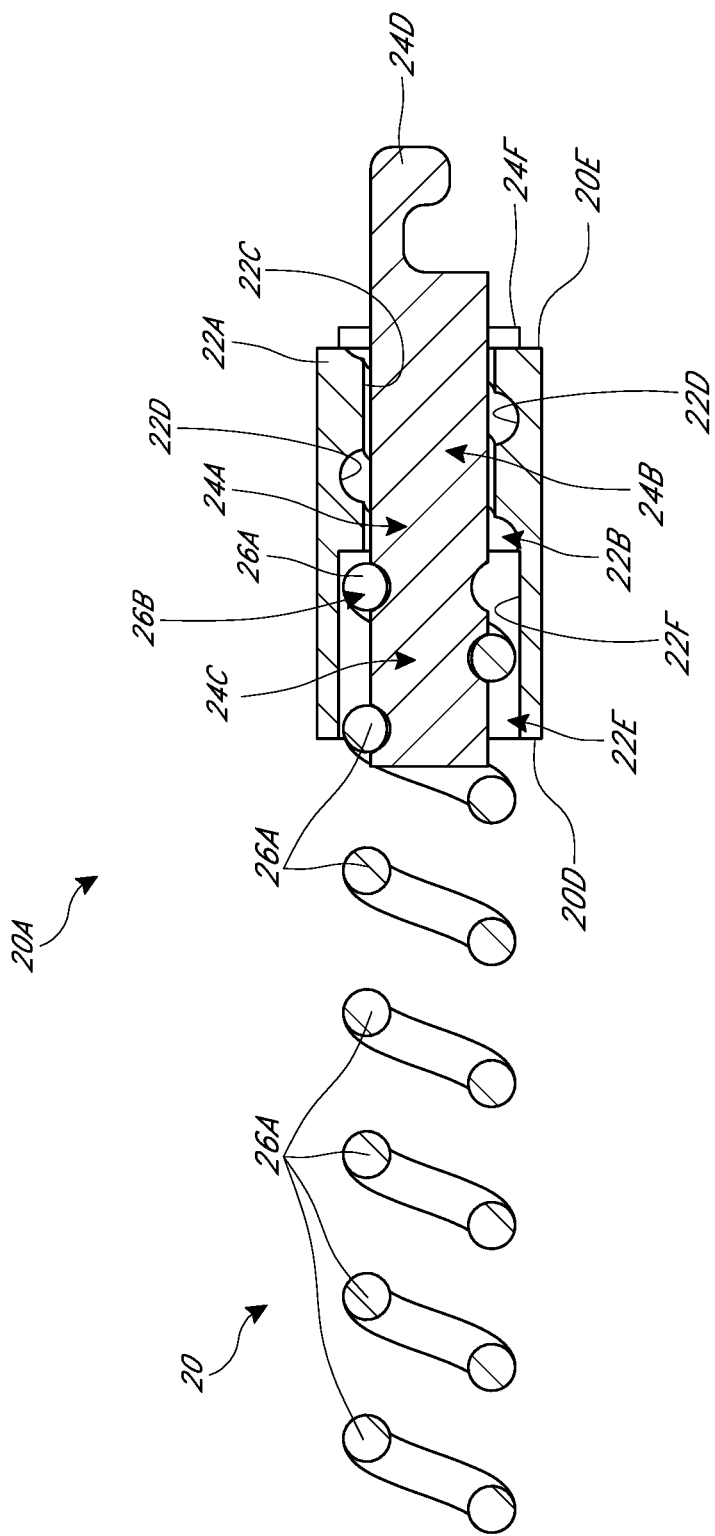
FIG. 52 is a partial cross-section view of the interface of FIG. 51 between the proximal end of the housing and the anchor, showing the distal helical tissue engagement portion moved proximally relative to the position shown in FIG. 51 and disengaged from the internal grooves in the anchor housing.

FIG. 52 depicts the anchor 20 in a distal position relative to the configuration shown in FIG. 51. As shown in FIG. 52, the helical portion 26A is located entirely within the distal portion 22E and outside the distal end of the housing 22A. The helical portion 26A has thus exited the groove 22D. Further rotation of the anchor 20 in this position will cause the anchor 20 to rotate while maintaining the axial position of the anchor 20. The anchor 20 will thus not advance farther distally due to rotation alone. The anchor 20 may therefore "freely spin" in this position. If desired, the anchor 20 may be pushed farther distally, for example with the driver. In some embodiments, the anchor 20 is prevented from farther distal advance relative to the position shown in FIG. 52, for example with use of a flange 24F at the head 24A of the anchor 20. The flange 24F may bear against the distal end 20E of the housing 22A, as shown in FIG. 52. In some embodiments, there may not be the flange 24F. In some embodiments, as further described herein, distal advance of the anchor 20 may be limited due to engagement with a coupling of a driver that rotates the anchor 20. In some embodiments, such driver may be incorporated with the flange 24F such that the flange 24F will limit distal axial advance of the anchor 20 after removal of the driver from the anchor 20. Further details of a driver and coupling are described herein, for example with respect to FIGS. 54 and 57-58.

The anchor 20 may engage tissue while the anchor 20 is "freely spinning" as described. Thus, the anchor 20 may distally advance into tissue while rotating within the distal portion 22E of the housing 22A. The housing 22A may also advance distally with the anchor 20. The housing 22A may advance distally due to distal force from a driver used to rotate the anchor 20, as described. The housing 22A may advance distally due to distal force from the flange 24F of the anchor 20 as the anchor advances distally into tissue due to rotation of the anchor 20 into the tissue. Thus, the anchor 20 and the housing 22A may advance distally together such that the anchor 20 and the housing 22A maintain a relatively constant axial position with each other. As the anchor 20 engages tissue, the housing 22A will advance distally toward the tissue. The distal end 20D of the housing 22A may contact the tissue. In some embodiments, the distal end 22D may be drawn toward the tissue with engagement of the anchor 20 and tissue, as described. In some embodiments, the implant 1 may initially be positioned with the distal end 22D of the anchor housing 22A contacting the tissue, and the anchor 20 may then be rotated through the housing 22A as described. After advance of the helical portion 26A into tissue, any remaining gap or space between the tissue and the housing 22A may be closed by using the "free spin" techniques described herein, for example further rotation of the anchor 20 while the helical portion 26A is located within the distal portion 22E of the housing 22A. The distal end 20D of the housing 22A may be flat or generally flat, for example planar and perpendicular to the longitudinal axis, or it may be contoured, for example curved.

Figure 53A:
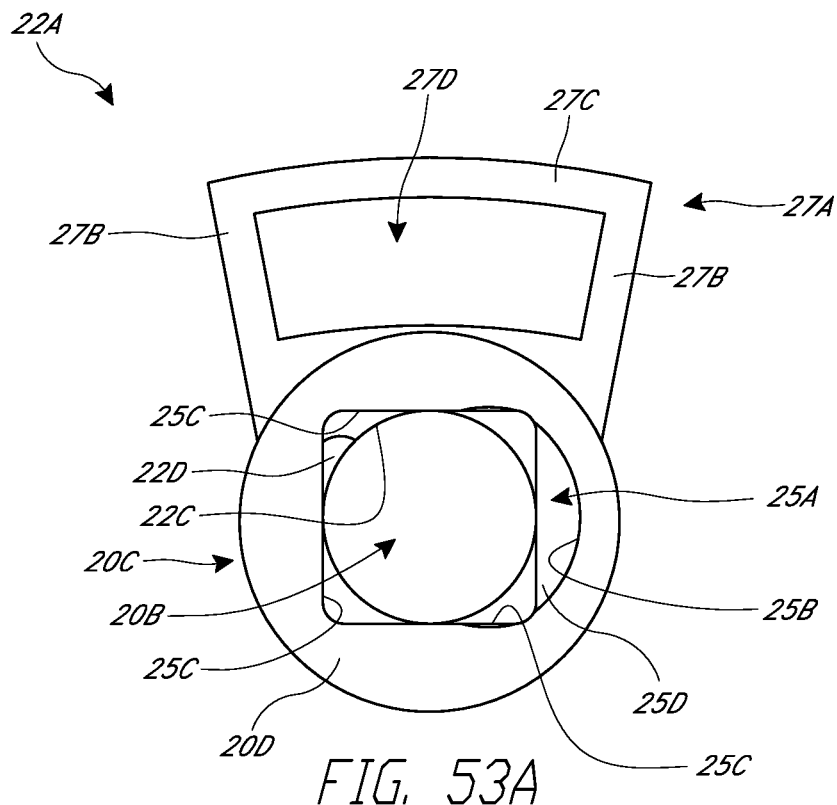
FIGS. 53A and 53B are respectively proximal end and perspective views of the anchor housing of FIG. 47A.
Figure 53B:
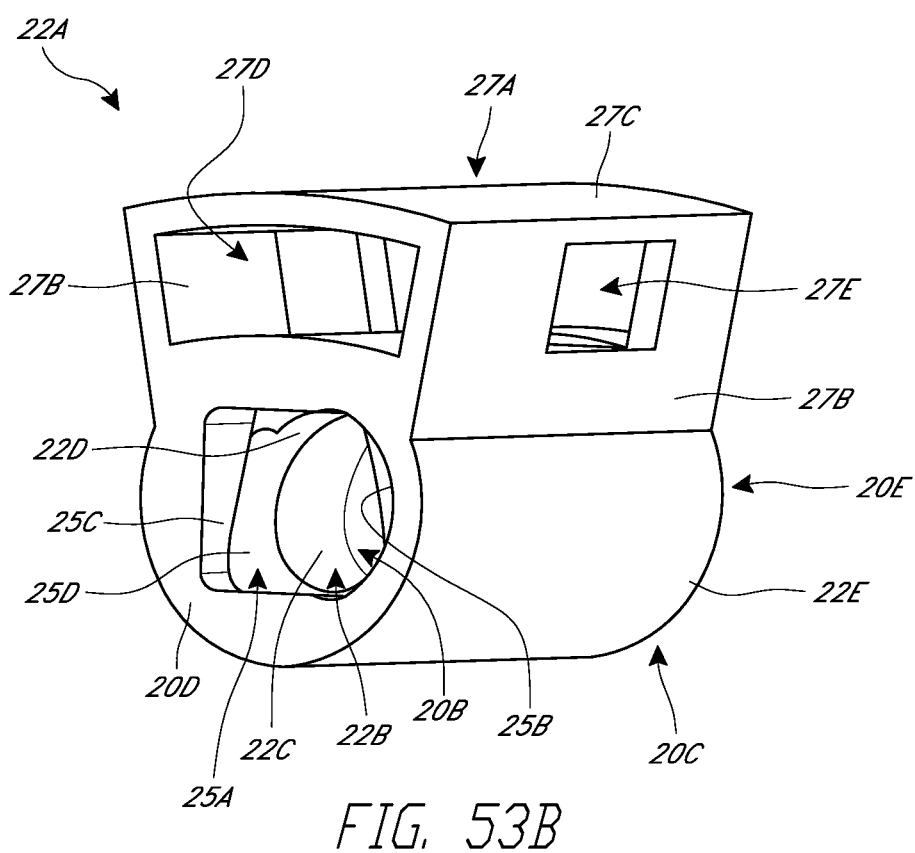

FIGS. 53A and 53B are respectively proximal end and perspective views of the housing 22A. The housing 22A includes a body 20C. The body 20C may include the opening 20B therethrough and receive the anchor 20 therein. The body 20C may be rounded, for example cylindrical as shown, or other shapes or profiles. The body 20C may have a substantially uniform outer width, for example diameter, while the internal opening 20B may have varied widths, as described. The body 20C adjacent the proximal end 20D may include a pocket 25A. The pocket 25A may be a recess in the proximal portion 22B of the housing 22A. Also, the pocket 25A is shown as having a somewhat square profile for receiving the anchor head 24, but it may have other shapes such as a somewhat star-shaped profile or others. This would facilitate the anchor head 24 seating with the pocket 25A. Furthermore, internal threading of the proximal portion 22B, such as the groove 22D, of the anchor housing 22A may terminate distally of the pocket 25A or extend up into the pocket 25A.

The pocket 25A may include a proximally-facing shelf 25D surrounded by one or more rounded side surfaces 25B and one or more straight side surfaces 25C. The side surfaces 25B, 25c may be shaped to complement the side contour if the anchor head 24A such that the anchor head 24A is prevented from rotating therein. The pocket 25A may receive a portion of the anchor head 24A therein and rotationally and/or axially lock the anchor 20 therein. A distal facing surface of the anchor 20, such as a distal facing surface of the flange 24F, may contact the shelf 25D to prevent farther distal advance of the anchor 20. The anchor 20 may contact and rest on the shelf 25D after engagement of the anchor 20 with tissue and removal of the anchor driver.

The housing 22A may include an attachment 27A. The attachment 27A may be located to a lateral side of the body 20C. The attachment 27A may include one or more sidewalls 27B extending laterally from the body 20C. The sidewalls 27B may extend laterally and outwardly to form an angle therebetween. The sidewalls 27b may open outwardly and flex inwardly to facilitate attachment with the frame 10. The attachment 27A may include an end wall 27C. The end wall 27C may connect laterally outward ends of the sidewalls 27B as shown. The end wall 27C may provide stiffness to the sidewalls 27B. The 27C may also flex to facilitate engagement of the sidewalls 27B with the frame 10. An opening 27D may extend through the attachment 27A and be defined by the sidewalls 27B and end wall 27D. The opening 27D may reduce the weight of the housing 22A. The sidewalls 27E may include a window 27E. The window 27E may receive corresponding tabs located on circumferentially inner sides of the window 16A of the distal apex 16. In some embodiments, the opening 27D may receive a portion of the frame 10 of the implant 1 therein. For example, the distal apex 16 may be received into the opening 27D for attachment of the housing 22A with the frame 10. The window 27E may receive therein corresponding circumferentially outer tabs of the distal apex 16. Thus, the anchor housing 22A may be attached with the frame 10 using a variety of techniques.

Figure 54:
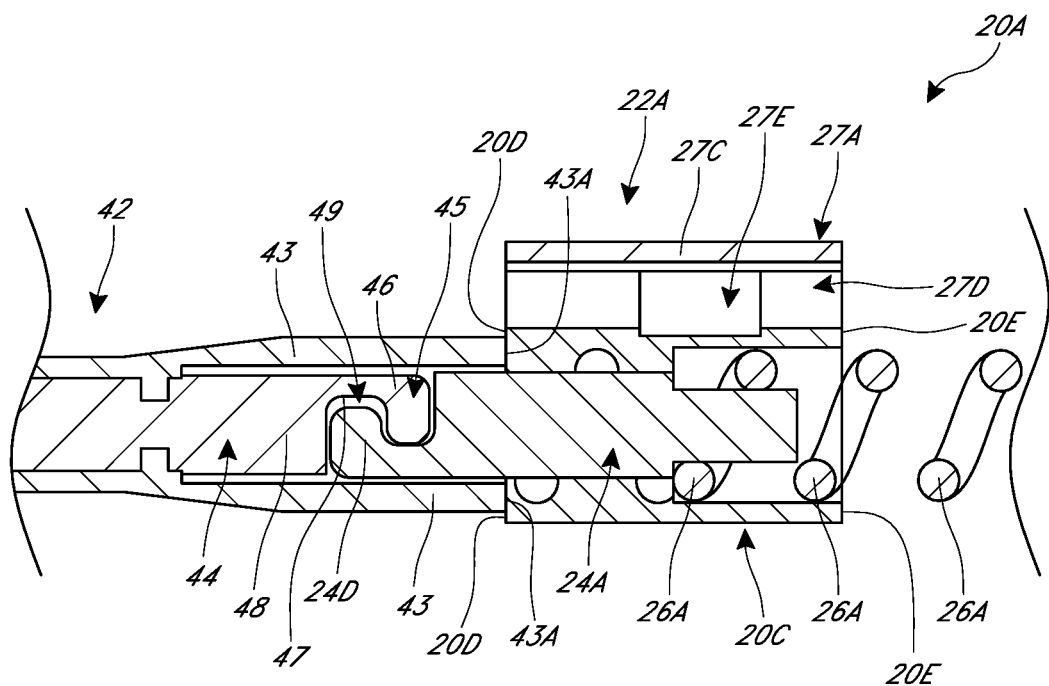
FIG. 54 is a partial cross-section view of the anchor assembly of FIG. 47A showing the anchor housing having the anchor therein engaged with a driver.

FIG. 54 is a partial cross-section view of the anchor assembly 20A showing the anchor housing 22A having the anchor 20 therein engaged with a driver 42. The driver 42 may extend through and exit the distal end of a driver tube 42A (see FIG. 57). The driver 42 may be rotated to transmit rotation forces to the anchor 20. The driver 42 includes a cover 43 surrounding a latch 44. A distal end 43A of the cover 43 may contact the proximal end 20D of the housing 22A. The driver 42 may be in this position while the implant 1 is being delivered through the delivery catheter. The latch 44 includes a coupling portion 45 that couples with the coupling 24D of the anchor head 24A. The coupling portion 45 as shown may include a lateral projection 46, a recess surface 47, a base 48, and an opening 49. These features of the driver 42 may be analogous to, respectively, the lateral projection 668A, the recess surface 670A, the base 671A, and the opening 672A of the anchor coupling 24D.

The lateral projection 46 of the driver coupling portion 45 may be received into the opening 672A of the anchor head 24A. The lateral projection 668A of the anchor head 24A may be received into the opening 49 of the driver coupling portion 45. The corresponding recess surfaces 670A and 47 may contact each other and prevent relative axial movement as well as lateral movement along a lateral axis. "Lateral" as used here indicates a direction that is perpendicular or generally perpendicular to the axis of the anchor 20 and/or driver 42. The cover 43 may surround the coupled connection between the two couplings 24D and 45 to prevent relative lateral slippage of the couplings 24D and 45. The driver 42 may then be rotated, for example by a surgeon rotating a proximal end of the driver 42, to transmit rotation to the anchor 20 via the anchor coupling 24D. This rotation will cause the anchor head 24A and helical portion 26A to rotate, and the anchor 20 can then advance distally as described. Rotation may be applied to the driver in an opposite direction to advance the anchor 20 proximally as described.

Figure 55:
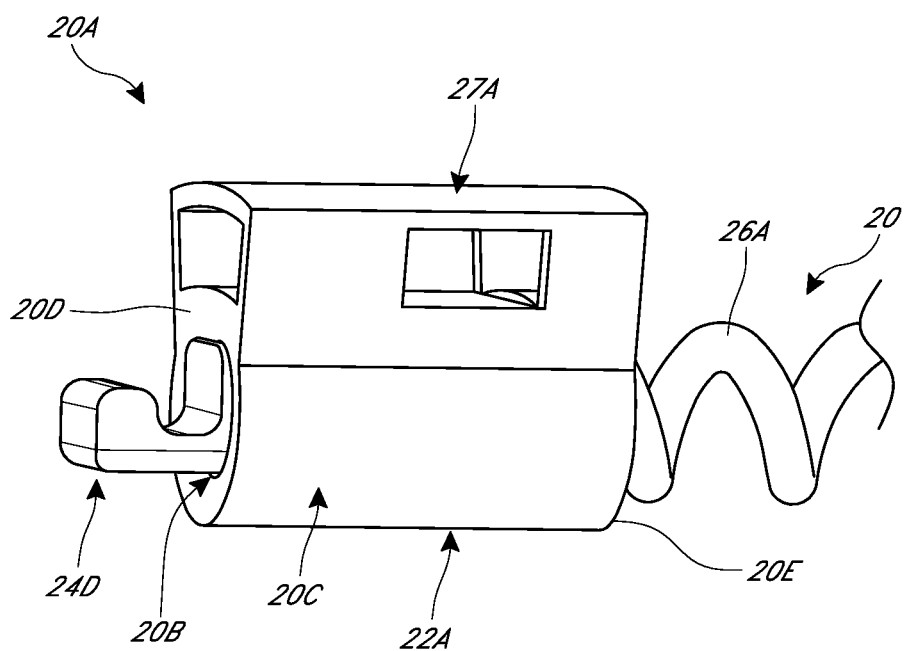
FIG. 55 depicts the anchor assembly of FIG. 47A showing the driver disengaged from the anchor head with the anchor head having been pulled into a self-locking position within the anchor housing.

As shown in FIG. 55, the anchor assembly 20A includes the anchor 20 advanced distally into and through the anchor housing 22A relative to the position shown in FIG. 54 and the driver 42 has been removed. The position shown in FIG. 55 may be the final securement position of the anchor 20. The coupling 24D is protruding proximally out of the opening 20B of the housing 22A. The coupling 24D may protrude proximally of the proximal end 20D of the housing 22A.

The driver 42 has been removed as shown in FIG. 55. The driver 42 may be removed by retracting the anchor 20 in the proximal direction to expose the coupling connection with the anchor 20, as is further described with respect to FIGS. 56-59. In some embodiments, the cover 43 may be retractable proximally while maintaining the axial position of the coupling connection of the driver 42 and anchor 20.

Further, when the helical portions 26A are rotationally driven into the heart valve annulus tissue and the implant 1 is forcibly reduced in width reducing the size of the valve annulus, a tensile force is developed on and stored in the anchor assembly 20A. This tensile force will tend to draw the anchor head 24A toward pocket 25A of the housing 22A. As shown in FIG. 54, the latch 44 of the driver 42 produces a counter tension and keeps the anchor head 24A from being pulled into the pocket 25A. When the driver 42 and latch 44 are disengaged from the anchor head 24, some of the tensile force stored in the anchor assembly 20A is released. The anchor head 24A is then pulled into the lock pocket 25A, as shown in FIG. 55. In this manner, the anchor head 24A, and anchor helical portion 26A, are rotationally constrained. This results in somewhat of a self-locking feature of the anchor assembly 20A. More specifically, owing to the potential energy stored in the anchor assembly 20A as a consequence of the anchoring and cinching of the implant 1, once the driver 42 is disengaged from the anchor 20, some of that stored energy is released causing the anchor head 24A to be pulled, or dropped, into the pocket 25A. These and other steps of anchoring and locking the anchor assembly 20A are described, more particularly, with reference to FIG. 56-59.

Figure 56:
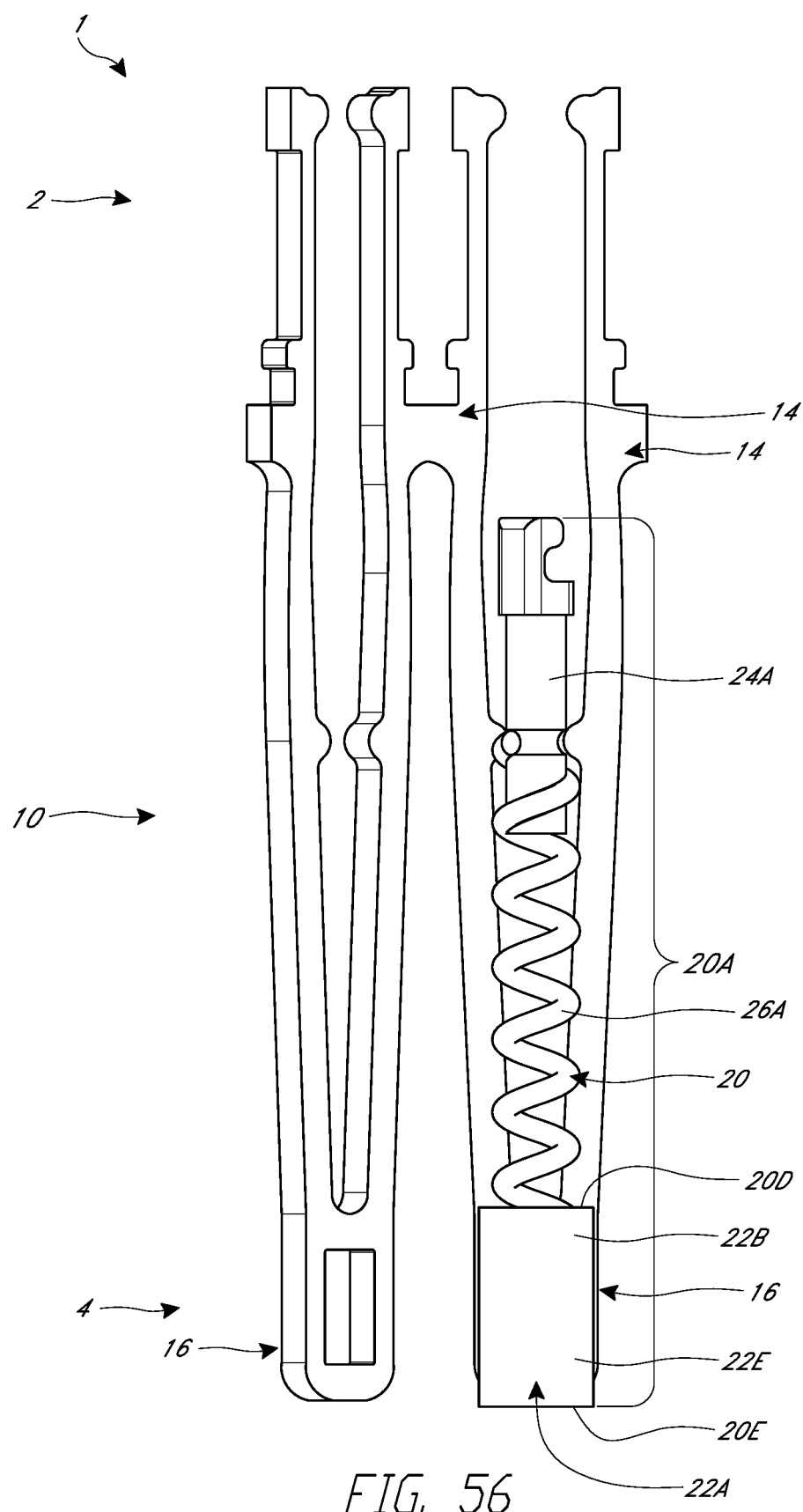
FIGS. 56-59 are partial perspective views depicting sequential positioning of the anchor with the driver, engagement of tissue with the anchor, de-coupling of the driver from the anchor, and settling in of the anchor with the housing.

FIGS. 56-59 are partial perspective views depicting sequential positioning of the anchor 20 with the driver 42, engagement of tissue with the anchor 20, de-coupling of the driver 42 form the anchor 20, and settling in of the anchor 20 with the housing 22A. FIG. 56 shows the anchor 20 in a relative proximal position relative to the housing 22A. The anchor 20 may be in this position during delivery and prior to securing the implant 1 to tissue. The driver 42, not shown for clarity purposes, may be engaged with the anchor 20 in this position. The helical portion 26A may be engaged with the proximal portion 22B of the housing 22A, as described. The helical portion 26A may or may not be located partially within the distal portion 22E of the housing 22A. The helical portion 26A may not extend past the distal end 20E of the housing 22A in this position. The driver 42 may be engaged with and be used to rotate the anchor 20, as described, to distally advance the anchor 20 to the positon shown in FIG. 57.

Figures 57, 58:
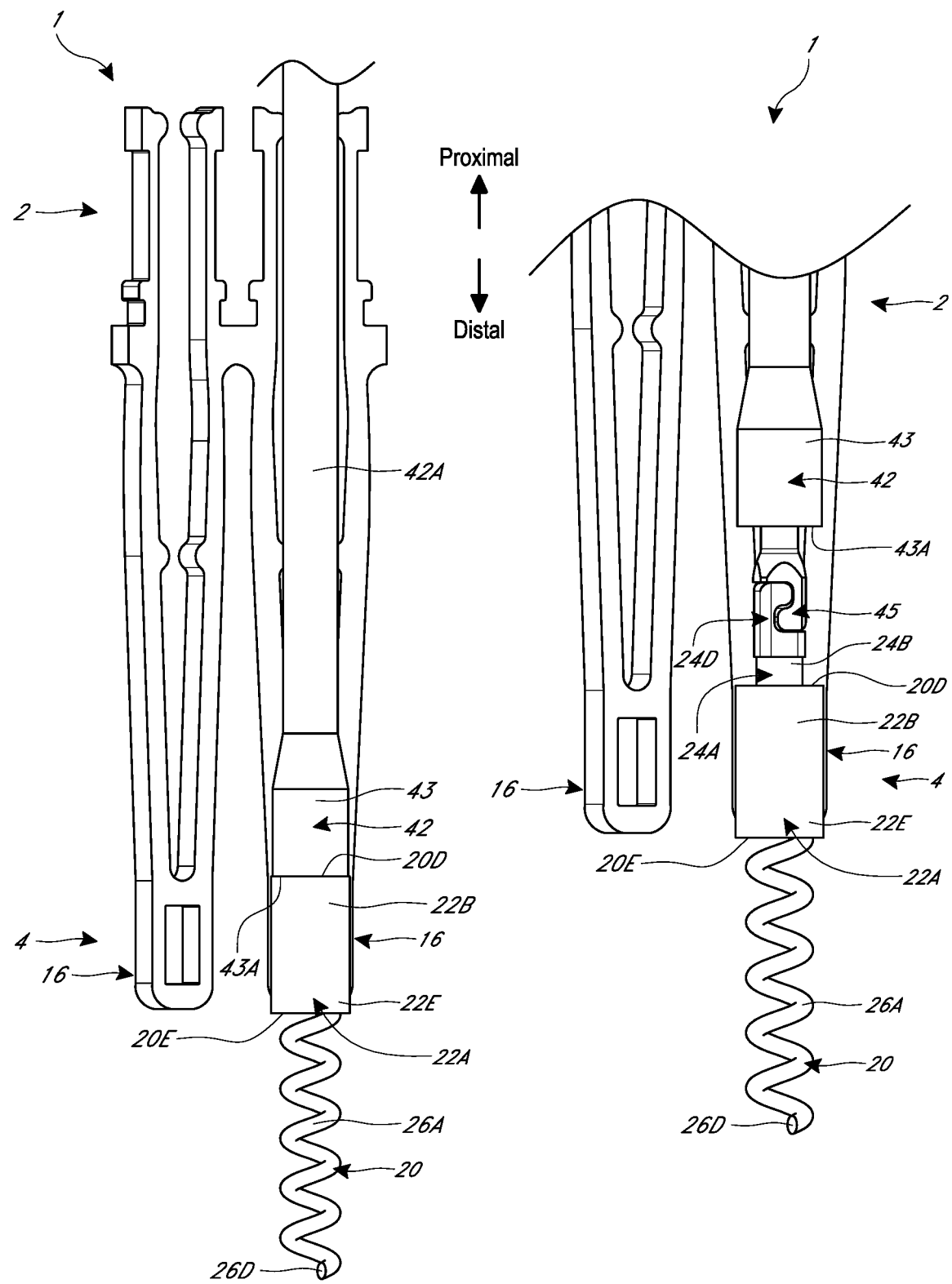

As shown in FIG. 57, the driver 42 extends through the driver tube 42A and is located distally of and adjacent to the housing 22A. The driver 42 may contact the proximal end 20D of the housing 22A. The driver 42 may provide an axial distal force to the anchor assembly 20A while rotating the anchor 20. Thus, the anchor housing 22A may advance distally due to force from the driver 42. The driver 42 may bear against the proximal end 20D. The driver 42 may rotate the anchor 20 to "freely spin" the anchor 20 as described. The helical portion 26A of the anchor 20 may be inside the distal portion 22E of the housing 22A such that the anchor can rotate 20 while maintaining an axial position relative to the housing 22A. The helical portion 26A may engage tissue and advance distally into the tissue while the anchor housing 22A, and thus at least the corresponding portion of the frame 10 to which the housing 22A is attached, moves distally toward the region of tissue into which the helical portion 26A of the anchor 20 is engaging. The anchor 20 may be rotated until the distal end 20E of the housing 22A has contacted or is within a sufficient distance of the tissue. A "sufficient" distance includes distances such that contraction of the implant 1, by advancement of the collar 18, will reduce or eliminate regurgitation of the blood through the valve.

In some embodiments, the anchor assembly 20A has the configuration shown in FIG. 57 after the anchor 20 has reached its final distal position. Some, most, or all of the helical portion 26A may be engaged with the tissue in the final position. In some embodiments, the anchor 20 may be in the final position with the helical portion 26A still partly engaged with the proximal portion 22B of the anchor housing 22A, such as the groove 22D, as described. For example, the housing 22A may contact tissue before the helical portion 26A advances distally beyond the distal end 20E of the housing 22A. The anchor 20 may then be rotated, and the helical portion 26A may or may not be engaged with the proximal portion 22B of the housing 22a in its final position. In some embodiments, the anchor housing 22A contacts the tissue, the anchor 20 is then rotated and advanced distally into tissue, and the anchor 20 "freely spins" in the distal portion of the housing 22A, as described, in order to remove any gap between the housing 22A and tissue or otherwise ensure a sufficiently small distance therebetween.

Figure 59:
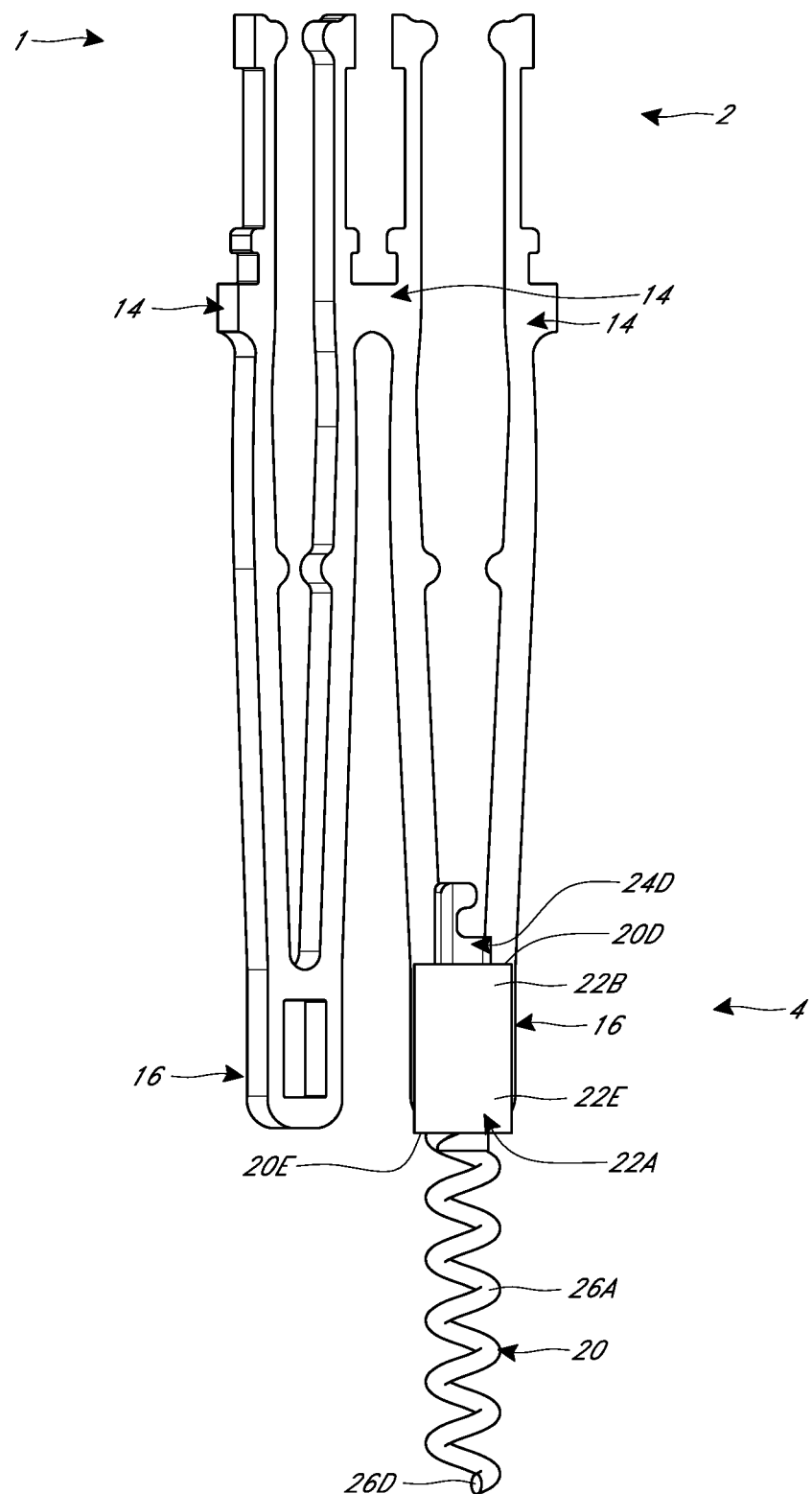

FIG. 58 depicts the driver 42 being disengaged from the anchor head 24. The driver 42 is first withdrawn slightly exposing its distal latch 44 which is mated with the anchor head 24. The coupling portion 45 of the driver 42 may be moved laterally to disengage from the coupling 24D of the anchor 20. The coupling portion 45 may be moved directly away from the coupling 24D (for example to the right as oriented in the figure) or slid along the coupling 24D (for example into or out of the plane of the figure as oriented). Once disengaged, the anchor head 24 drops into and self-locks into the anchor housing 22A, as shown in FIG. 59. FIG. 59 depicts the anchor 20 in its fully deployed and locked state, with the driver 42 disengaged from the anchor head 24.

The implant 1 may be repositioned and, if necessary, retrieved from the patient after implantation. For example, the collars 18 may be adjusted to further contract or expand the implant 1. The shafts 646 may be rotated in opposite directions to cause the collars 18 to advance proximally or distally as desired. The anchors 20 may be rotated in opposite directions to cause proximal or distal advance of the anchors 20.

In particular, to reposition the implant 1, the shafts 646 may be rotated to advance the collars proximally or distally to obtain the desired shape of the frame 10 and thus of the annulus. Some collar 18 may be advanced farther distally than other collars 18 to allow for different angles between different pairs of adjacent struts 12. Some of the angles C (see FIG. 44C) may be larger or smaller than other of the angles C as desired.

The implant 1 may be removed from securement with tissue if needed. The anchors 20 may be secured to tissue and then removed from engagement with the tissue by rotation in the opposite direction. The anchors 20 may be retracted via the "free spin" technique described herein, where the housing 22A also moves distally with the anchors 20. The anchors 20 may be retracted into the housing 22A so that the helical portion 26A engages the proximal grooved portion 22B of the housing 22A. The anchors 20 may be retracted back to a same starting position as prior to delivery. Prior to retraction of the anchors 20 from tissue, the collars 18 may be advanced proximally or distally to facilitate anchor 20 removal. For example, the collars 18 may be advanced proximally to remove contraction stresses on the frame 10 which may assist with removal of the anchors 20, such as by removing circumferential forces on the anchors 20 from the frame 10.

The implant 1 may be retrieved by proximal retraction of the anchors 20 from tissue engagement as described and proximal advance of the collars 18 as described. The anchors 20 may be disengaged from the tissue and proximally retracted some, most or all of the possible retraction distance, such as back to their starting position. The collars 18 may be advanced proximally some, most, or all of the possible proximally distance, such as back to their starting position at the proximal apex 14. In some embodiments, after removal of the anchors 20 from engagement with tissue, one or more collars 18 may be advanced distally to contract the implant 1 to a retrieval configuration. The collars 18 may be advanced distally to reduce the angle C between pairs of adjacent struts 12 such that the implant 1 reduces in overall width and can be re-sheathed for removal with the delivery catheter.

In some embodiments, after implantation of various implants described herein, such as implant 1, the heart valve annulus may remodel. Thus dynamic post implantation constriction of the annulus may be achieved. The annulus may remodel due to residual stresses in the annulus imparted by the contracted and stressed implant 1 acting on the annulus. The inward forces imparted on the annulus by the contracted implant 1 may thus cause the tissue to remodel and further contract. The implant 1 may cause such remodeling due to the structure of the implant 1. For example, the reduction of the angle C between every pair of adjacent struts 12 will impart an inward force on the annulus at every distal apex 16. The uniform distribution of these inward forces at each anchor 20 about the annulus may cause it to remodel and further contract with the passage of time. Thus, the implant 1 may be used to further reduce regurgitation after a period of time post implantation of the implant 1. In some embodiments, the annulus may reduce in width after implantation of the implant 1 from about 0.5 millimeters to about 3 millimeters, from about 1 millimeter to about 2 millimeters, or other ranges or amounts. In some embodiments, the annulus may reduce in width after implantation of the implant 1 from about 1% to about 15%, from about 2% to about 10%, from about 5% to about 8%, or other ranges or percentages. This percentage may be a percentage of the annulus width after implantation and removal of the adjustment catheter or driver. The annulus may continue to reduce in width for a period of time after implantation of the implant 1 of about 2 days to about 30 days, of about 3 days to about 20 days, of about 4 days to about 15 days, of about 5 days to about 10 days, or other ranges or periods of time. The implant 1 may reduce in width post-implantation a corresponding amount and time as described herein with respect to the annulus post-implantation reduction in width.

The implant 1 may thus be used for dynamic post implantation constriction of the annulus surrounding a heart valve. In some embodiments, the implant 1 may have a moveable restraint such as the collar 18, that may be at least partially surrounding the pair of adjacent struts 12 and can be moved along the pair of adjacent struts 12 away from the apex to reduce the angle C between the pair of adjacent struts 12. This may cause the implant body such as the frame 10 to contract the annulus from a first diameter to a second, smaller diameter, with at least one strut 12 initially elastically deflected by resistance to movement imposed by the annulus when in the second diameter. The struts 12 may be under a bending moment and store potential mechanical energy due to the bending. The bending may be in or out of plane bending. The implant 1 may be configured to contract post implantation from the second diameter to a third, smaller diameter as elastic tension in the strut 12 relaxes and overcomes resistance to movement imposed by the annulus. In some embodiments, the elastic tension, for example elastic energy due to bending, is stored in the struts 12 in between the movable restraint 18 and tissue anchor 20. This energy may be released or partially released as the annulus remodels and further constricts post implantation of the implant 1. One, some or all of the struts 12 may contribute to the remodeling as described.

Various methods for dynamic post implantation constriction of an annulus surrounding a heart valve may be performed with the various implants described herein. The method may comprise the steps of securing the implant 1 to the wall of the atrium surrounding a mitral valve annulus having a first diameter. The implant 1 may be actively adjusted with an adjustment catheter to reduce the annulus from the first diameter to a second, smaller diameter. The adjustment catheter may be removed. The diameter may continue to be reduced to a third diameter that is smaller than the second diameter following removal of the catheter, in response to potential energy stored in the implant 1.

Various sizes and dimensions for dynamic post implantation constriction of the annulus may be achieved. For example, the second diameter may be no more than about 27 mm and the third diameter may be at least 1 mm smaller than the second diameter. The second diameter may be no more than about 27 mm and the third diameter may be at least 2 mm smaller than the second diameter. The implant 1 may be configured to contract post implantation from the second diameter to the third, smaller diameter within about 30 days after removing the adjustment catheter. Further, mitral leaflet coaptation may increase by at least about 25% in response to reduction of the annulus from the second diameter to the third diameter. Mitral leaflet coaptation may increase by at least about 50% in response to reduction of the annulus from the second diameter to the third diameter. The diameter may continue to reduce for at least about five days following removing the adjustment catheter. The diameter may continue to reduce for at least about 10 days following the removing the adjustment catheter.

In some embodiments, following removing the catheter, the dynamic implant 1 increases leaflet coaptation by at least about 25% from the coaptation corresponding to the second diameter. In some embodiments, following removing the catheter, the dynamic implant 1 increases leaflet coaptation by at least about 50% from the coaptation corresponding to the second diameter. In some embodiments, following removing the catheter, the dynamic implant increases leaflet coaptation by at least about 2 mm. In some embodiments, following removing the catheter, the dynamic implant 1 increases leaflet coaptation by at least about 4 mm.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. An implant comprising:
    a tubular frame having a proximal end, a distal end and a central lumen extending therethrough, the tubular frame comprising a plurality of pairs of struts joined to form a plurality of proximal apices and a plurality of distal apices;
    an adjustment mechanism coupled to a first pair of struts that form a proximal apex, the adjustment mechanism configured to control a spacing between distal ends of the first pair of struts;
    an anchor housing carried by a distal apex formed by a second pair of struts; and
    an anchor translationally disposed within an opening of the anchor housing and axially moveable within the anchor housing between a first position and a second position, wherein in the first position the anchor advances axially relative to the tubular frame in response to rotation of the anchor in a first direction within the anchor housing, and in the second position the anchor is freely rotatable in the first direction within the anchor housing without axially advancing relative to the anchor housing.

2. The implant of claim 1, wherein the anchor housing includes an opening extending axially therethrough, and the anchor is configured to engage tissue of the mitral valve annulus in the second position by rotating within the anchor housing without advancing axially relative to the anchor housing.

3. The implant of claim 1, wherein the anchor comprises a proximal coupling portion and a helical coil portion.

4. The implant of claim 1, wherein the second position is a position wherein the helical coil portion of the anchor is fully within the distal portion of the anchor housing.

5. A method of anchoring an implant as described in claim 1 to patient tissue proximate to a valve annulus, the method comprising:
    transluminally advancing the implant towards the valve annulus;
    expanding the implant to an annulus engagement diameter;
    rotating an anchor carried by the implant in a first direction to engage a helical coil portion of the anchor into tissue around the valve annulus; and
    continuing to rotate the anchor in the first direction relative to the implant without further axially advancing the anchor relative to the implant when the anchor is in an axially extended position on the implant to pull tissue around the valve annulus toward the implant.

* * * * *